US011723990B2

(12) United States Patent
Gao et al.

(10) Patent No.: US 11,723,990 B2
(45) Date of Patent: *Aug. 15, 2023

(54) LIBRARY OF PH RESPONSIVE POLYMERS AND NANOPROBES THEREOF

(71) Applicant: The Board of Regents of the University of Texas System, Austin, TX (US)

(72) Inventors: Jinming Gao, Plano, TX (US); Gang Huang, Plano, TX (US); Tian Zhao, Irving, TX (US); Xinpeng Ma, Dallas, TX (US); Yiguang Wang, Dallas, TX (US); Yang Li, Dallas, TX (US); Baran D. Sumer, Dallas, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 3 days.

This patent is subject to a terminal disclaimer.

(21) Appl. No.: 17/231,922

(22) Filed: Apr. 15, 2021

(65) Prior Publication Data

US 2021/0338840 A1    Nov. 4, 2021

Related U.S. Application Data

(63) Continuation of application No. 16/114,187, filed on Aug. 27, 2018, now Pat. No. 11,013,818, which is a
(Continued)

(51) Int. Cl.
*A61K 8/73* (2006.01)
*A61K 8/06* (2006.01)
(Continued)

(52) U.S. Cl.
CPC ...... *A61K 49/0054* (2013.01); *A61K 49/0021* (2013.01); *A61K 49/0032* (2013.01);
(Continued)

(58) Field of Classification Search
None
See application file for complete search history.

(56) References Cited

U.S. PATENT DOCUMENTS 9,511,152 B2   12/2016   Gao et al.
9,751,970 B2   9/2017    Gao et al.
(Continued)

FOREIGN PATENT DOCUMENTS

WO   WO 2012/039741   3/2012
WO   WO 2012/039855   3/2012
(Continued)

OTHER PUBLICATIONS

Zhou, K., et al., Multicolored pH-Tunable and Activatable Fluorescence Nanoplatform Responsive to Physiologic pH Stimuli, J. Am. Soc. Chem., 134 (2012) pp. 7803-7811. (Year: 2012).*
(Continued)

*Primary Examiner* — Dominic Lazaro
(74) *Attorney, Agent, or Firm* — Parker Highlander PLLC

(57) ABSTRACT

The present disclosure relates to polymers which contain a hydrophobic and hydrophilic segment which is sensitive to pH. In some aspects, the polymers form a micelle which is sensitive to pH and results in a change in fluorescence based upon the particular pH. In some aspects, the disclosure also provides methods of using the polymers for the imaging of cellular or extracellular environment or delivering a drug.

20 Claims, 108 Drawing Sheets

Related U.S. Application Data continuation of application No. 15/369,701, filed on Dec. 5, 2016, now Pat. No. 10,098,971, which is a continuation of application No. PCT/US2015/034575, filed on Jun. 5, 2015.

(60) Provisional application No. 62/009,019, filed on Jun. 6, 2014.

(51) Int. Cl.
  *A61K 49/00* (2006.01)
  *G01N 21/64* (2006.01)
  *C08F 8/30* (2006.01)
  *C08F 8/32* (2006.01)
  *C08F 8/34* (2006.01)
  *C08F 8/42* (2006.01)
  *C09B 69/10* (2006.01)
  *G01N 33/58* (2006.01)
  *G01N 33/84* (2006.01)

(52) U.S. Cl.
  CPC .......... *A61K 49/0041* (2013.01); *C08F 8/30* (2013.01); *C08F 8/32* (2013.01); *C08F 8/34* (2013.01); *C08F 8/42* (2013.01); *C09B 69/103* (2013.01); *C09B 69/105* (2013.01); *C09B 69/106* (2013.01); *C09B 69/109* (2013.01); *G01N 21/643* (2013.01); *G01N 21/6428* (2013.01); *G01N 21/6456* (2013.01); *G01N 33/582* (2013.01); *G01N 33/84* (2013.01); *G01N 2021/6432* (2013.01); *G01N 2021/6439* (2013.01); *G01N 2021/6441* (2013.01)

(56) References Cited

U.S. PATENT DOCUMENTS

| | | | |
|---|---|---|---|
| 10,098,971 B2 * | 10/2018 | Gao | G01N 33/582 |
| 11,013,818 B2 * | 5/2021 | Gao | G01N 21/643 |
| 2002/0028474 A1 | 3/2002 | Shibamura et al. | |
| 2008/0241873 A1 | 10/2008 | Bornhob et al. | |
| 2013/0011336 A1 | 1/2013 | Niitsu et al. | |
| 2013/0017147 A1 | 1/2013 | Ogiwara et al. | |
| 2013/0330278 A1 | 12/2013 | Gao et al. | |
| 2013/0331426 A1 | 12/2013 | Gao et al. | |
| 2014/0023590 A1 | 1/2014 | Gao et al. | |
| 2017/0049911 A1 | 2/2017 | Gao et al. | |

FOREIGN PATENT DOCUMENTS

| | | |
|---|---|---|
| WO | WO 2012/040513 | 3/2012 |
| WO | WO 2013/152059 | 10/2013 |

OTHER PUBLICATIONS

Zhou, K., et al., Multicolored pH-Tunable and Activatable Fluorescence Nanoplatform Responsive to Physiologic pH Stimuli, J. Am. Soc. Chem., 134 (2012) pp. 7803-7811, Supplementary Information. (Year: 2012).*

Albertazzi et al., "Delivery and subcellular targeting of dendrimer-based fluorescent pH sensors in living cells," *J. Am. Chem. Soc.*, 132:18158-18167, 2010.

Almutairi et al., "Biodegradable pH-sensing dendritic nanoprobes for near-infrared fluorescence lifetime and intensity imaging," *J. Am. Chem. Soc.*, 130:444-445, 2008.

Benjaminsen et al., "Evaluating nanoparticle sensor design for intracellular pH measurements," *ACS Nano*, 5:5864-5873, 2011.

Han and Burgess, "Fluorescent indicators for intracellular pH," *Chem. Rev.*, 110:2709-2728, 2010.

Huang et. al., "A reexamination of active and passive tumor targeting by using rod-shaped gold nanocrystals and covalently conjugated peptide ligands," *ACS Nano*, 4:5887-5896, 2010.

Kobayashi et al., "New strategies for fluorescent probe design in medical diagnostic imaging," *Chem. Rev.*, 110:2620-2640, 2010.

Li et al., "Chaotropic-anion-induced supramolecular self-assembly of ionic polymeric micelles," *Angew. Chem. Int. Ed. Engl.*, 53(31):8074-8078, 2014.

Li et al., "pH-Activated Near-Infrared Fluorescence Nanoprobe Imaging Tumors by Sensing the Acidic Microenvironment," *Adv. Funct. Mater.*, 20:2222-2230, 2010.

Ma et al., "Ultra-pH-sensitive nanoprobe library with broad pH tenability and fluorescence emissions," *J. Am. Chem. Soc.*, 136(31):11085-11092, 2014.

Office Communication issued in European Patent Application No. 15803416.5, dated Apr. 9, 2019.

Office Communication issued in Japanese Patent Application No. 2016-571093, dated Feb. 20, 2019. (English translation).

Office Communication issued in U.S. Appl. No. 15/369,701, dated Apr. 27, 2017.

Office Communication issued in U.S. Appl. No. 15/369,701, dated Sep. 21, 2017.

Office Communication issued in U.S. Appl. No. 15/369,701, dated Feb. 6, 2018.

Office Communication issued in U.S. Appl. No. 15/369,701, dated Apr. 12, 2018.

Office Communication issued in U.S. Appl. No. 15/369,701, dated May 4, 2018.

Partial Supplementary European Search Report and Search Opinion issued in European Application No. 15803416.5, dated Dec. 14, 2017.

PCT International Preliminary Report on Patentability issued in International Application No. PCT/US2015/034575, dated Jul. 21, 2016.

PCT International Search Report and Written Opinion issued in International Application No. PCT/US2015/034575, dated Aug. 27, 2015.

Srikun et al., "A dendrimer-based platform for simultaneous dual fluorescence imaging of hydrogen peroxide and pH gradients produced in living cells," *J. Chang. Chem. Sci.*, 2:1156-1165, 2011.

Urano et al., "Selective molecular imaging of viable cancer cells with pH-activatable fluorescence probes," *Nat. Med.*, 15:104-109, 2009.

Wang et al., "A nanobuffer reporter library for fine-scale imaging and perturbation of endocytic organelles," *Nat. Commun.*, 6:8524, 2015.

Wang et al., "A nanoparticle-based strategy for the imaging of a broad range of tumours by nonlinear amplification of microenvironment signals," *Nature Materials*, 13(2):204-212, 2014.

Wang et al., "Functional imaging of brown fat in mice with 18F-FDG micro-PET/CT," *Journal of Visualized Experiments*, 2012.

Zheng et al., "Enhanced tumor treatment using biofunctional indocyanine green-containing nanostructure by intratumoral or intravenous injection," *Molecular Pharmaceutics*, 9(3):514-522, 2012.

Zhou et al., "Multicolored pH-tunable and activatable fluorescence nanoplatform responsive to physiologic pH stimuli," *J. Am. Chem. Soc.*, 134:7803-7811, 2012.

Zhou et al., "Supplementary Information: Multicolored pH-tunable and activatable fluorescence nanoplatform responsive to physiologic pH stimuli," *Journal of the American Chemical Society*, 2012.

Zhou et al., "Supporting information: Tunable, ultrasensitive pH-responsive nanoparticles targeting specific endocytic organelles in living cells," *Angew. Chem. Int. Ed.*, 123:623-6238, 2011.

Zhou et al., "Tunable, ultrasensitive pH-responsive nanoparticles targeting specific endocytic organelles in living cells," *Angew. Chem. Int. Ed.*, 50:6109-6114, 2011.

* cited by examiner

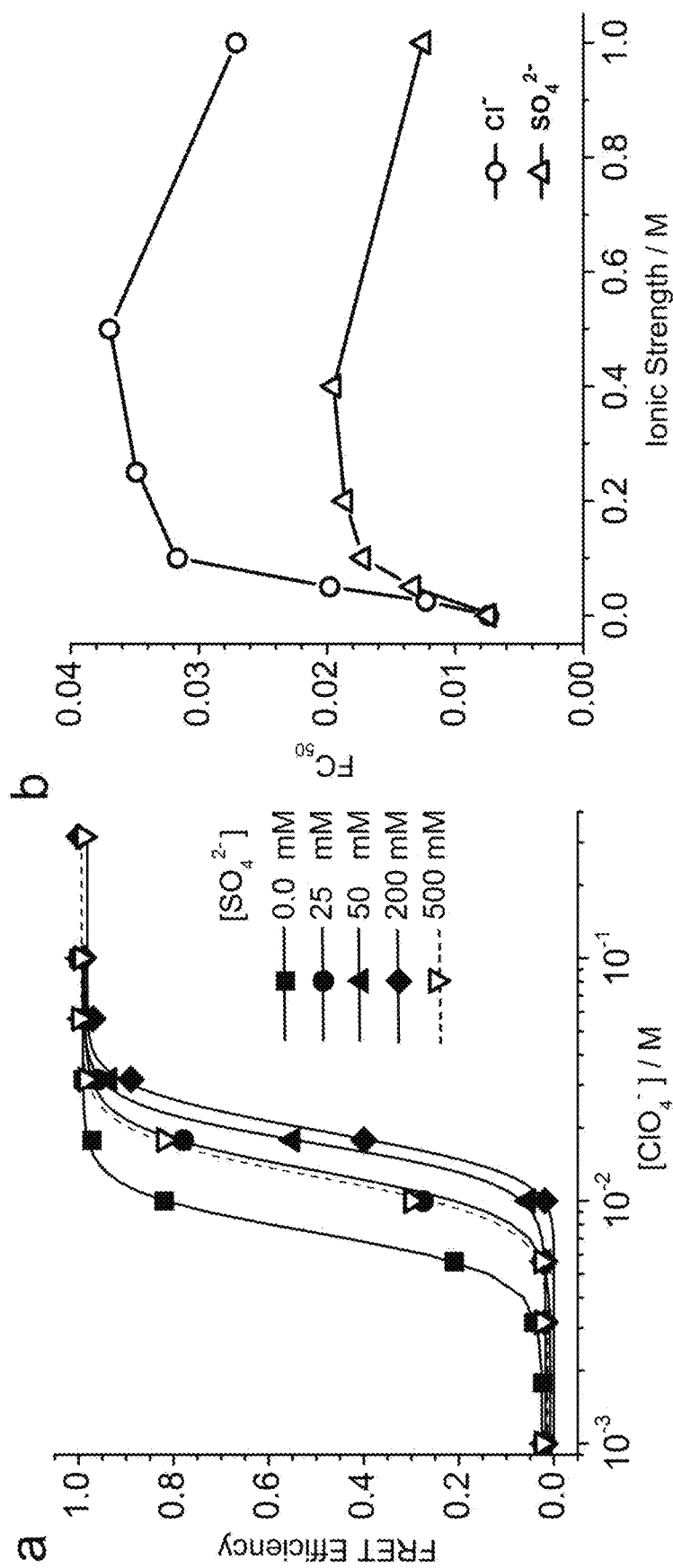
FIGS. 37A & B

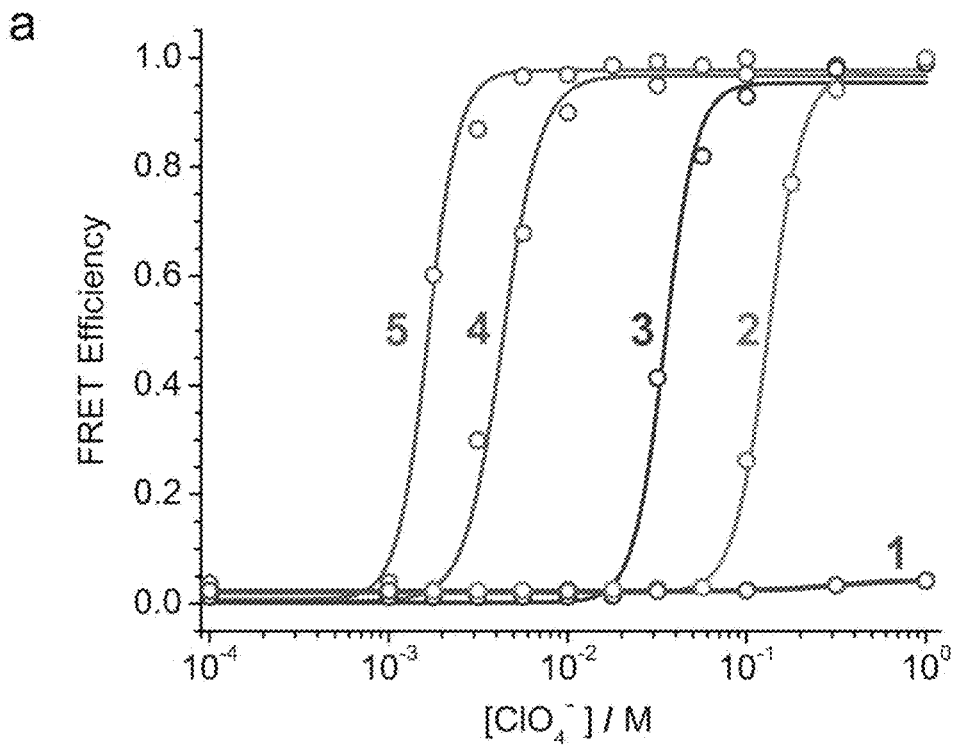
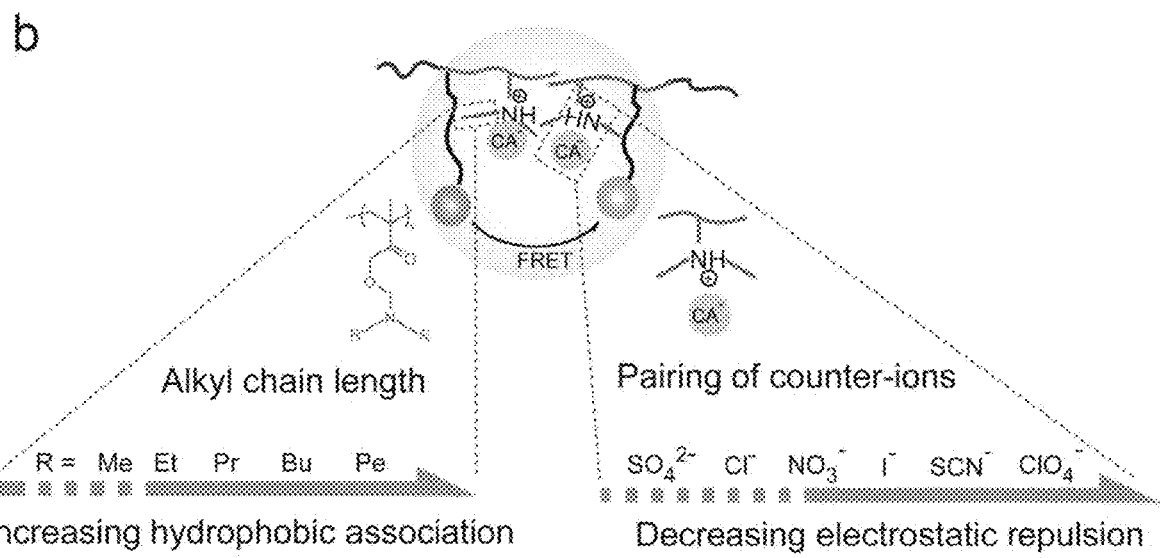
FIGS. 38A & B

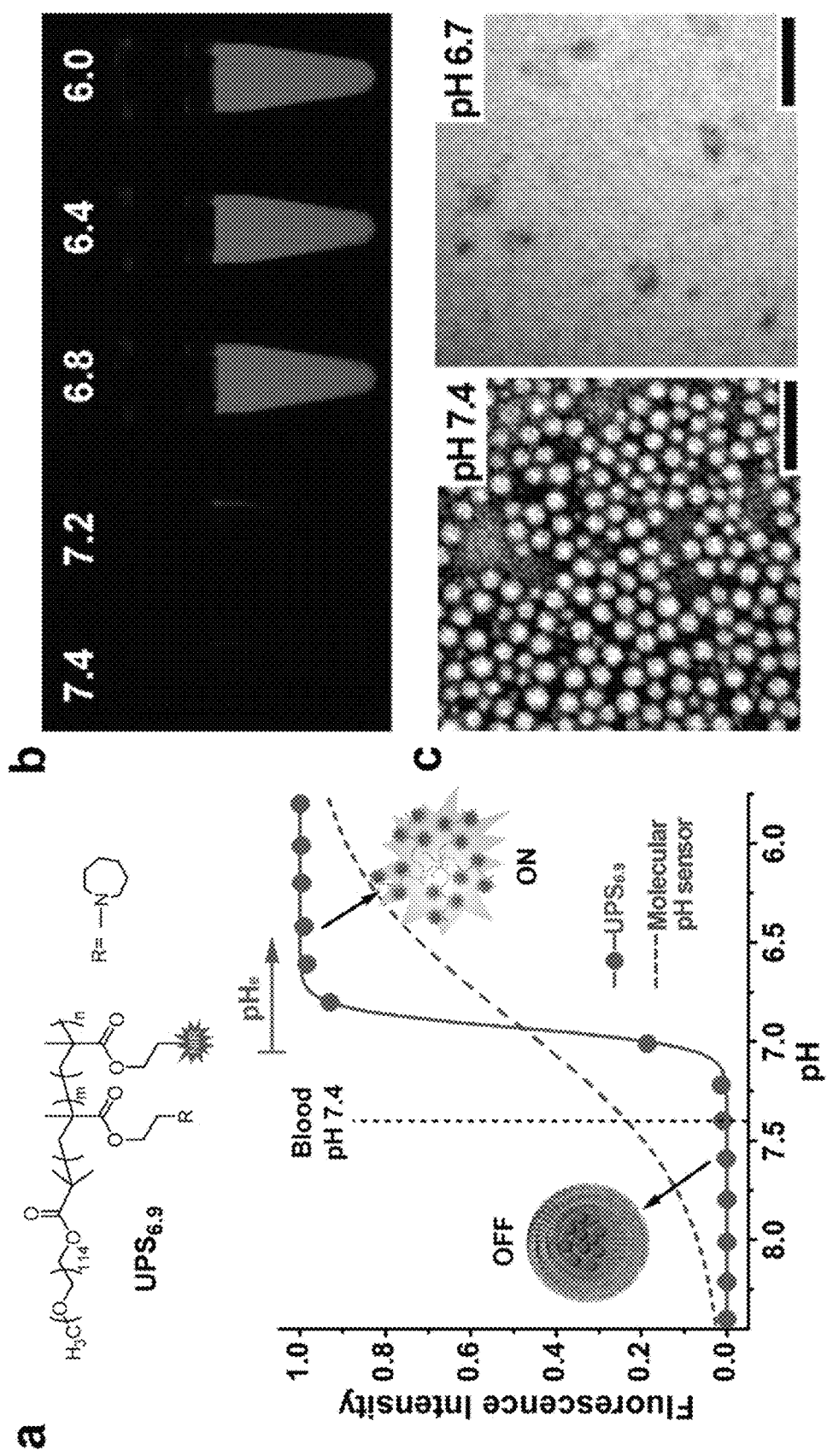
FIGS. 40A-C

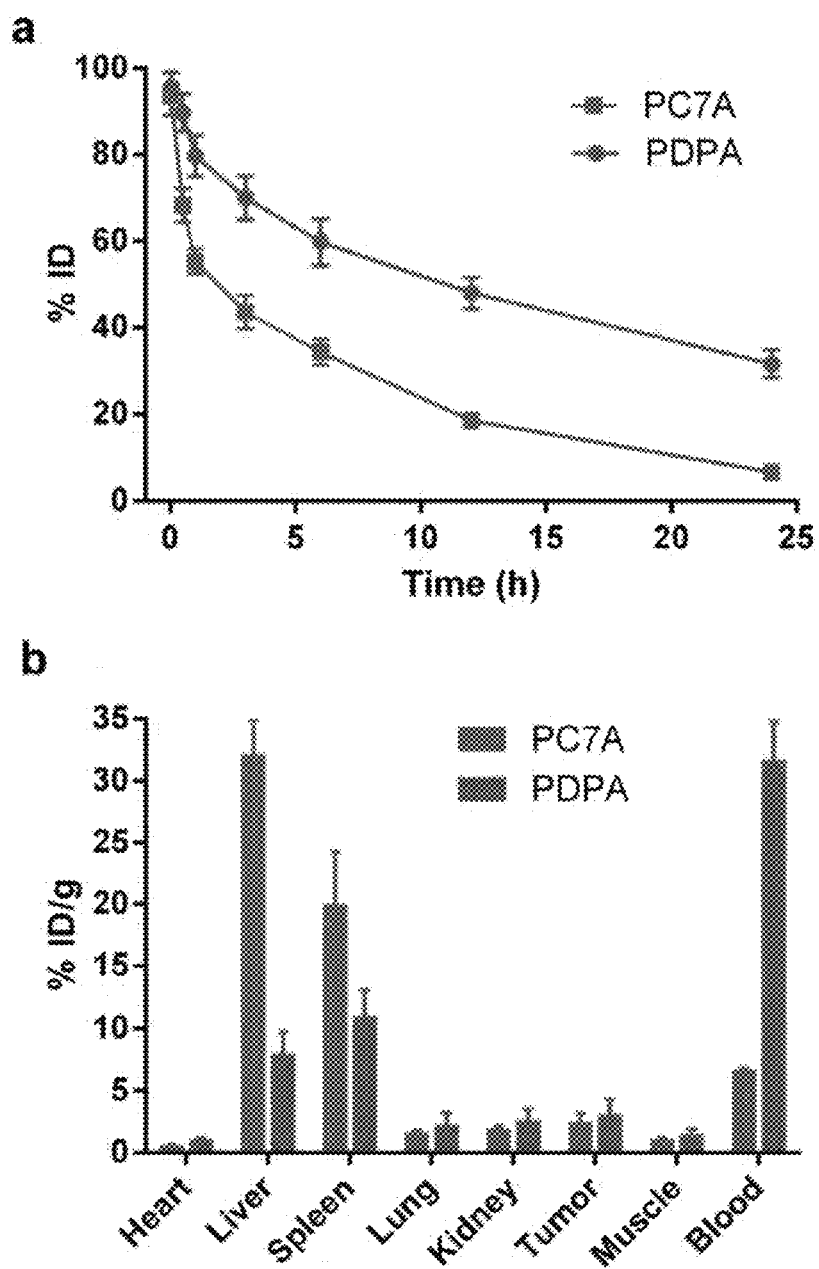
FIGS. 41A & B

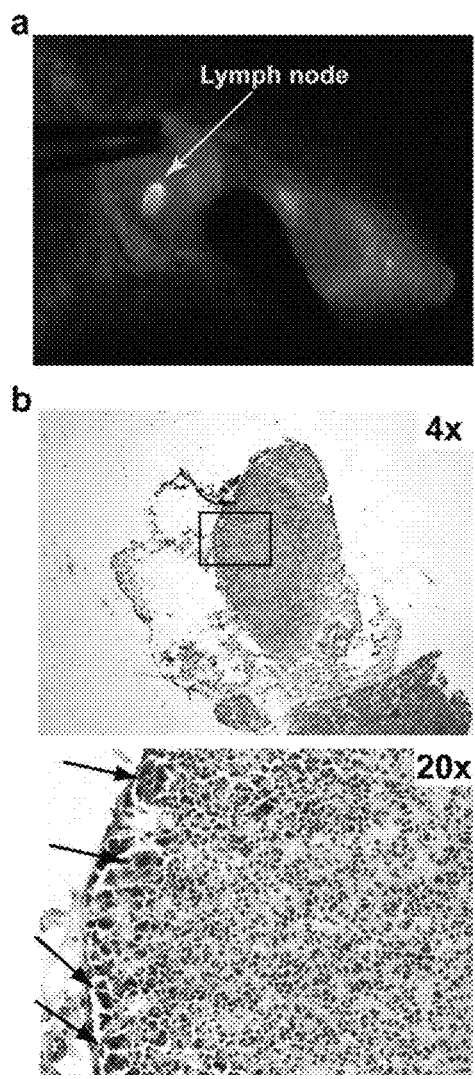
FIG. 42A & B

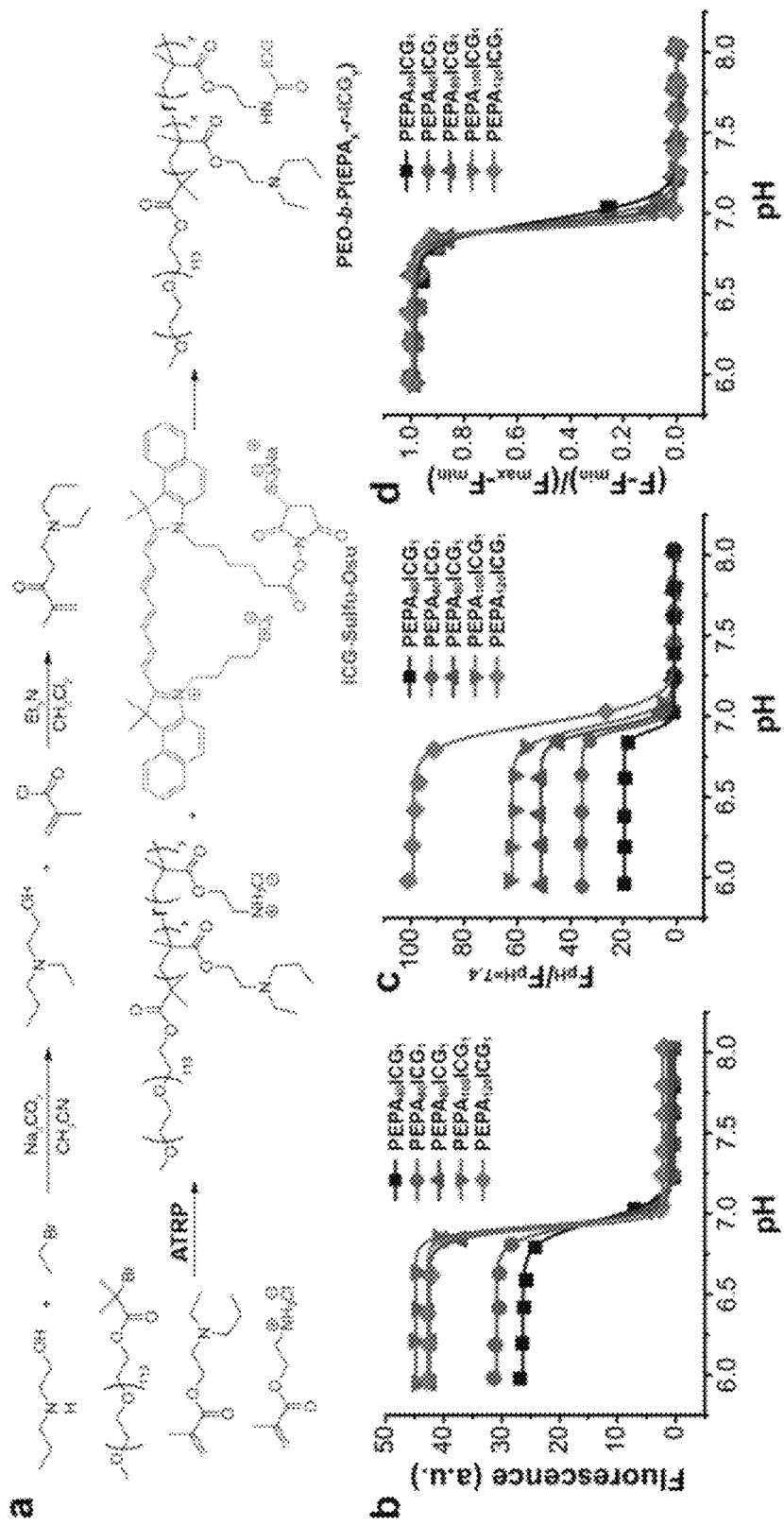
FIGS. 43A-D

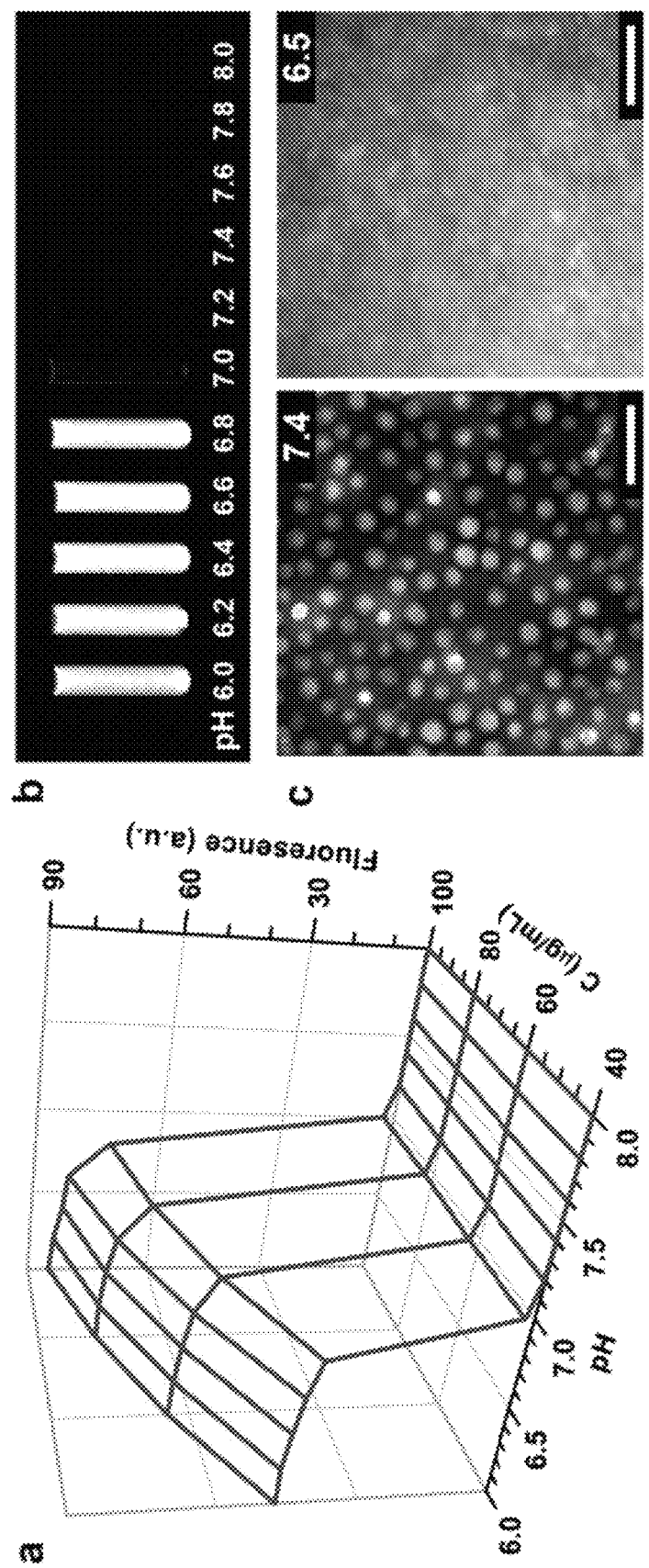
FIGS. 44A-C

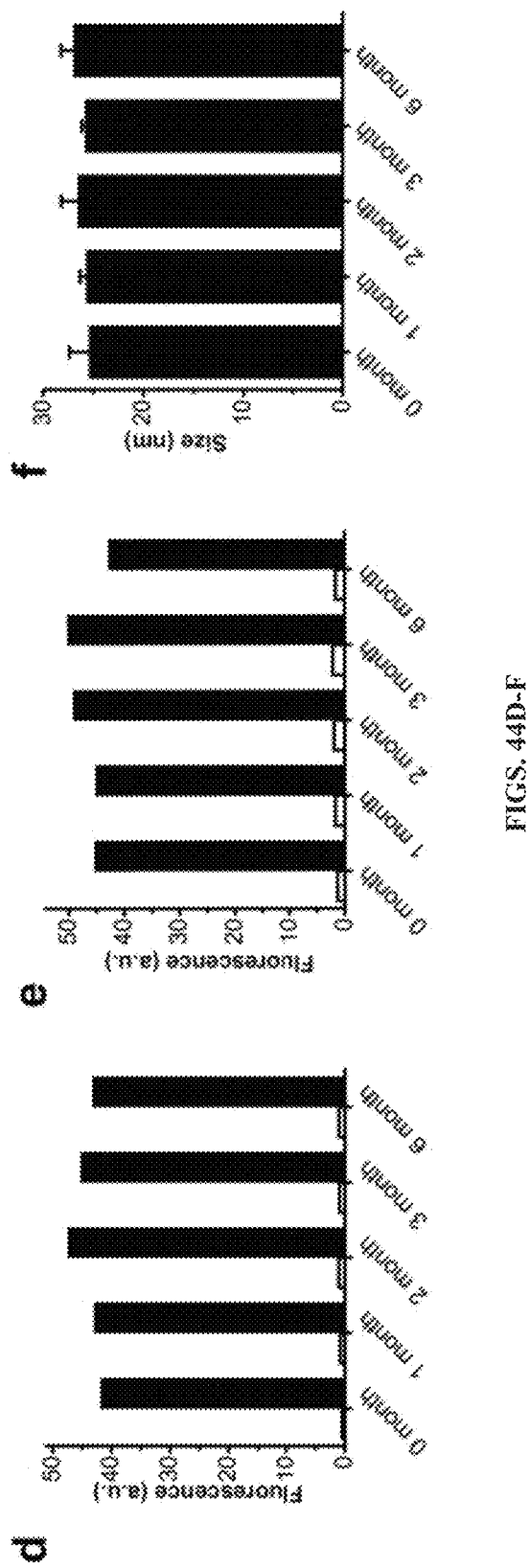
FIGS. 44D-F

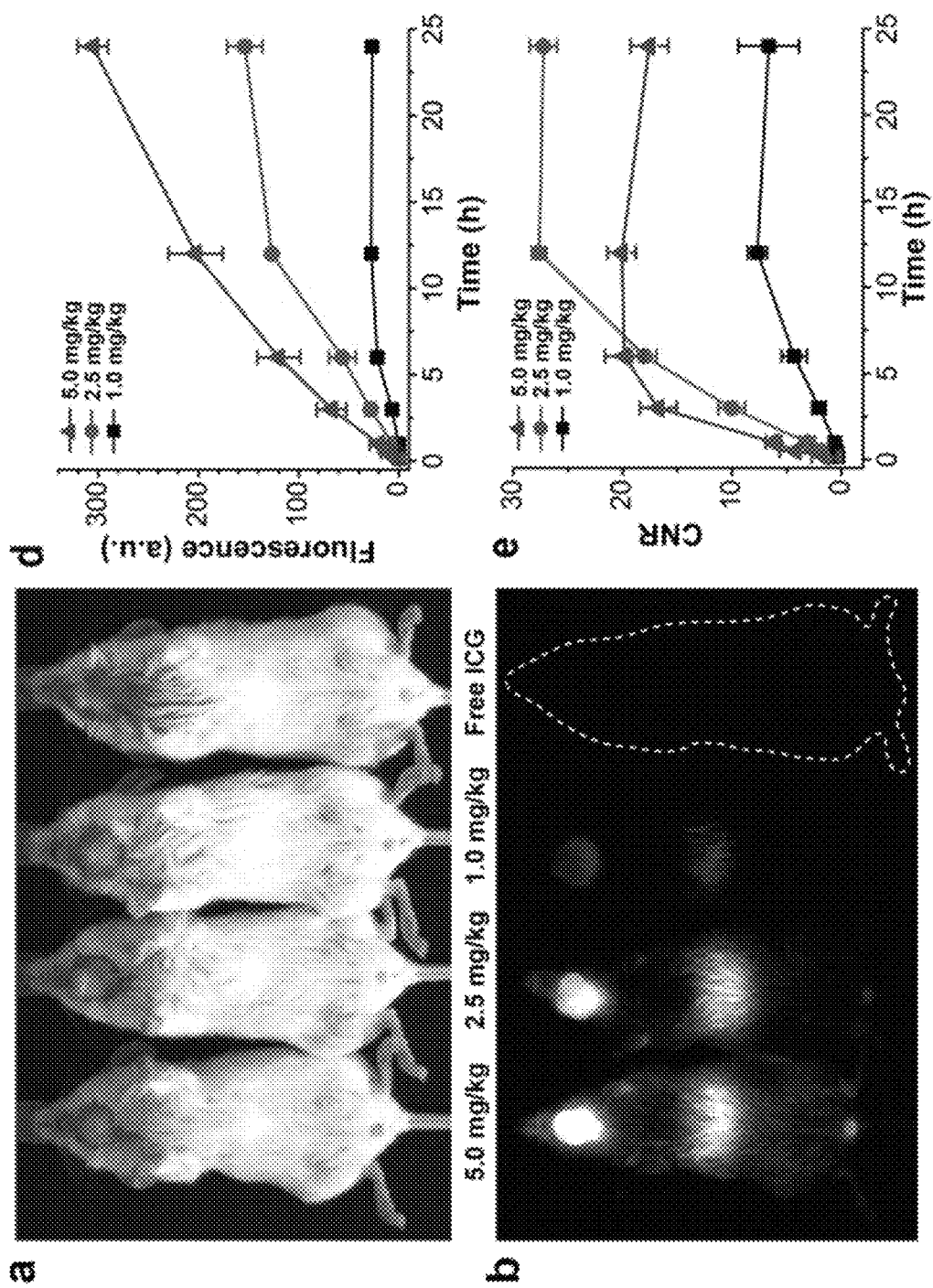
FIGS. 45A-B and 45D-E

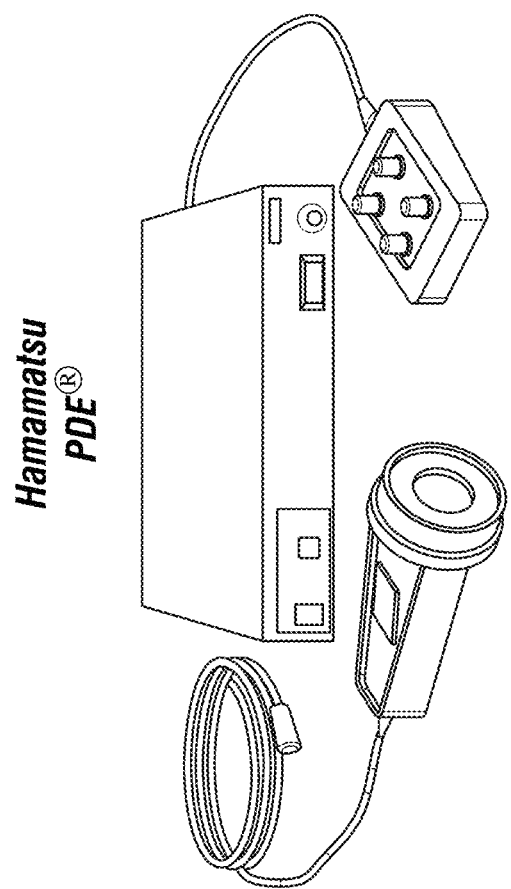
FIG. 49A2
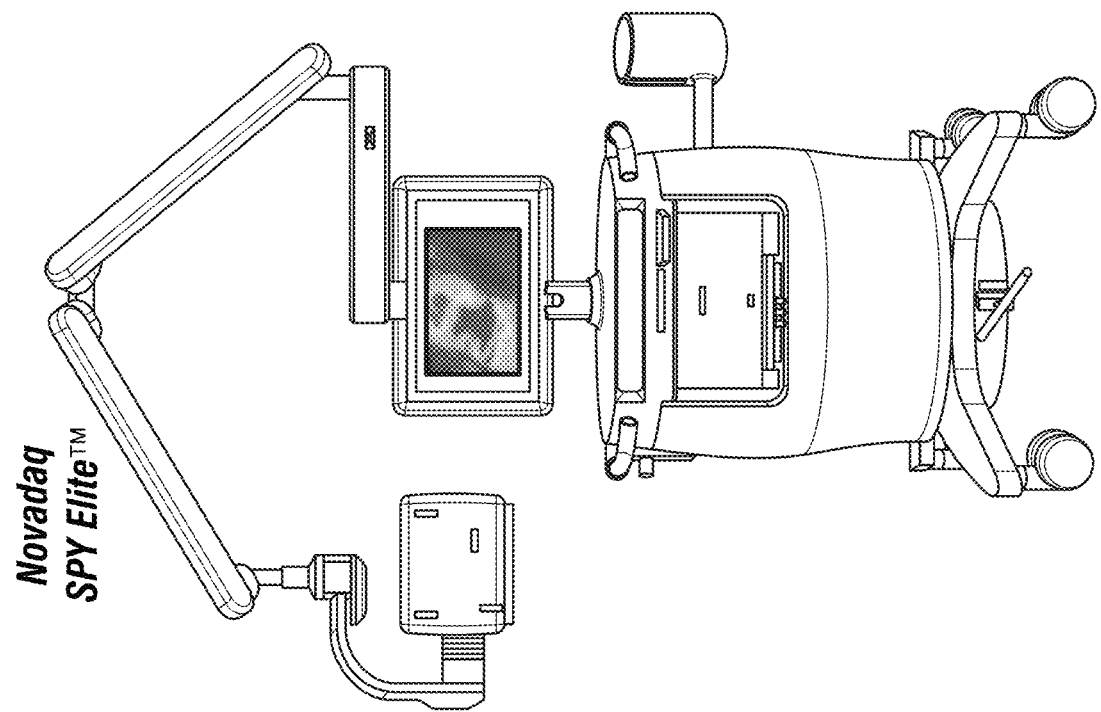
FIG. 49A1

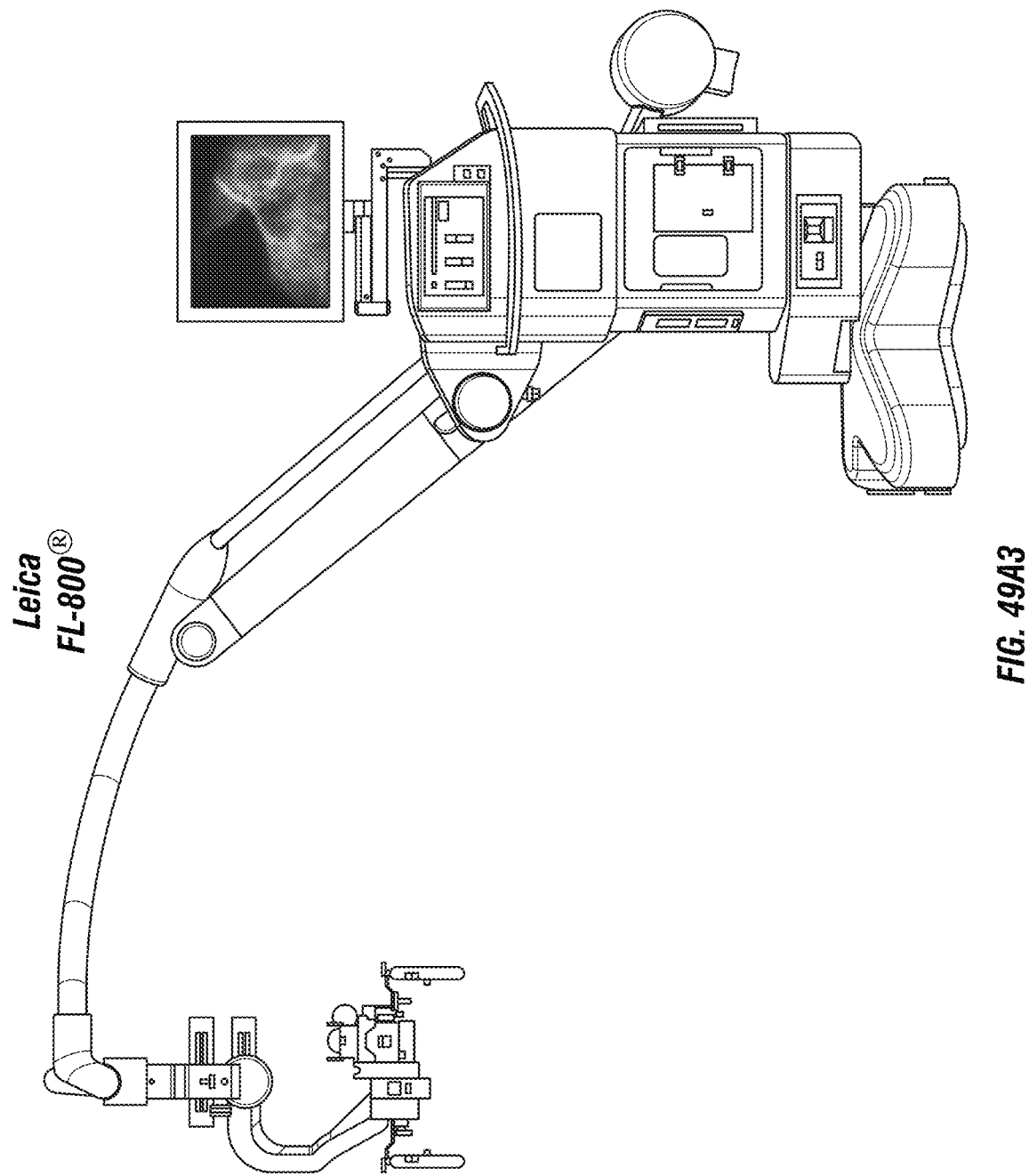
FIG. 49A3

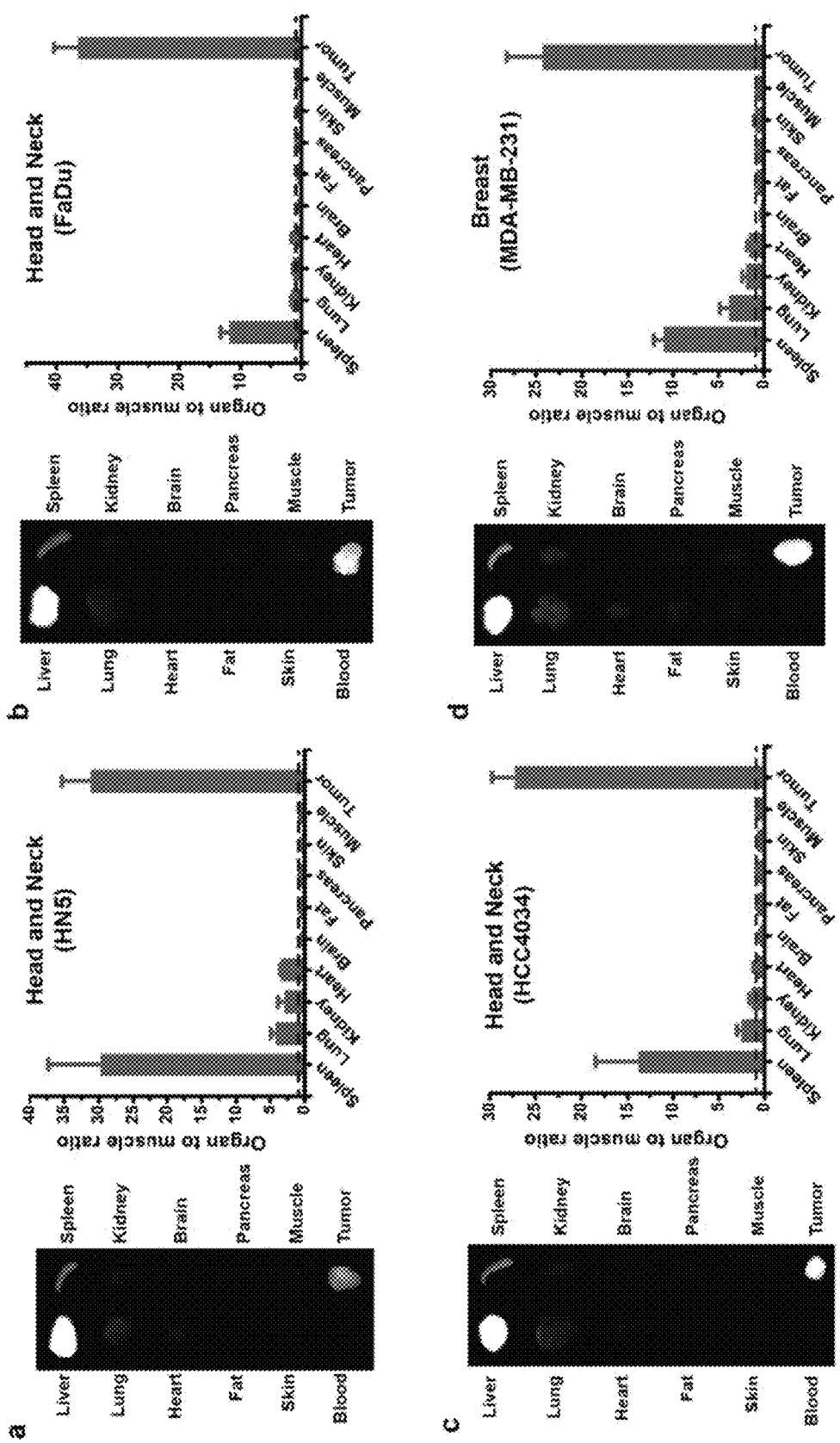
FIGS. 50A-D

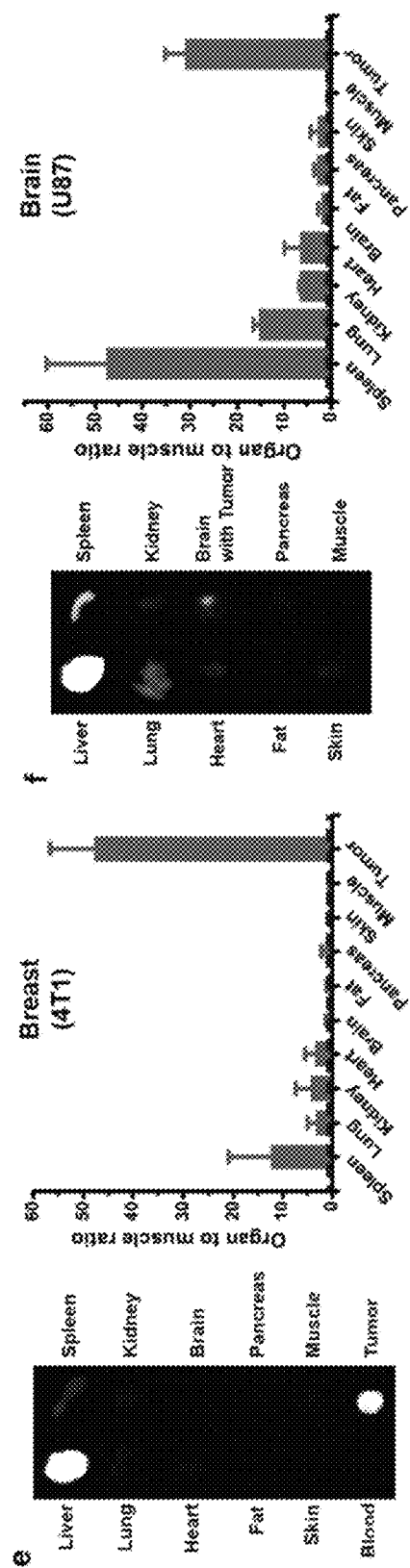
FIGS. 50E-F

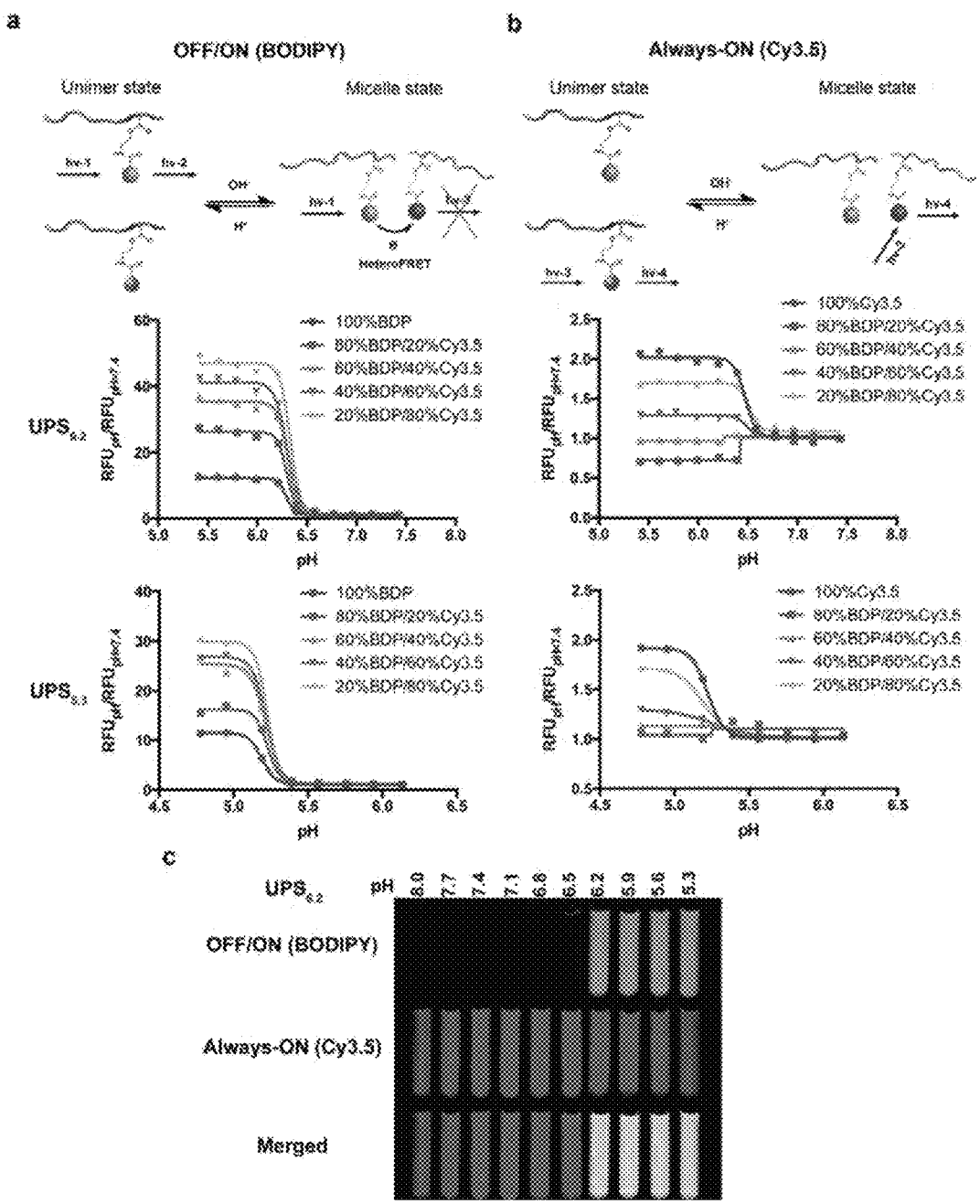
FIGS. 61A-C b
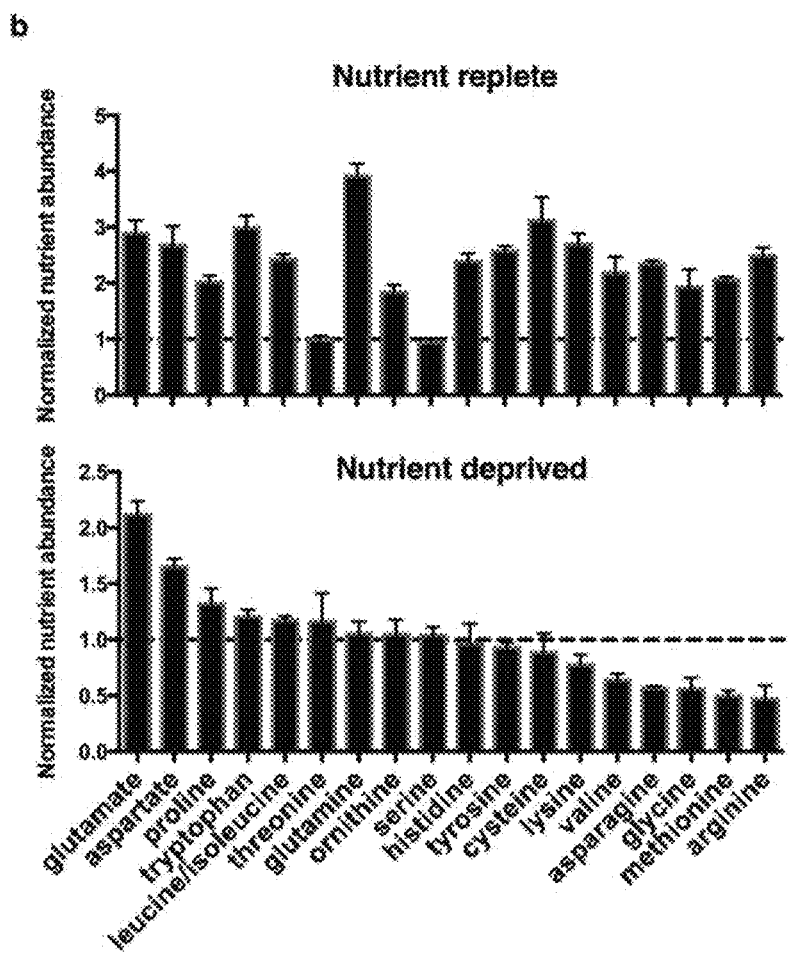
c
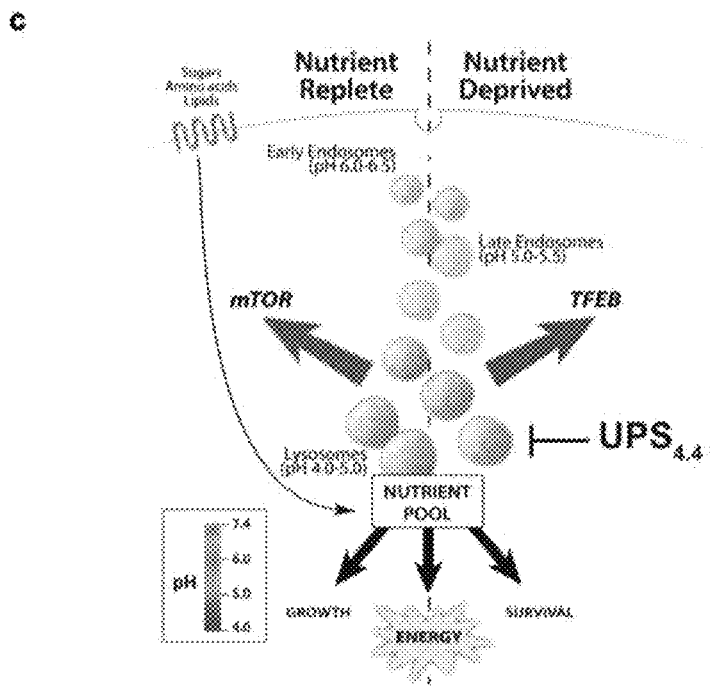
FIGS. 68B-C

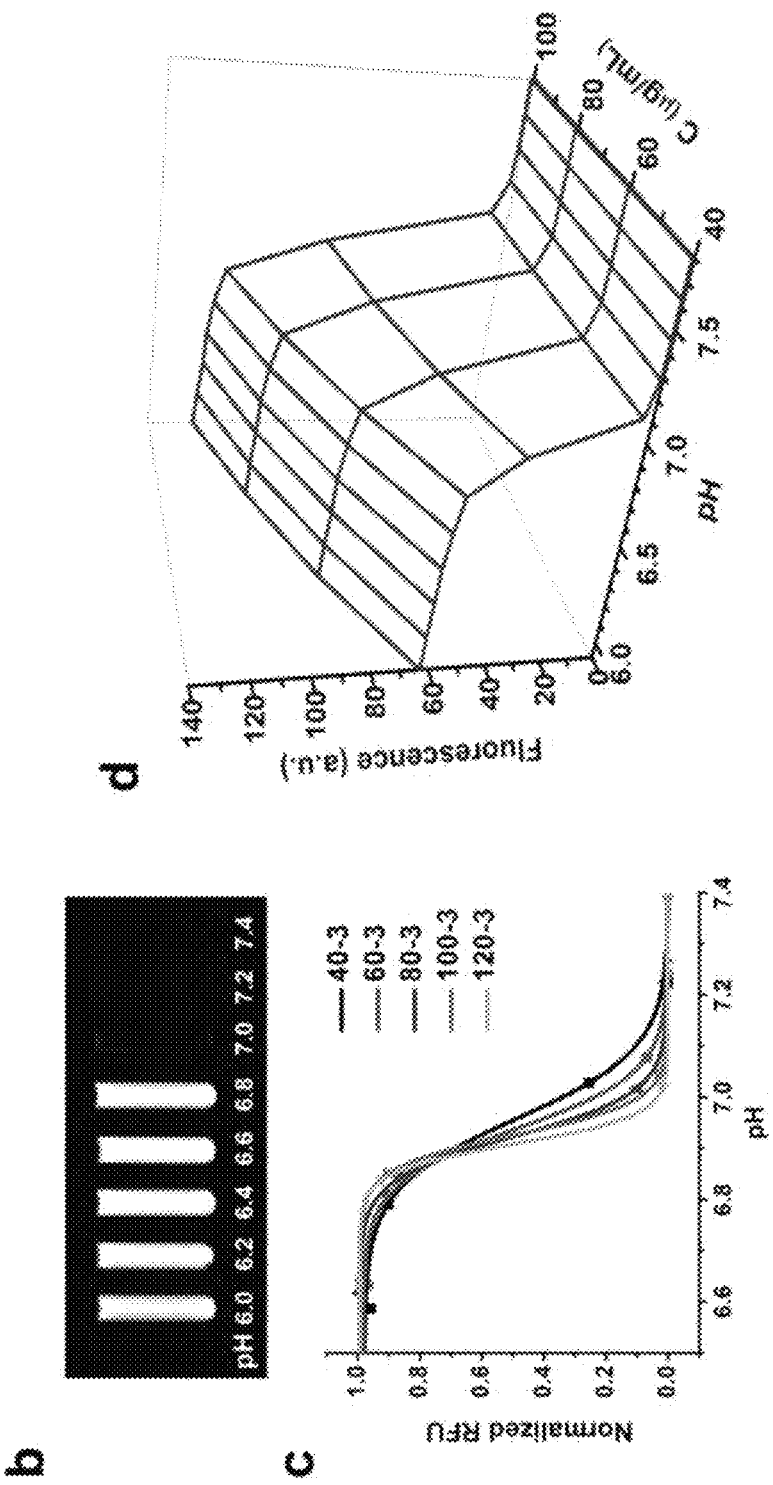
FIGS. 70B-D

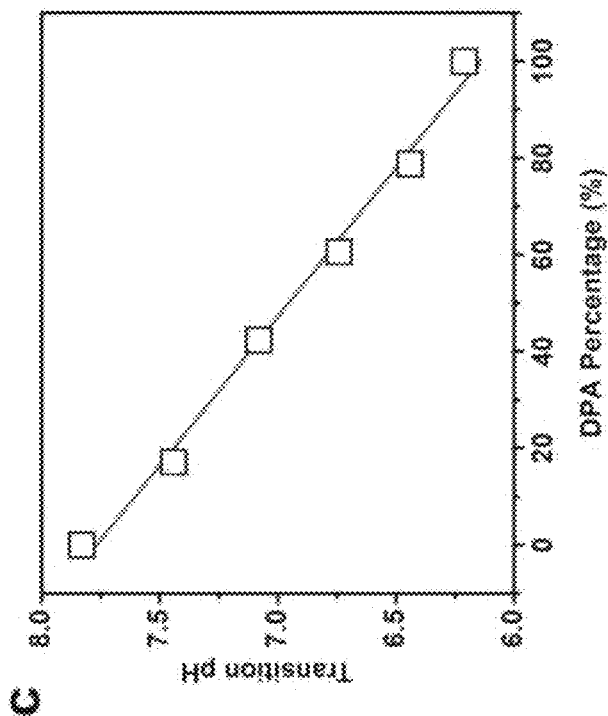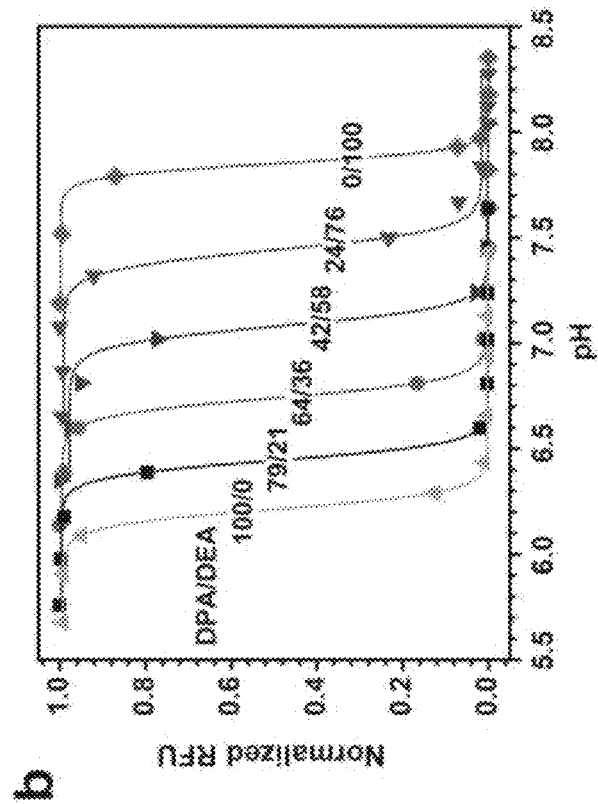
FIGS. 76B-C

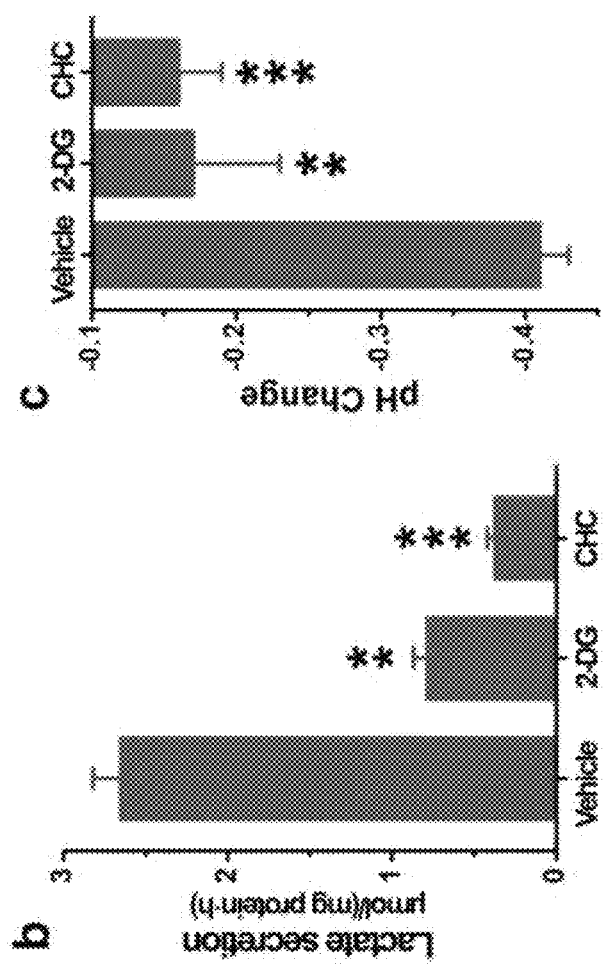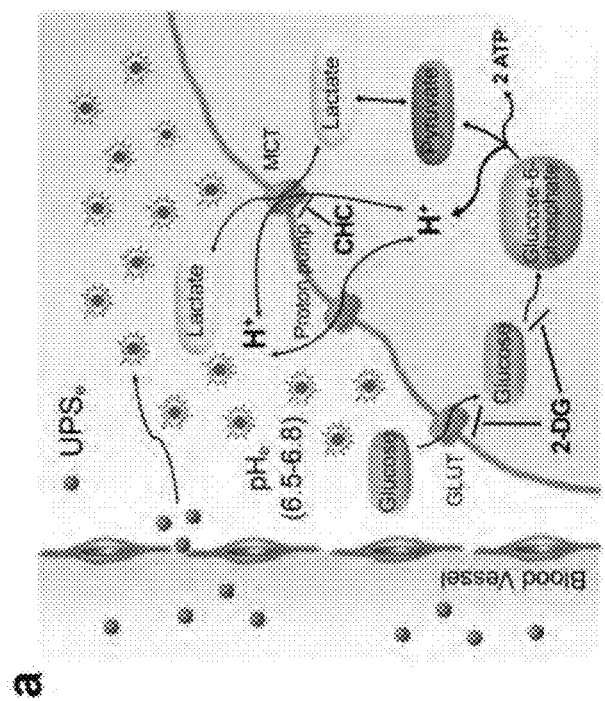
FIGS. 78A-C

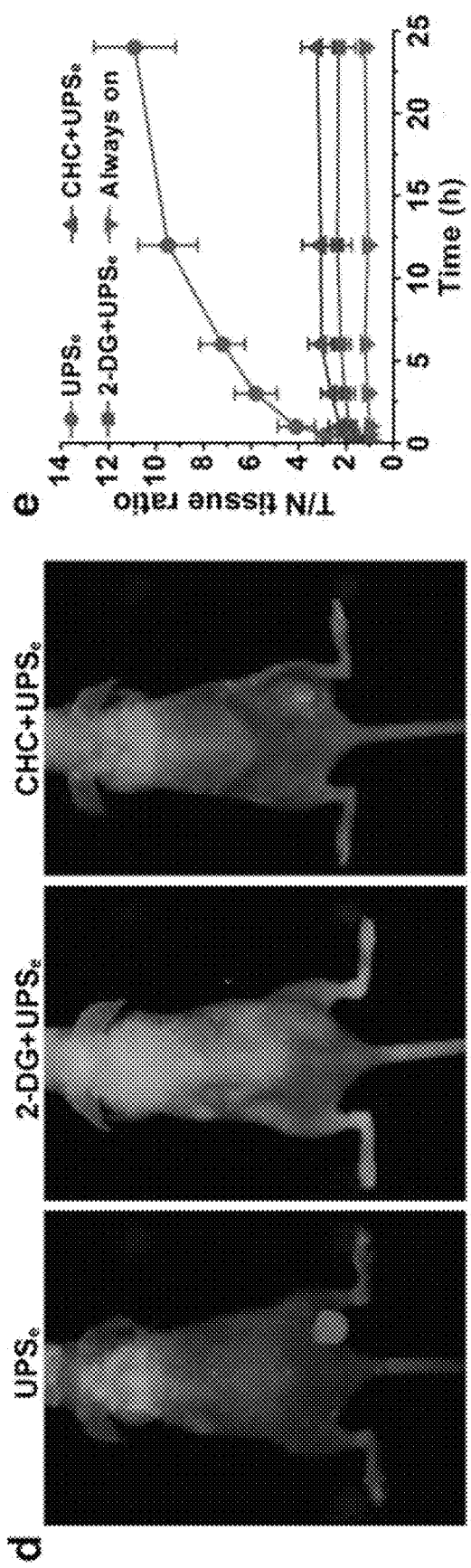
FIGS. 78D-E

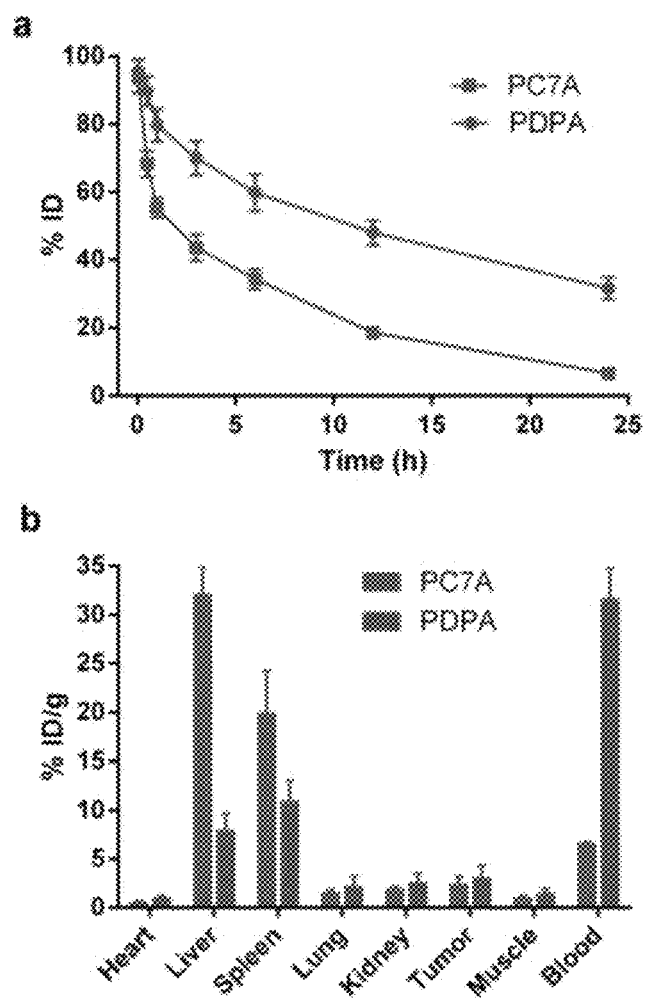
FIGS. 83A-B

LIBRARY OF PH RESPONSIVE POLYMERS AND NANOPROBES THEREOF

This application is a continuation of U.S. application Ser. No. 16/114,187, filed Aug. 27, 2018, which is a continuation of U.S. application Ser. No. 15/369,701, filed Dec. 5, 2016, now U.S. Pat. No. 10,098,971, which is a continuation of International Application No. PCT/US2015/034575, filed Jun. 5, 2015, which claims the benefit of priority from U.S. Provisional Application Ser. No. 62/009,019, filed on Jun. 6, 2014, the entire contents of each of which are incorporated herein by reference.

This invention was made with government support under Grant Number R01 EB013149 awarded by the National Institutes of Health. The government has certain rights in the invention.

BACKGROUND

1. Field

The present disclosure relates generally to the fields of molecular and cellular biology, cancer imaging, nanotechnology, and fluorescence sensors. More particularly, it relates to nanoplatforms for the detection of pH changes.

2. Description of Related Art

Fluorescence imaging has become an important tool in the study of biological molecules, pathways and processes in living cells thanks to its ability to provide spatial-temporal information at microscopic, mesoscopic and macroscopic levels (see, e.g., Tsien, R. Y. *Nat. Rev. Mol. Cell Biol.* 2003, 4, SS16; Weissleder, R., *Nature* 2008, 452, 580; Fernandez-Suarez, M., *Nat. Rev. Mol. Cell Biol.* 2008, 9, 929). Recently, activatable imaging probes that are responsive to physiological stimuli such as ionic and redox potentials, enzymatic expressions, and pH have received considerable attention to probe cell physiological processes (see, e.g., de Silva, A. P., Chem. Rev. 1997, 97, 1515; Zhang, J., *Nat. Rev. Mol. Cell Biol.* 2002, 3, 906; Fee, S., *Chem. Commun.* 2008, 4250; Kobayashi, H.; *Chem. Res.* 2010, 44, 83; Fovell, J. F., *Chem. Rev.* 2010, 110, 2839; Ueno, T., *Nat. Methods* 2011, 8, 642). Among these stimuli, pH stands out as an important physiological parameter that plays a critical role in both the intracellular ($pH_i$) and extracellular ($pH_e$) milieu (Alberts, B., *Molecular Biology of the Cell;* 5th ed.; Garland Science: New York, 2008).

Although various pH-sensitive fluorescent probes have been reported (Kobayashi, H., *Chem. Rev.* 2010, 110, 2620; Han, J. Y., *Chem. Rev.* 2010, 110, 2709), their pH sensitivity primarily arises from ionizable residues with pH-dependent photo-induced electron transfer (PeT) properties to the fluorophores. One potential drawback for these fluorescent agents is their broad pH response ($\Delta pH \sim 2$) as dictated by the Henderson-Hasselbalch equation (Atkins, P., *Physical Chemistry*, Oxford University Press, 2009). This lack of sharp pH response makes it difficult to detect subtle pH differences between the acidic intracellular organelles (e.g., <1 pH difference between early endosomes and lysosomes) (Maxfield, F. R., *Nat. Rev. Mol. Cell Biol.* 2004, 5, 121; Casey, J. R., *Nat. Rev Mol. Cell Biol.* 2010, 11, 50) or pHe in solid tumors (6.5-6.9) (Webb, B. A., *Nat. Rev. Cancer* 2011, 11, 671; Zhang, X., *J. Nucl. Med.* 2010, 51, 1167.) over normal tissue environment (7.4). Moreover, simultaneous control of pH transition point and emission wavelengths (in particular, in the near IR range) is difficult for small molecular dyes. Recent attempts to develop pH-sensitive fluorescent nanoparticles primarily employ polymers conjugated with small molecular pH-sensitive dyes (Srikun, D., *J. Chem. Sci.* 2011, 2, 1156; Benjaminsen, R. V., *ACS Nano* 2011, 5, 5864; Albertazzi, L., *J. Am. Chem. Soc.* 2010, 132, 18158; Urano, Y., *Nat. Med.* 2009, 15, 104) or the use of pH-sensitive linkers to conjugate pH-insensitive dyes (Li, C., *Adv. Eunct. Mater.* 2010, 20, 2222; Almutairi, A., *J. Am. Chem. Soc.* 2007, 130, 444.). These nanoprobe designs also yield broad pH response and lack the ability to fine-tune pH transition point.

Recently, the use of polymers to create a pH responsive system has been described in WO 2013/152059, which produces a relatively narrow range of pH transition points based upon the specific monomer used but lacks the flexibility to fine-tune the pH transition point specifically.

Furthermore, imaging of tumor cells can provide enhanced methods of delineating the tumor boundaries and increasing the efficacy of surgery to resect a tumor. A variety of methods have been proposed to assist in the delineation of tumor boundaries. Conventional imaging modalities such as CT, MRI or ultrasound using image navigators such as the Brainlab™ first use pre-operative images followed by the intra-operative use of surgical fiducial markers to guide resection of skull base and sinus cancers as well as brain tumors. A major drawback is that only tumors that are immobile relative to firm bony landmarks can be accurately imaged and the pre-operative images cannot be updated to account for intra-operative manipulations to provide real-time feedback. Intra-operative MRI is being used in a few centers for imaging brain tumors but requires expensive installation of magnets into the operative suite for real time imaging and a recent review suggest that this may be of marginal benefit over conventional surgical navigation (Kubben et al., 2011). Ultrasound has been used to assess tumor depth for oral cavity HNSCC but is difficult to use in less accessible primary sites of the head and neck (Lodder et al., 2011).

These anatomy-based imaging modalities have great resolution but provide little disease specific information. Optical imaging strategies have rapidly been used to image tissues intra-operatively based on cellular imaging, native autofluorescence, and Raman scattering (Vahrmeijer et al., 2013; Nguyen & Tsien, 2013; Dacosta et al., 2006; Draga et al., 2010; Haka et al., 2006; Schwarz et al., 2009 and Mo et al., 2009). Unfortunately, using tissue autofluorescence for tumor margin detection is limited by high false positive and false negative results due to the lack of robust spectroscopic differences between cancer and normal tissues (Liu et al., 2010; Kanter et al., 2009; Ramanujam et al., 1996 and Schomacker et al., 1992).

A variety of exogenous fluorophores have been developed for intra-operative margin assessment. Most common strategies have focused on cell-surface receptors such as folate receptor-α (FR-α) (van Dam et al., 2011), chlorotoxin (Veiseh et al., 2007), epidermal growth factor receptor (EGFR) (Ke et al., 2003 and Urano et al., 2009), Her2/neu (Koyama et al., 2007), tumor associated antigens (e.g., prostate-specific membrane antigen, PSMA) (Tran Cao et al., 2012, carcinoembryonic antigen and carbohydrate antigen 19-9 (CA19-9) (Tran Cao et al., 2012; McElroy et al., 2008). Among these, folate-FITC and chlorotoxin-Cy5.5 conjugate have already advanced to Phase I clinical trials in surgery of ovarian and skin cancers, respectively. Despite these successes, one of the major limitations is the lack of broad tumor applicability in cancer patients. For the cell-surface receptor strategy of tumor visualization, lack of a uniform marker makes it difficult to create a universal platform to visualize tumors with a diverse oncogenotypes and anatomical sites. In addition, the relatively low (fmol-nmol) and highly variable expression levels (100-300 folds) makes it challenging for conventional stoichiometric strategy (e.g., 1:1 for ligand:receptor) without signal amplification. This is particularly challenging for mAb-dye conjugates (e.g., Erbitux-ICG) due to the long circulation times of humanized mAb that raise the blood background because of the always-on probe design.

As such, new polymers that can generate pH responsive systems for the imaging of tumors are of value to development diagnostic and imaging protocols.

SUMMARY

In some aspects, the present disclosure provides a polymer of the formula:

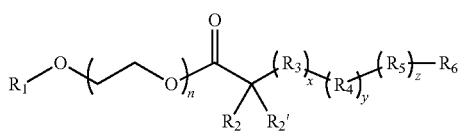
(I)

wherein: $R_1$ is hydrogen, alkyl$_{(C \leq 12)}$, cycloalkyl$_{(C \leq 12)}$, substituted alkyl$_{(C \leq 12)}$, substituted cycloalkyl$_{(C \leq 12)}$, or

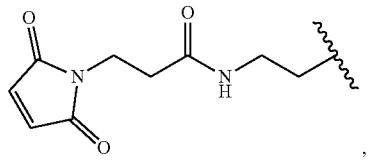 [SMILES: *CCNC(=O)CCN1C(=O)C=CC1=O]

or a metal chelating group; n is an integer from 1 to 500; $R_2$ and $R_2'$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; $R_3$ is a group of the formula:

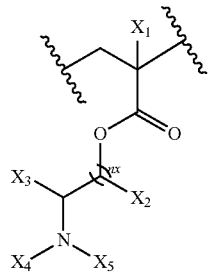
(II)

wherein: $n_x$ is 1-10; $X_1$, $X_2$, and $X_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $X_4$ and $X_5$ are each independently selected from alkyl$_{(C \leq 12)}$, cycloalkyl$_{(C \leq 12)}$, aryl$_{(C \leq 12)}$, heteroaryl$_{(C \leq 12)}$ or a substituted version of any of these groups, or $X_4$ and $X_5$ are taken together and are alkanediyl$_{(C \leq 12)}$, alkoxydiyl$_{(C \leq 12)}$, alkylaminodiyl$_{(C \leq 12)}$, or a substituted version of any of these groups; x is an integer from 1 to 150; $R_4$ is a group of the formula:

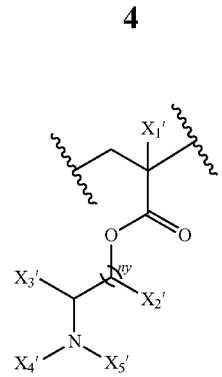
(III)

wherein: $n_y$ is 1-10; $X_1'$, $X_2'$, and $X_3'$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $X_4'$ and $X_5'$ are each independently selected from alkyl$_{(C \leq 12)}$, cycloalkyl$_{(C \leq 12)}$, aryl$_{(C \leq 12)}$, heteroaryl$_{(C \leq 12)}$ or a substituted version of any of these groups, or $X_4'$ and $X_5'$ are taken together and are alkanediyl$_{(C \leq 12)}$, alkoxydiyl$_{(C \leq 12)}$, alkylaminodiyl$_{(C \leq 12)}$, or a substituted version of any of these groups; y is an integer from 1 to 150; $R_5$ is a group of the formula:

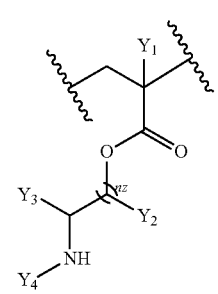
(IV)

wherein: $n_z$ is 1-10; $Y_1$, $Y_2$, and $Y_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $Y_4$ is hydrogen, alkyl$_{(C \leq 12)}$, acyl$_{(C \leq 12)}$, substituted alkyl$_{(C \leq 12)}$, substituted acyl$_{(C \leq 12)}$, a dye, or a fluorescence quencher; z is an integer from 0-6; and $R_6$ is hydrogen, halo, hydroxy, alkyl$_{(C \leq 12)}$, or substituted alkyl$_{(C \leq 12)}$, wherein $R_3$, $R_4$, and $R_5$ can occur in any order within the polymer, provided that $R_3$ and $R_4$ are not the same group. In some embodiments, the compound is further defined by the formula wherein: $R_1$ is hydrogen, alkyl$_{(C \leq 12)}$, substituted alkyl$_{(C \leq 12)}$, or

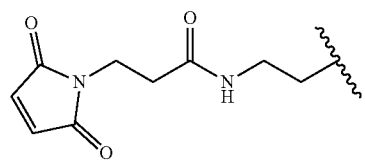

or a metal chelating group; n is an integer from 10 to 500; $R_2$ and $R_2'$ are each independently selected from hydrogen, alkyl$_{(C \leq 12)}$, or substituted alkyl$_{(C \leq 12)}$; $R_3$ is a group of the formula:

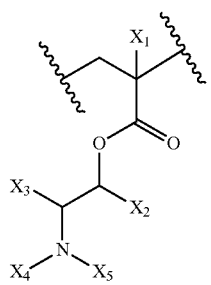

(II)

wherein: $X_1$, $X_2$, and $X_3$ are each independently selected from hydrogen, alkyl$_{(C\leq12)}$, or substituted alkyl$_{(C\leq12)}$; and $X_4$ and $X_5$ are each independently selected from alkyl$_{(C\leq12)}$, aryl$_{(C\leq12)}$, heteroaryl$_{(C\leq12)}$ or a substituted version of any of these groups, or $X_4$ and $X_5$ are taken together and are alkanediyl$_{(C\leq8)}$, alkoxydiyl$_{(C\leq8)}$, alkylaminodiyl$_{(C\leq8)}$, or a substituted version of any of these groups; x is an integer from 1 to 100; $R_4$ is a group of the formula:

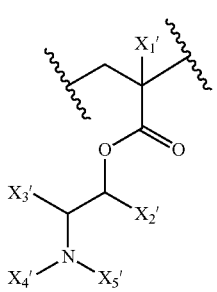

(III)

wherein: $X_1'$, $X_2'$, and $X_3'$ are each independently selected from hydrogen, alkyl$_{(C\leq12)}$, or substituted alkyl$_{(C\leq12)}$ and $X_4'$ and $X_5'$ are each independently selected from alkyl$_{(C\leq12)}$, aryl$_{(C\leq12)}$, heteroaryl$_{(C\leq12)}$ or a substituted version of any of these groups, or $X_4'$ and $X_5'$ are taken together and are alkanediyl$_{(C\leq8)}$, alkoxydiyl$_{(C\leq8)}$, alkylaminodiyl$_{(C\leq8)}$, or a substituted version of any of these groups; y is an integer from 1 to 100; $R_5$ is a group of the formula:

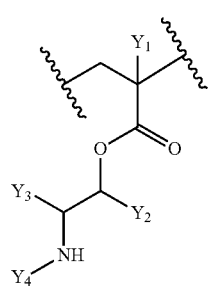

(IV)

wherein: $Y_1$, $Y_2$, and $Y_3$ are each independently selected from hydrogen, alkyl$_{(C\leq12)}$, substituted alkyl$_{(C\leq12)}$; and $Y_4$ is hydrogen, acyl$_{(C\leq12)}$, substituted acyl$_{(C\leq12)}$, a dye, or a fluorescence quencher; z is an integer from 0-6; and $R_6$ is hydrogen, halo, alkyl$_{(C\leq12)}$, or substituted alkyl$_{(C\leq12)}$, wherein $R_3$, $R_4$, and $R_5$ can occur in any order within the polymer, provided that $R_3$ and $R_4$ are not the same group. In some embodiments, the compound is further defined by the formula wherein: $R_1$ is hydrogen, alkyl$_{(C\leq8)}$, substituted alkyl$_{(C\leq8)}$, or

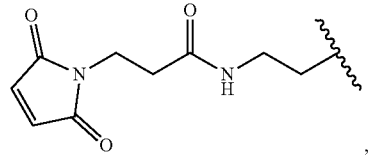 [SMILES: *CCNC(=O)CCN1C(=O)C=CC1=O]

, or a metal chelating group; n is an integer from 10 to 200; $R_2$ and $R_2'$ are each independently selected from hydrogen, alkyl$_{(C\leq8)}$, or substituted alkyl$_{(C\leq8)}$; $R_3$ is a group of the formula:

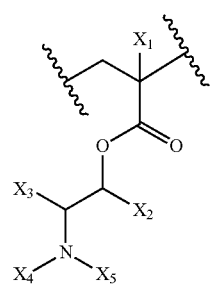

(II)

wherein: $X_1$, $X_2$, and $X_3$ are each independently selected from hydrogen, alkyl$_{(C\leq8)}$, or substituted alkyl$_{(C\leq8)}$; and $X_4$ and $X_5$ are each independently selected from alkyl$_{(C\leq12)}$, aryl$_{(C\leq12)}$, heteroaryl$_{(C\leq12)}$ or a substituted version of any of these groups, or $X_4$ and $X_5$ are taken together and are alkanediyl$_{(C\leq8)}$ or substituted alkanediyl$_{(C\leq8)}$; x is an integer from 1 to 100; $R_4$ is a group of the formula:

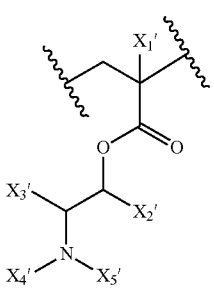

(III)

wherein: $X_1'$, $X_2'$, and $X_3'$ are each independently selected from hydrogen, alkyl$_{(C\leq8)}$, or substituted alkyl$_{(C\leq8)}$; and $X_4'$ and $X_5'$ are each independently selected from alkyl$_{(C\leq12)}$, aryl$_{(C\leq12)}$, heteroaryl$_{(C\leq12)}$ or a substituted version of any of these groups, or $X_4'$ and $X_5'$ are taken together and are alkanediyl$_{(C\leq8)}$ or substituted alkanediyl$_{(C\leq8)}$; y is an integer from 1 to 100; $R_5$ is a group of the formula:

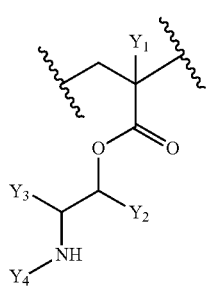

(IV)

wherein: $Y_1$, $Y_2$, and $Y_3$ are each independently selected from hydrogen, alkyl$_{(C\leq 8)}$, substituted alkyl$_{(C\leq 8)}$; and $Y_4$ is hydrogen, a dye, or a fluorescence quencher; z is an integer from 0-6; and $R_6$ is hydrogen, halo, alkyl$_{(C\leq 6)}$, or substituted alkyl$_{(C\leq 6)}$, wherein $R_3$, $R_4$, and $R_5$ can occur in any order within the polymer, provided that $R_3$ and $R_4$ are not the same group. In some embodiments, $R_1$ is hydrogen. In some embodiments, $R_1$ is alkyl$_{(C\leq 6)}$. In some embodiments, $R_1$ is methyl. In some embodiments, $R_1$ is

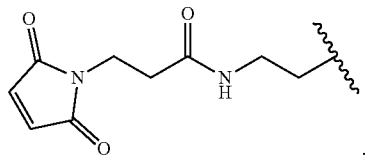 [SMILES: *CCNC(=O)CCN1C(=O)C=CC1=O]

In some embodiments, $R_1$ is a metal chelating group such as a metal chelating group selected from 1,4,7,10-tetraazacyclododecane-1,4,7,10-tetraacetic acid, (DOTA), 1,4,8,11-tetraazacyclotetradecane-1,4,8,11-tetraacetic acid, (TETA), 1,8-Diamino-3,6,10,13,16,19-hexaazabicyclo[6,6,6]-eicosane (Diamsar), 1,4,7-triazacyclononane-1,4,7-triacetic acid, (NOTA), {4-[2-(bis-carboxymethylamino)-ethyl]-7-carboxymethyl-[1,4,7]triazonan-1-yl}-acetic acid (NETA), N,N',N'', tris(2-mercaptoethyl)-1,4,7-triazacyclononane (TACN-TM), diethylenetriaminepentaacetic acid (DTPA), 1,4,7-triazacyclononane-1,4,7-tris[methyl(2-carboxyethyl) phosphinic acid] (TRAP), 1,4,7-triazacyclononane-1,4-bis [methylene(hydroxymethyl)phosphinic acid]-7-[methylene (2-carboxyethyl)phosphinic acid] (NOPO), 1,4-bis (carboxymethyl)-6-[bis(carboxymethyl)]amino-6-methylperhydro-1,4-diazepine (AAZTA), 2,2'-(6-((carboxymethyl)amino)-1,4-diazepane-1,4-diyl)diacetic acid (DATA), N,N'-bis(2-hydroxybenzyl)-ethylenediamine-N,N'-diacetic acid, (HBED), N,N'-bis(2-hydroxy-5-sulfobenzyl)-ethylenediamine-N,N'-diacetic acid (SHBED), bis(2-pyridylcarbonyl) amine (BPCA), 4-acetylamino-4-[2-[(3-hydroxy-1,6-dimethyl-4-oxo-1,4-dihydro-pyridin-2-yl-methyl)-carbamoyl]-ethyl]-heptanedioicacid bis-[(3-hydroxy-1,6-dimethyl-4-oxo-1,4-dihydro-pyridin-2-ylmethyl)-amide] (CP256), desferrioxamine B (DFO), 3,6, 9,15-tetraazabicyclo[9.3.1]-pentadeca-1(15),11,13-triene-3, 6,9,-triacetic acid (PCTA), 1,4,7,10,13,16-hexaazacyclohexadecane-N,N',N'',N''',N'''',N'''''-hexaacetic acid (HEHA), 1,4,7,10,13-pentaazacyclopentadecane-N,N', N'',N''',N''''-pentaacetic acid (PEPA), or a derivative thereof. In some embodiments, the metal chelating group is a nitrogen containing macrocycle. In some embodiments, the nitrogen containing macrocycle is a compound of the formula:

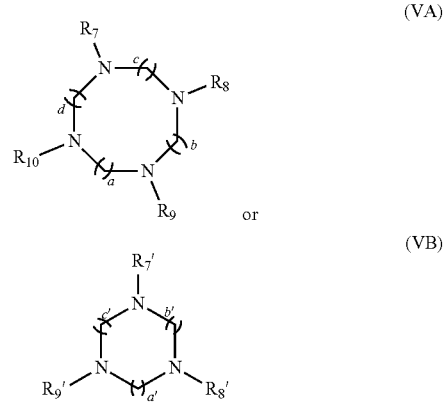

(VA)

or (VB)

wherein:
$R_7$, $R_8$, $R_9$, $R_{10}$, $R_7'$, $R_8'$, and $R_9'$ are each independently selected from hydrogen, alkyl$_{(C\leq 12)}$, acyl$_{(C\leq 12)}$, -alkanediyl$_{(C\leq 12)}$, or a substituted version of any of these groups; or a linker, wherein the linker is an alkanediyl$_{(C\leq 12)}$-C(O)NH— or a substituted alkanediyl$_{(C\leq 12)}$-C(O)NH—; or $R_7$ is taken together with one of $R_8$, $R_9$, or $R_{10}$ and is alkanediyl$_{(C\leq 6)}$; or $R_8$ is taken together with one of $R_7$, $R_9$, or $R_{10}$ and is alkanediyl$_{(C\leq 6)}$; or $R_9$ is taken together with one of $R_7$, $R_8$, or $R_{10}$ and is alkanediyl$_{(C\leq 6)}$; or $R_{10}$ is taken together with one of $R_7$, $R_8$, or $R_9$ and is alkanediyl$_{(C\leq 6)}$; or $R_7'$ is taken together with one of $R_8'$ or $R_9'$ and is alkanediyl$_{(C\leq 6)}$; or $R_8'$ is taken together with one of $R_7'$ or $R_9'$ and is alkanediyl$_{(C\leq 6)}$; or $R_9'$ is taken together with one of $R_7'$ or $R_8'$ and is alkanediyl$_{(C\leq 6)}$; and a, b, c, d, a', b', and c' are each independently selected from 1, 2, 3, or 4.

In some embodiments, a, b, c, d, a', b', and c' are each independently selected from 2 or 3. In some embodiments, the metal chelating group is:

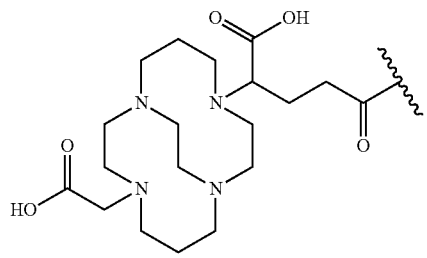

In some embodiments, the metal chelating complex is bound to a metal ion. In some embodiments, the metal ion is a radionuclide or radiometal. In some embodiments, the metal ion is suitable for PET or SPECT imaging. In some embodiments, the metal chelating complex is bound to a transition metal ion. In some embodiments, the metal ion is a copper ion, a gallium ion, a scandium ion, an indium ion, a lutetium ion, a ytterbium ion, a zirconium ion, a bismuth ion, a lead ion, a actinium ion, or a technetium ion. In some embodiments, the metal ion is an isotope selected from $^{99m}$Tc, $^{60}$Cu, $^{61}$Cu, $^{62}$Cu, $^{64}$Cu, $^{86}$Y, $^{90}$Y, $^{89}$Zr, $^{44}$Sc, $^{47}$Sc, $^{66}$Ga, $^{67}$Ga, $^{68}$Ga, $^{111}$In, $^{177}$Lu, $^{225}$Ac, $^{212}$Pb, $^{212}$Bi, $^{213}$Bi, $^{114m}$In, $^{114}$In, $^{186}$Re, or $^{188}$Re. In some embodiments, the transition metal is a copper(II) ion. In some embodiments, the copper(II) ion is a $^{64}$Cu$^{2+}$ ion. In some embodiments, the metal chelating complex is:

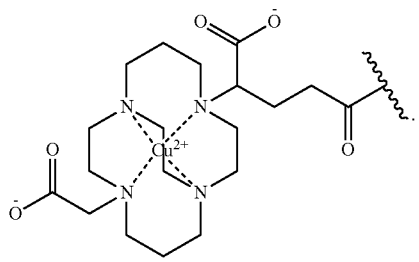

In some embodiments, $R_2$ is alkyl$_{(C \le 6)}$. In some embodiments, $R_2$ is methyl. In some embodiments, $R_2'$ is alkyl$_{(C \le 6)}$. In some embodiments, $R_2'$ is methyl. In some embodiments, $R_3$ is further defined by the formula:

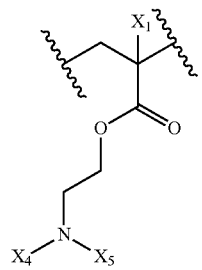

(V)

wherein: $X_1$ is selected from hydrogen, alkyl$_{(C \le 8)}$, or substituted alkyl$_{(C \le 8)}$; and $X_4$ and $X_5$ are each independently selected from alkyl$_{(C \le 12)}$, aryl$_{(C \le 12)}$, heteroaryl$_{(C \le 12)}$ or a substituted version of any of these groups, or $X_4$ and $X_5$ are taken together and are alkanediyl$_{(C \le 8)}$ or substituted alkanediyl$_{(C \le 8)}$; In some embodiments, $X_1$ is alkyl$_{(C \le 6)}$. In some embodiments, $X_1$ is methyl. In some embodiments, $X_4$ is alkyl$_{(C \le 8)}$. In some embodiments, $X_4$ is methyl, ethyl, propyl, butyl, or pentyl. In some embodiments, $X_5$ is alkyl$_{(C \le 8)}$. In some embodiments, $X_5$ is methyl, ethyl, propyl, butyl, or pentyl.

In some embodiments, $R_4$ is further defined by the formula:

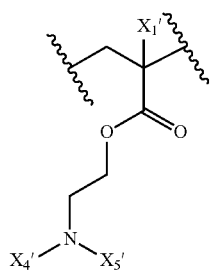

(VI)

wherein: $X_1'$ is selected from hydrogen, alkyl$_{(C \le 8)}$, or substituted alkyl$_{(C \le 8)}$; and $X_4'$ and $X_5'$ are each independently selected from alkyl$_{(C \le 12)}$, aryl$_{(C \le 12)}$, heteroaryl$_{(C \le 12)}$ or a substituted version of any of these groups, or $X_4'$ and $X_5'$ are taken together and are alkanediyl$_{(C \le 8)}$ or substituted alkanediyl$_{(C \le 8)}$. In some embodiments, $X_1'$ is alkyl$_{(C \le 6)}$. In some embodiments, $X_1$ is methyl. In some embodiments, $X_4'$ is alkyl$_{(C \le 8)}$. In some embodiments, $X_4'$ is methyl, ethyl, propyl, butyl, or pentyl. In some embodiments, $X_5'$ is alkyl$_{(C \le 8)}$. In some embodiments, $X_5'$ is methyl, ethyl, propyl, butyl, or pentyl. In some embodiments, $R_5$ is further defined by the formula:

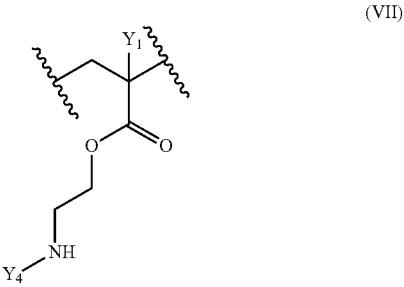

(VII)

wherein: $Y_1$ is selected from hydrogen, alkyl$_{(C \le 8)}$, substituted alkyl$_{(C \le 8)}$; and $Y_4$ is hydrogen, a dye, or a fluorescence quencher. In some embodiments, $Y_1$ is alkyl$_{(C \le 6)}$. In some embodiments, $Y_1$ is methyl. In some embodiments, $Y_4$ is hydrogen. In some embodiments, $Y_4$ is a dye. In some embodiments, $Y_4$ is fluorescent dye. In some embodiments, the fluorescent dye is a coumarin, fluorescein, rhodamine, xanthene, BODIPY® (boron-dipyrromethene), Alexa Fluor® (sulfonated derivative of coumarin, rhodamine, xanthene or cyanine dye), or cyanine dye. In some embodiments, the fluorescent dye is indocyanine green, AMCA-x, Marina Blue, PyMPO, Rhodamine Green™ (rhodamine), Tetramethylrhodamine, 5-carboxy-X-rhodamine, Bodipy493, Bodipy TMR-x, Bodipy630, Cyanine5, Cyanine5.5, and Cyanine7.5. In some embodiments, the fluorescent dye is indocyanine green. In some embodiments, $Y_4$ is a fluorescence quencher. In some embodiments, the fluorescence quencher is QSY7, QSY21, QSY35, BHQ1, BHQ2, BHQ3, TQ1, TQ2, TQ3, TQ4, TQ5, TQ6, and TQ7. In some embodiments, n is 75-150. In some embodiments, n is 100-125. In some embodiments, x is 1-99. In some embodiments, x is from 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99 or any range derivable therein. In some embodiments, y is 1-99. In some embodiments, y is from 1-5, 5-10, 10-15, 15-20, 20-25, 25-30, 30-35, 35-40, 40-45, 45-50, 50-55, 55-60, 60-65, 65-70, 70-75, 75-80, 80-85, 85-90, 90-95, 95-99 or any range derivable therein. In some embodiments, z is 0-6. In some embodiments, z is 1-6. In some embodiments, z is from 0-2, 2-4, 4-6, or any range derivable therein. In some embodiments, $R_3$, $R_4$, and $R_5$ can occur in any order within the polymer. In some embodiments, $R_3$, $R_4$, and $R_5$ occur in the order described in formula I. In some embodiments, the polymer further comprises a targeting moiety. In some embodiments, the targeting moiety is a small molecule, an antibody, an antibody fragment, or a signaling peptide. In some embodiments, $R_3$ and $R_4$ are selected from:

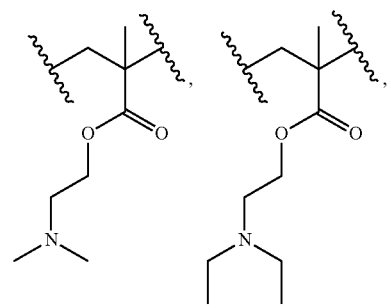

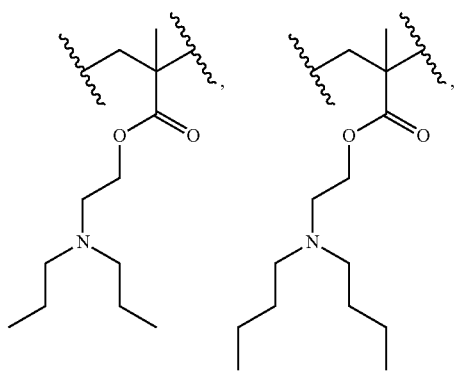

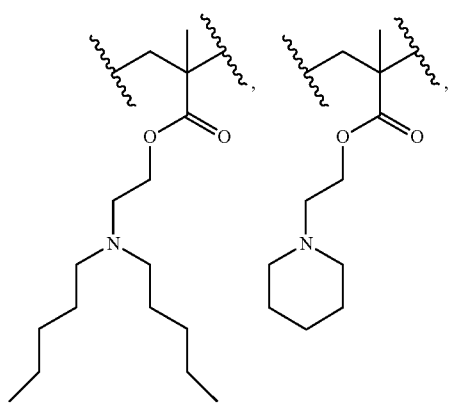

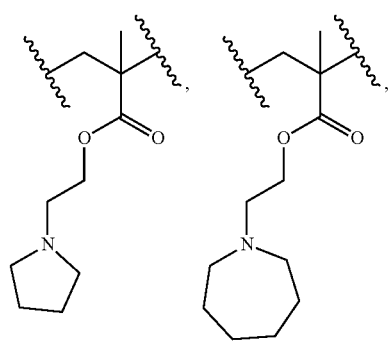

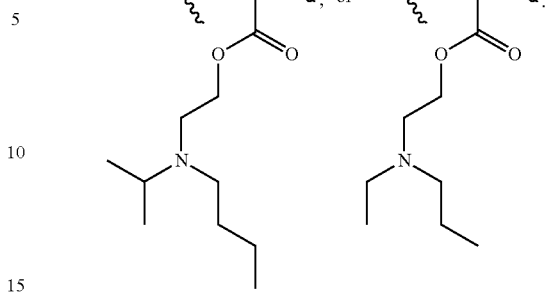

In some embodiments, the polymer is $PEO_{114}$-$P(DEA_{20}$-$D5A_{60})$, $PEO_{114}$-$P(DEA_{40}$-$D5A_{40})$, $PEO_{114}$-$P(DEA_{60}$-$D5A_{20})$, $PEO_{114}$-$P(DPA_{60}$-$DBA_{20})$, $PEO_{114}$-$P(DPA_{40}$-$DBA_{40})$, $PEO_{114}$-$P(DPA_{20}$-$DBA_{60})$, $PEO_{114}$-$P(DEA_{76}$-$DPA_{24})$, $PEO_{114}$-$P(DEA_{58}$-$DPA_{42})$, $PEO_{114}$-$P(DEA_{39}$-$DPA_{61})$, $PEO_{114}$-$P(DEA_{2}1$-$DPA_{79})$, $PEO_{114}$-$P(DPA_{30}$-$DBA_{50})$, $PEO_{114}$-$P(DBA_{28}$-$D5A_{52})$, $PEO_{114}$-$P(DBA_{56}$-$D5A_{24})$, $PEO_{114}$-$P(DEA_{20}$-$D5A_{60}$-$AMA_{3})$, $PEO_{114}$-$P(DEA_{40}$-$D5A_{40}$-$AMA_{3})$, $PEO_{114}$-$P(DEA_{60}$-$D5A_{20}$-$AMA_{3})$, $PEO_{114}$-$P(DPA_{60}$-$DBA_{20}$-$AMA_{3})$, $PEO_{114}$-$P(DPA_{40}$-$DBA_{40}$-$AMA_{3})$, $PEO_{114}$-$P(DPA_{20}$-$DBA_{60}$-$AMA_{3})$, $PEO_{114}$-$P(DEA_{76}$-$DPA_{24}$-$AMA_{3})$, $PEO_{114}$-$P(DEA_{58}$-$DPA_{42}$-$AMA_{3})$, $PEO_{114}$-$P(DEA_{39}$-$DPA_{61}$-$AMA_{3})$, $PEO_{114}$-$P(DEA_{2}1$-$DPA_{79}$-$AMA_{3})$, $PEO_{114}$-$P(DPA_{30}$-$DBA_{50}$-$AMA_{3})$, $PEO_{114}$-$P(DBA_{28}$-$D5A_{52}$-$AMA_{3})$, or $PEO_{114}$-$P(DBA_{56}$-$D5A_{24}$-$AMA_{3})$, $PEO_{114}$-$P(DEA_{11}$-$EPA_{89})$, $PEO_{114}$-$P(DEA_{22}$-$EPA_{78})$, $PEO_{114}$-$P(EPA_{90}$-$DPA_{10})$, $PEO_{114}$-$P(EPA_{79}$-$DPA_{2}i)$; wherein PEO is polyethylene glycol; P is poly; DBA is 2-(dibutylamino)ethyl methacrylate; D5A is 2-(dipentylamino)ethyl methacrylate; AMA is 2-aminoethyl methacrylate; DEA is 2-(diethylamino)ethyl methacrylate; DPA is 2-(dipropylamino)ethyl methacrylate; and EPA is 2-(ethylpropylamino)ethyl methacrylate.

In another aspect, the present disclosure provides a polymer of the formula:

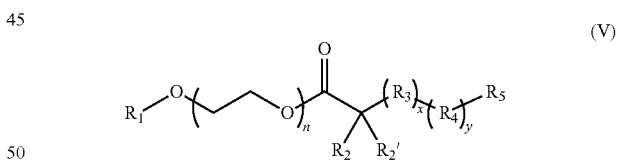

(V)

wherein: $R_1$ is hydrogen, $alkyl_{(C\leq12)}$, $cycloalkyl_{(C\leq12)}$, substituted $alkyl_{(C\leq12)}$, substituted $cycloalkyl_{(C\leq12)}$, or

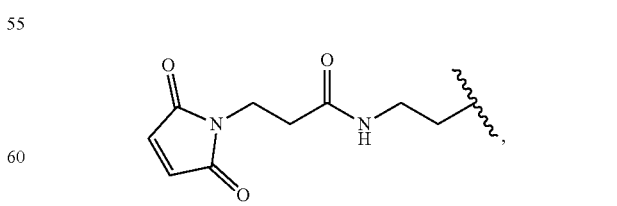

or a metal chelating group; n is an integer from 1 to 500; $R_2$ and $R_2'$ are each independently selected from hydrogen, $alkyl_{(C\leq12)}$, $cycloalkyl_{(C\leq12)}$, substituted $alkyl_{(C\leq12)}$, or substituted $cycloalkyl_{(C\leq12)}$; $R_3$ is a group of the formula:

(II)

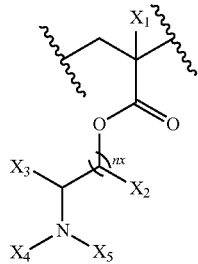

wherein: $n_x$ is 1-10; $X_1$, $X_2$, and $X_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; $X_4$ is pentyl, n-propyl, or ethyl; and $X_5$ is pentyl or n-propyl; x is an integer from 1 to 100; $R_4$ is a group of the formula:

(IV)

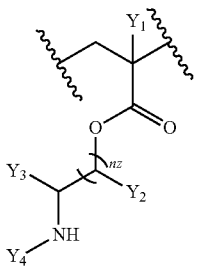

wherein: $Y_1$, $Y_2$, and $Y_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $Y_4$ is hydrogen, alkyl$_{(C \leq 12)}$, acyl$_{(C \leq 12)}$, substituted alkyl$_{(C \leq 12)}$, substituted acyl$_{(C \leq 12)}$, a dye, or a fluorescence quencher; y is an integer from 1 to 6; and $R_5$ is hydrogen, halo, hydroxy, alkyl$_{(C \leq 12)}$, or substituted alkyl$_{(C \leq 12)}$. In some embodiments, $Y_4$ is a fluorescent dye. In some embodiments, the fluorescent dye is indocyanine green. In some embodiments, the polymer is PEO$_{114}$-P(D5A$_{80}$), PEO$_{114}$-P(D5A$_{100}$), PEO$_{114}$-P(DPA$_{80}$), PEO$_{114}$-P(DPA$_{100}$), PEO$_{114}$-P(EPA$_{80}$), and PEO$_{114}$-P(EPA$_{100}$); wherein PEO is polyethylene glycol; P is poly; D5A is 2-(dipentylamino)ethyl methacrylate; DPA is 2-(dipropylamino)ethyl methacrylate; and EPA is 2-(ethylpropylamino)ethyl methacrylate.

In yet another aspect, the present disclosure provides a compound of the formula:

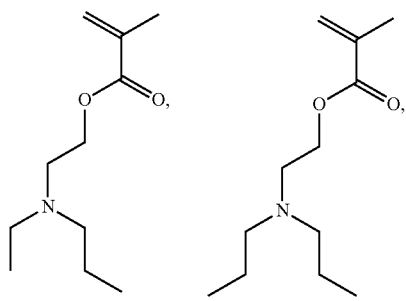

-continued

In another aspect, the present disclosure provides a micelle of a polymer of the present disclosure.

In yet another aspect, the present disclosure provides a pH responsive system comprising a micelle of a first polymer of the present disclosure, wherein z is not 0 and $Y_4$ is a dye, and wherein the micelle has a pH transition point and an emission spectra. In some embodiments, the micelle further comprises a second polymer of the present disclosure, wherein z is not 0 and $Y_4$ is a fluorescence quencher. In some embodiments, the second polymer has the same formula as the first polymer except that $Y_4$ is a fluorescence quencher. In some embodiments, the pH transition point is between 3-9. In some embodiments, the pH transition point is between 4-8. In some embodiments, the pH transition point is between 4-6. In some embodiments, the pH transition point is between 6-7.5. In some embodiments, the pH transition point is 4.38, 4.67, 4.96, 5.27, 5.63, 5.91, 6.21, 6.45, 6.76, 7.08, or 7.44. In some embodiments, the emission spectra is between 400-850 nm. In some embodiments, the system has a pH response ($\Delta pH_{10-90\%}$) of less than 1 pH unit. In some embodiments, the pH response is less than 0.25 pH units. In some embodiments, the pH response is less than 0.15 pH units. In some embodiments, the fluorescence signal has a fluorescence activation ratio of greater than 25. In some embodiments, the fluorescence activation ratio is greater than 50. In yet another aspect, the present disclosure provides a method of imaging the pH of a intracellular or extracellular environment comprising:
    (a) contacting a micelle of the present disclosure with the environment; and
    (b) detecting one or more optical signals from the environment, wherein the detection of the optical signal indicates that the micelle has reached its pH transition point and disassociated.

In some embodiments, the optical signal is a fluorescent signal. In some embodiments, when the intracellular environment is imaged, the cell is contacted with the micelle under conditions suitable to cause uptake of the micelle. In some embodiments, the intracellular environment is part of a cell. In some embodiments, the part of the cell is lysosome or an endosome. In some embodiments, the extracellular environment is of a tumor or vascular cell. In some embodiments, the extracellular environment is intravascular or extravascular. In some embodiments, the imaging the pH of the tumor environment comprises imaging the sentinel lymph node or nodes. In some embodiments, imaging sentinel lymph node or nodes allows for the surgical resection of the tumor and staging of the tumor metastasis. In some embodiments, imaging the pH of the tumor environment allows determination of the tumor size and margins. In some embodiments, imaging the pH of the tumor environment allows for more precise removal of the tumor during surgery. In some embodiments, imaging the pH of the sentential lymph node or nodes allows for more precise removal of the sentential lymph node or nodes during surgery. In some embodiments, the method further comprises:
  (a) contacting the cell with a compound of interest;
  (b) detecting one or more optical signals in the environment; and
  (c) determining whether a change in the optical signal occurred following contacting the cell with the compound of interest.

In some embodiments, the compound of interest is a drug, antibody, peptide, protein, nucleic acid, or small molecule.

In yet another aspect, the present disclosure provides a method of delivering a compound of interest to a target cell comprising:
  (a) encapsulating the compound of interest with a micelle of a polymer described herein; and
  (b) contacting the target cell with the micelle under such conditions that the pH of the target cell triggers the disassociation of the micelle and release of the compound, thereby delivering the compound of interest.

In some embodiments, the compound of interest is delivered into the cell. In some embodiments, the compound of interest is delivered to the cell. In some embodiments, the compound of interest is a drug, antibody, peptide, protein, nucleic acid, or small molecule. In some embodiments, the method comprises administering the micelle to a patient.

In still yet another aspect, the present disclosure provides method of resecting a tumor in a patient comprising:
  (a) administering to the patient an effective dose of a pH responsive system of the present disclosure;
  (b) detecting one or more optical signals for the patient; wherein the optical signals indicate the presence of a tumor; and
  (c) resecting the tumor via surgery.

In some embodiments, the optical signals indicate the margins of the tumor. In some embodiments, the tumor is 90% resected, or the tumor is 95% resected., or the tumor is 99% resected. In some embodiments, the tumor is a solid tumor such as a solid tumor is from a cancer. In some embodiments, the cancer is a breast cancer or a head and neck cancer such as a head and neck squamous cell carcinoma. In some embodiments, the pH responsive system is comprised of a polymer of the formula:

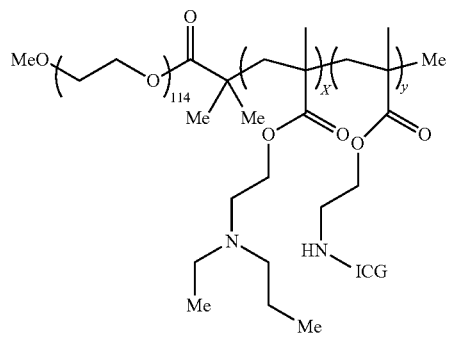

wherein: x is an integer from 30 to 150, y is an integer from 1 or 2; x and y are randomly distributed throughout the polymer; and ICG is the fluorescent dye indocyanine green.

In yet another aspect, the present disclosure provides methods of treating a cancer susceptible to endosomal/lysosomal pH arrest in a patient comprising administering to the patient in need thereof a pH responsive system of the present disclosure. In some embodiments, the cancer is a lung cancer such as a non-small cell lung cancer. In some embodiments, the cancer comprises a mutation in the KRAS gene or a mutation in the LKB1 gene. In other embodiments, the cancer comprises a mutation in both the KRAS and LKB1 gene. In some embodiments, methods are sufficient to induce apoptosis.

In still yet another aspect, the present disclosure provides methods of identifying the presence of a genetic mutation in a cell:
  (a) contacting a pH responsive systems comprising two or more micelles with the cell or cellular environment; and
  (b) detecting two or more optical signals from the environment, wherein the detection of the optical signal indicates that one of the micelles has reached its pH transition point and disassociated; and
  (c) correlate the two or more optical signals to determine the presence of the genetic mutation in the cell.

In some embodiments, the genetic mutation is a mutation in the KRAS gene. In some embodiments, the two or more micelles comprises three micelles with a pH transition point at 6.9, 6.2, and 5.3. In some embodiments, each of the three micelles is prepared from a polymer selected from poly(2-dipropylaminoethyl methacrylate)-tetramethyl rhodamine (PDPA-TMR), poly((2-ethylpropylamino)ethyl methacrylate)-BODIPY 493 (PEPA-BDY493; wherein BDY is BODIPY), and poly((2-dibutylamino)ethyl methacrylate)-Cyanine 5(PDBA-Cy5). In some embodiments, the method is performed in vivo and contact a cell comprising administering the one or more micelles to a patient.

In still yet another aspect, the present disclosure provides methods of identifying the tumor acidosis pathway comprising:
  (a) contacting a pH responsive system of the present disclosure comprising one or more micelles with a cell or a cellular environment;
  (b) contacting the cell with an inhibitor of the pH regulatory pathway;
  (c) detecting two or more optical signals from the cell or cellular environment, wherein the detection of the optical signal indicates that one of the micelles has reached its pH transition point and disassociated; and
  (d) correlating the two or more optical signals with a modification in the tumor acidosis pathway.

In some embodiments, the inhibitor of the pH regulatory pathway is an inhibitor of a monocarboxylate transporter, a carbonic anhydrase, an anion exchanger, a $Na^+$-bicarbonate exchanger, a $Na^+/H^+$ exchanger, or a V-ATPase. In some embodiments, the one or more micelles comprise a polymer with two or more fluorophores attached to the polymer backbone. In some embodiments, the method comprises one micelle and the micelle comprises two or more polymers with different fluorophores or different $R_3$ groups. In some embodiments, the micelle comprises two or more polymers with different fluorophores and different $R_3$ groups.

140. A method of imaging a patient to determine the presence of a tumor comprising:
  (a) contacting a pH responsive system comprising one or more micelles of the present disclosure with the tumor, wherein the micelle further comprises a metal chelating group at $R_1$;
  (b) collecting one or more PET or SPECT imaging scans; and (c) collecting one or more optical imaging scans, wherein the detection of the optical signal indicates that one of the micelles has reached its pH transition point and disassociated;

wherein the one or more PET or SPECT imaging scans and the one or more optical imaging scans result in the identification of a tumor.

In some embodiments, the optical imaging scans are collected before the PET or SPECT imaging scans. In other embodiments, the optical imaging scans are collected after the PET or SPECT imaging scans. In other embodiments, the optical imaging scans are collected simultaneously with the PET or SPECT imaging scans. In some embodiments, the imaging scans are PET imaging scans. In other embodiments, the imaging scans are SPECT imaging scans. In some embodiments, the metal chelating group is bound to a $^{64}$Cu ion. In some embodiments, the metal chelating group is a nitrogen containing macrocycle. In some embodiments, the nitrogen containing macrocycle is:

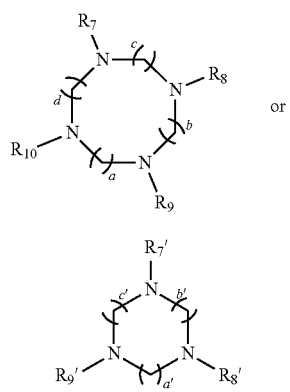

(VA)

or (VB)

wherein: $R_7$, $R_8$, $R_9$, $R_{10}$, $R_7R_8'$, $R_9'$ a, b, c, d, a', b', and c' are as defined above. In some embodiments, the nitrogen containing macrocycle is:

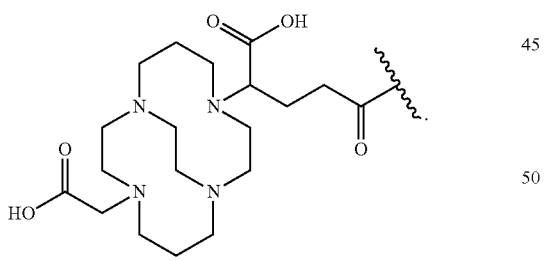

In still yet another aspect, the present disclosure provides polymers of the formula:
wherein:

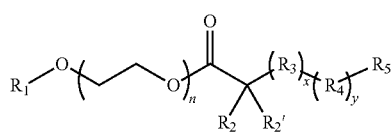

(IX)

$R_1$ is a metal chelating group;

n is an integer from 1 to 500;

$R_2$ and $R_2'$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$;

$R_3$ is a group of the formula:

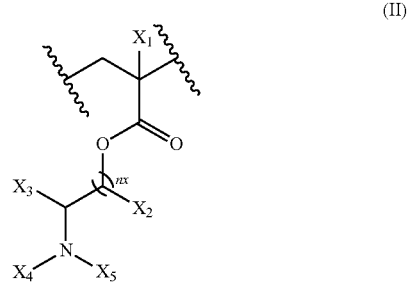

(II)

wherein:

$n_x$ is 1-10;

$X_1$, $X_2$, and $X_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $X_4$ and $X_5$ are each independently selected from alkyl$_{(C \leq 12)}$, cycloalkyl$_{(C \leq 12)}$, aryl$_{(C \leq 12)}$, heteroaryl$_{(C \leq 12)}$ or a substituted version of any of these groups, or $X_4$ and $X_5$ are taken together and are alkanediyl$_{(C \leq 12)}$, alkoxydiyl$_{(C \leq 12)}$, alkylaminodiyl$_{(C \leq 12)}$, or a substituted version of any of these groups;

x is an integer from 1 to 150;

$R_4$ is a group of the formula:

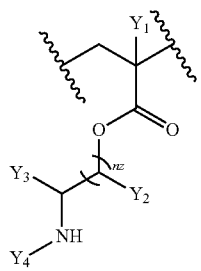

(IV)

wherein:

$n_z$ is 1-10;

$Y_1$, $Y_2$, and $Y_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $Y_4$ is hydrogen, alkyl$_{(C \leq 12)}$, acyl$_{(C \leq 12)}$, substituted alkyl$_{(C \leq 12)}$, substituted acyl$_{(C \leq 12)}$, a dye, or a fluorescence quencher;

y is an integer from 0-6; and $R_4$ is hydrogen, halo, hydroxy, alkyl$_{(C \leq 12)}$, or substituted alkyl$_{(C \leq 12)}$, wherein $R_3$ and $R_4$ can occur in any order within the polymer, provided that $R_3$ and $R_4$ are not the same group.

In some embodiments, $R_3$ is:

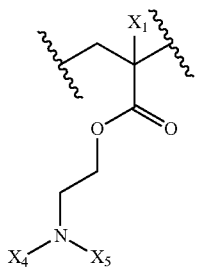

wherein: $X_1$, $X_4$, and $X_5$ are as defined above.

In some embodiments, $X_1$ is alkyl$_{(C \leq 12)}$ such as $X_1$ is methyl. In some embodiments, $X_4$ and $X_5$ are taken together and are alkanediyl$_{(C \leq 12)}$ or substituted alkanediyl$_{(C \leq 12)}$. In some embodiments, wherein $X_4$ and $X_5$ are taken together and are —CH$_2$CH$_2$CH$_2$CH$_2$CH$_2$CH$_2$—. In some embodiments, $R_4$ is:

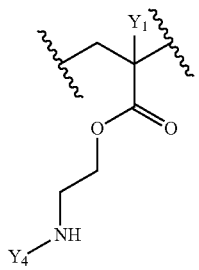

wherein: $Y_1$ and $Y_4$ are as defined above. In some embodiments, $Y_4$ is a dye. In some embodiments, $Y_4$ is a fluorescent dye. In some embodiments, $Y_1$ is alkyl$_{(C \leq 12)}$ such as $Y_1$ is methyl. In some embodiments, x is 40, 60, 80, 100, or 120. In some embodiments, y is 1, 2, or 3, such as when y is 3. In some embodiments, the polymer is PEO$_{114}$-P(C7A$_{40}$-r-ICG$_3$), PEO$_{114}$-P(C7A$_{60}$-r-ICG$_3$), PEO$_{114}$-P(C7A$_{80}$-r-ICG$_3$), PEO$_{114}$-P(C7A$_{100}$-r-ICG$_3$), or PEO$_{114}$-P(C7A$_{120}$-r-ICG$_3$), wherein the PEO group is capped with a metal chelating group; PEO is polyethylene glycol; P is poly; C7A is 2-(hexamethyleneimino)ethyl methacrylate; ICG is indocyanine green; and r is for describing that the arrangement of the two monomeric units that are connected is random.

As used herein, "pH responsive system," "micelle," "pH-responsive micelle," "pH-sensitive micelle," "pH-activatable micelle" and "pH-activatable micellar (pHAM) nanoparticle" are used interchangeably herein to indicate a micelle comprising one or more block copolymers, which disassociates depending on the pH (e.g., above or below a certain pH). As a non-limiting example, at a certain pH, the block copolymer is substantially in micellar form. As the pH changes (e.g., decreases), the micelles begin to disassociate, and as the pH further changes (e.g., further decreases), the block copolymer is present substantially in disassociated (non-micellar) form.

As used herein, "pH transition range" indicates the pH range over which the micelles disassociate.

As used herein, "pH transition value" (pH$_t$) indicates the pH at which half of the micelles are disassociated.

It is contemplated that any method or composition described herein can be implemented with respect to any other method or composition described herein.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. As a result, a method, composition, kit, or system that "comprises," "has," "contains," or "includes" one or more recited steps or elements possesses those recited steps or elements, but is not limited to possessing only those steps or elements; it may possess (i.e., cover) elements or steps that are not recited. Likewise, an element of a method, composition, kit, or system that "comprises," "has," "contains," or "includes" one or more recited features possesses those features, but is not limited to possessing only those features; it may possess features that are not recited.

Any embodiment of any of the present methods, composition, kit, and systems may consist of or consist essentially of—rather than comprise/include/contain/have—the described steps and/or features. Thus, in any of the claims, the term "consisting of" or "consisting essentially of" may be substituted for any of the open-ended linking verbs recited above, in order to change the scope of a given claim from what it would otherwise be using the open-ended linking verb.

The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the standard deviation of error for the device or method being employed to determine the value. Following long-standing patent law, the words "a" and "an," when used in conjunction with the word "comprising" in the claims or specification, denotes one or more, unless specifically noted.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

ratios in the random copolymers. The peaks at 0.9 ppm and 1.1 ppm were used to estimate the monomer composition in the hydrophobic PR block.

Figure 3:
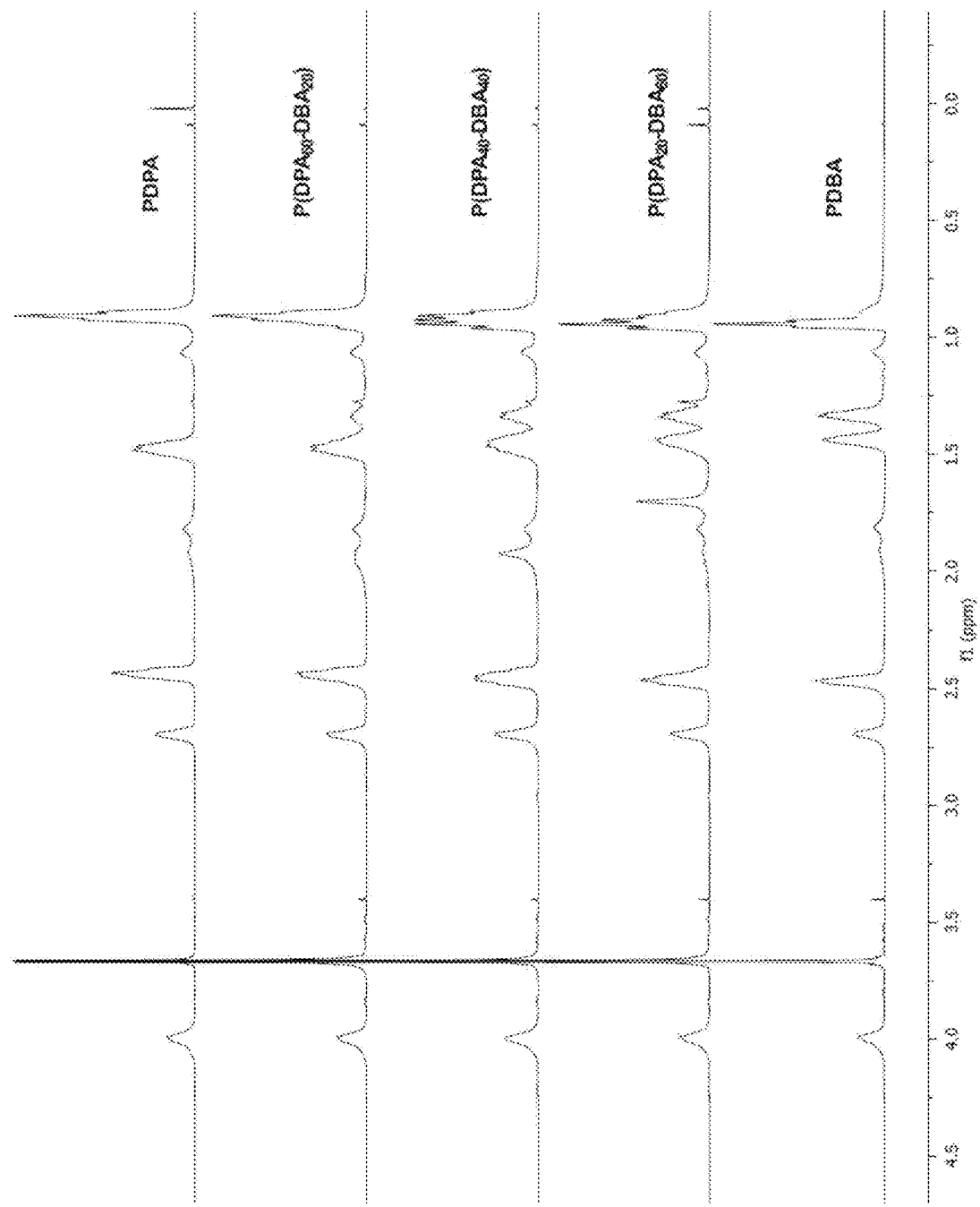

FIG. 3 shows the NMR spectra of PEO-P(DPA$_x$-DBA$_y$) (x+y=80) copolymers at different monomer (DPA and DBA) ratios in the random copolymers. The peaks at 1.3 ppm and 1.4 ppm were used to estimate the monomer composition in the hydrophobic PR block.

Figure 4:
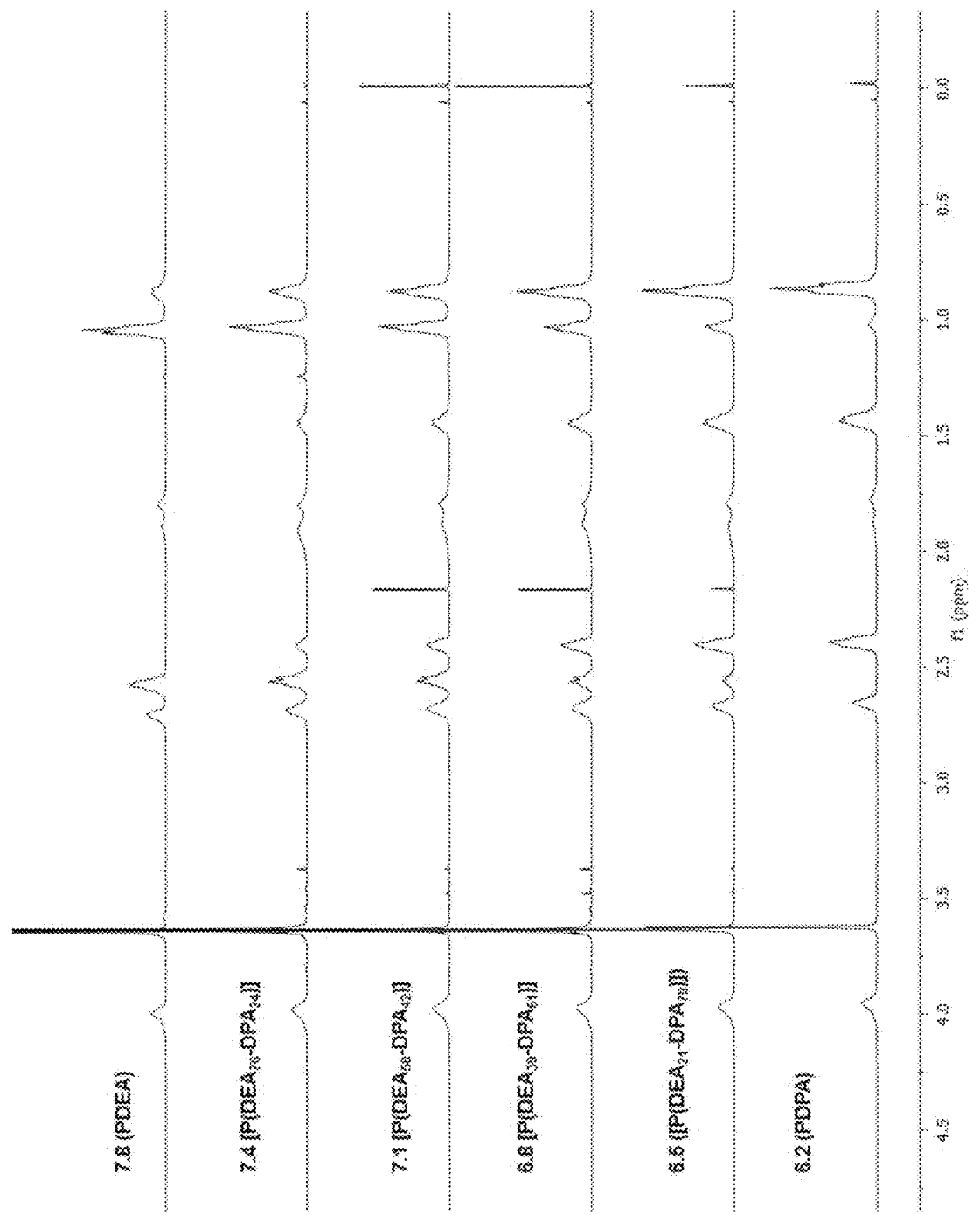

FIG. 4 shows the NMR spectra of nanoprobe compositions with pH$_t$ values at 7.8, 7.4, 7.1, 6.8, 6.5 and 6.2 by adjusting the monomer (DEA and DPA) ratios in the hydrophobic PR block. The peaks at 0.9 ppm and 1.0-1.1 ppm were used to estimate the monomer composition in the hydrophobic PR block.

Figure 5:
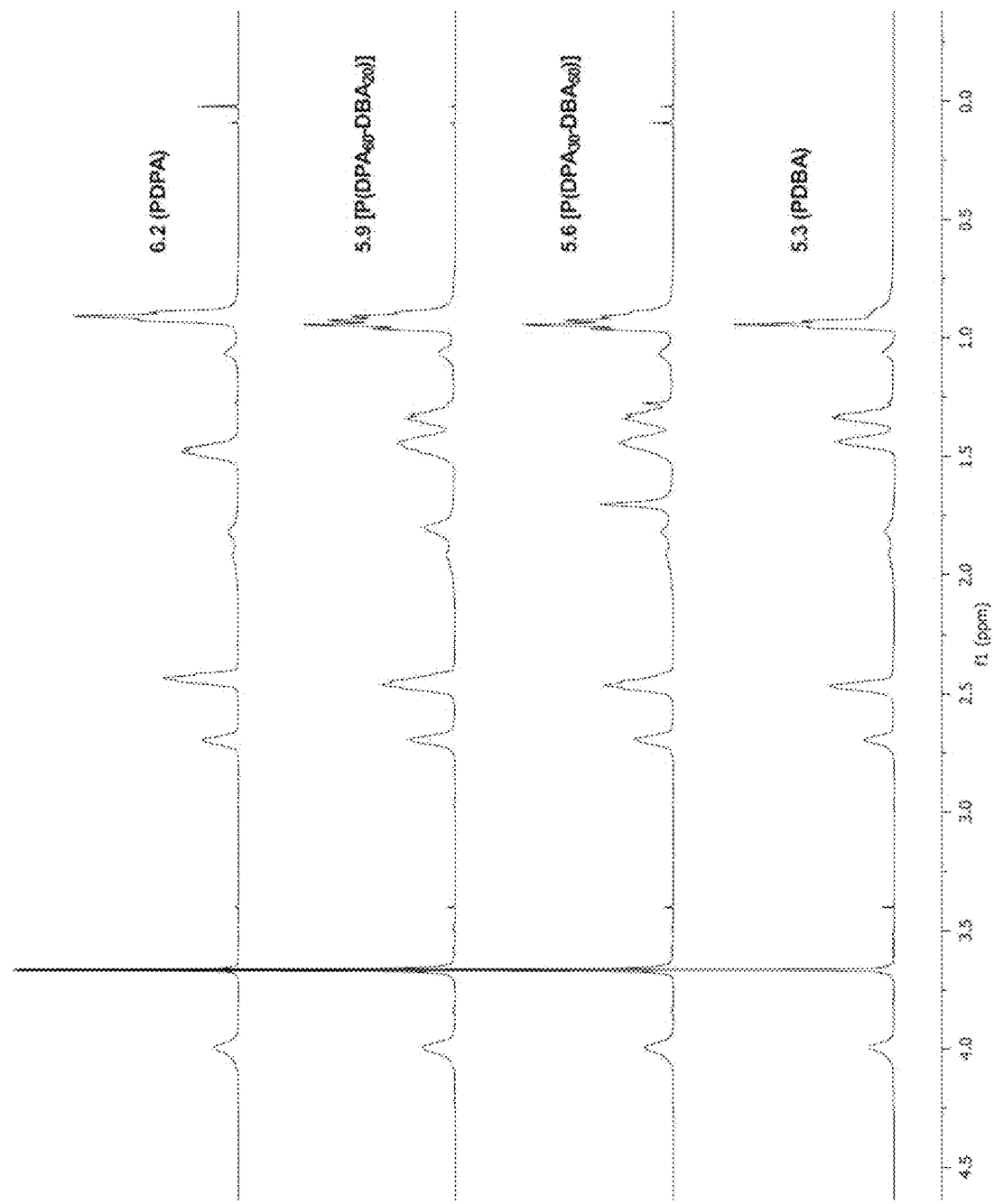

FIG. 5 shows the NMR spectra of nanoprobe compositions with pH$_t$ values at 6.2, 5.9, 5.6 and 5.3 by adjusting the monomer (DPA and DBA) ratios in the hydrophobic PR block. The peaks at 1.3 ppm and 1.4 ppm were used to estimate the monomer composition in the hydrophobic PR block.

Figure 6:
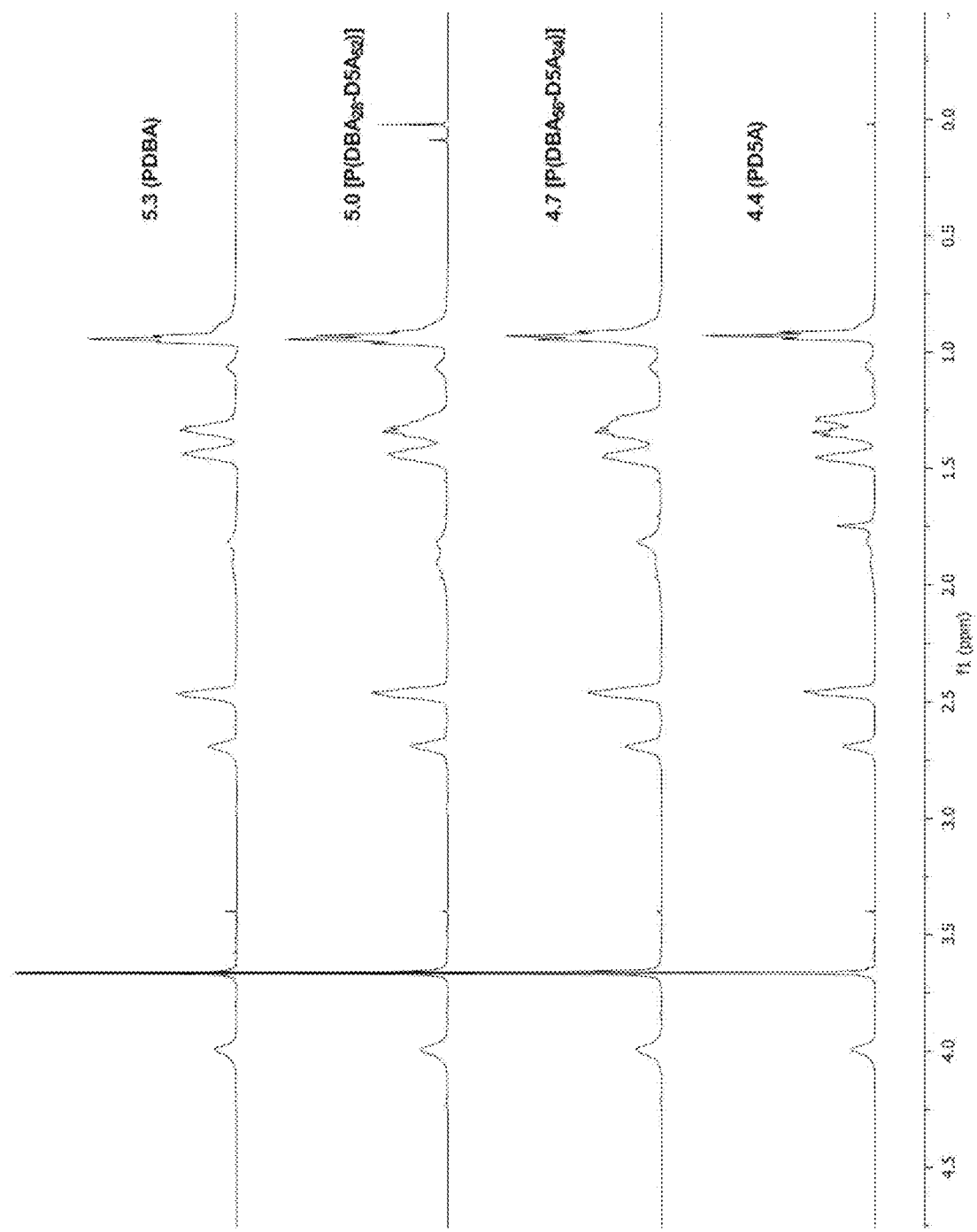

FIG. 6 shows the $^1$H NMR spectra of nanoprobe compositions with pH$_t$ values at 5.3, 5.0, 4.7 and 4.4 by adjusting the monomer (DBA and D5A) ratios in the hydrophobic PR block. The peaks at 1.3 ppm and 1.4 ppm were used to estimate the monomer composition in the hydrophobic PR block.

Figure 7:
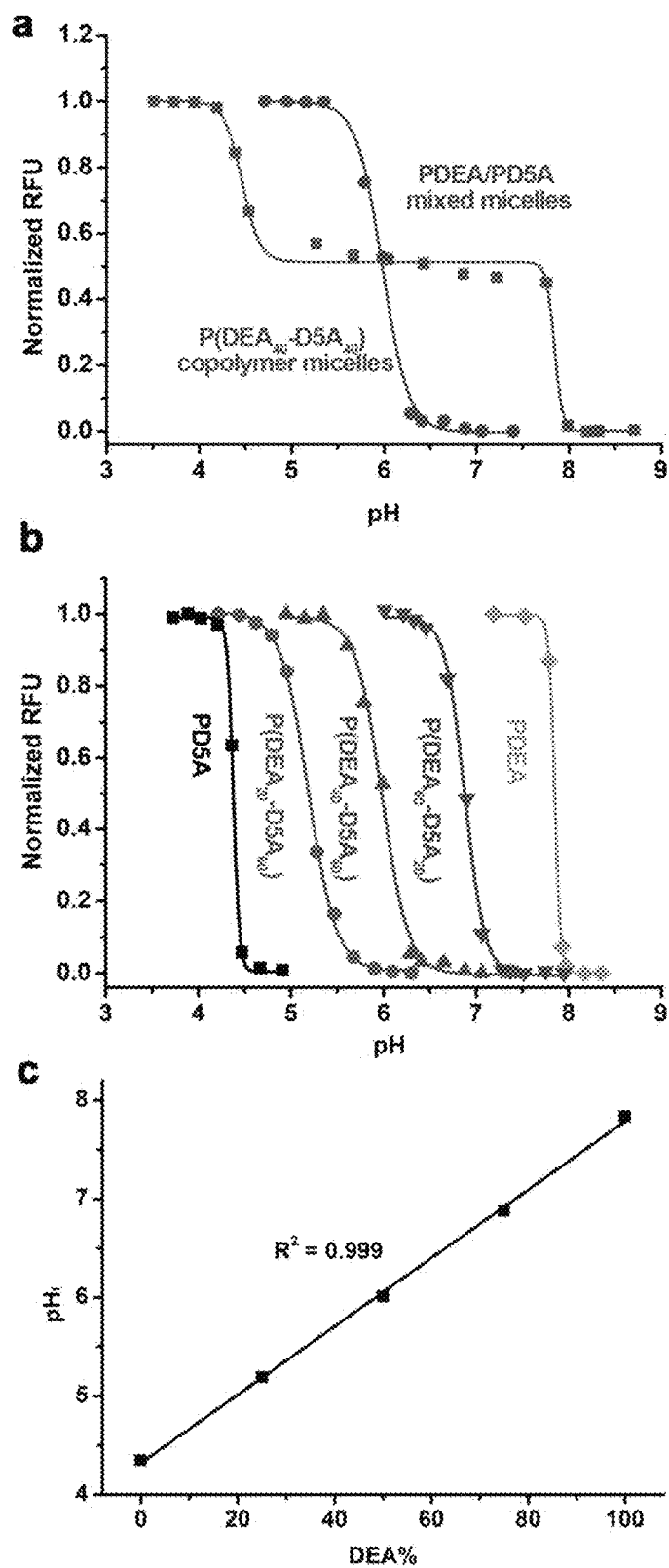

FIGS. 7A-C: (FIG. 7A) Comparison of PDEA/PD5A molecular mixture vs. P(DEA$_{40}$-D5A$_{40}$) copolymer strategies for the control of pH$_t$. (FIG. 7B) Normalized fluorescence intensity of P(DEA$_x$-D5A$_y$) nanoprobes with different ratios of the two monomers as a function of pH. (FIG. 7C) Nanoprobe pH$_t$ is linearly correlated with the molar fraction of the DEA-MA monomer in the PR segment. Polymer concentrations were 0.1 mg/mL in these studies.

Figure 8:
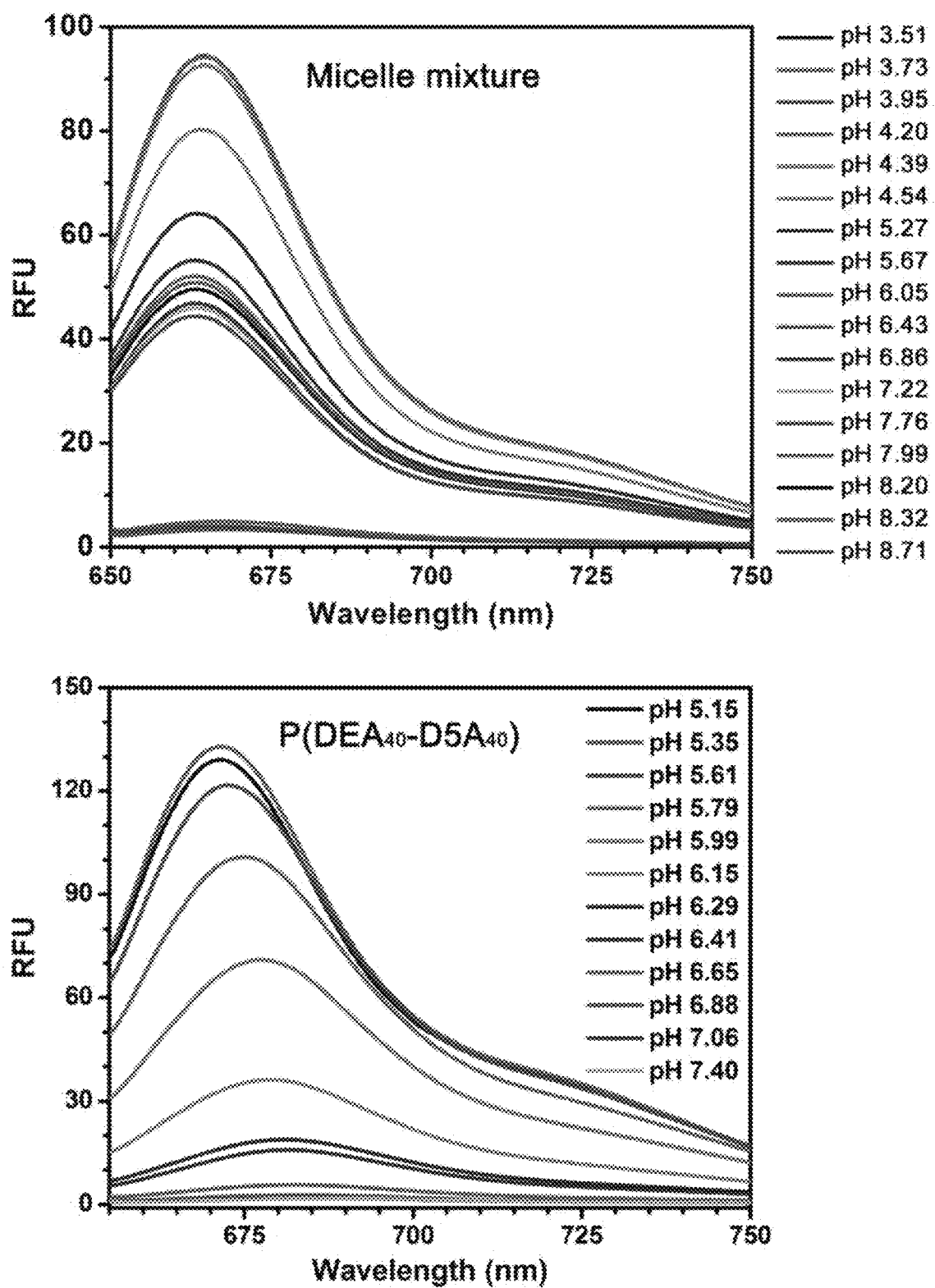

FIG. 8 shows the pH-dependent fluorescence spectra of PDEA/PD5A micelle blend vs. P(DEA$_{40}$-D5A$_{40}$) copolymer nanoprobes. Cy5 dye ($\lambda_{ex}/\lambda_{em}$=646/662 nm) was conjugated to the PR blocks of the corresponding copolymers. The normalized fluorescence intensity vs. pH relationships were shown in FIG. 7A.

Figure 9:
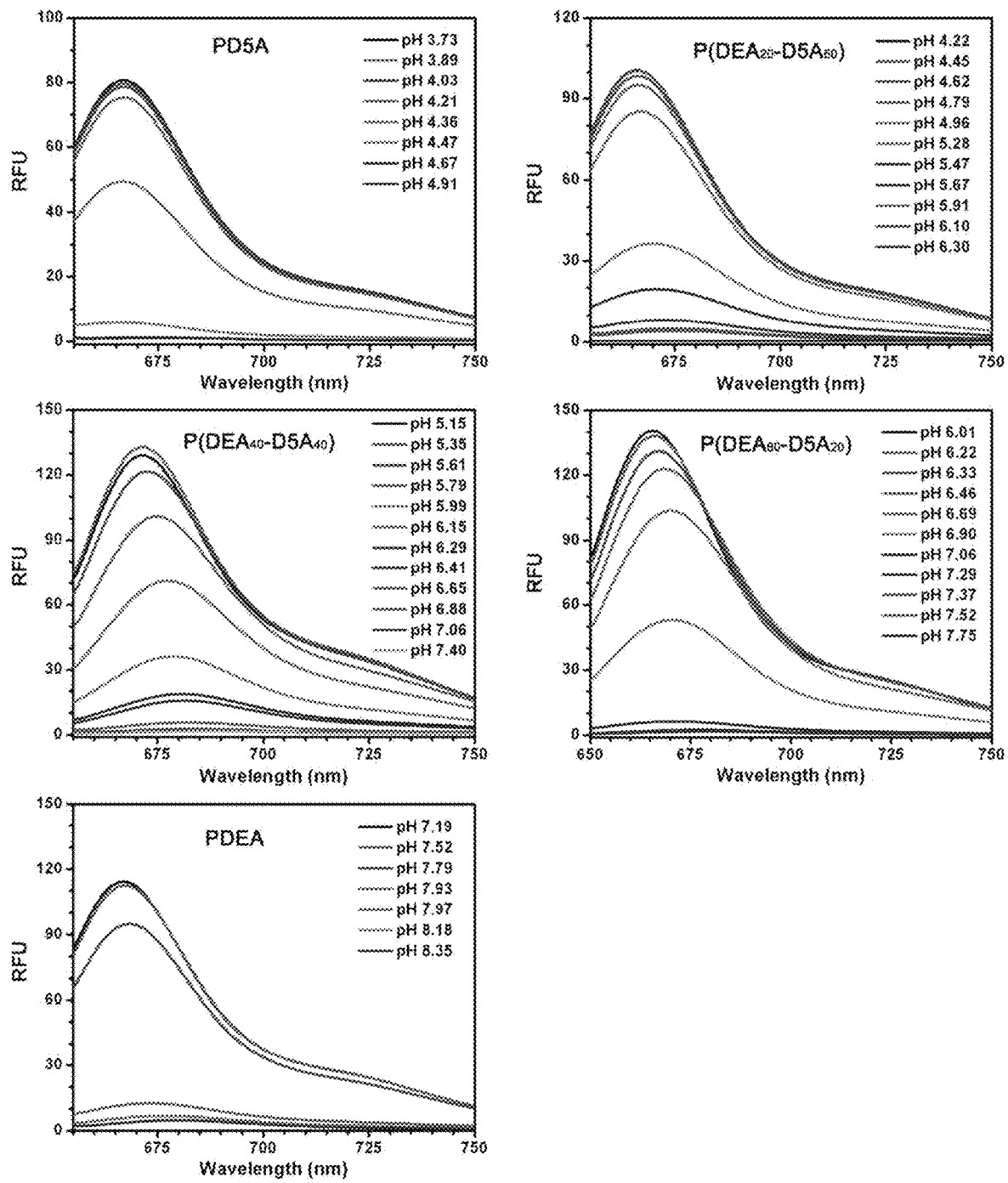

FIG. 9 shows pH-dependent fluorescence spectra of coarse-tuned P(DEA$_x$-D5A$_y$) nanoprobes. Cy5 dye ($\lambda_{ex}/\lambda_{em}$=646/662 nm) was conjugated to the PR blocks of the copolymers. The normalized fluorescence intensity vs. pH relationships were shown in FIG. 7B.

FIGS. 10A-D: (FIG. 10A) Normalized fluorescence intensity as a function of pH for Cy5-conjugated P(DPA$_x$-DBA$_y$) nanoprobes. (FIG. 10B) A derivatized fluorescence plot (d$_F$/d$_{pH}$, data from 4a) as a function of pH for P(DPA$_x$-DBA$_y$) vs. P(DEA$_{40}$-D5A$_{40}$) nanoprobes. Use of methacrylate monomers with close hydrophobicity (i.e., DPA/DBA vs. DEA/D5A) resulted in much sharper pH transitions. (FIG. 10C) Linear relationships of the nanoprobe pH$_t$ as a function of molar fractions of the less hydrophobic monomer for different copolymer compositions. These correlations serve as the standard curves for selecting the optimal copolymer composition to achieve an operator-predetermined pH$_t$. (FIG. 10D) A representative library of UPS nanoprobes with 0.3 pH increment covering the entire physiologic range of pH (4-7.4). All the nanoprobes were conjugated with the Cy5 dye. Polymer concentrations were at 0.1 mg/mL.

Figure 11:
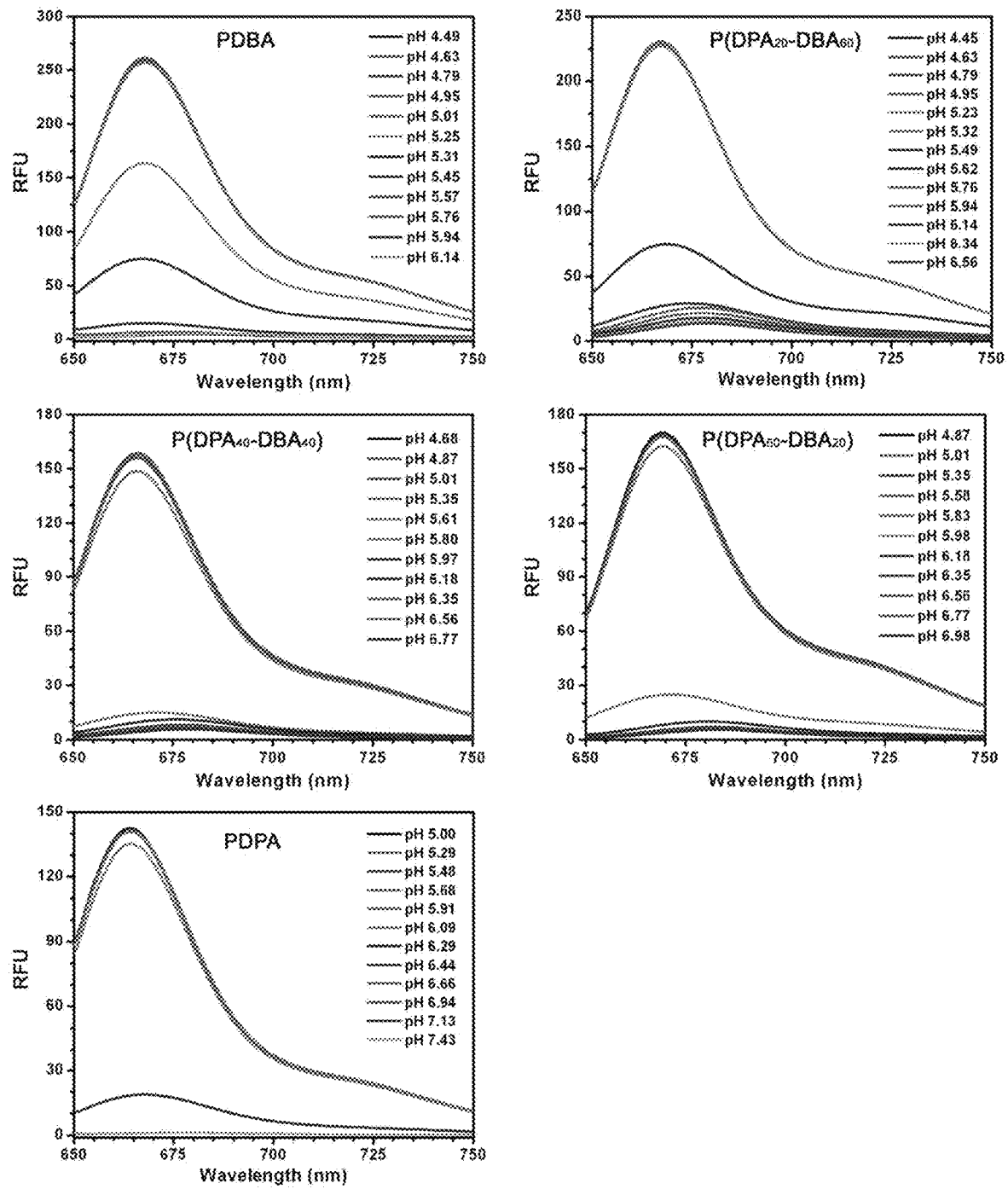

FIG. 11 shows pH-dependent fluorescence spectra of fine-tuned P(DPA$_x$-DBA$_y$) nanoprobes. Cy5 dye ($\lambda_{ex}/\lambda_{em}$=646/662 nm) was conjugated to the PR blocks of the copolymers. The normalized fluorescence intensity vs. pH relationships were shown in FIG. A.

Figure 12:
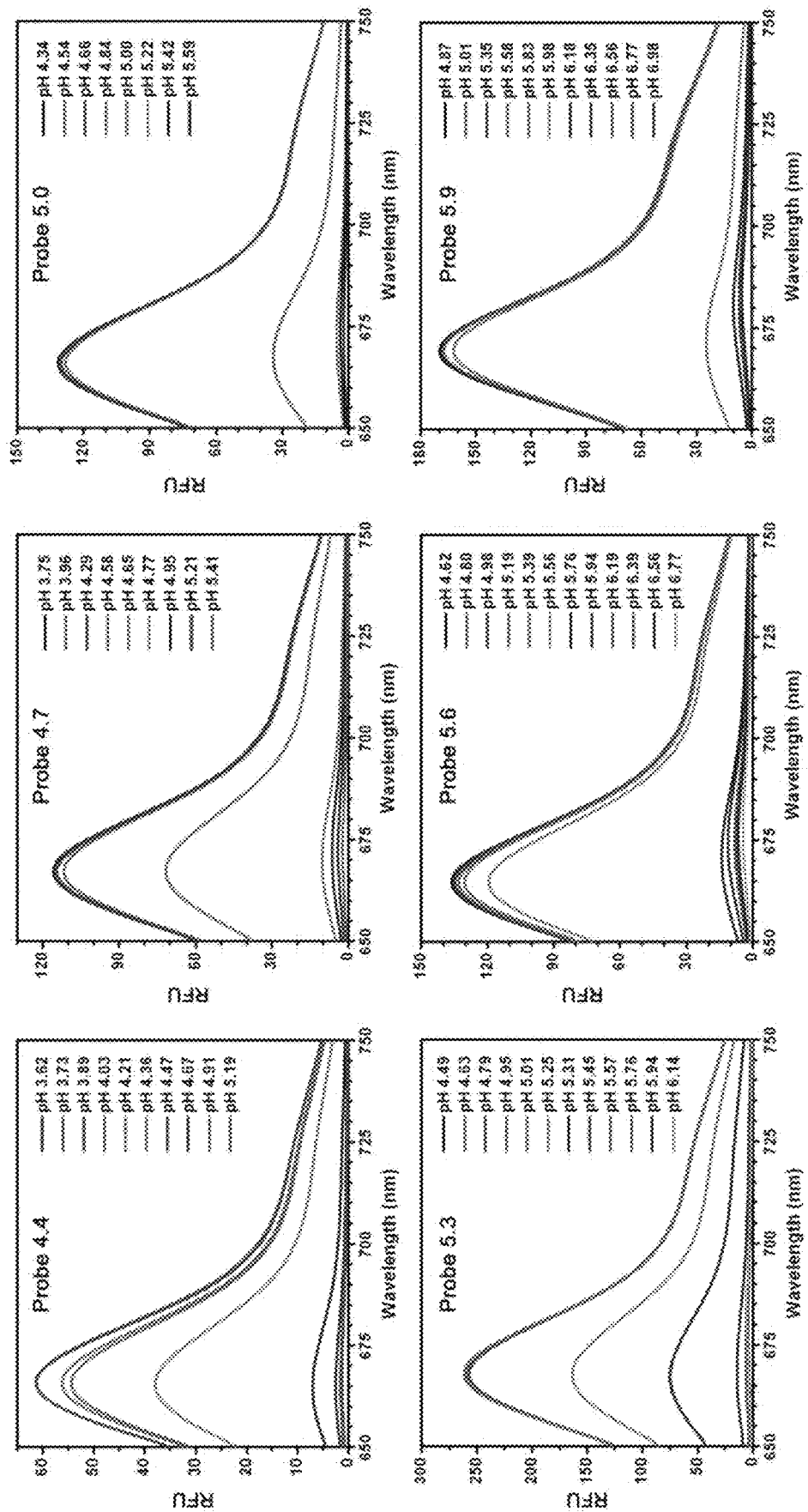
Figure 12:
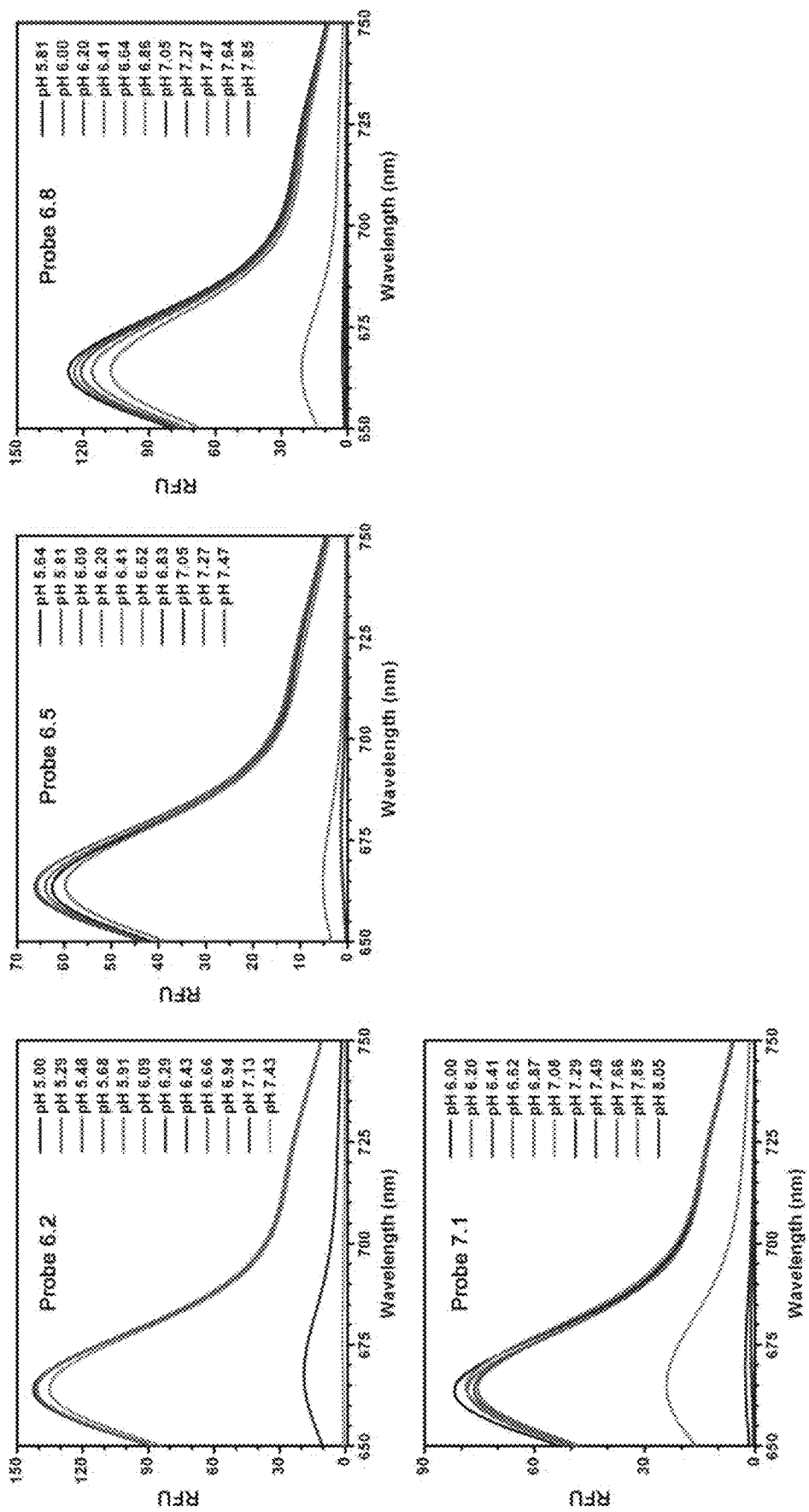

FIG. 12 shows pH-dependent fluorescence spectra of the UPS library nanoprobes. The composition for each UPS nanoprobe is shown in Table 3. Cy5 dye ($\lambda_{ex}/\lambda_{em}$=646/662 nm) was conjugated to the PR blocks of the copolymers. The normalized fluorescence intensity vs. pH relationships were shown in FIG. 10D.

Figure 13:
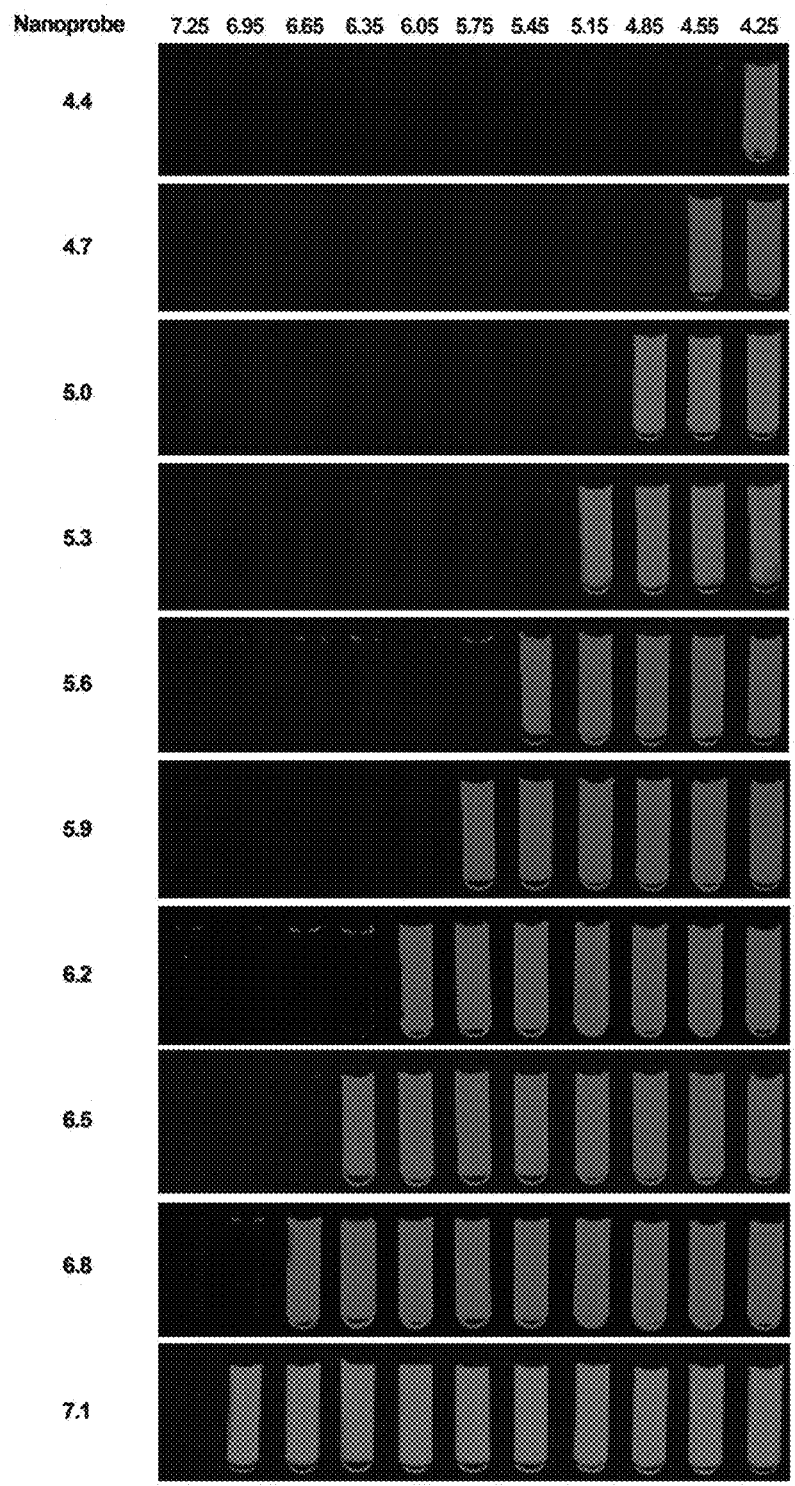

FIG. 13 shows the fluorescence imaging of the UPS library consisting of 10 nanoprobes with 0.3 pH increment. The composition for each UPS nanoprobe is shown in Table 3. Cy5 dye ($\lambda_{ex}/\lambda_{em}$=646/662 nm) was conjugated to the PR blocks of the copolymers. Images of the nanoprobes were taken on a Maestro Imaging system.

FIGS. 14A-F show (FIG. 14A) Structures of the PEO-PDPA-Dye/FQ copolymers. (FIG. 14B) Structures of selected fluorophores with large Stokes shift. (FIG. 14C) Structures of selected Rhodamine dyes. (FIG. 14D) Structures of selected Bodipy dyes. (FIG. 14E) Structures of selected cyanine dyes. The excitation/emission wavelengths for all the fluorophores were shown in FIGS. 14B-E, respectively. (FIG. 14F) Structures of the selected fluorescence quenchers. The active quenching range of each quencher was shown in parenthesis.

Figure 15:
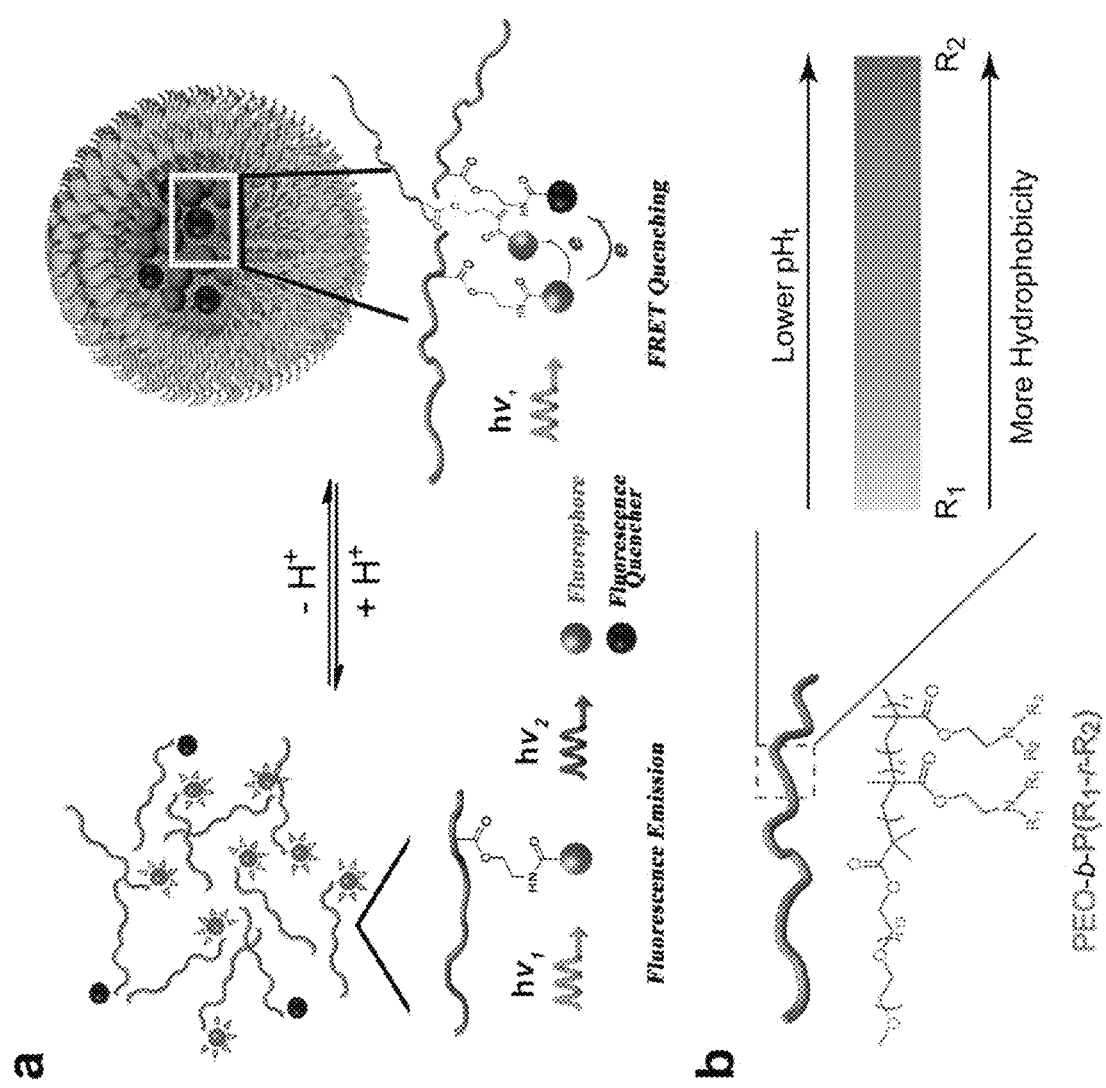

FIGS. 15A & B show a schematic design of ultra-pH sensitive (UPS) micellar nanoprobes. (FIG. 15A) In the unimer state (pH<pH$_t$), polymer dissociation resulted in fluorophore-quencher separation and strong fluorescence emission. In the micelle state (pH>pH$_t$), fluorescence quenching dramatically suppress the emission intensity of fluorophores. (FIG. 15B) A copolymer strategy was used to achieve an operator-predetermined control of nanoprobe pH$_t$ by the ability to continuously fine tuning the hydrophobicity of the PR segment.

Figure 16:
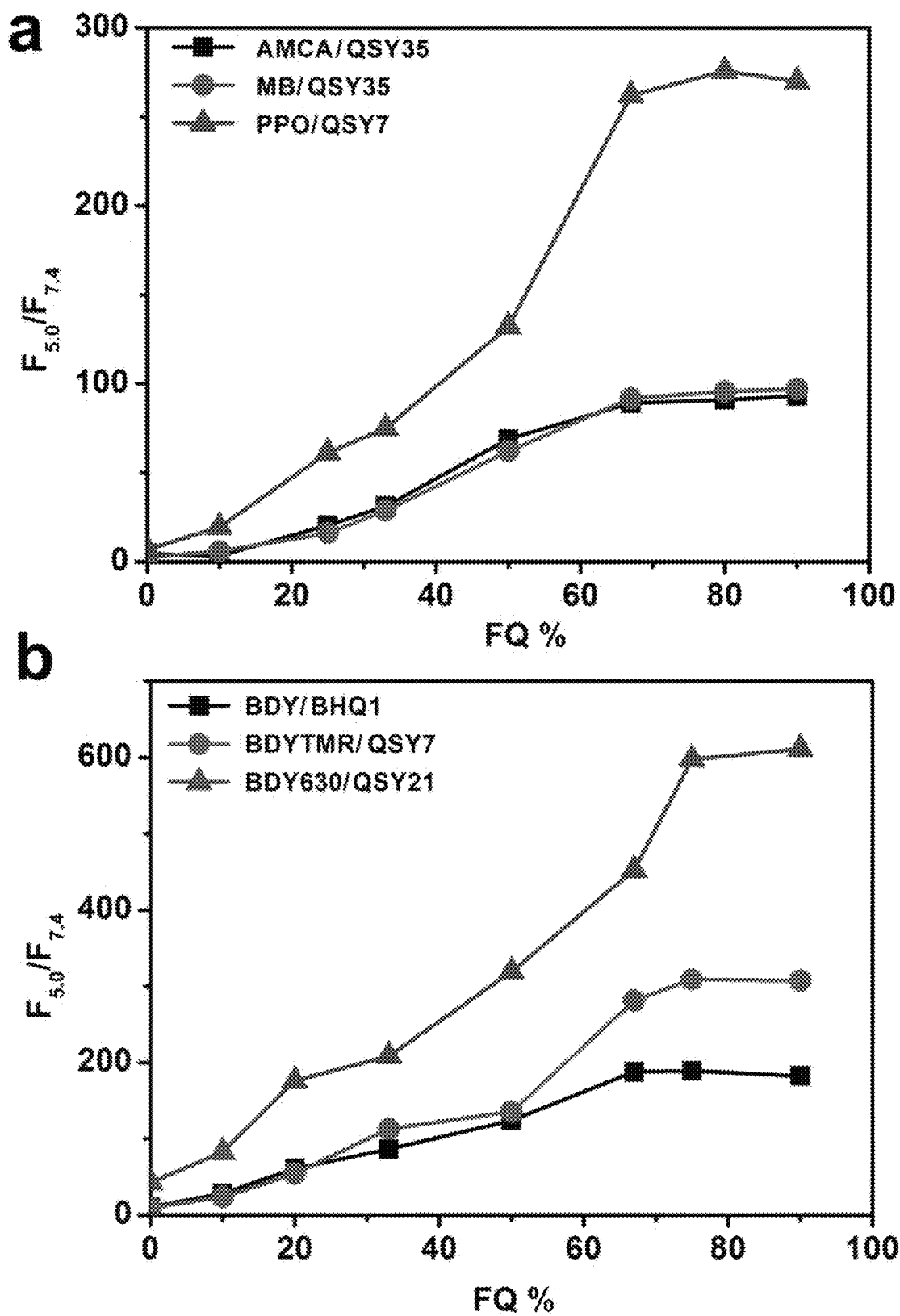
Figure 17:
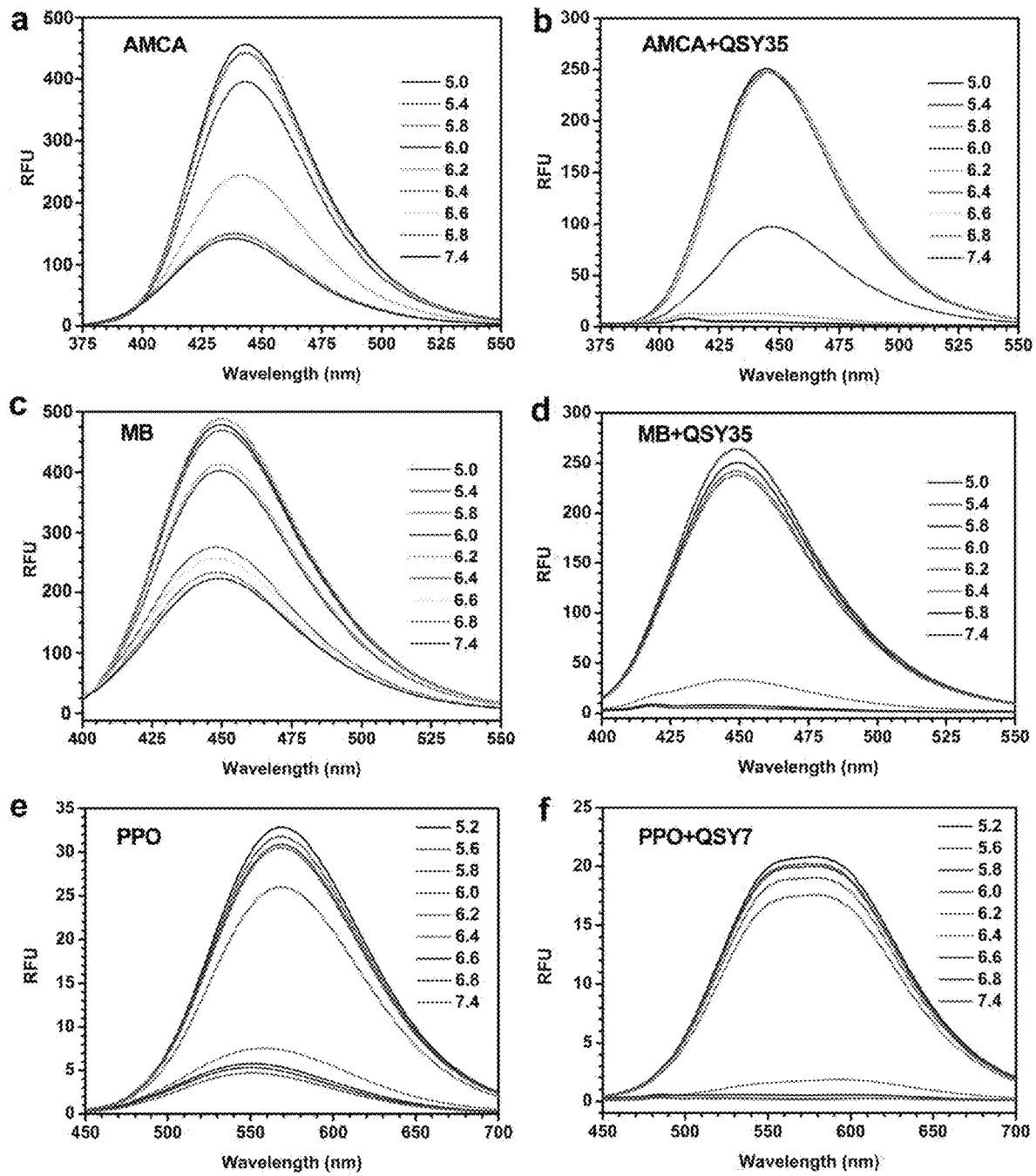

FIGS. 16A & B show the fluorescence intensity ratios of mixed nanoparticles at pH 5.0 (ON) and pH 7.4 (OFF) at different ratios of PDPA-Dye/PDPA-FQ. (FIG. 16A) Results for fluorophores with large Stokes shift (AMCA, MB and PPO). (FIG. 16B) Results for BODIPY® families of fluorophores. The structures of the fluorophores and FQs were shown in FIGS. 14A-F.

FIGS. 17A-F show the pH-dependent fluorescence spectra of nanoprobes without (left column) or with (right column) fluorescence quenchers. Fluorophores with large Stokes shift were presented in this study. The structures of the fluorophores and FQs were shown in FIGS. 14A-F.

Figure 18:
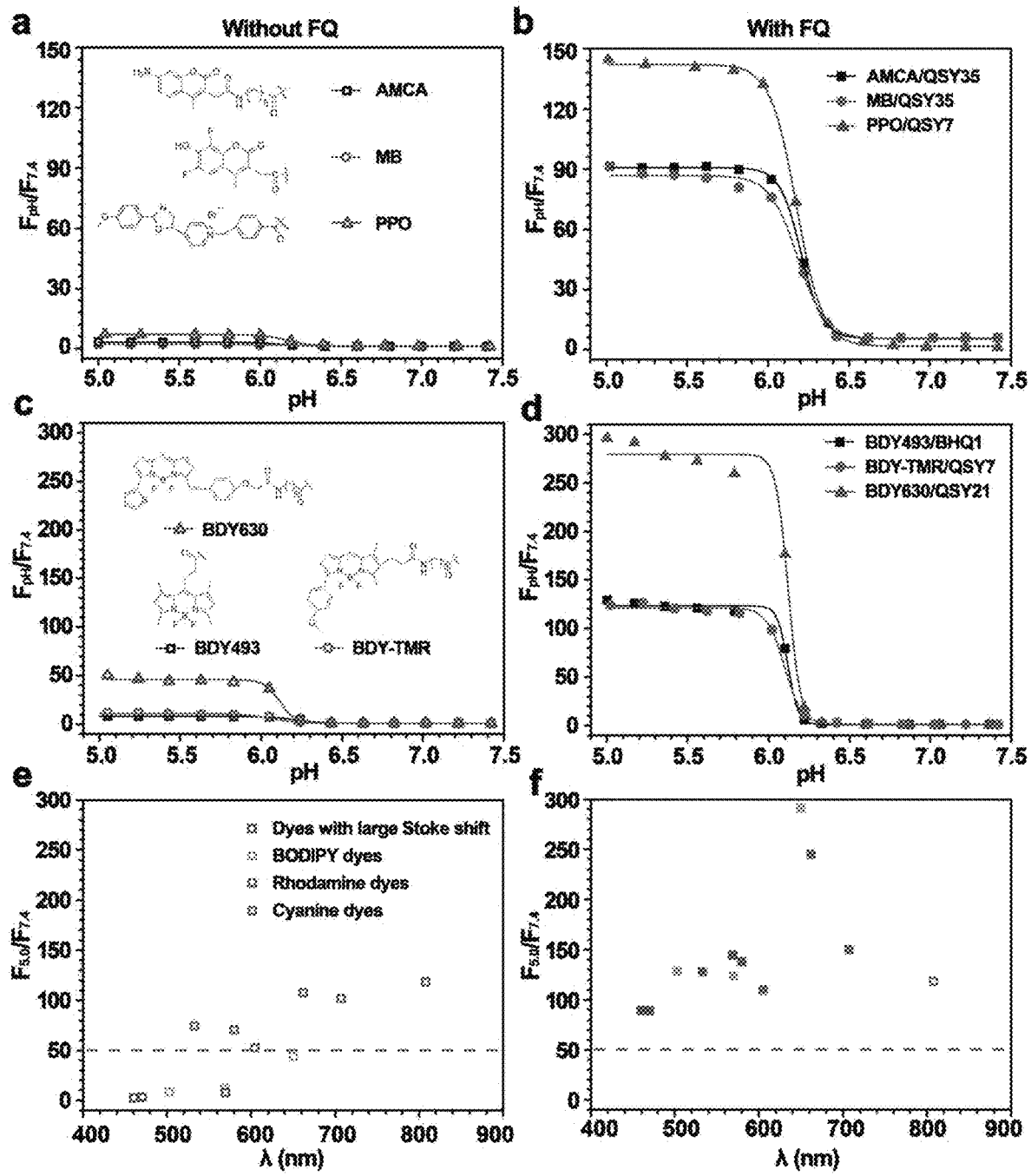
Figure 19:
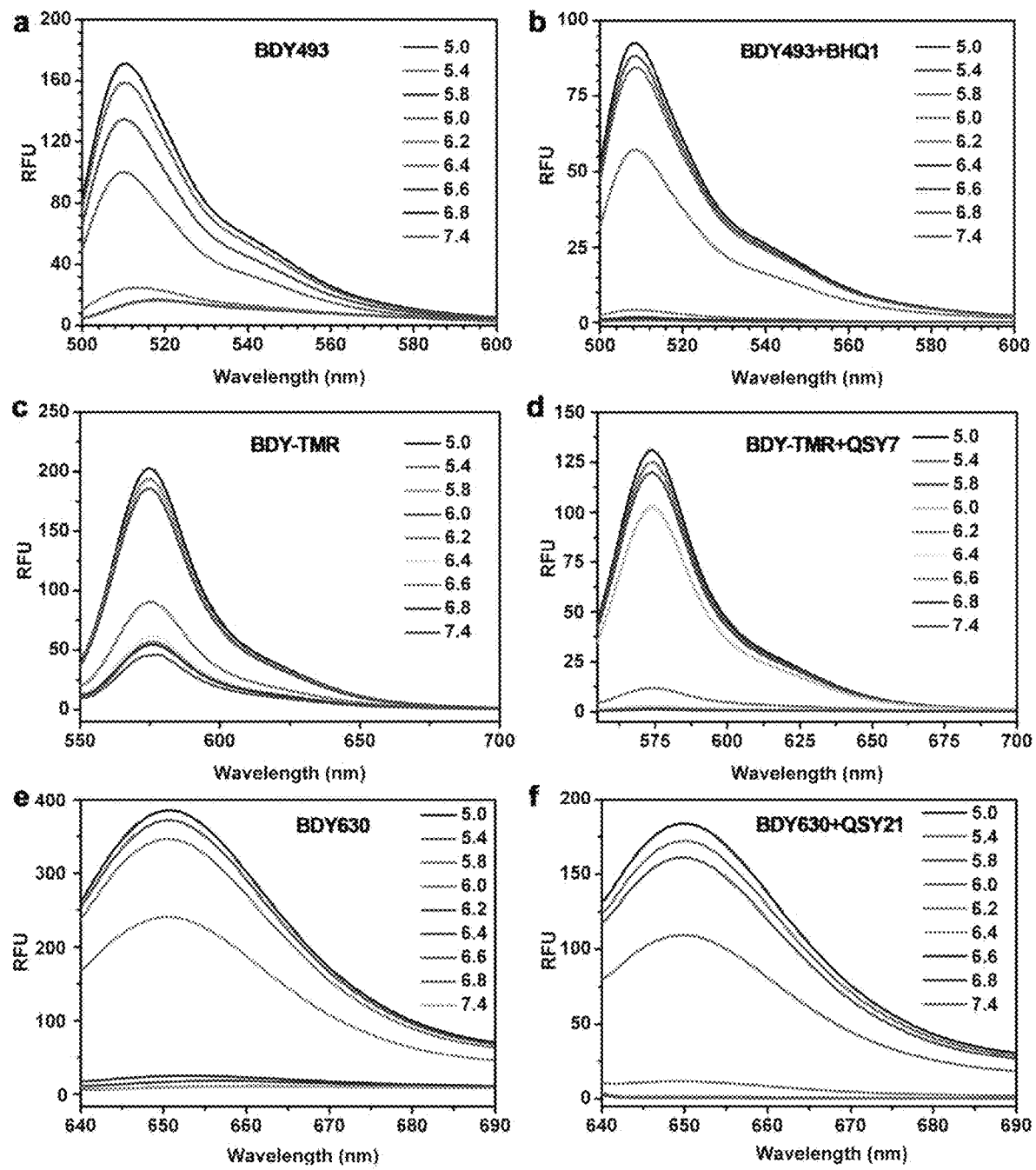
Figure 20:
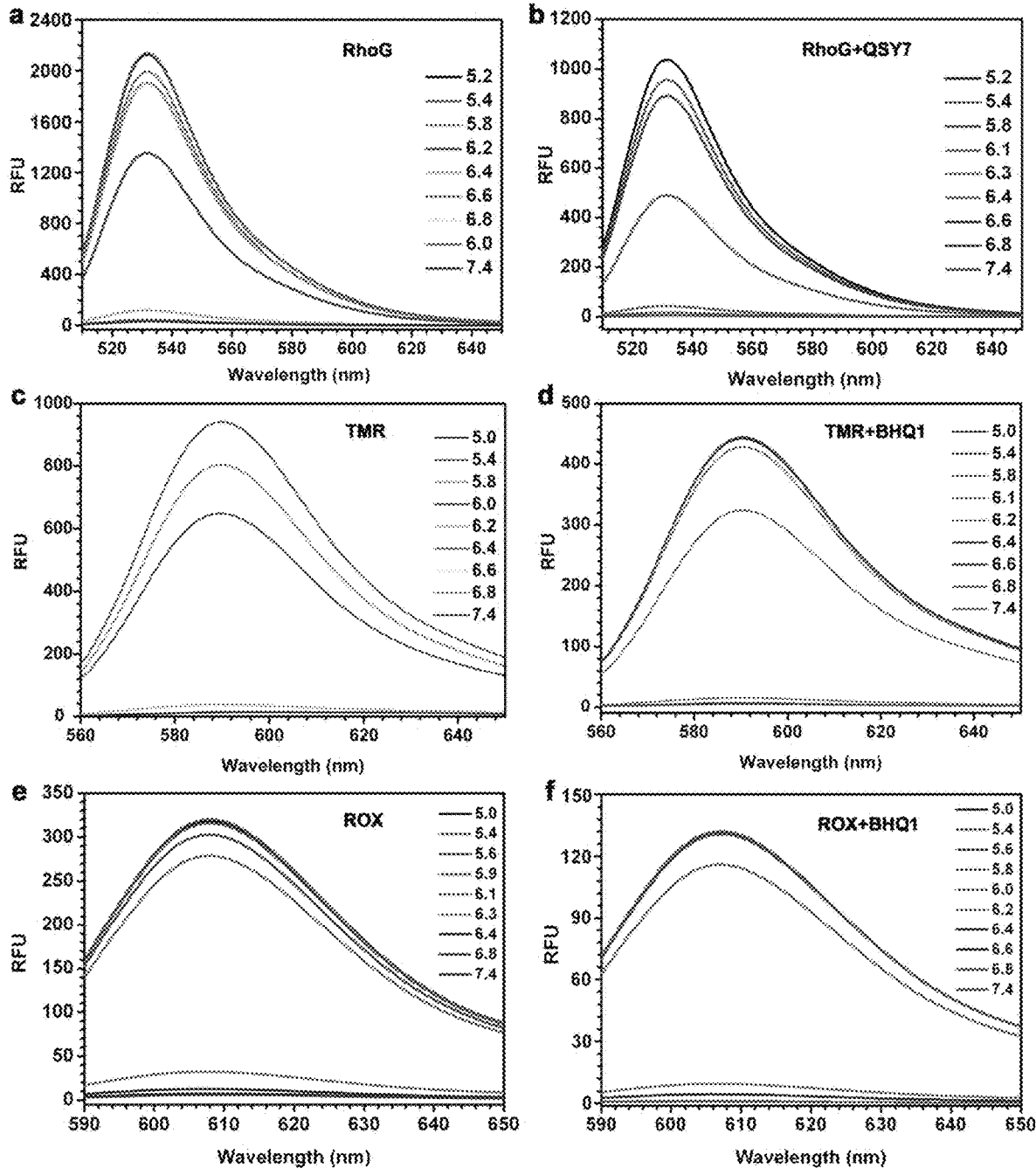
Figure 21:
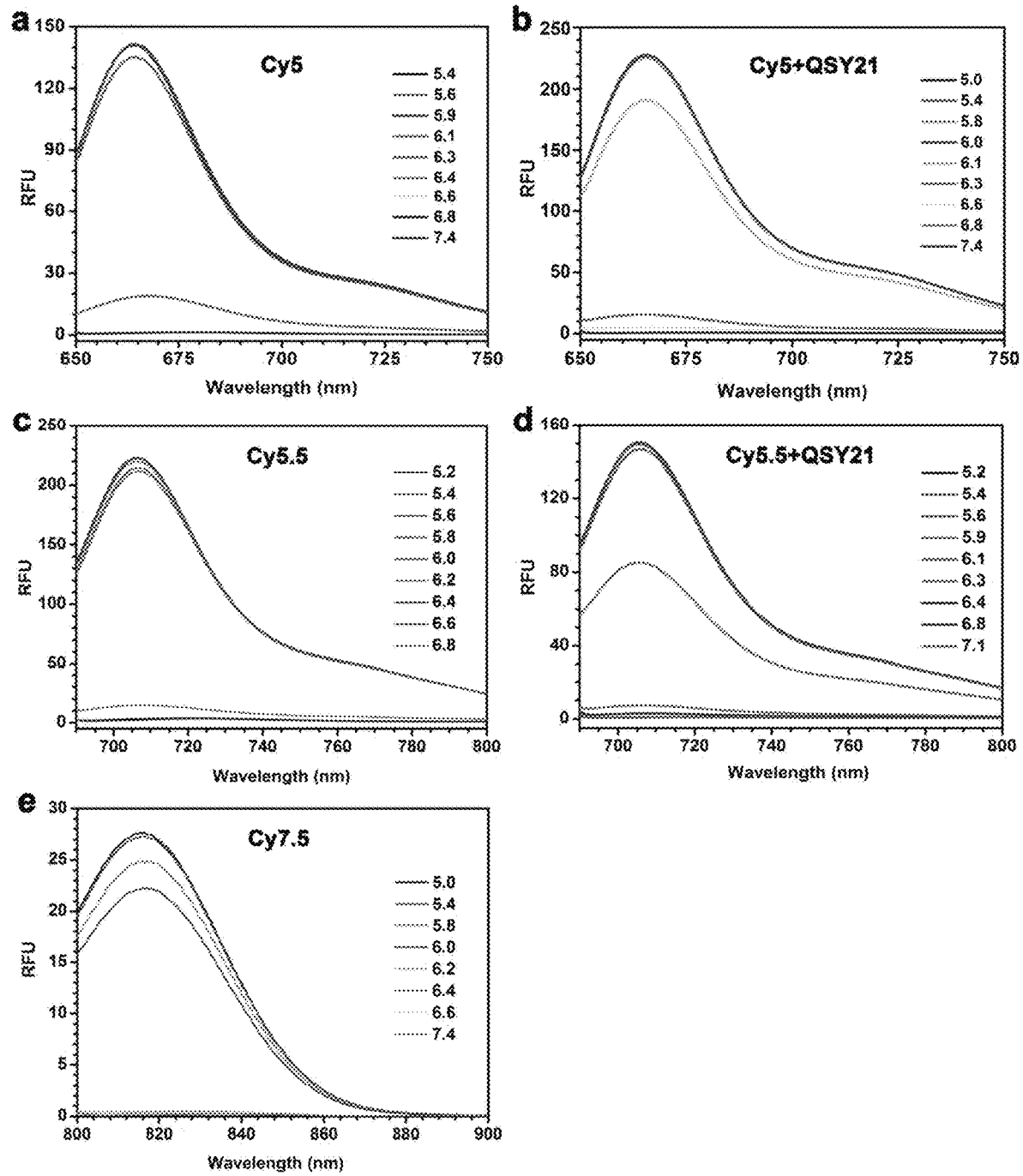
Figure 22:
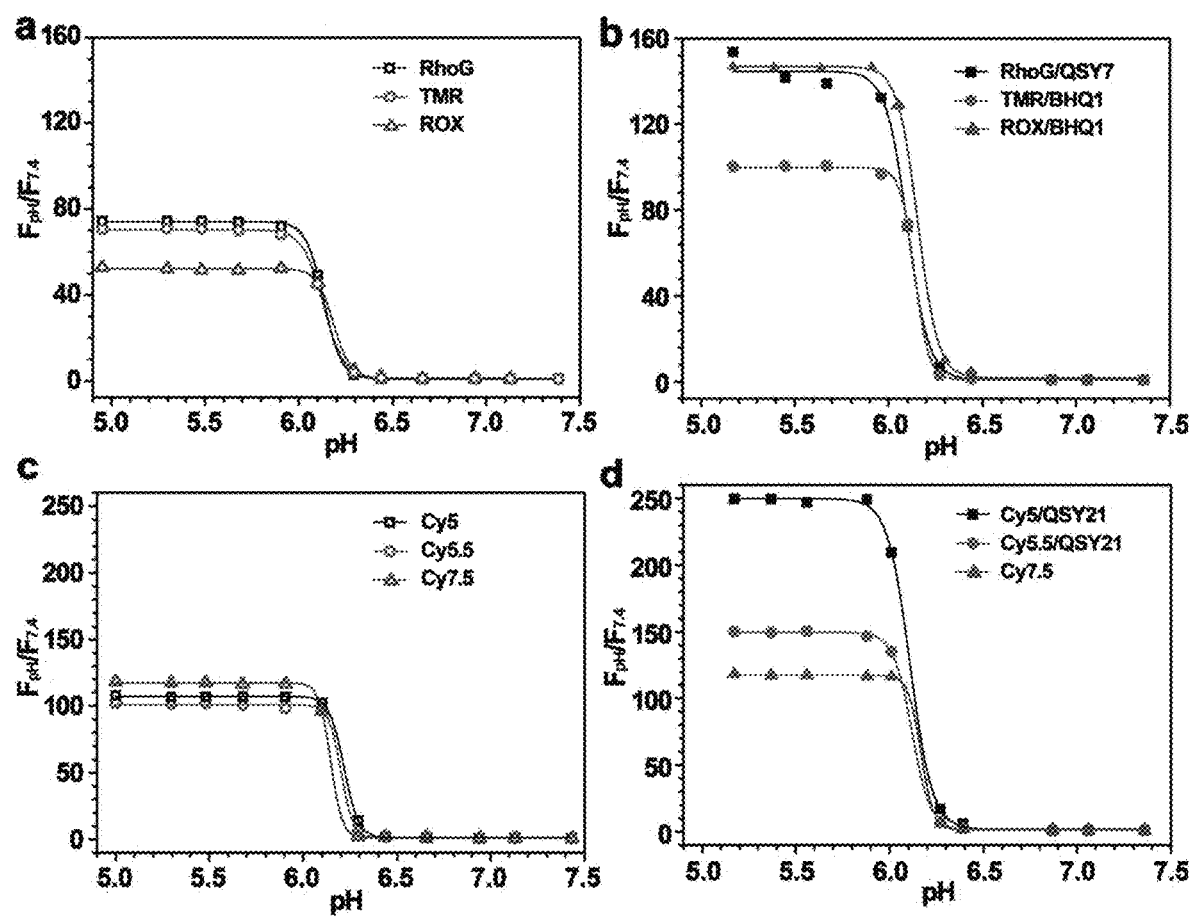

FIGS. 18A-F show the introduction of FQ-conjugated PDPA copolymer significantly increased the fluorescence activation ratio of different PDPA-dye nanoprobes. Fluorescence intensity ratio at different pH to pH 7.4 (F$_{pH}$/F$_{7.4}$) was plotted for copolymer alone (FIGS. 18A, 18C, and 18E) and with the addition of FQ-conjugated copolymers (FIGS. 18B, 18D, and 18F). The structures of the fluorophores and FQs were shown in FIGS. 14A-F.

FIGS. 19A-F show the pH-dependent fluorescence spectra of nanoprobes without (left column) or with (right column) fluorescence quenchers. BODIPY® family of fluorophores were presented in this study. The structures of the fluorophores and FQs were shown in FIGS. 14A-F.

FIGS. 20A-F show the pH-dependent fluorescence spectra of nanoprobes without (left column) or with (right column) fluorescence quenchers. Rhodamine family of fluorophores were presented in this study. The structures of the fluorophores and FQs were shown in FIGS. 14A-F.

FIGS. 21A-E show the pH-dependent fluorescence spectra of nanoprobes without (left column) or with (right column) fluorescence quenchers. Cyanine family of fluorophores were presented in this study. The structures of the fluorophores and FQs were shown in FIGS. 14A-F.

FIGS. 22A-D show the fluorescence intensity ratio at different pH to pH 7.4 ($F_{pH}/F_{7.4}$) was plotted for copolymer alone (FIG. 22A, 22C) and with the addition of FQ-conjugated copolymers (FIG. 22B, 22D) for rhodamine and cyanine families of dyes. The structures of the fluorophores and FQs were shown in FIGS. 14A-F.

Figure 23:
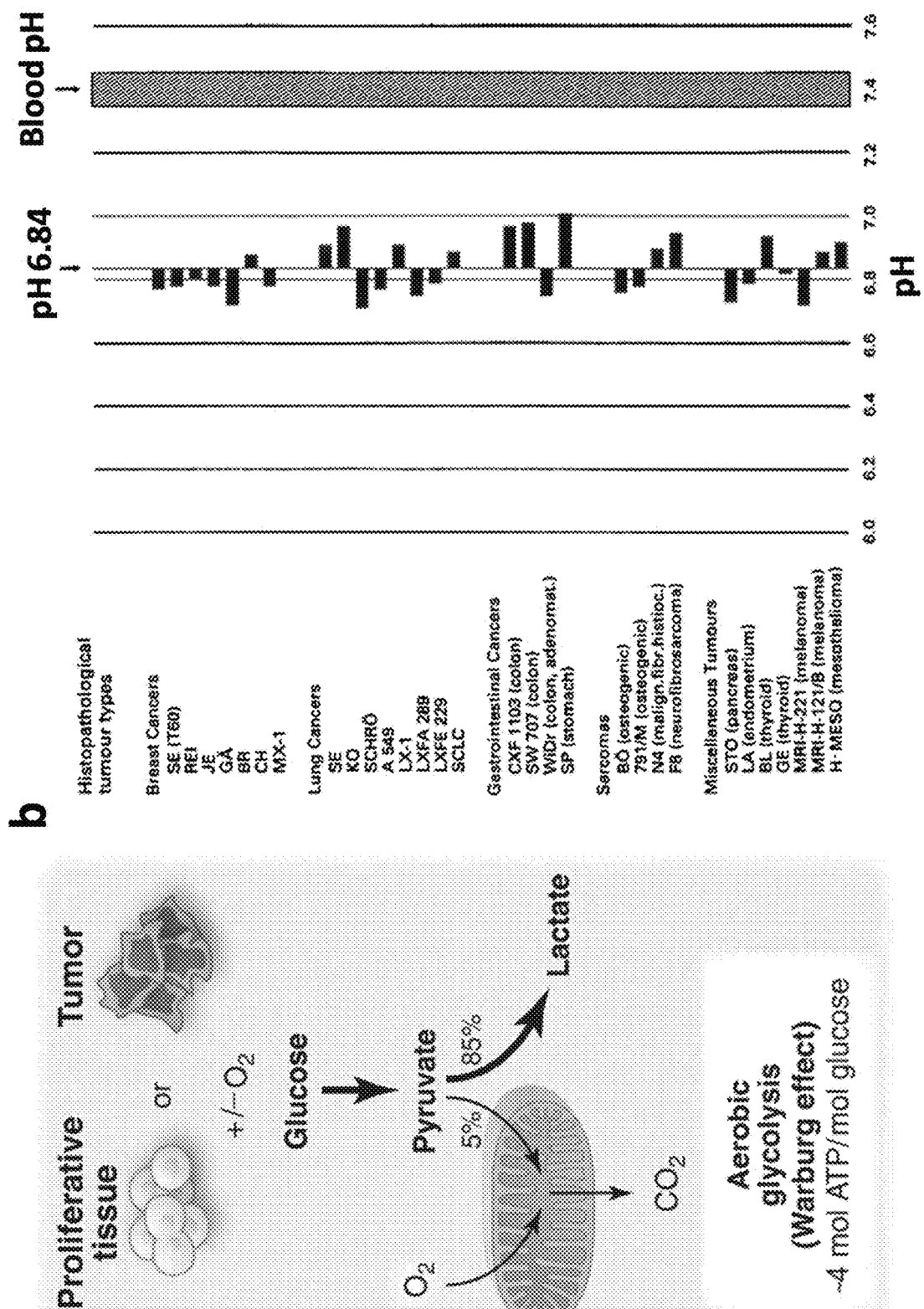

FIGS. 23A & B show Aerobic glycolysis and acidic extracellular pH ($pH_e$) in the tumor. (FIG. 23A) Cancer cells convert glucose mostly to lactate regardless of whether oxygen is present (Warburg effect). The figure is adapted from Heiden, et al., 2009. (FIG. 23B) Acidic $pH_e$ measured in 269 tumors from 30 different human cancer cell lines. The average $pH_e$=6.84 with variation range from 6.71-7.01, which is below the blood pH (7.4). The figure is adapted from Volk, et al., 1993.

Figure 24:
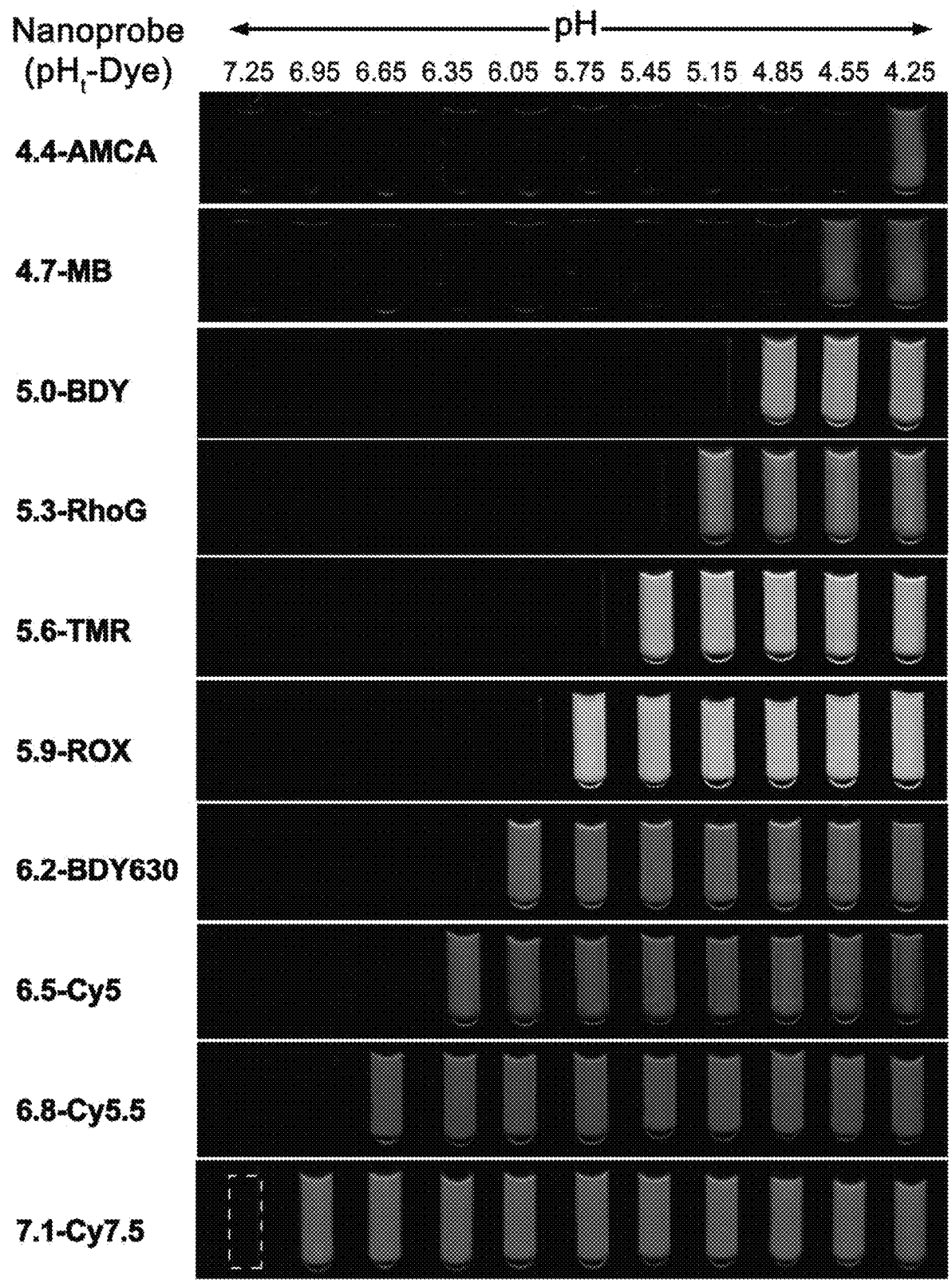

FIG. 24 shows an exemplary UPS library consisting of 10 nanoprobes spanning a wide pH range (4-7.4) and large fluorescent emissions (400-820 nm). Each nanoprobe is encoded by its transition pH and fluorophore. Images of 4.4-AMCA and 4.7-MB were taken by a camera at the excitation light of 365 nm. Images of the rest of the nanoprobe solutions were taken on a Maestro Imaging system.

Figure 25:
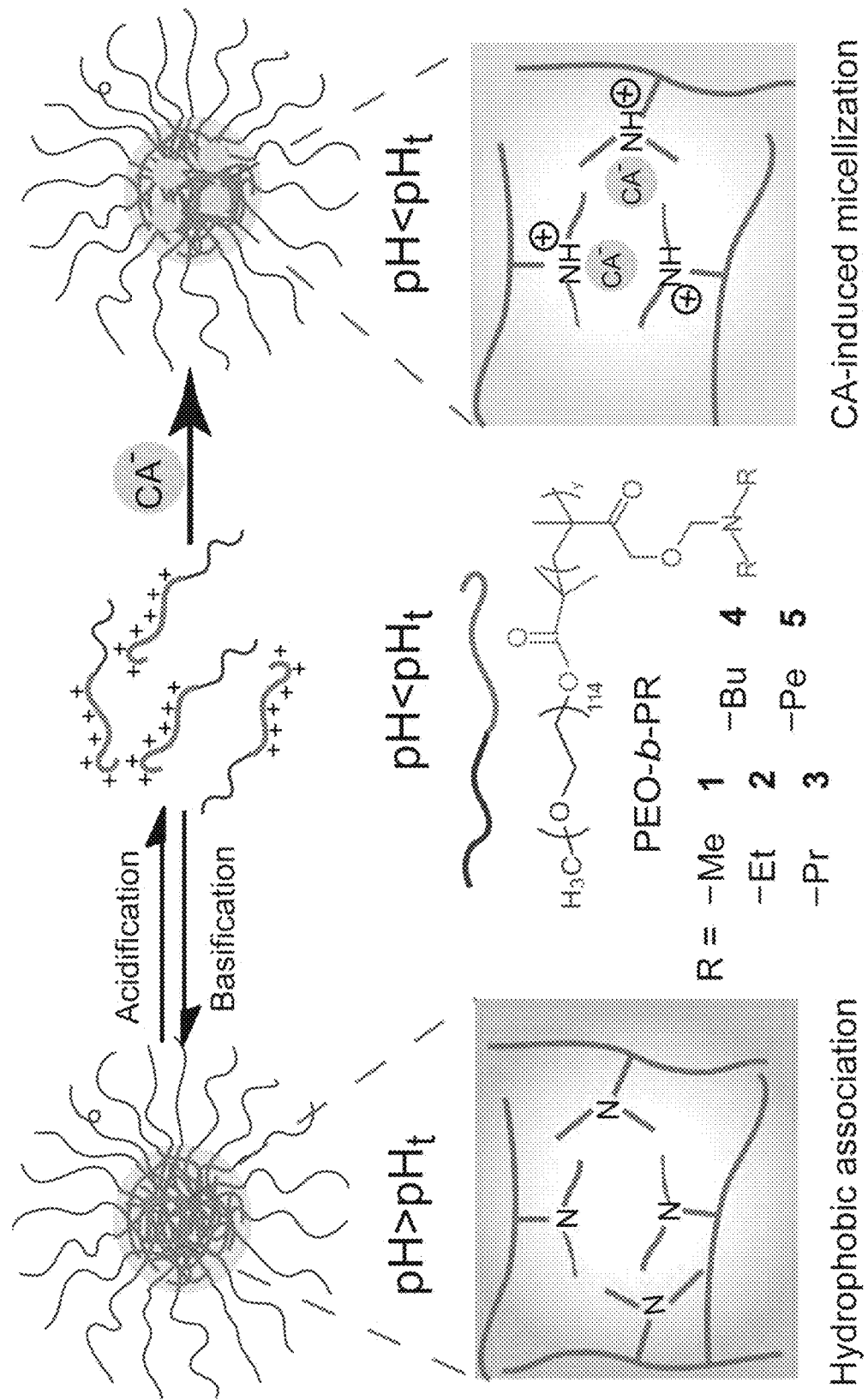

FIG. 25 shows the self-assembly of ionizable polymeric micelles by two independent mechanisms. The left panel shows the induction of micellization by pH increase, where the PR segments become neutralized and hydrophobic to drive micelle formation. Surprisingly, addition of chaotropic ions (CA, such as $ClO_4^-$) at low pH also leads to micellization with ammonium PR segments (right panel). Structures of a series of PEO-6-PR copolymers (1-5) with different hydrophobic side chains are shown in the inset.

Figure 26:
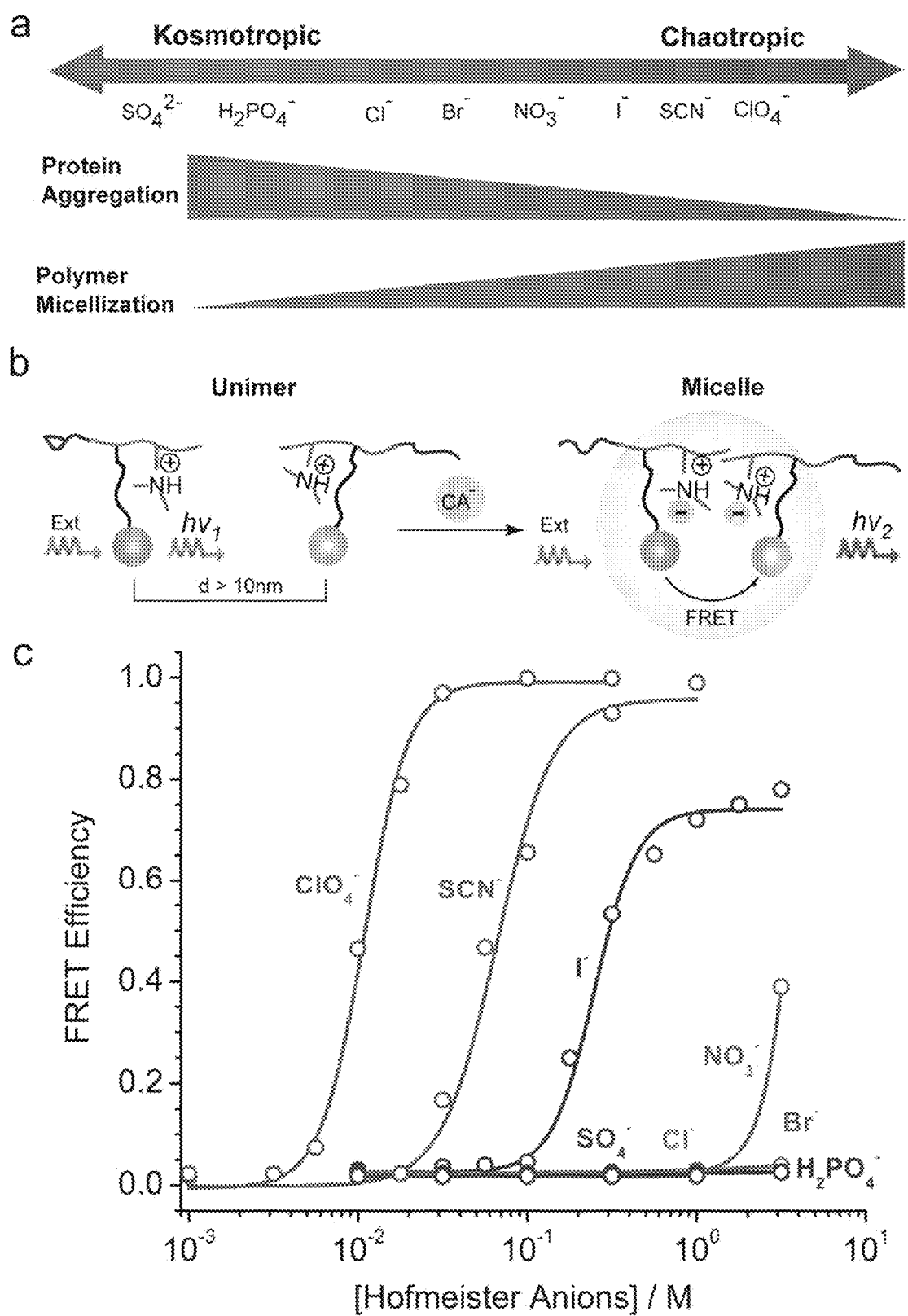

FIGS. 26A-C show (FIG. 26A) Chaotropic anions induce micelle self-assembly from PEO-6-PR copolymers with protonated PR segment, a reversed "salt-out" effect from their abilities to solubilize proteins (salt-in). (FIG. 26B) Illustration of FRET design to investigate CA-induced micelle self-assembly. Addition of CA results in micelle formation and efficient energy transfer from donor (TMR) to acceptor (Cy5) dyes. (FIG. 26C) Chaotropic anion-induced micelle self-assembly showing the anti-Hofmeister trend.

Figure 27:
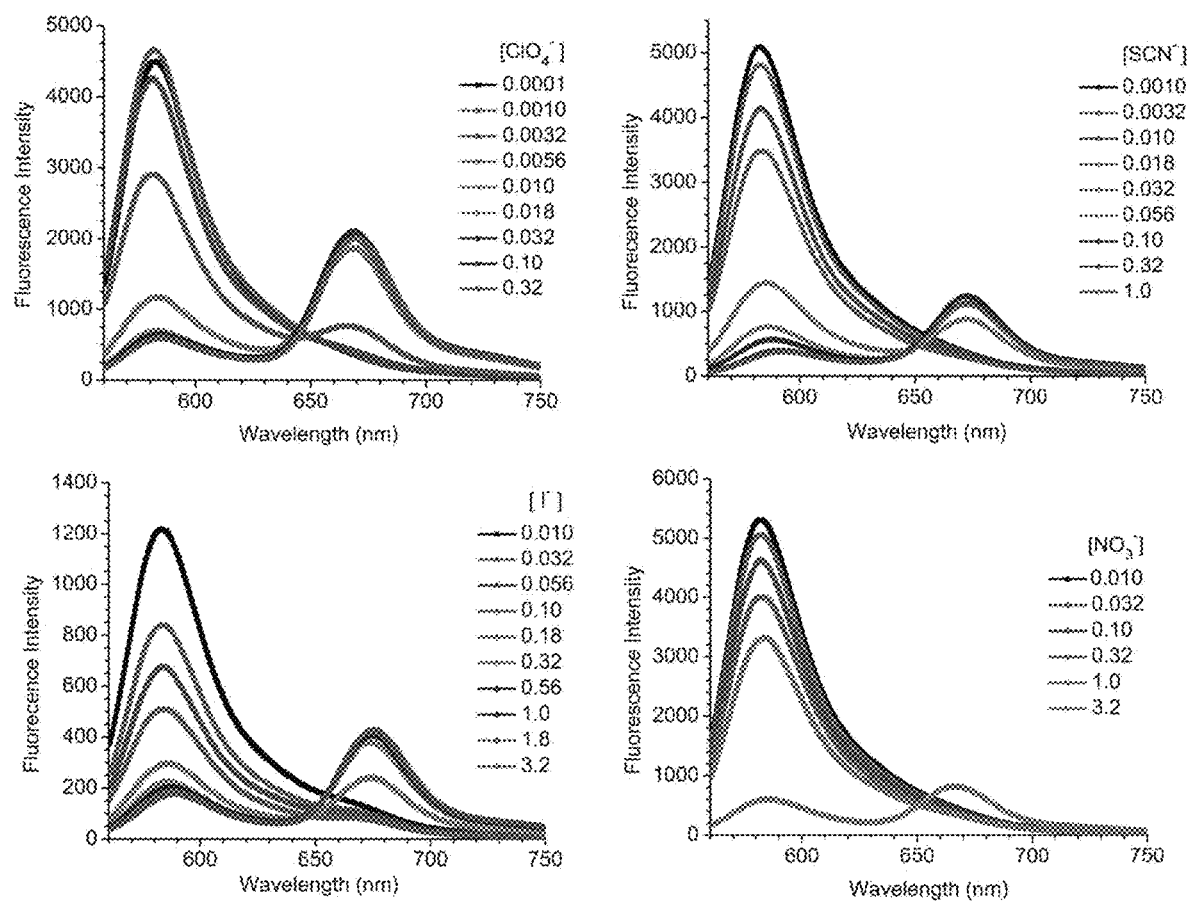

FIG. 27 shows the fluorescence spectra of FRET polymer pairs of PEO-b-P(DPA-r-TMR)/PEO-b-P(DPA-r-Cy5) at different concentrations of chaotropic anions. The samples were excited at $\lambda_{ex}$=545 nm and emission spectra were collected from 560-750 nm. All the experiments were conducted at pH=4, below the transition pH of PEO-6-PDPA ($pH_t$=6.1).

Figure 28:
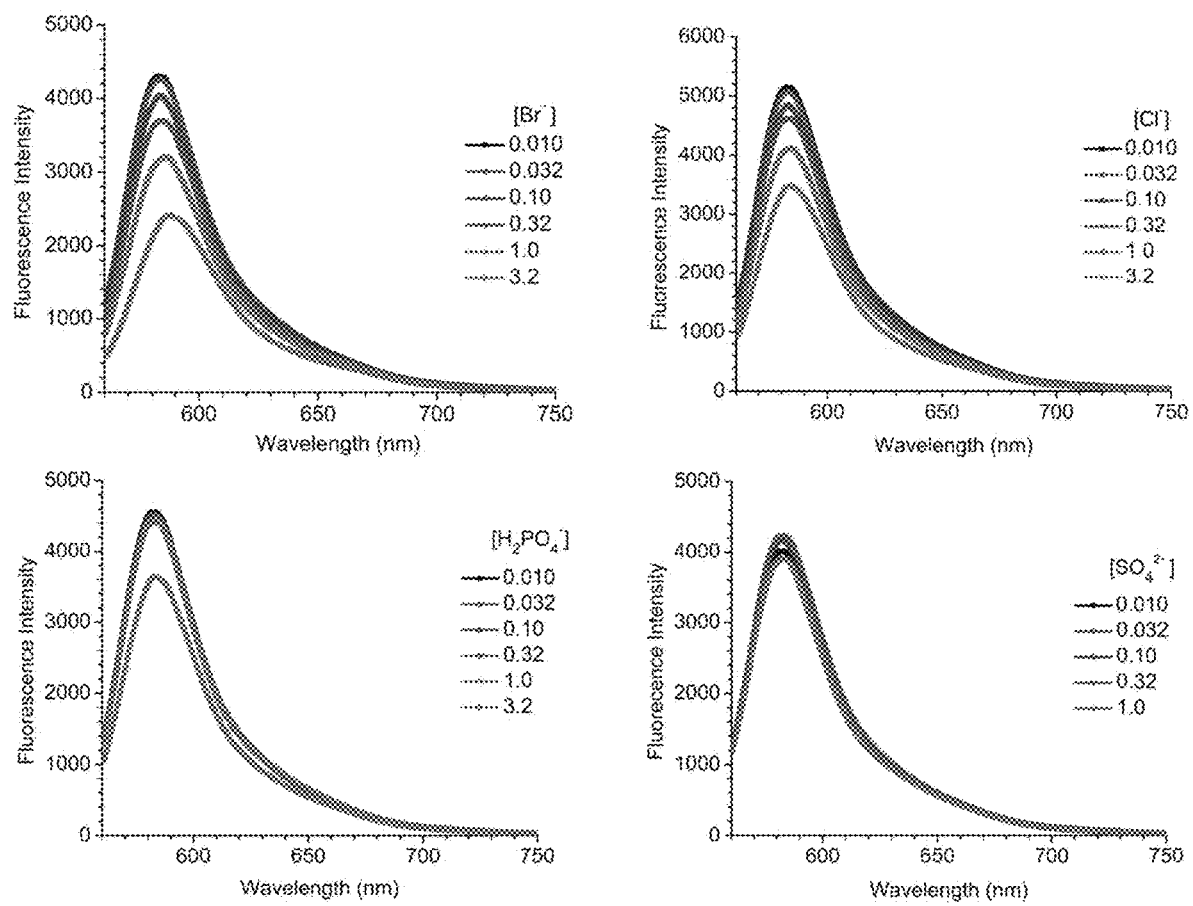

FIG. 28 shows the fluorescence spectra of FRET polymer pairs of PEO-b-P(DPA-r-TMR)/PEO-b-P(DPA-r-Cy5) at different concentrations of kosmotropic and borderline anions. The samples were excited at $\lambda_{ex}$=545 nm and emission spectra were collected from 560-750 nm. All the experiments were conducted at pH=4, below the transition pH of PEO-6-PDPA ($pH_t$=6.1).

FIGS. 29A & B show TEM and DLS analyses of micelle transition of copolymer 3 in the presence of Cl⁻ (FIG. 29A) and $ClO_4^-$ anions (FIG. 29B). Concentrations of both anions were controlled at 50 mM (pH=5.0). The scale bars are 100 nm in the TEM images.

FIGS. 30A & B show (FIG. 30A) TEM and (FIG. 30B) DLS analyses of micelle morphology and hydrodynamic diameter of copolymer 3 micelles in the presence of Cl⁻ (50 mM) at pH 7.4. The scale bar is 100 nm in the TEM image.

FIGS. 31A & B show (FIG. 31A) TEM and (FIG. 31B) DLS analyses of micelle morphology and hydrodynamic diameter of copolymer 3 micelles in the presence of $ClO_4^-$ (50 mM) at pH 7.4. The scale bar is 100 nm in the TEM image.

FIGS. 32A & B show (FIG. 32A) TEM and (FIG. 32B) DLS analyses of micelle morphology and hydrodynamic diameters of PEO-6-PLA copolymer in the presence of $ClO_4^-$ (50 mM) at pH 7.4 and 5.0. The scale bars are 100 nm in the TEM images.

Figure 33:
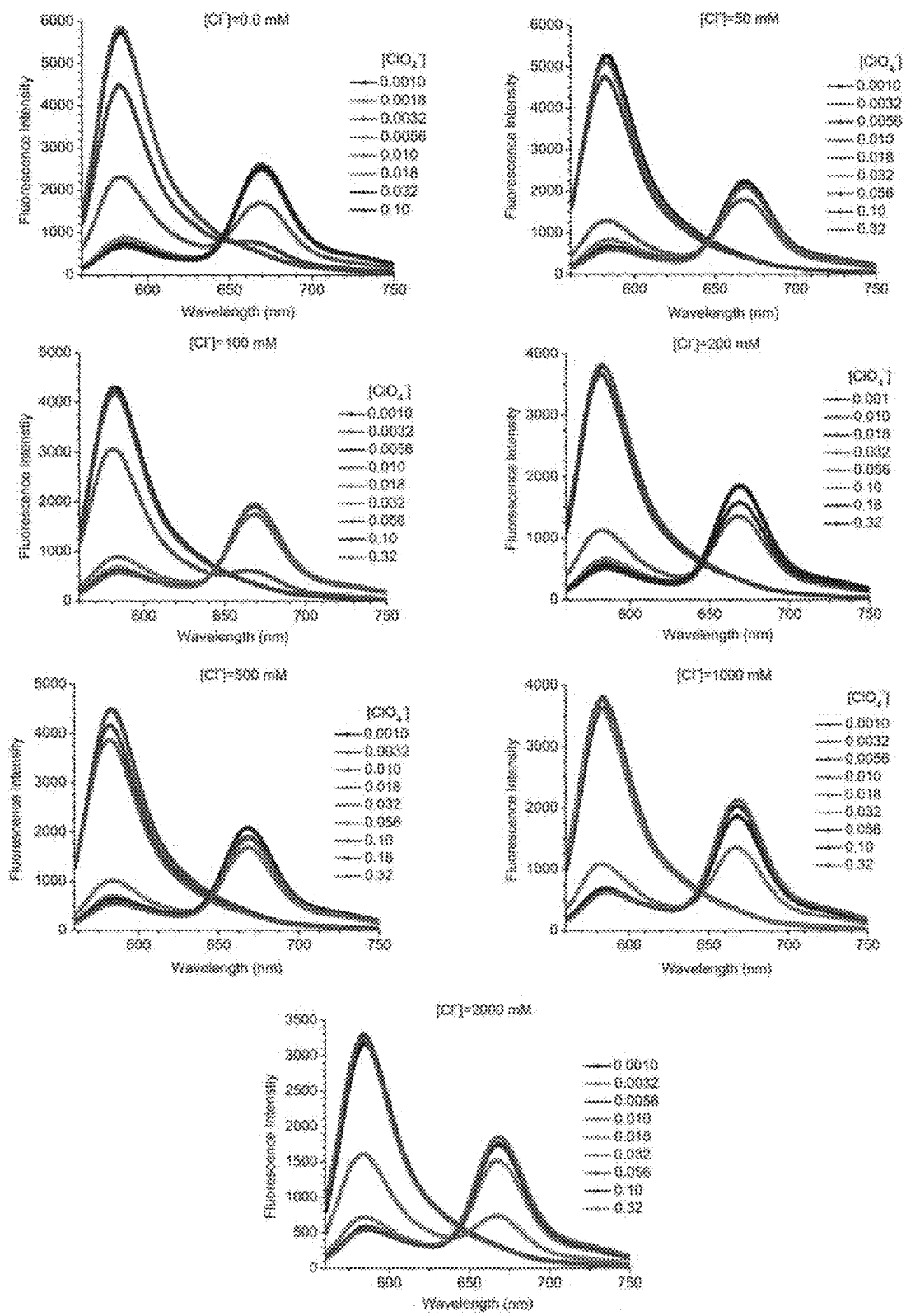

FIG. 33 shows the fluorescence spectra of FRET polymer pairs of PEO-b-P(DPA-r-TMR)/PEO-b-P(DPA-r-Cy5) at different initial concentration of Cl⁻ (0-2,000 mM). Different concentrations of $ClO_4^-$ (in M) anions were added to induce micelle formation. The samples were excited at $\lambda_{ex}$=545 nm and emission spectra were collected from 560-750 nm. All the experiments were conducted at pH=4, below the transition pH of PEO-6-PDPA ($pH_t$=6.1).

Figure 34:
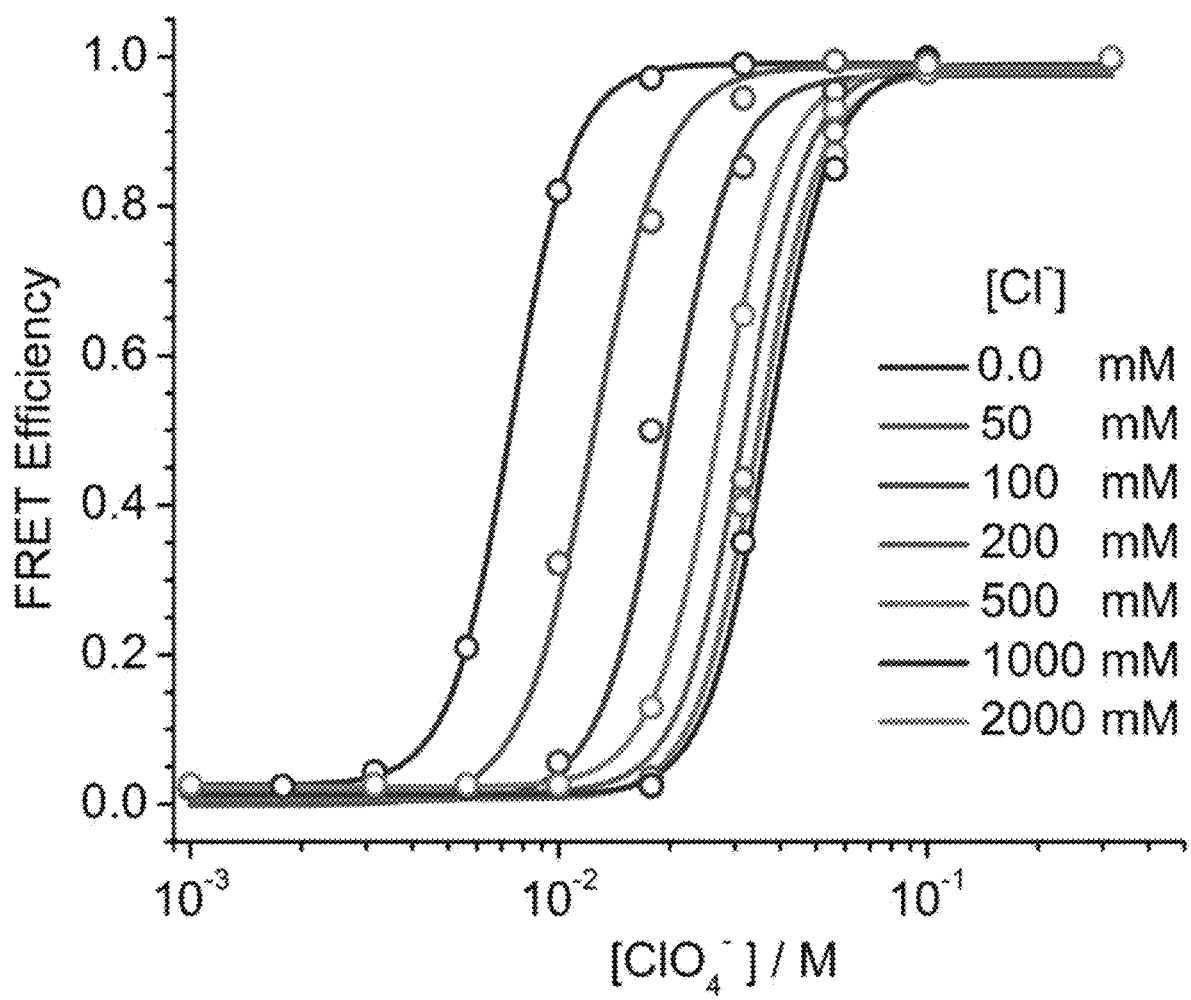

FIG. 34 shows the FRET transfer efficiency as a function of $ClO_4^-$ concentration at different competing Cl⁻ concentrations (0-2,000 mM).

Figure 35:
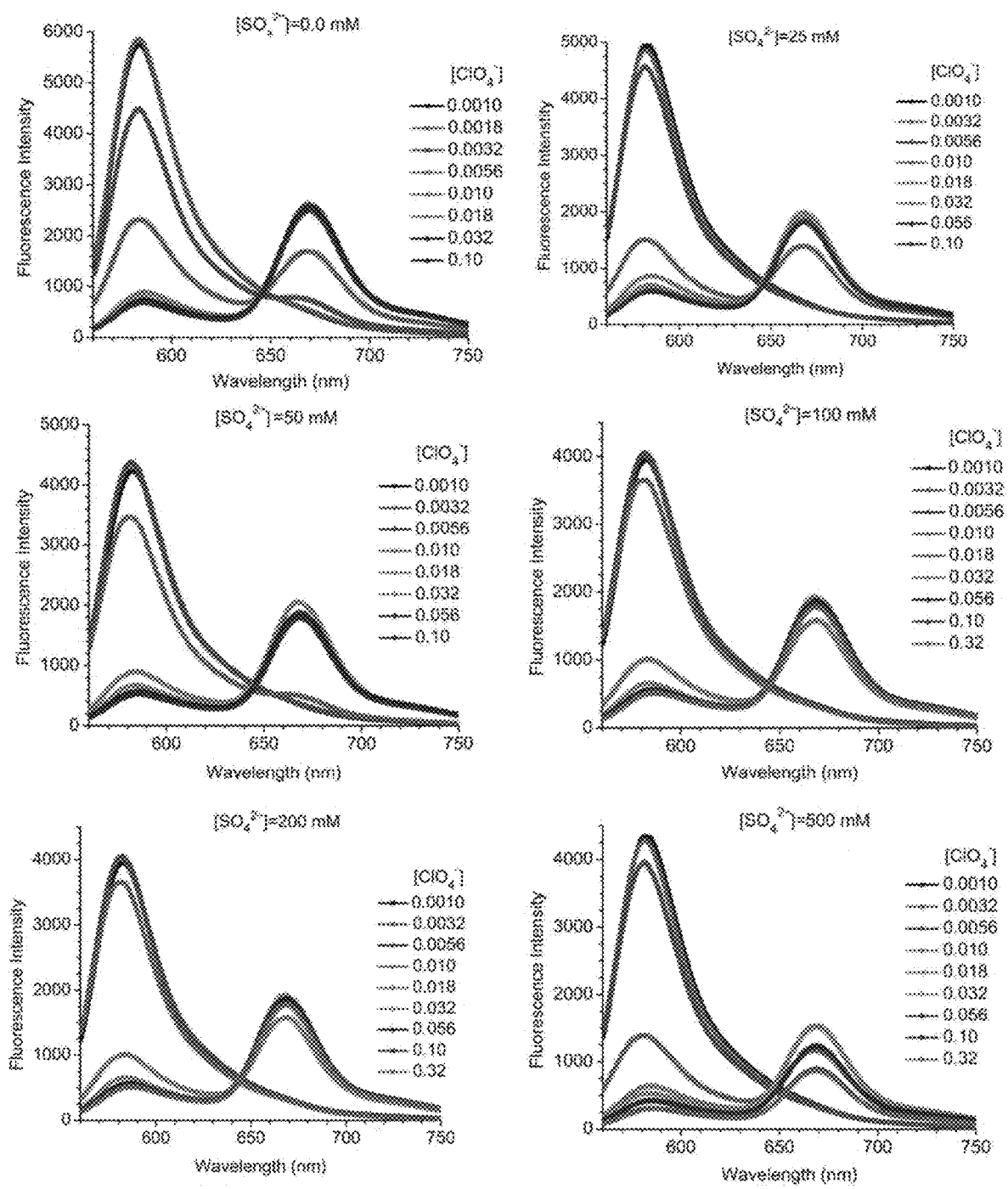

FIG. 35 shows the fluorescence spectra of FRET polymer pairs of PEO-b-P(DPA-r-TMR)/PEO-b-P(DPA-r-Cy5) at different initial concentration of $SO_4^{2-}$ (0-500 mM). Different concentrations of $ClO_4^-$ (in M) anions were added to induce micelle formation. The samples were excited at $\lambda_{ex}$=545 nm and emission spectra were collected from 560-750 nm. All the experiments were conducted at pH=4, below the transition pH of PEO-6-PDPA ($pH_t$=6.1).

Figure 36:
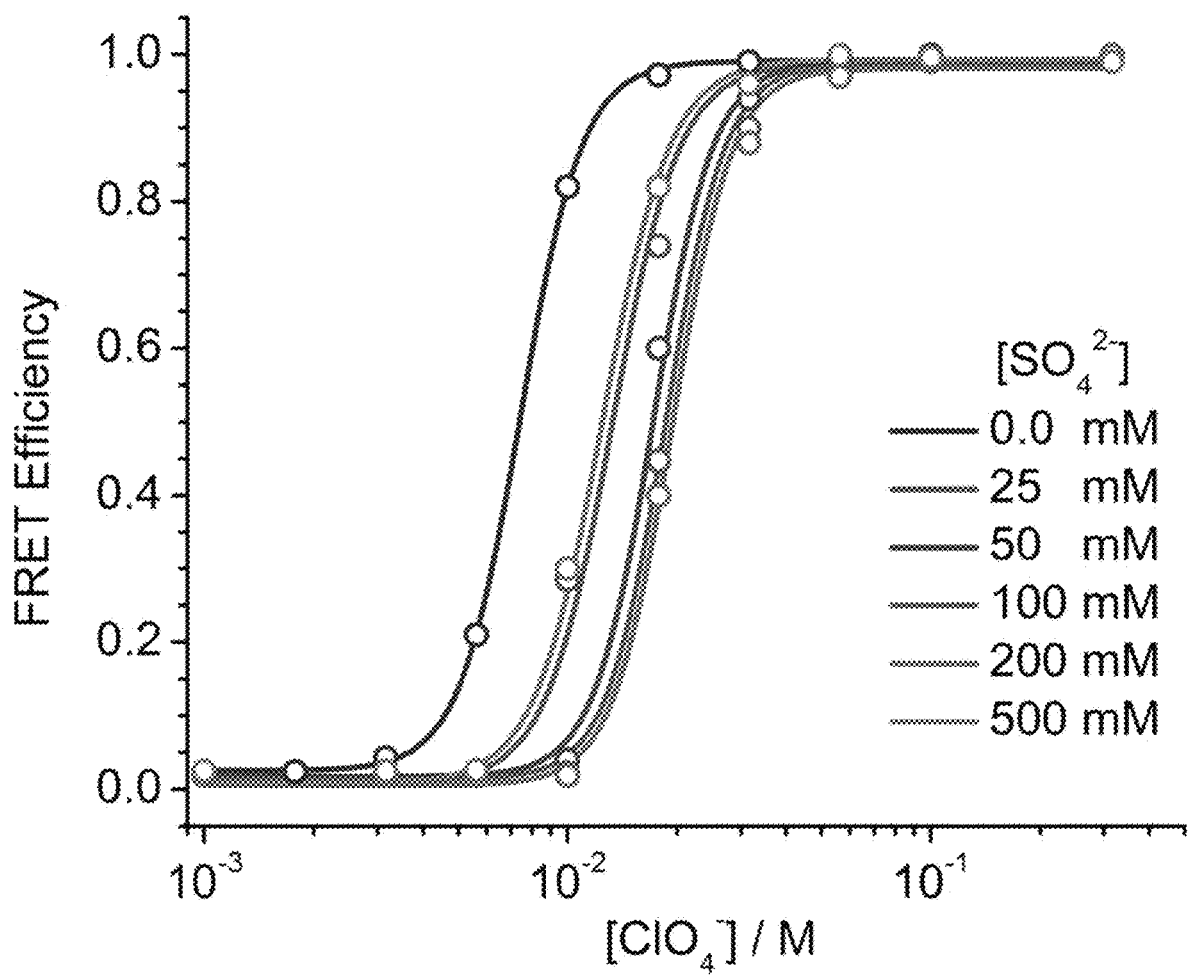

FIG. 36 shows the FRET transfer efficiency as a function of $ClO_4^-$ concentration at different competing $SO_4^{2-}$ concentrations (0-500 mM).

FIGS. 37A & B show (FIG. 37A) $ClO_4^-$-induced self-assembly of copolymer 3 in the presence of different concentrations of competing $SO_4^{2-}$ anions. (FIG. 37B) The FRET efficiency ($FC_{50}$) from $ClO_4^-$-induced self-assembly as a function of ionic strength of competing Cl⁻ and $SO_4^{2-}$ anions. The solution pH was controlled at 4 in these studies.

FIGS. 38A & B show (FIG. 38A) hydrophobic strength of PR segment affects the ability of $ClO_4^-$ in micelle induction. More hydrophobic PR segment (e.g., pentyl groups in 5) increases the $ClO_4^-$ sensitivity to induce micelle formation. (FIG. 38B) An empirical model depicting two important contributing factors (hydrophobic alkyl chain length and chaotropic anions) on the self-assembly of ionic polymeric micelles.

Figure 39:
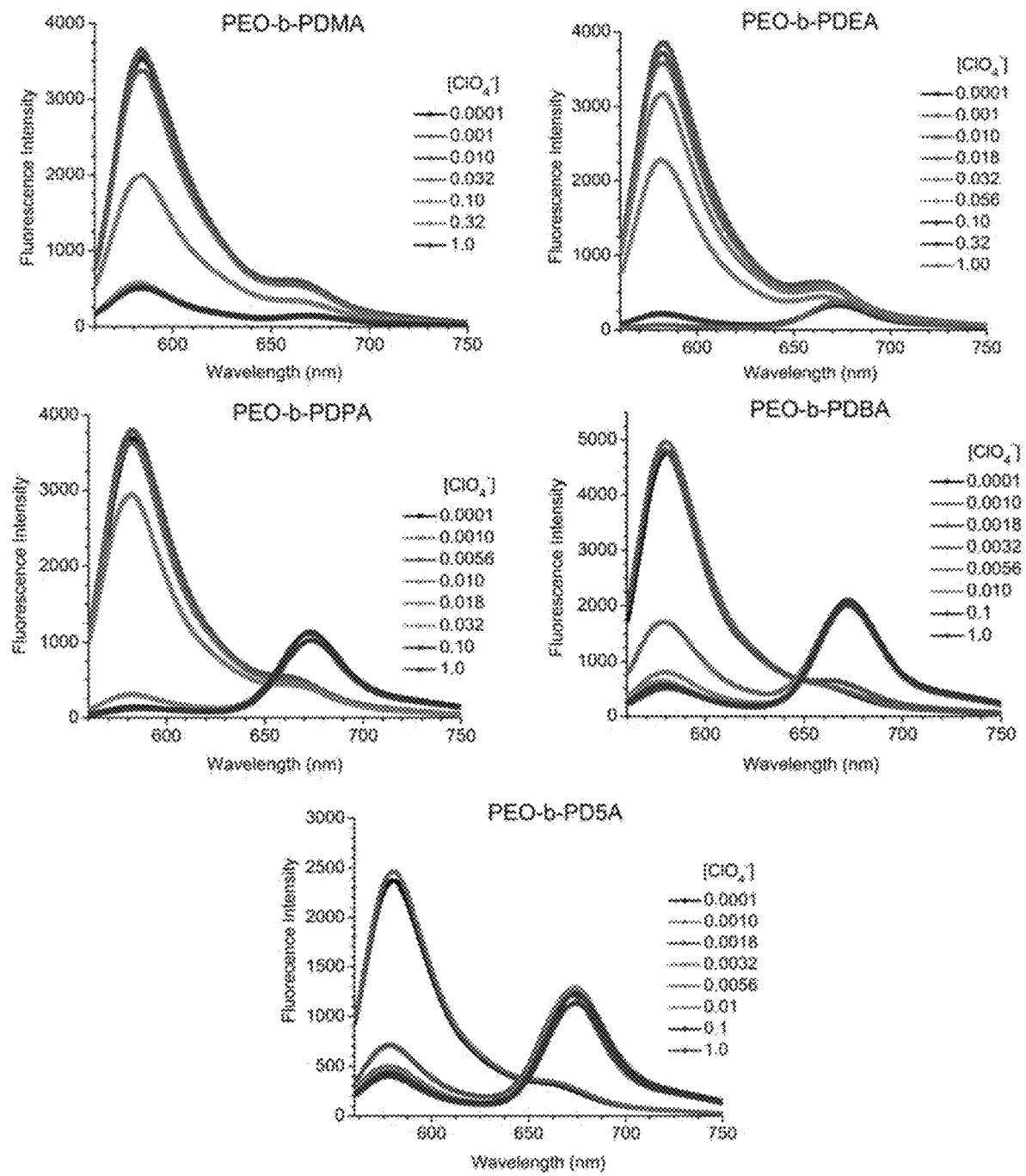

FIG. 39 shows the fluorescence spectra of FRET polymer pairs of PEO-b-P(R-r-TMR)/PEO-b-P(R-r-Cy5) of different hydrophobic strengths (PR segments were varied from methyl to pentyl side chains). Different concentrations of $ClO_4^-$ (in M) anions were added to induce micelle formation. The samples were excited at $\lambda_{ex}$=545 nm and emission spectra were collected from 560-750 nm. All the experiments were conducted at pH=4, which was below the transition pH of PEO-6-PDPA ($pH_t$=6.1).

FIGS. 40A-C show the $UPS_{6.9}$ nanoprobe with exquisitely sharp pH transition at 6.9. (FIG. 40A) Structure of the ionizable block copolymer and its pH-dependent fluorescence emission properties. At high pH (i.e., 7.4 or 7.2), UPS stays silent. At pH below 6.9, UPS is activated as a result of micelle dissociation. The pH response is much sharper than a hypothetical small molecular pH sensor (blue dashed line). (FIG. 40B) Fluorescent images of $UPS_{6.9}$ solution in different pH buffers. (FIG. 40C) Transmission electron micrographs of $UPS_{6.9}$ in the micelle and unimer states at pH 7.4 and 6.7, respectively (polymer concentration=1 mg/mL, scale bar=100 nm).

FIGS. 41A & 41B show the PK/BD of two UPS nanoprobes with comparable size but different pH transitions (pH$_t$=6.3 and 6.9).

FIGS. 42A & 42B show (FIG. 42A) NIR image of a representative sentinel lymph node on the side of the neck after removal of primary HNSCC tumors. (FIG. 42B) Histology (H&E) was able to validate the nodal structures. The selected node showed presence of HN5 cells (black arrows) in the cortex region of the node.

Figures 1, 43E:
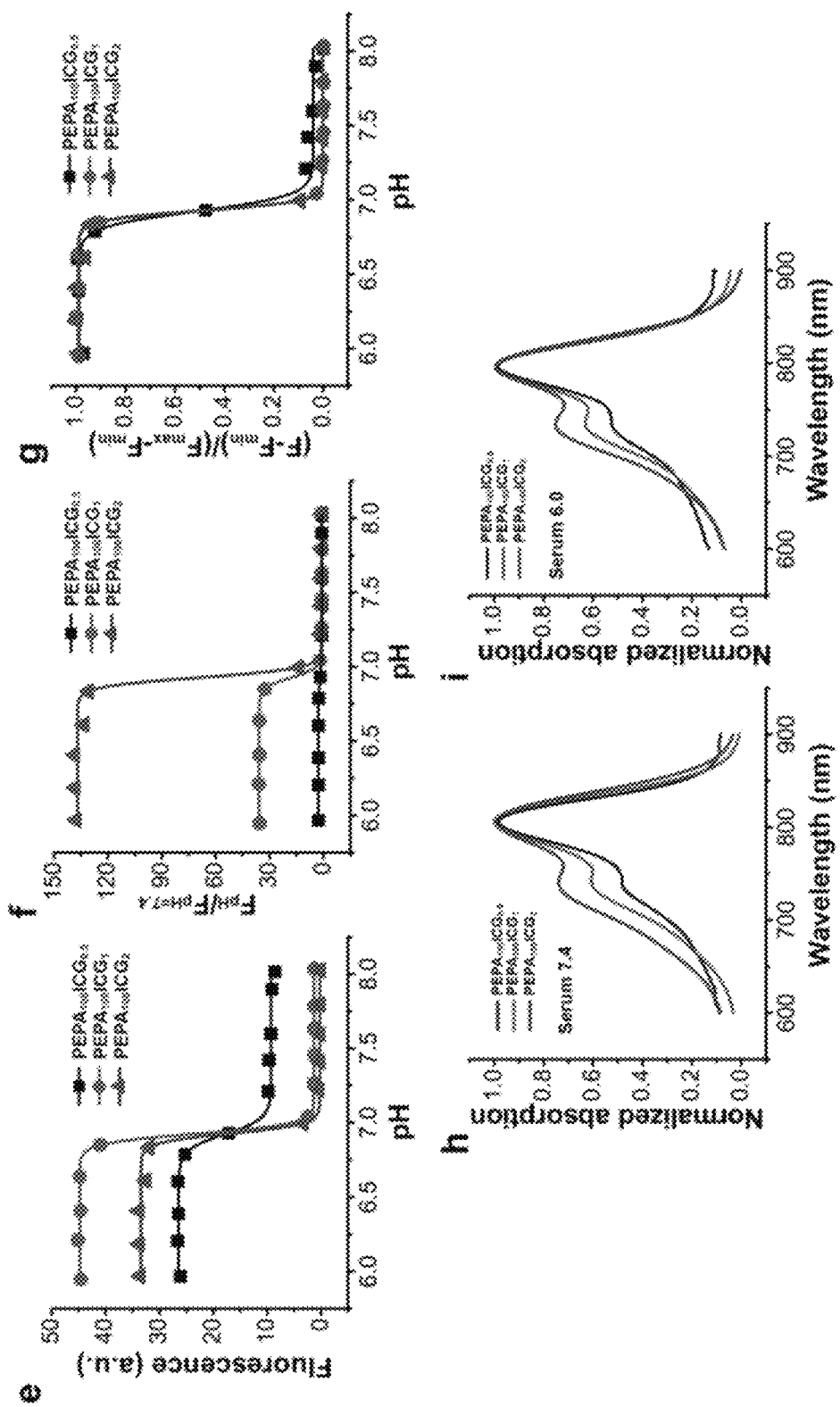

FIGS. 43A-43I show the syntheses and optimization of PINS nanoprobes. FIG. 43A Schematic syntheses of ICG-conjugated PEG-b-P (EPA$_x$-r-ICG$_y$) block copolymers. FIGS. 43B-43D Investigation of the influence of the PEPA segment length on the pH-dependent fluorescence properties: (FIG. 43B) fluorescence intensity, (FIG. 43C) fluorescence activation ratio at pH of interest over 7.4, and (FIG. 43D) normalized fluorescence intensity. The PEPA segment length was varied (x=40, 60, 80, 100, 120) while the number of ICG per polymer chain was maintained at 1. FIGS. 43E-G: Investigation of the influence of ICG conjugation number on the pH-dependent fluorescence properties: (FIG. 43E) fluorescence intensity, (FIG. 43F) fluorescence activation ratio at pH of interest over 7.4, and (FIG. 43G) normalized fluorescence intensity. The number of ICG per polymer chain was varied (y=0.5, 1, 2) while the PEPA segment length was controlled at 100. FIGS. 43H & 43I: UV-Vis absorption spectra with normalization to the monomer peak intensity ($\lambda$=808 nm) of PEPA$_{100}$-ICG$_y$ (n=0.5, 1, 2) in (FIG. 43H) human serum at pH 7.4 and (FIG. 43I) human serum at pH 6.0. Based on these data, PEG-b-P (EPA$_{100}$-r-ICG$_1$) was chosen as the optimal composition for animal imaging studies.

FIGS. 44A-44F show characterization of PINS. FIG. 44A A 3D plot of fluorescence intensity as a function of PINS concentration and pH. FIG. 44B Near IR images of PINS solution by SPY Elite® surgical camera showing pH-sensitive off/on activation. FIG. 44C Transmission electron micrographs of PINS in the micelle and unimer states at pH 7.4 and 6.5, respectively. Polymer concentration=1 mg/mL; scale bars=100 nm. PINS fluorescence intensity at pH 6.5 (black bars) and 7.4 (white bars) in PBS (FIG. 44D) or 50% human serum (FIG. 44E) upon storage. FIG. 44F Number-weighted hydrodynamic radius of PINS nanoprobes upon storage. Storage condition for (FIG. 44D)-(FIG. 44F): 10% w/v sucrose solution at −20° C. These results show PINS was stable in storage over 6 months in 10% w/v sucrose solution at −20° C.

Figure 1:
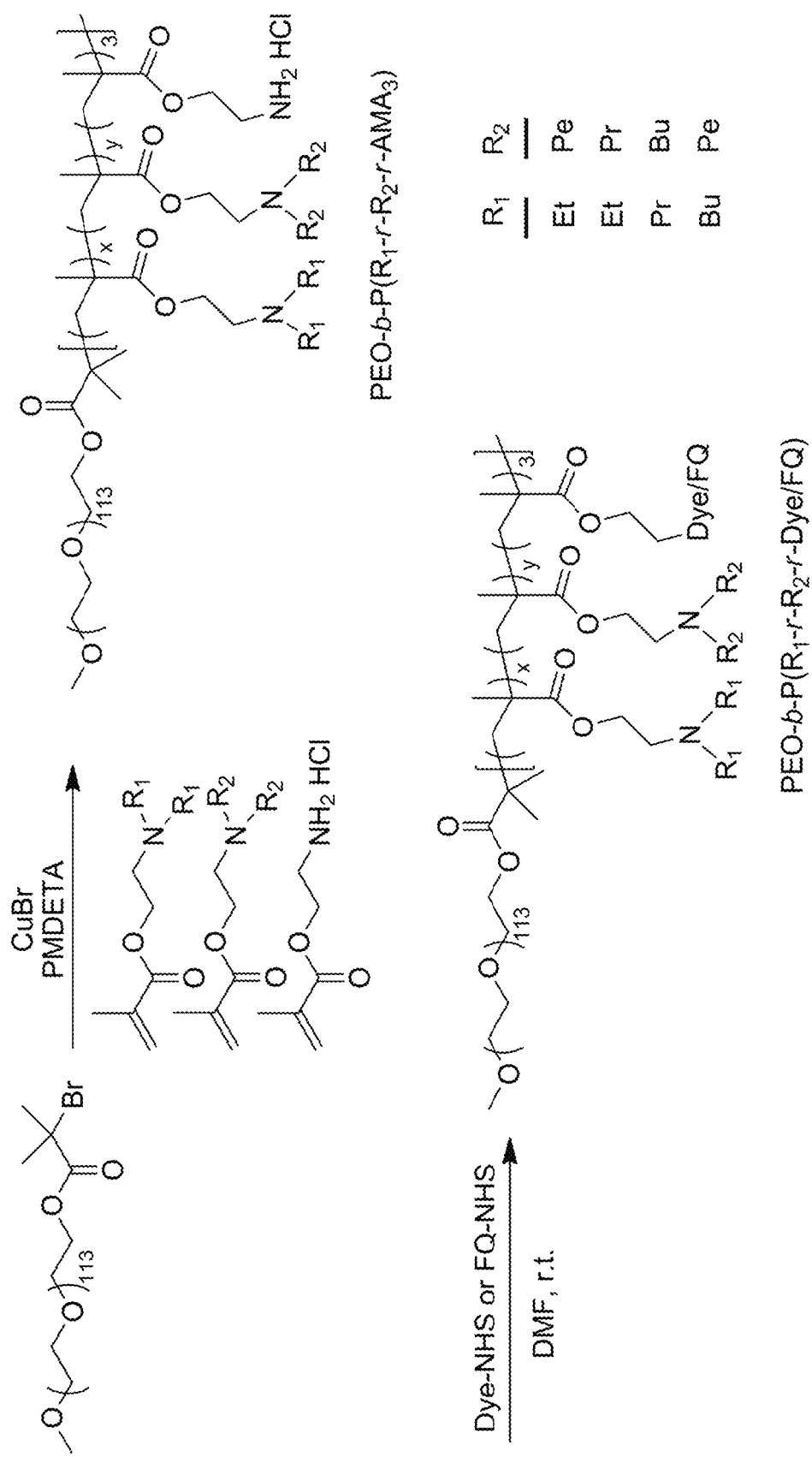
FIG. 1 shows the syntheses of dye- or fluorescence quencher (FQ)-conjugated PEO-b-P(R$_1$-r-R$_2$) copolymers. The hydrophobicity of the PR segment can be continuously controlled by varying the molar fractions of the two monomers (R$_1$ or R$_2$: Et, ethyl; Pr, propyl; Bu, butyl; Pe, pentyl).
Figure 2:
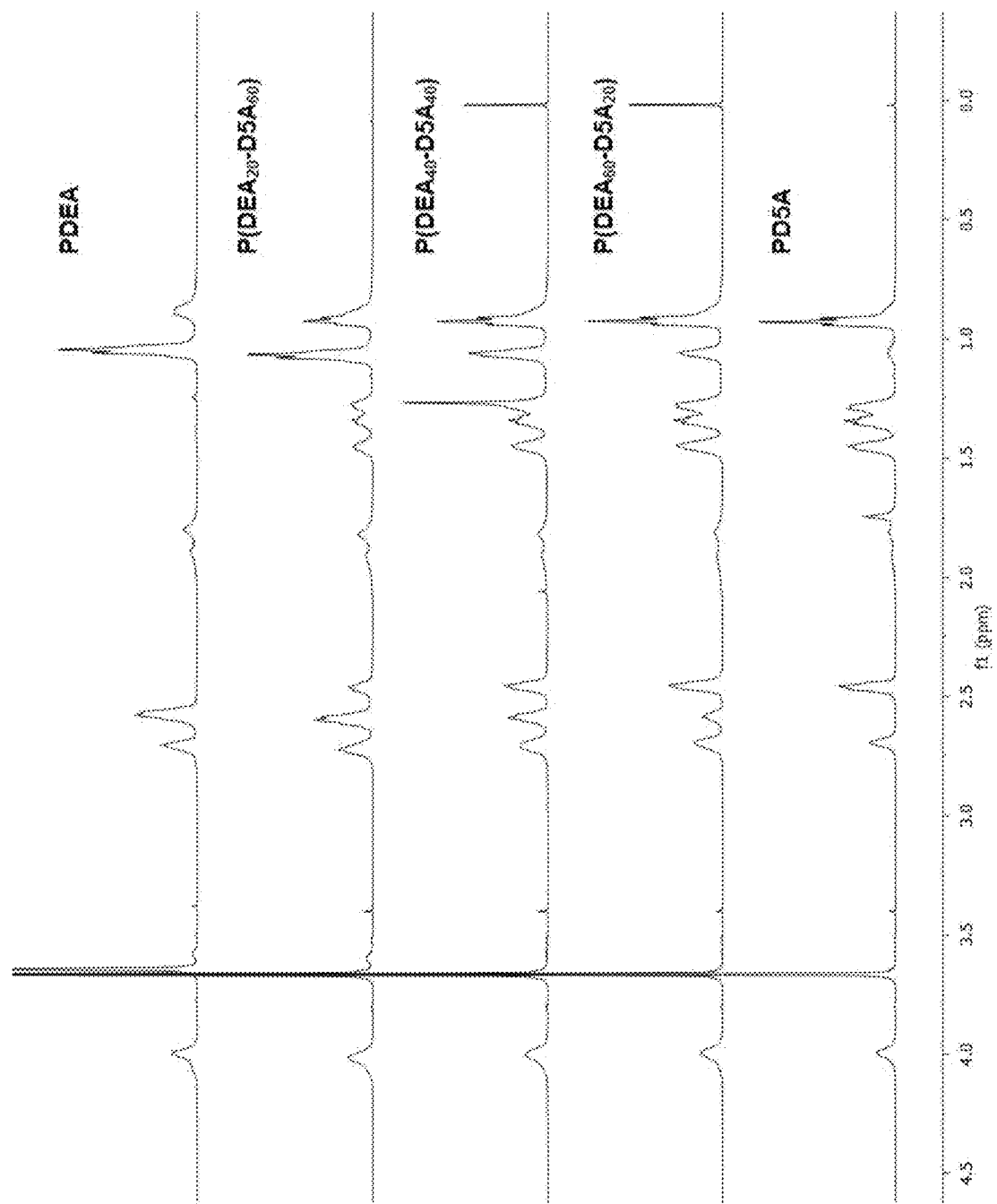
FIG. 2 shows the NMR spectra of PEO-P(DEA$_x$-D5A$_y$) (x+y=80) copolymers at different monomer (DEA and D5A)
Figure 45C:
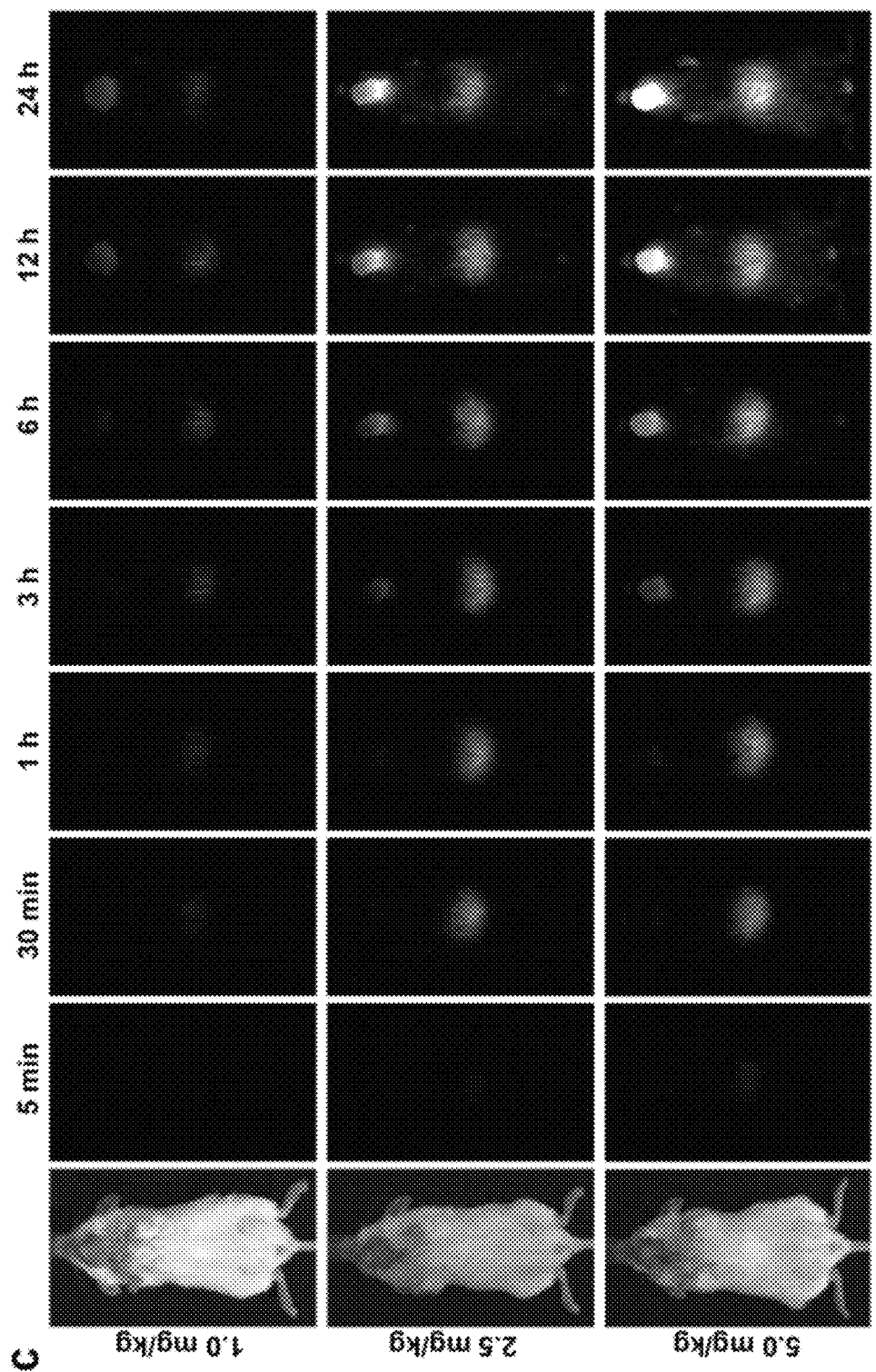

FIGS. 45A-45E show the dose-response of PINS in mice bearing human HN5 orthotopic tumors. White light (FIG. 45A) and near IR (FIG. 45B) images of mice injected with different doses of PINS (1.0, 2.5 and 5.0 mg/kg) via the tail veins. HN5 tumor intensity increased with increasing PINS dose. Free ICG control at an equivalent dye dose to 2.5 mg/kg PINS did not show observable tumor contrast. FIG. 45C: NIR images of representative mice injected with different doses of PINS at selected time points. Quantification of tumor fluorescence intensity (FIG. 45D) and tumor contrast over noise ratio (FIG. 45E) as a function of time after intravenous injection (n=3). Higher PINS dose at 5.0 mg/kg led to reduced CNR value due to the higher background signal in muscle tissue. Based on results from FIG. 45E, 2.5 mg/kg was chosen as the optimal PINS dose for tumor acidosis imaging.

Figures 46A, 46B:
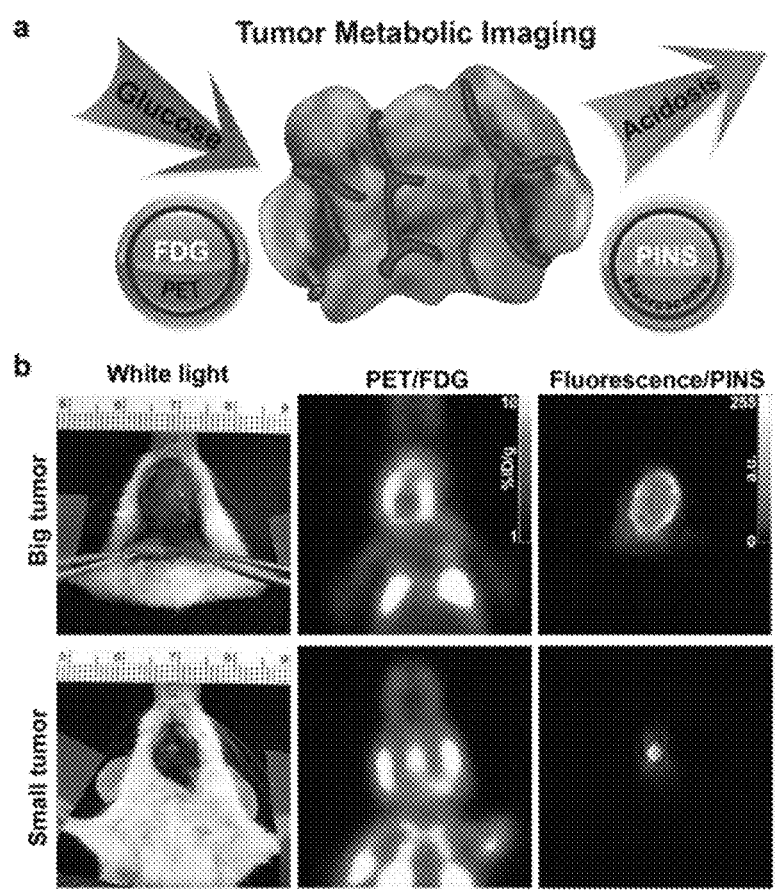

FIGS. 46A & 46B show tumor acidosis imaging by PINS. FIG. 46A Schematic of tumor metabolic imaging by PET with FDG or NIR fluorescence imaging with PINS. FIG. 46B Comparison of FDG-PET with PINS imaging in SCID mice bearing large or small HN5 orthotopic tumors. PINS imaging showed dramatically improved sensitivity and specificity of tumor detection over FDG-PET. Additional comparisons are available in FIGS. 47A-47E (n=3 for each animal group).

Figures 47A, 47B, 47C, 47D, 47E:
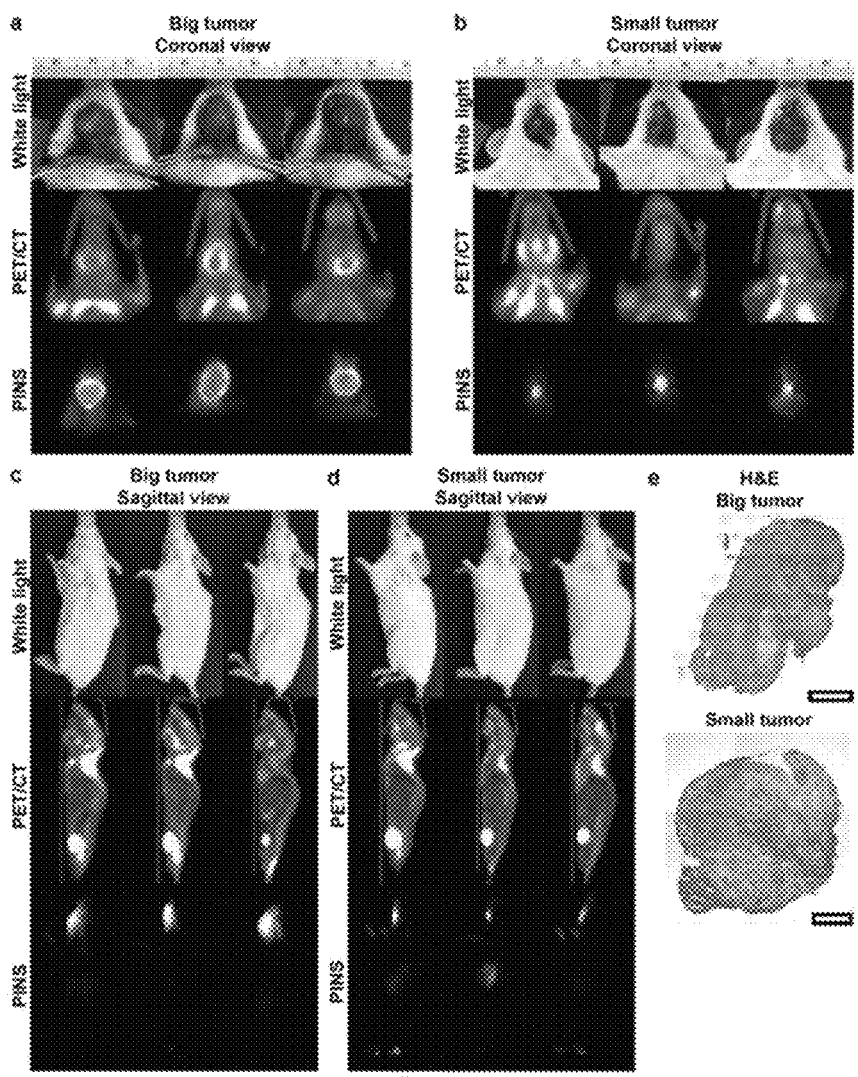

FIGS. 47A-47E show the comparison of FDG-PET with PINS imaging in mice bearing orthotopic HN5 tumors. White light, FDG-PET/CT and NIR images for the same group of mice with large tumors (200 mm$^3$, FIG. 47A) or small tumors (15 mm$^3$, FIG. 47B). PINS imaging allowed clear tumor margin delineation for all big and small tumors. For big tumors, FDG-PET showed higher signal on the periphery of the tumors consist with PINS activation. Sagittal view of the same group of mice with large (FIG. 47C) and small tumors (FIG. 47D). FIG. 47E Stitched H&E images for the big and small tumors shown in FIGS. 46A & 46B. Scale bars: 2 mm in big tumor and 500 μm in small tumor images.

Figure 48:
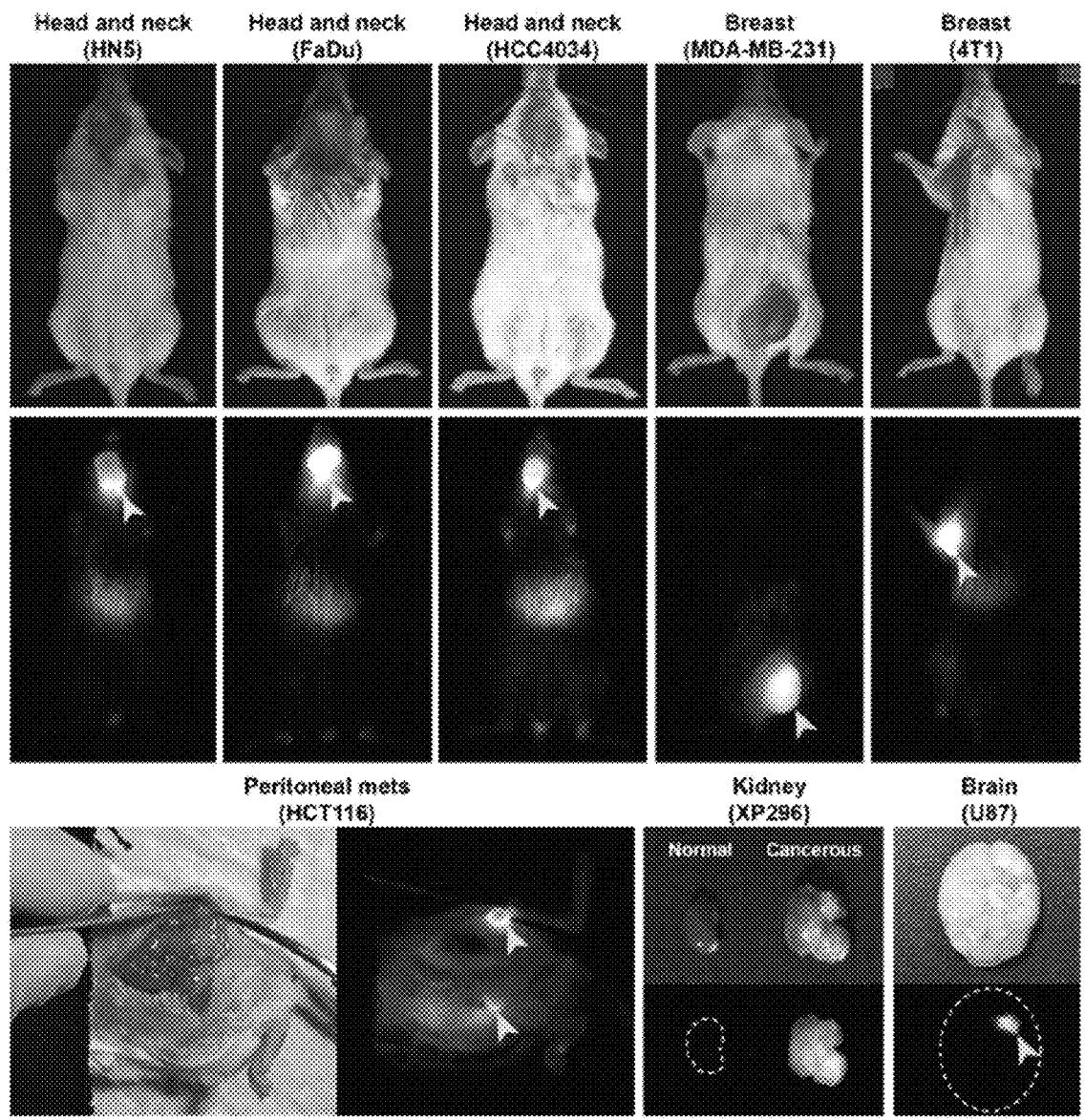

FIG. 48 shows PINS imaging achieved broad tumor specificity. PINS nanoprobes (2.5 mg/kg, i.v. injection 24 h prior to imaging by SPY Elite® clinical camera) demonstrate broad tumor imaging efficacy in different tumor models (head and neck, breast, peritoneal mets, kidney, brain) and organ sites. Arrow heads indicate the location of tumors.

Figure 49B:
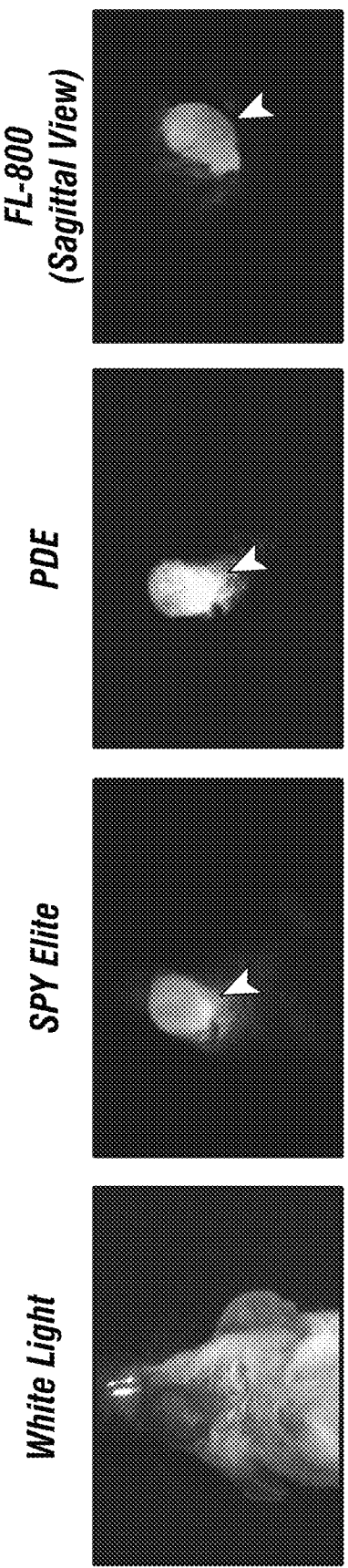

FIGS. 49A1, 49A2, 49A3 & 49B show the compatibility of PINS nanoprobes with different clinical cameras. FIGS. 49A1-3: Clinically used ICG imaging systems: Novadaq SPY Elite® (FIG. 49A1), Hamamastu PDE (FIG. 49A2) and Feica FL-800 (FIG. 49A3) models. FIG. 49B: White light and NIR images of the same tumor bearing mouse under different clinical ICG imaging systems.

FIGS. 50A-50F show ex vivo organ and tumor fluorescence imaging after PINS injection. NIR images of main organs and quantification of organ to muscle ratios of fluorescence intensity 24 h after injection of nanoprobes in mice bearing (FIG. 50A) HN5, (FIG. 50B) FaDu and (FIG. 50C) HCC4034 head and neck tumors, (FIG. 50D) MBA-MD-231 and (FIG. 50E) 4T1 breast tumors, and (FIG. 50F) U87 glioma. Data are presented as mean±s.d. (n=3). Livers were not calculated due to signal saturation.

Figures 51A, 51B:
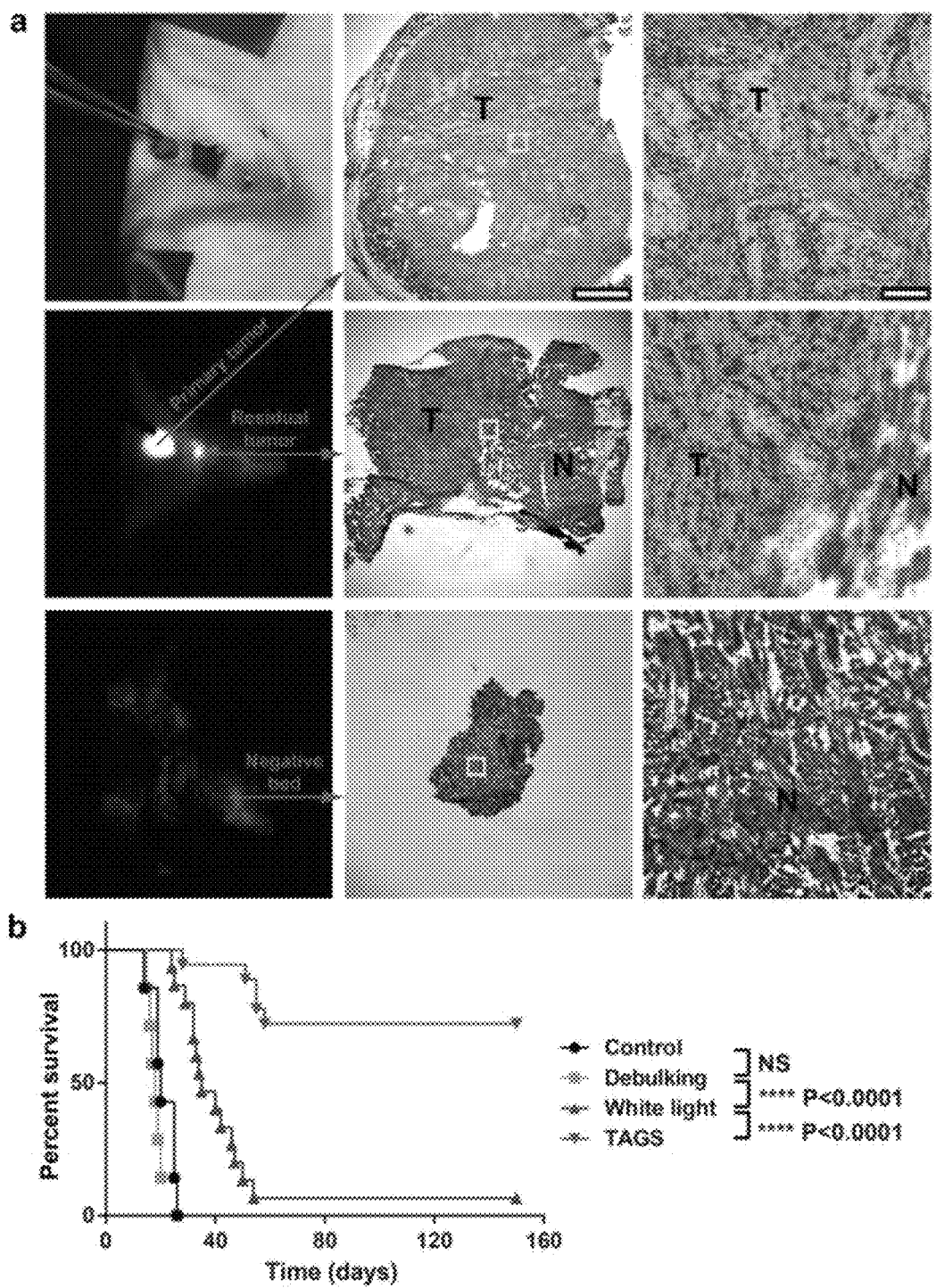

FIGS. 51A & 51B show tumor acidosis guided surgery (TAGS) in mice bearing orthotopic head and neck tumors. FIG. 51A Surgical resection of primary HN5 tumors and successful detection of residual tumors by SPY Elite® camera. Visual inspection of tumor bed by eyes was not able to differentiate residual tumors from surrounding muscle tissue (top left). Tumor tissue (T) and normal tissue (N) were verified by histology. Scale bar=1 mm (low magnification) or 100 μm (high magnification). FIG. 51B As expected debulking surgery provided no survival benefit over untreated control. TAGS shows significantly improved long-term survival over white light and other control groups (****P<0.0001). For control and debulking group n=7; for white light group n=15; for TAGS group n=18.

Figure 52:
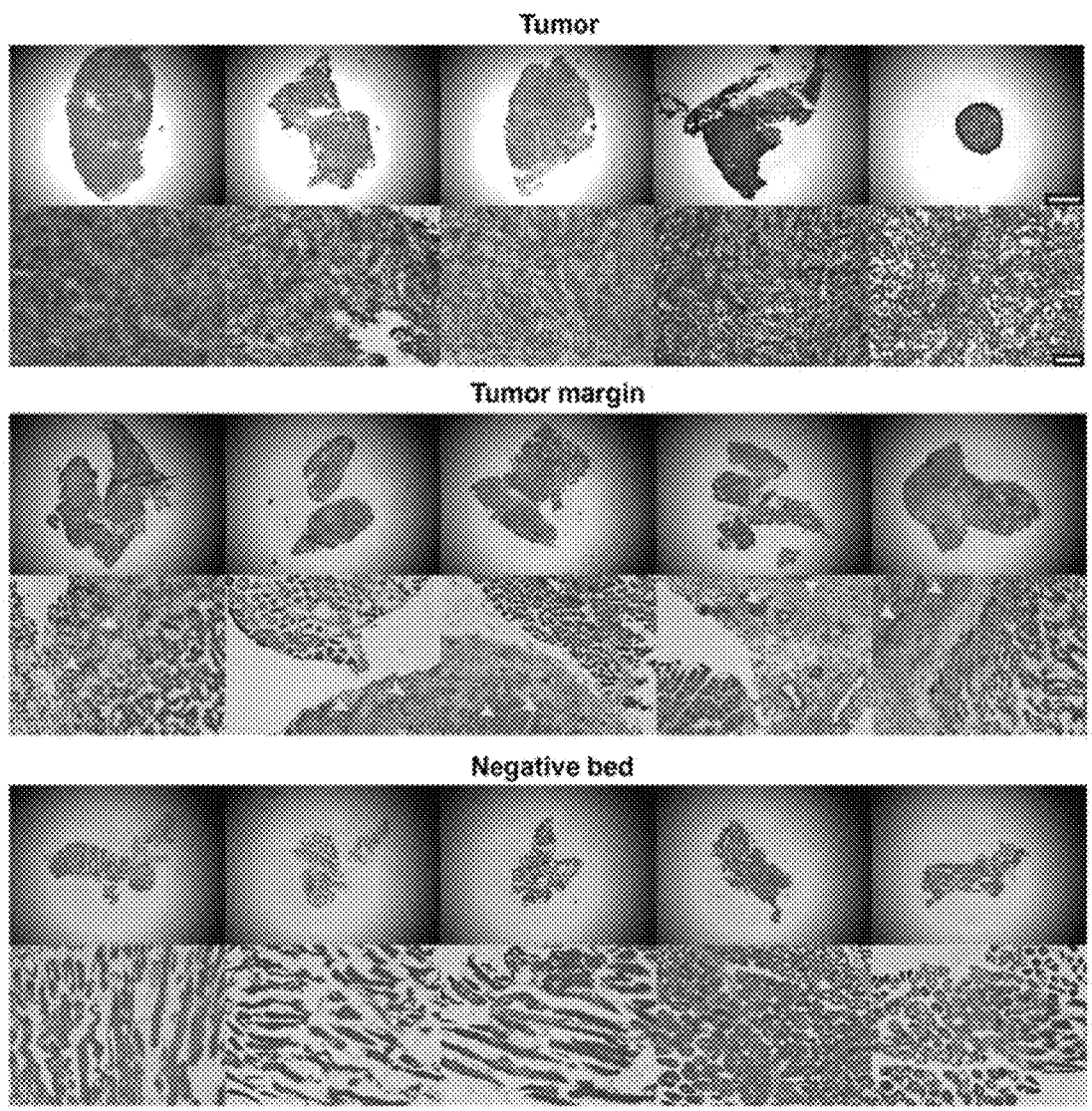

FIG. 52 shows histology validation of primary tumor, tumor margin and negative bed. Five representative H&E histology images from each type of specimens collected during the non-survival surgeries. Arrow heads indicate the presence of cancer cells in the tumor margin specimens. Scale bar=1 mm (top rows, low magnification) or 100 μm (bottom rows, high magnification).

Figures 53A, 53B, 53C, 53D:
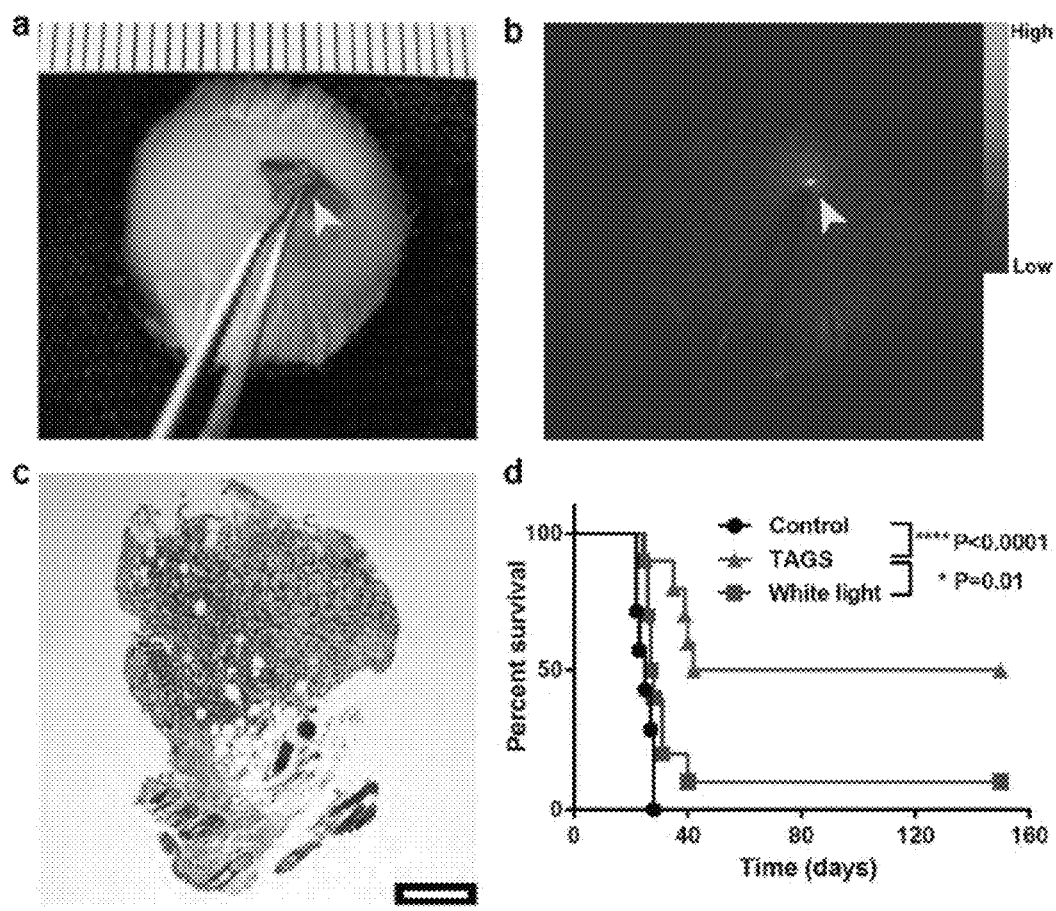

FIGS. 53A-53D show tumor acidosis guided surgery in mice bearing small occult breast tumor nodules. Tumor foci (<1 million cells) was visible under SPY camera (FIG. 53B) but not by visual detection (FIG. 53A). FIG. 53C: A representative histology section of a small breast tumor nodule resected during TAGS; scale bar=200 μm. FIG. 53D:

Kaplan-Meier curve demonstrates significantly improved long-term survival by TAGS over white light and untreated control groups. For control groups n=7; white light and TAGS groups n=10; *P<0.05.

Figures 54A, 54B, 54C:
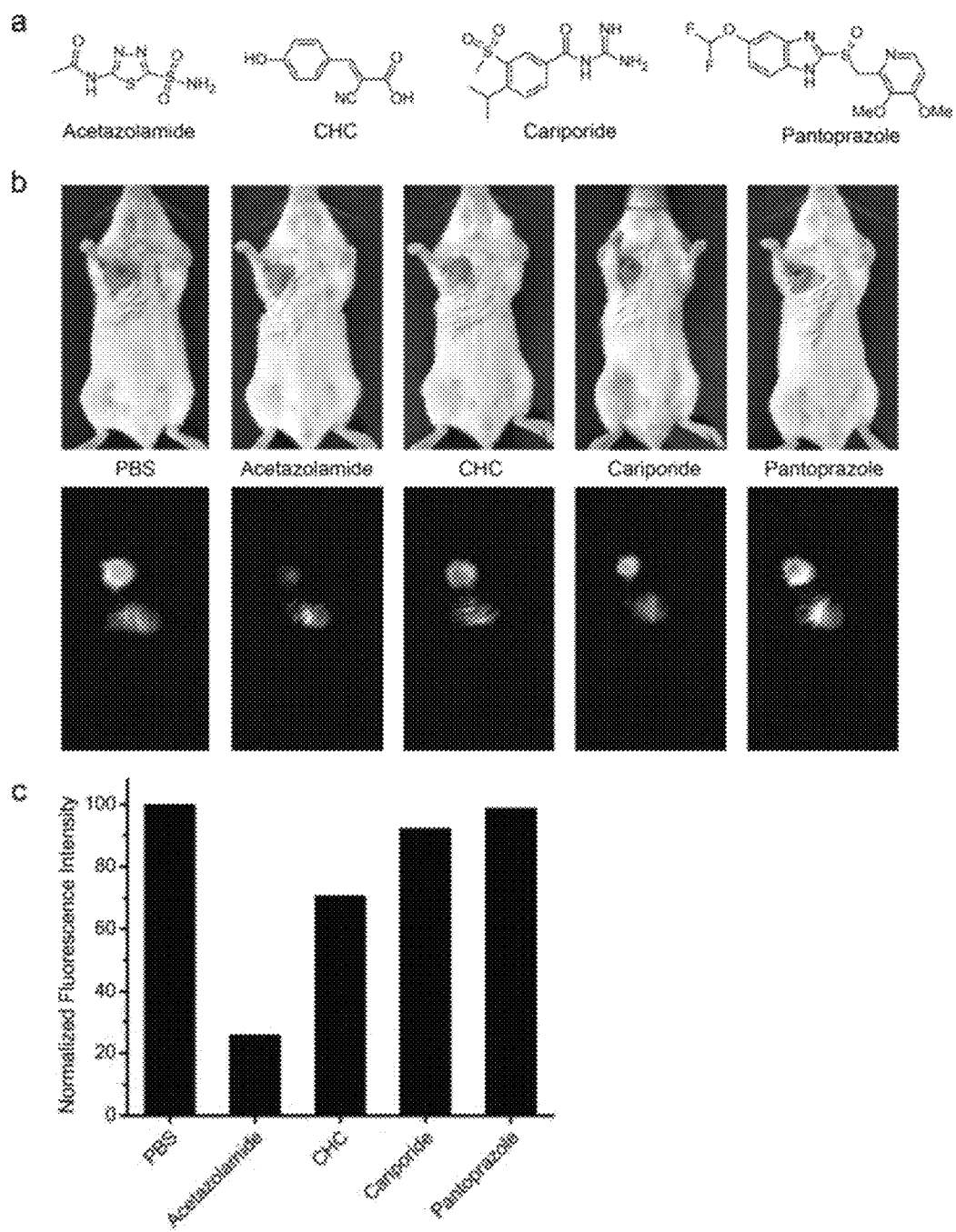

FIGS. 54A-54C show the evaluation of small molecular inhibitors targeting different tumor acidosis pathways by PINS. FIG. 54A: Chemical structure of selected small molecular inhibitors and their corresponding targets in parenthesis: acetazolamide (CAIX), α-cyano-4-hydroxycinnamate or CHC (MCT), cariporide (NHE1) and pantoprazole (proton pump). FIG. 54B: Representative images of mice bearing triple negative 4T1 breast tumors in immunocompetent BalB/C mice after injection of PBS or other tumor acidosis inhibitors. FIG. 54C: Quantification of NIR fluorescence images shown in FIG. 54B. The fluorescence intensity was normalized to the PBS control. CAIX inhibition by acetazolamide resulted in the most efficient suppression of tumor acidosis.

Figures 55A, 55B, 55C, 55D, 55E:
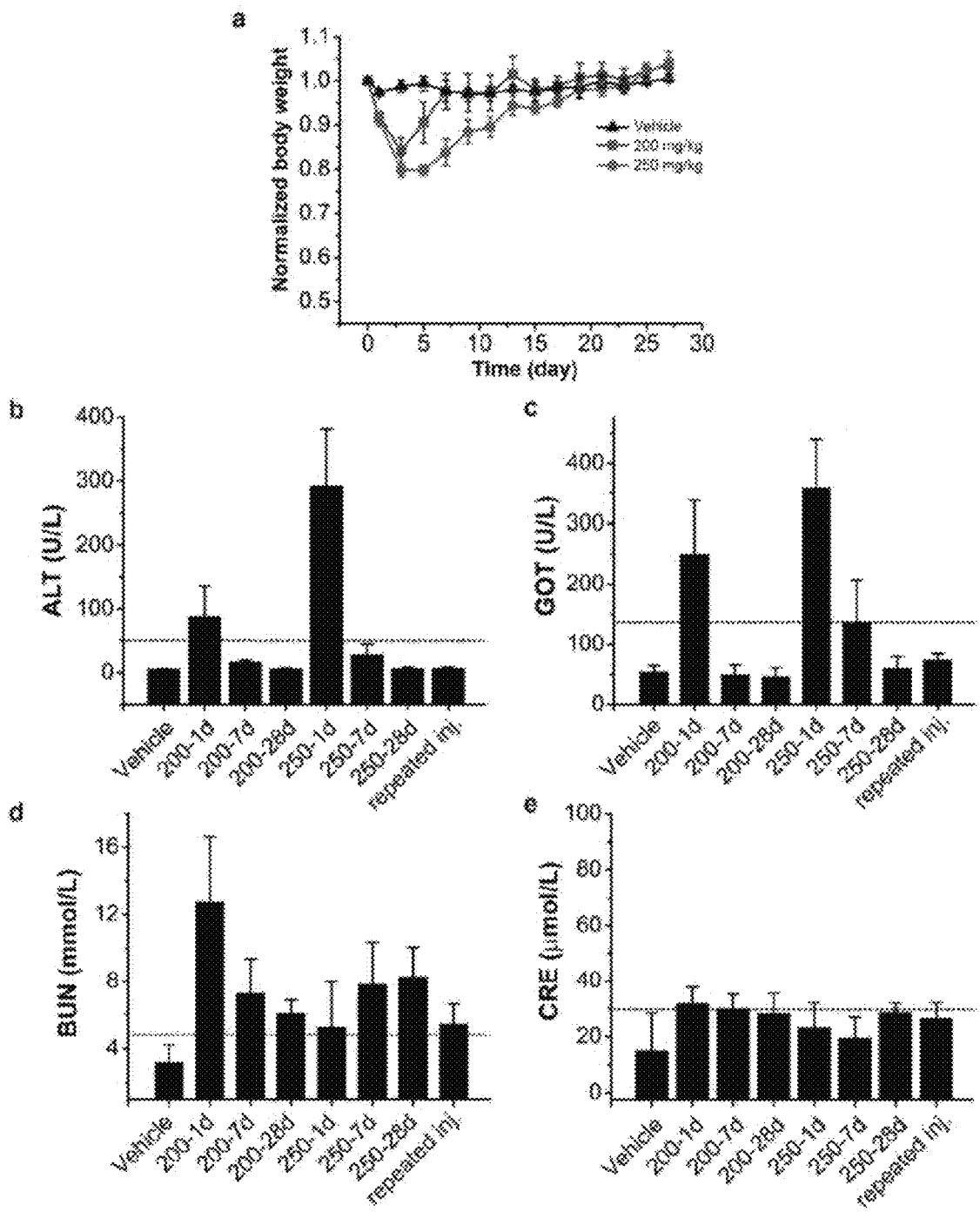

FIGS. 55A-55E show the safety assessment of intravenously administered PINS in healthy C57BL/6 mice. FIG. 55A: Normalized change of body weight of C57BL/6 immunocompetent mice after bolus injection of 200 or 250 mg/kg PINS compared to PBS control. FIGS. 55B-55E: Serum tests for liver (FIGS. 55B & 55C) and kidney (FIGS. 55D & 55E) functions of C57BL/6 immunocompetent mice after bolus injection of PINS at different doses and sacrificed after selected time points. For all groups n=5. Abbreviations: ALT, alanine aminotransferase; GOT, glutamic oxaloacetic transaminase; BUN, blood urea nitrogen; CRE, creatinine; dotted lines indicate typical wild-type mean values for C57BL/6 mice.

Figure 56:
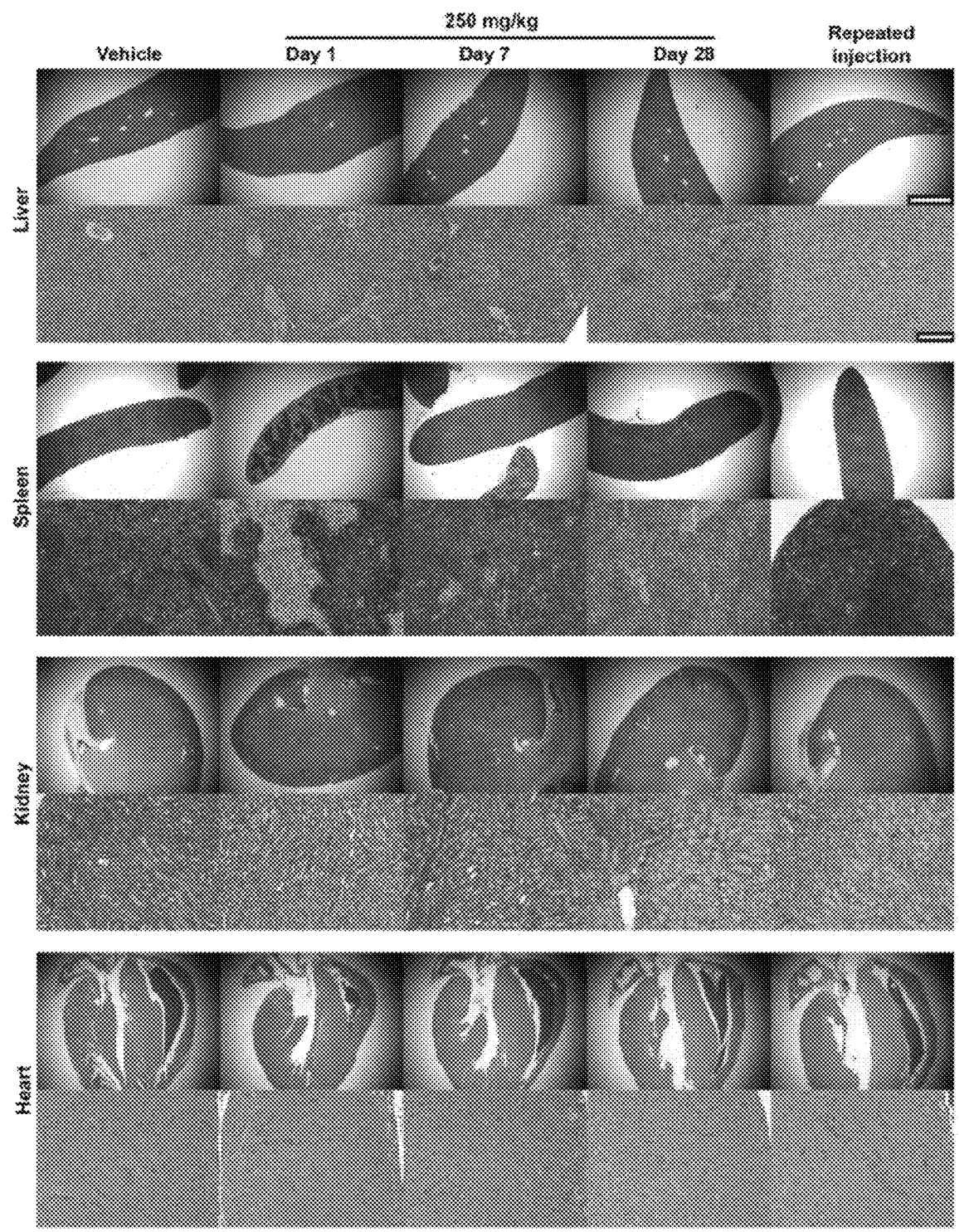

FIG. 56 shows the histology analyses of major organs for safety assessment of PINS. Representative H&E sections of the main organs from C57BL/6 immunocompetent mice after bolus injection (250 mg/kg) or repeated injection (25 mg/kg/week, 5 injections) of PINS and sacrificed after selected time points (n=5 for each group). At 250 mg/kg, microsteatosis was observed in the liver at earlier time points (day 1 and day 7), but recovered on day 28. Spleen, kidney and heart showed no abnormalities. For repeated injection, no abnormalities were observed in any of the main organs.

Figures 57A, 57B, 57C:
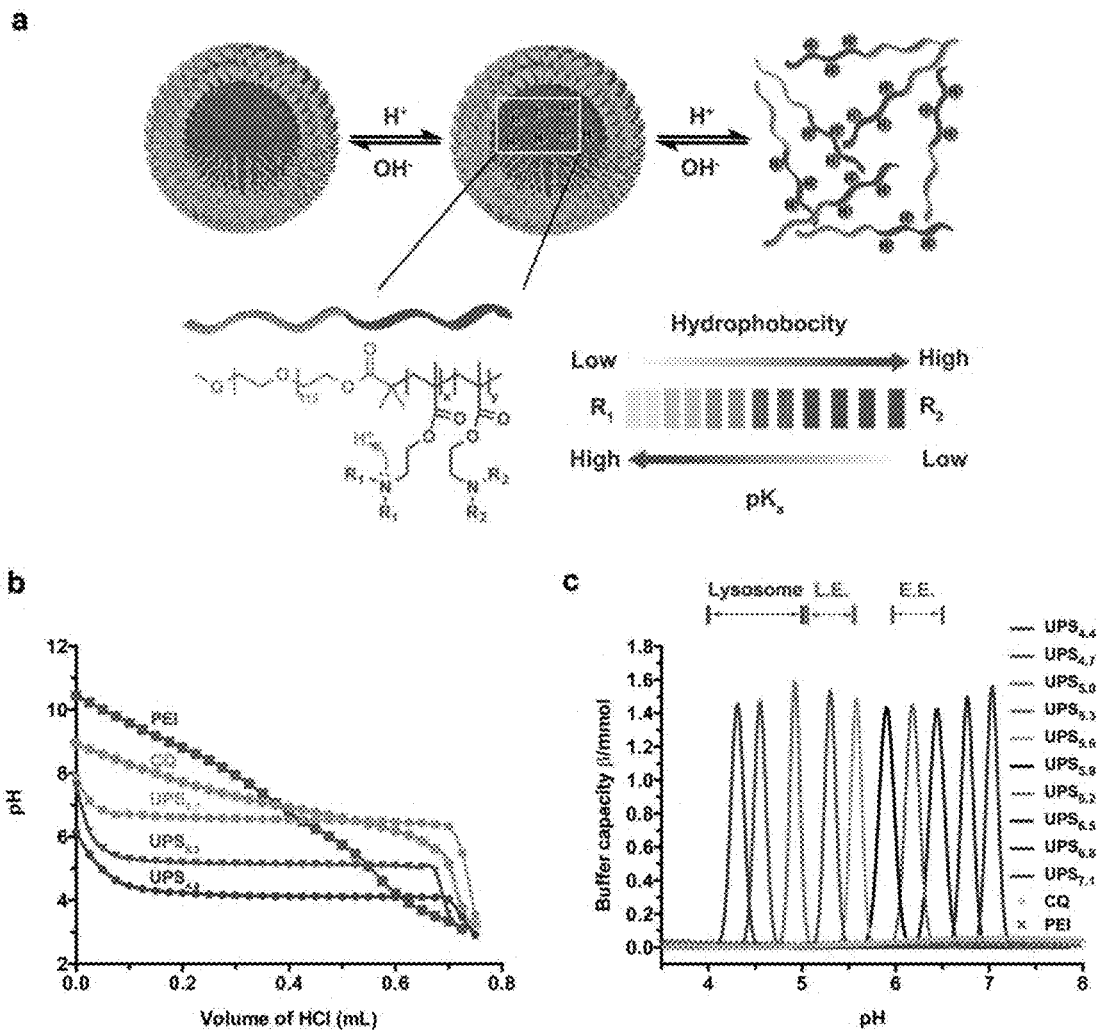

FIGS. 57A-57C show a UPS nanoparticle library with sharply defined buffer capacity across a broad physiological pH range. (FIG. 57A) Schematic illustration of the buffer effect of UPS nanoparticles and the chemical structures of PEO-b-P($R_1$-r-$R_2$) copolymers with finely tunable hydrophobicity and $pK_a$. The composition for each copolymer is shown in Table 11. (FIG. 57B) pH titration of solutions containing $UPS_{6.2}$, $UPS_{5.3}$ and $UPS_{4.4}$ nanoparticles using 0.4 M HCl. The maximum buffer pH corresponds to the apparent $pK_a$ of each copolymer. Chloroquine (CQ, $pK_a$=8.3 and 10.4), a small molecular base, and polyethyleneimines (PEI) were included for comparison. (FIG. 57C) Buffer capacity (P) for each component of the UPS library was plotted as a function of pH in the pH range of 4.0 to 7.4. At different pH values, UPS nanoparticles were 30-300 fold higher in buffer strength over CQ. L.E. and E.E. are abbreviations for late endosomes and early endosomes, respectively.

Figure 58:
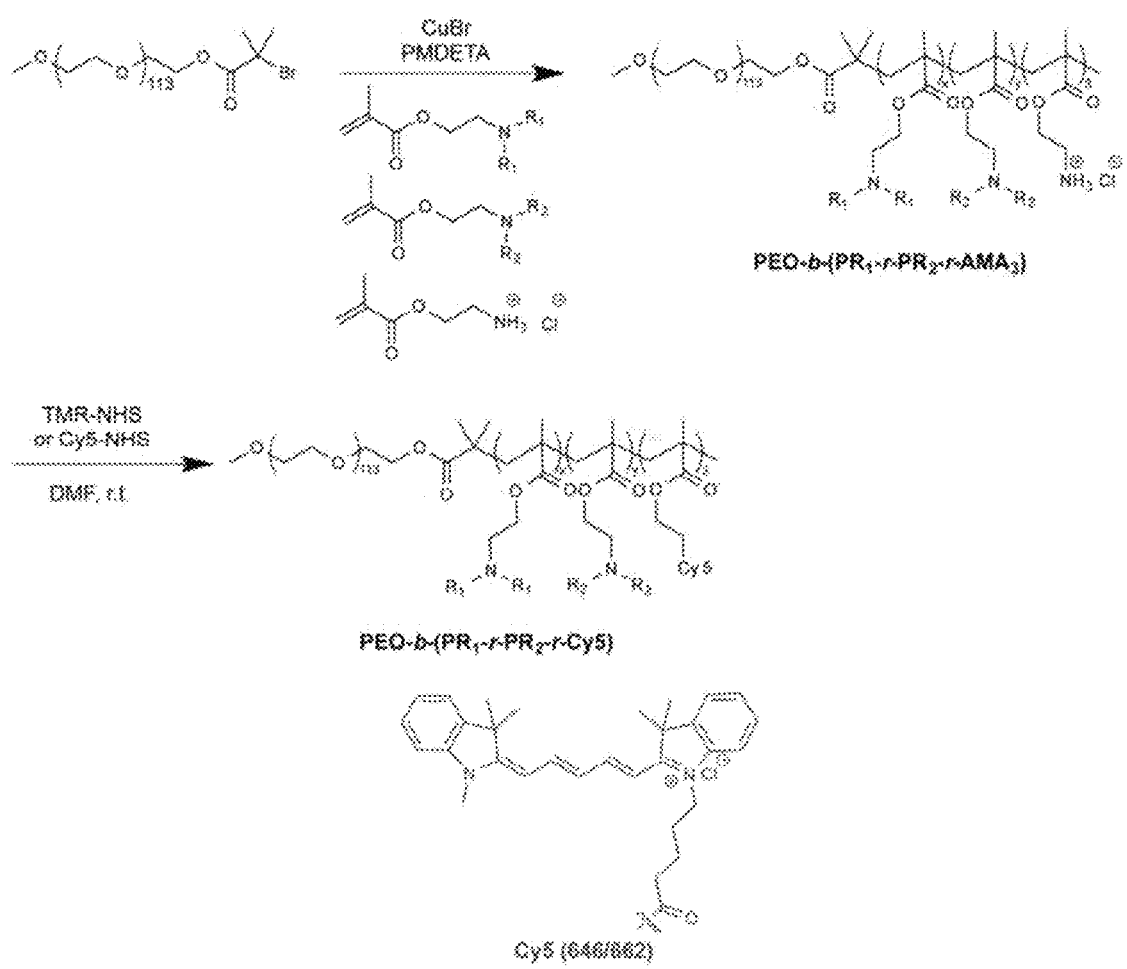

FIG. 58 shows the syntheses of dye-conjugated diblock copolymers. The PR segment consists of a random block from two monomers with different molar fractions to fine-tune its hydrophobicity and pH transition (see Table 10). The structure of Cy5 dye is also shown.

Figure 59:
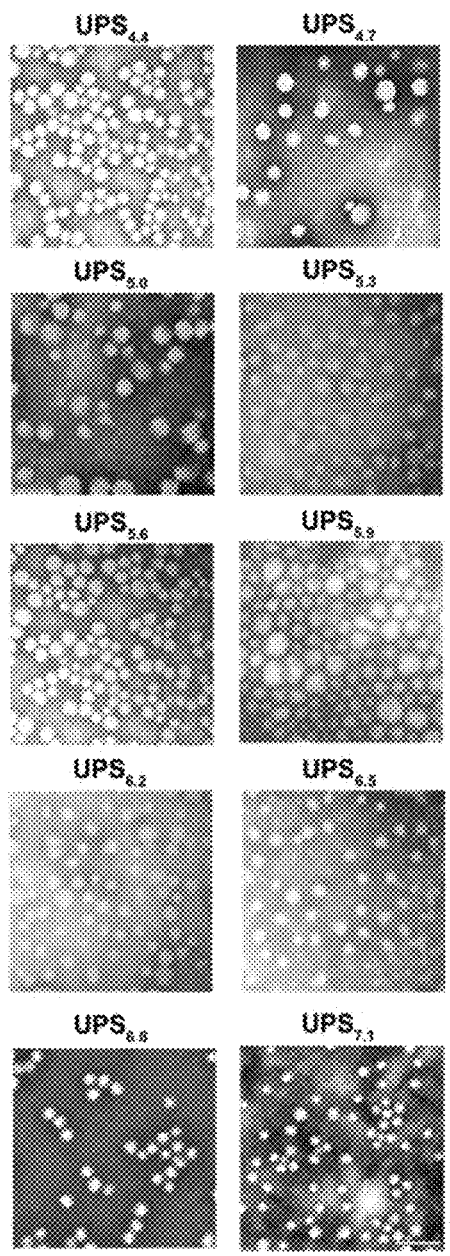

FIG. 59 shows the TEM images of the UPS nanoprobe library. Nanoprobes were dissolved in PBS buffer (pH 7.4) and dried on a carbon grid prior to TEM analysis. Phosphotungstic acid was used for negative staining. Scale bar=100 nm for all images.

Figure 60:
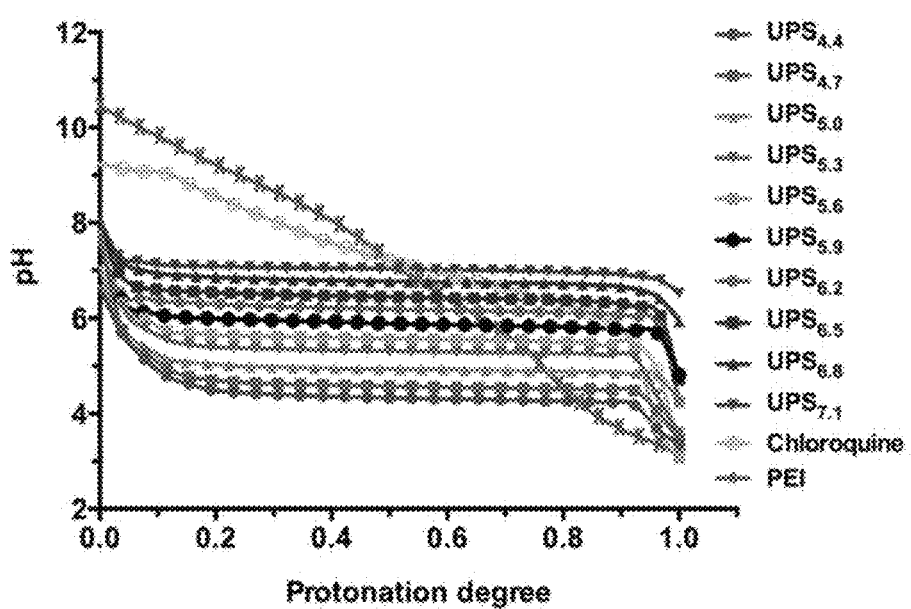

FIG. 60 shows the pH titration of each component of the UPS nanoprobe library. HCl (0.4 M) was added incrementally to titrate micelle solution (2 mg/mL polymer concentration or 8 mM based on the amount of amine groups) of all ten UPS nanoprobes, choloroquine solution (2 mg/mL or 12.5 mM based on the amount of amine groups) and PEI (branched, MW 10,000 Da, Polyscience, Inc.) solution (0.3 mg/mL or 7.3 mM based on the amount of amine groups). A pH/conductivity meter (Mettler Toledo) was used to monitor the change of pH in the solution during titration.

FIGS. 61A-61C show the syntheses and characterization of Always-ON/OFF-ON UPS nanoparticles. (FIG. 61A) and (FIG. 61B) Schematic of the dual-reporter nanoparticle. In the micelle state, the Always-ON dyes serve as the quencher for the ON/OFF fluorophores. When the micelle is disassembled, the Always-ON and ON/OFF fluorophores can fluoresce independently. The ON/OFF ratio of BODIPY (FIG. 61A) and Cy3.5 (FIG. 61B) varies when the ratio of polymers conjugated with these two dyes varies. Weight fraction of 60% BODIPY-conjugated copolymer with 40% Cy3.5-conjugated copolymer was chosen as the final combination. (FIG. 61C) Fluorescence signal amplification of $UPS_{6.2}$ nanoprobes as a function of pH. Images were captured on Maestro in vivo imaging system (CRI) using the green and yellow filters.

Figures 62A, 62B, 62C:
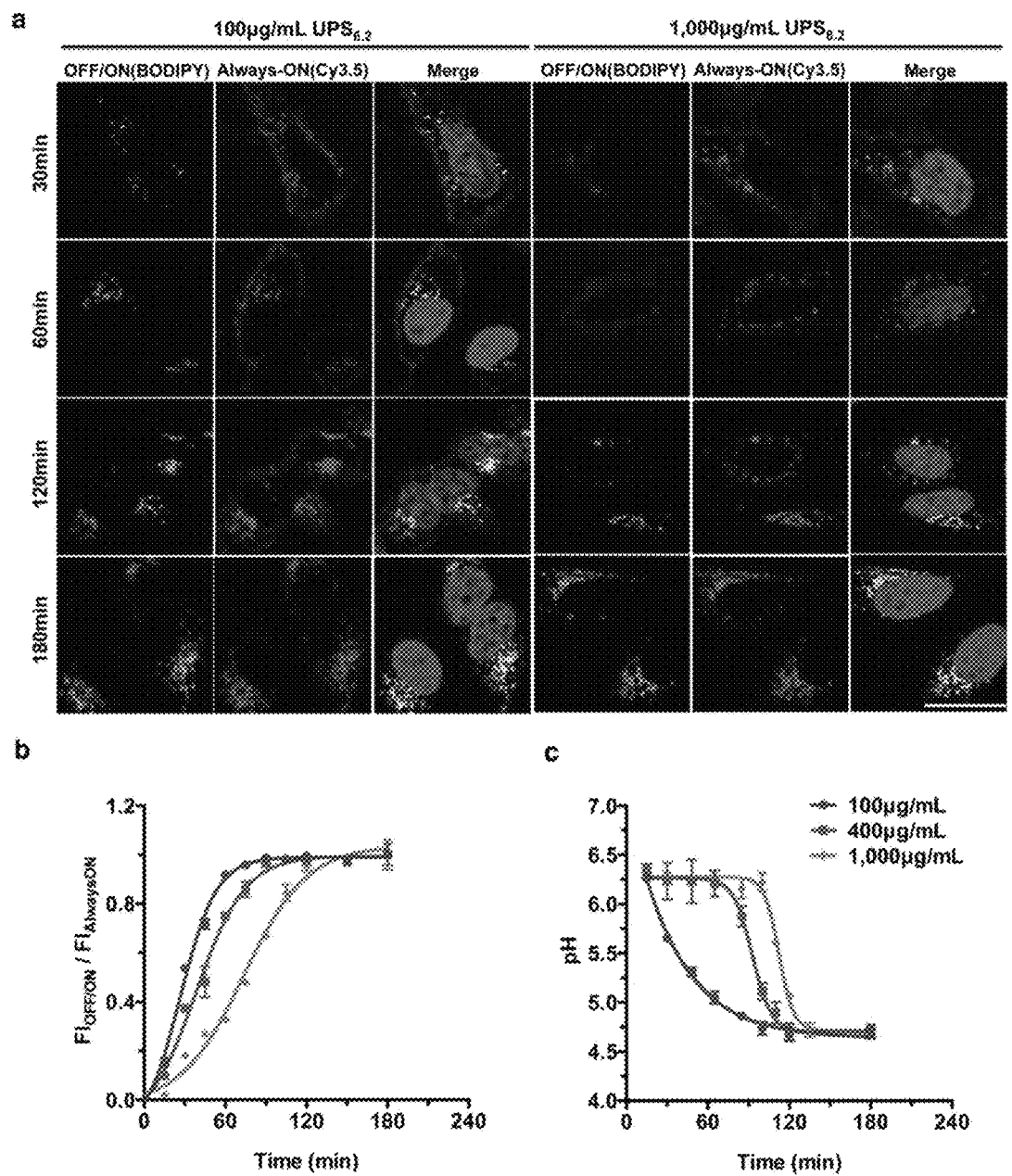

FIGS. 62A-62C show the pH-sensitive imaging and buffering of endocytic organelles in HeLa cells. (FIG. 62A) Representative confocal images of HeLa cells at the indicated time points following a 5 min exposure to low (100 μg/mL) and high dose (1,000 μg/mL) of $UPS_{6.2}$. Nuclei were stained blue with Hoechst. Scale bar=10 μm. (FIG. 62B) Quantitative analysis of the activation kinetics of always-ON/OFF-ON $UPS_{6.2}$. The fluorescent intensity of punctae in BODIPY channel (OFF-ON) was normalized to that of Cy3.5 (always-ON). (FIG. 62C) Real-time measurement of endo/lysosomal pH in HeLa cells treated with the indicated doses of $UPS_{6.2}$. Lysosensor ratiometric imaging probe was used for in situ pH measurement. The error bars represent standard deviations from 50 organelles at each time point.

Figures 63A, 63B, 63C:
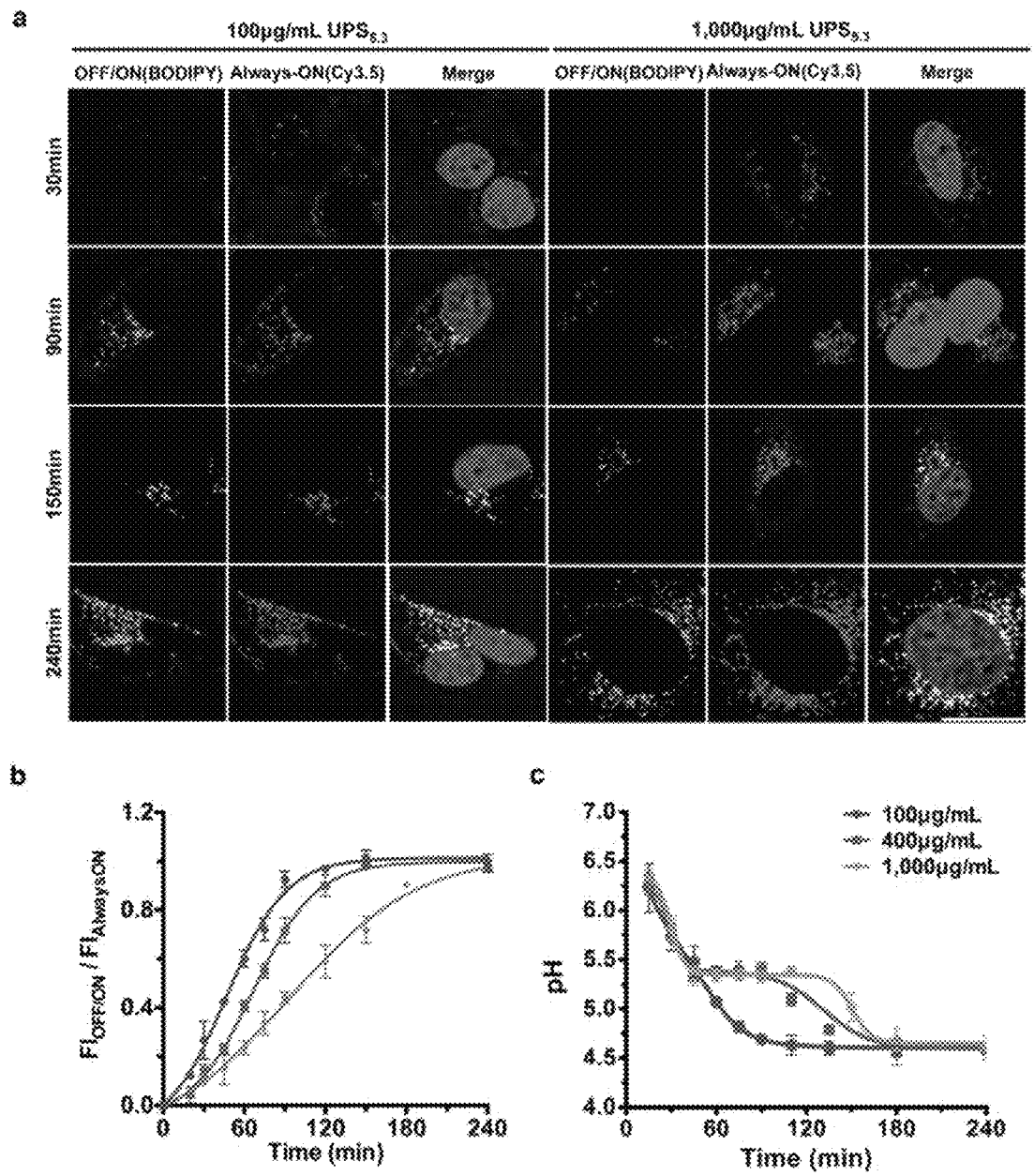

FIGS. 63A-63C show the Buffering endocytic organelles of HeLa cells with $UPS_{5.3}$ nanoprobes. (FIG. 63A) Confocal images of HeLa cells at the indicated time points following a 5 min exposure to low dose (100 μg/mL) and high dose (1,000 μg/mL) Always-ON (Cy3.5)/OFF-ON (BODIPY) $UPS_{5.3}$. Nuclei were stained blue with Hoechst. Scale bar=10 μm. (FIG. 63B) Quantitative analysis of the OFF-ON activation process of $UPS_{5.3}$. The fluorescent intensity of punctae in cells in BODIPY channel was normalized to the fluorescent intensity of the same puncta in TMR channel. (FIG. 63C) Real-time measurement of endo/lysosomal pH fluctuation in HeLa cells treated with always-ON (Cy3.5)/OFF-ON (BODIPY) $UPS_{5.3}$ at indicated doses. Lysosensor Yellow/Blue DND160 ratiometric imaging probe was used for in situ pH measurement. The error bars represent standard deviations from 50 organelles at each time point.

FIGS. 64A-64F show the buffering the pH of endocytic organelles affects their membrane protein dynamics. HeLa cells were treated with 1,000 μg/mL $UPS_{6.2}$-Cy5 or $UPS_{4.4}$-Cy5 for 5 min for cell uptake. Then they were incubated for 15 min (FIG. 64A), 1 h (FIG. 64B) and 2 h (FIG. 64C) before fixation. Immunofluorescence (IF) images show the localization of UPS nanoprobes in early endosomes (Rab5) or lysosomes (LAMP2). Scale bar=10 μm and 5 μm (inset). Imaris software was used to analyze colocalization of z-stacked confocal images. The faction of UPS colocalized with Rab5 (FIG. 64D) and LAMP2 (FIG. 64E) and the faction of Rab5 colocalized with LAMP2 (FIG. 64F) were calculated from Mander's coefficient, n=10, $\alpha$=0.05, ****$p<0.0001$. Two-way ANOVA and Sidak's multiple comparison tests were performed to assess the statistical significance.

FIGS. 65A-65E show the clamping luminal pH of endolysosomes with UPS selectively inhibits amino acid-dependent mTORC1 activation. HeLa cells were starved in EBSS for 2 h and then stimulated with essential amino acids (EAAs) for indicated time intervals in the presence of (FIG. 65A) $UPS_{6.2}/UPS_{5.3}/UPS_{50}$ and (FIG. 65B) $UPS_{4.7}/UPS_{4.4}$. Water and 50 µM chloroquine (CQ) were used as control. Accumulation of the indicated phosphoproteins was assessed by immunoblot of whole cell lysates. (FIG. 65C) Quantitative analysis of the nuclear/cystosolic distribution of GFP-TFEB following the indicated treatments. Error bars represent standard deviation, n=10. (FIG. 65D) Representative images for FIG. 65C. Scale bar=10 µm. (FIG. 65E) Working model of pH transitions required for free amino acid versus albumin-derived amino acid dependent activation of the mTORC1 signaling pathway.

Figures 66A, 66B, 66C:
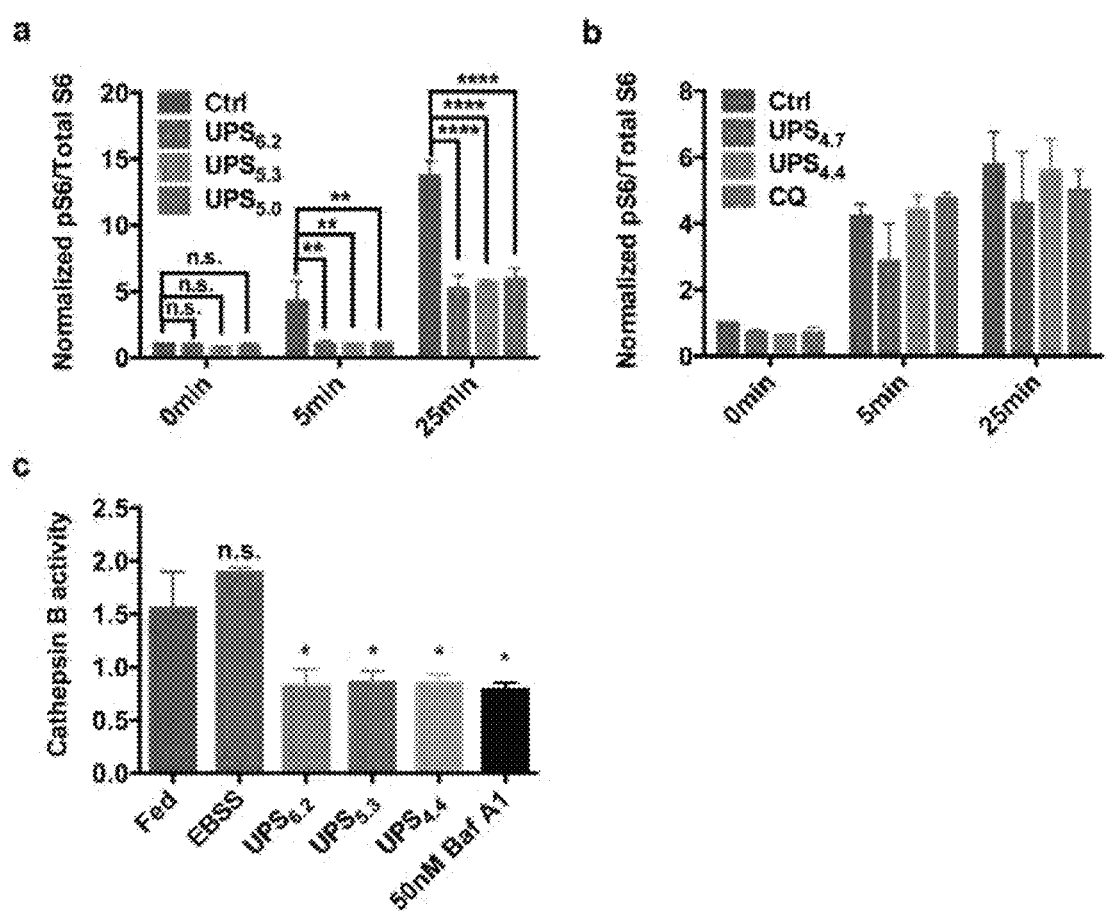

FIGS. 66A-66C show the mTORC1 signal quantitation and cathepsin B activity upon UPS exposure. (FIGS. 66A & 66B) Quantitative analysis of phosphorylated S6 protein normalized by its total protein levels in FIGS. 64A & 64B. Statistic difference between control (water) and UPS treated groups at each time point was detected by two-way ANOVA and Dunnett's multiple comparison test, $\alpha$=0.05, $p<0.01$, **$p<0.0001$ or not significant (n.s.). The statistical differences between control and UPS treated groups were not significant at any time point in FIG. 66B. Error bars indicate standard deviation, n=3. (FIG. 66C) Cathepsin B activity was measured in response to the indicated treatments (n=2). Statistical difference between 'Fed' and all the other groups was detected by one-way ANOVA and Dunnett's multiple comparison test, $\alpha$=0.05, *$p<0.05$ or not significant (n.s.).

Figures 67A, 67B, 67C, 67D:
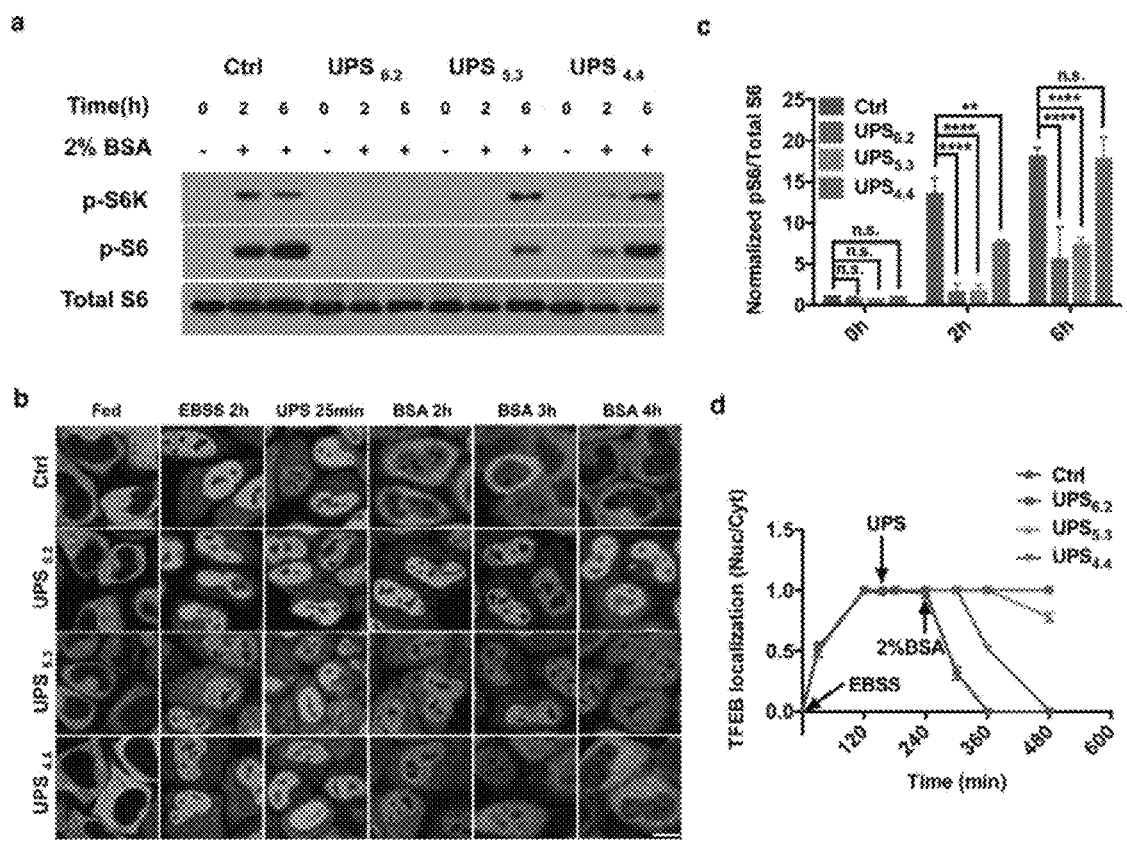

FIGS. 67A-67D show the albumin-dependent mTORC1 pathway activation is inhibited by $UPS_{4.4}$. (FIG. 67A) HeLa cells were deprived of nutrients for 2 h followed by BSA uptake (2%) in the presence or absence of the indicated UPS nanoparticles (1,000 µg/ml). Accumulation of the indicated phosphoproteins was monitored by immunobot of whole cell lysates. (FIG. 67B) Nuclear/cytosolic distribution of GFP-tagged TFEB was monitored in response to the indicated conditions. (FIG. 67C) Quantitative analysis of phosphorylated S6 protein normalized by its total protein levels in (FIG. 67A). Error bars indicate standard deviation, n=3. Statistic difference between control and UPS treated groups at each time point was detected by two-way ANOVA and Dunnett's multiple comparison test, $\alpha$=0.05, $p<0.01$, **$p<0.0001$ or not significant (n.s.). (FIG. 67D) Quantitative analysis of the location of TFEB in the results shown in (FIG. 67B) (in the cytosol=0, in the nucleus=1). The error bars represent standard deviation. Scale bar=10 µm.

Figure 68A:
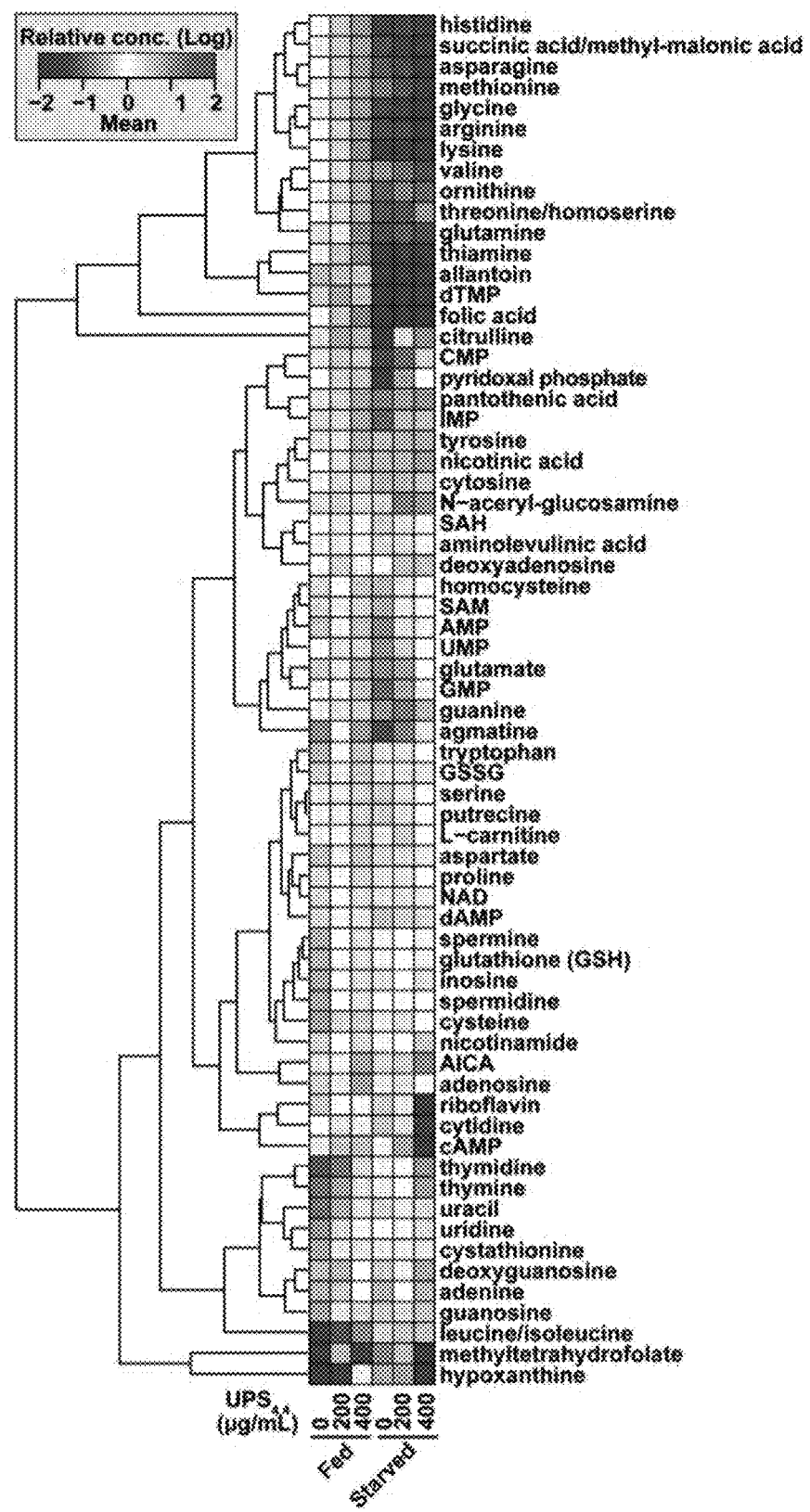

FIGS. 68A-68C show the selective buffering of lysosomal pH modulates the cellular metabolite pool. (FIG. 68A) Dendrogram indicates relative abundance of the indicated metabolites in nutrient replete (fed) or deprived (starved) medium as normalized to the total protein content. Cells were treated with $UPS_{4.4}$ at the indicated doses. (FIG. 68B) Normalized abundance of the selected amino acids under nutrient replete and nutrient deprived conditions. Error bars represent standard deviation, n=6. (FIG. 68C) A schematic indicating the consequence of environment and lysosomal pH on the balance of cellular metabolite pools.

FIGS. 69A-69G show the UPS nanoparticles selectively kill NSCLC cells that are sensitive to lysosomal stress. (FIG. 69A) Schematic of the cell models employed and their corresponding vulnerabilities to lysosomal maturation. (FIG. 69B) DIC images indicating the relative viability of HBEC30 KT and HCC4017 cells with and without exposure to UPS at effective doses ($UPS_{6.2}$ and $UPS_{5.3}$=400 µg/ml, $UPS_{4.4}$=1,000 µg/ml). Scale bar=100 µm. (FIGS. 69C-69E) Caspase3/7 activity in HBEC30KT, HBEC30KT KP, HBEC30KT KPL and HCC4017 cells was measured 72 h after exposure to the indicated doses of UPS. Two-way ANOVA and Sidak's multiple comparison tests were performed to assess statistical significance of observed differences between HBEC30KT and HCC4017, and HBEC30KT KP and HBEC30KT KPL, $\alpha$=0.05, $p<0.01$, **$p<0.0001$. (FIGS. 69F & 69G) Cellular ATP levels were measured after exposure of HCC4017 (FIG. 69F) and HBEC30 KT KPL (FIG. 69G) to 1,000 µg/mL $UPS_{6.2}$ for 72 h together with the indicated concentrations of methyl pyruvate (MP), dimethyl-2-oxoglutarate (MOG), or water (dash line). Values were normalized to no treatment (without UPS) controls. Error bars indicate standard deviation, n=4.

FIGS. 70A-70D show I-$UPS_{6.9}$ nanoprobes. (FIG. 70A) Schematic syntheses of ICG-conjugated block copolymers, PEG-b-P(C7A-r-ICG). (FIG. 70B) Near IR images of I-$UPS_{6.9}$ solution by SPY Elite® surgical camera showing pH-sensitive off/on activation. (FIG. 70C) Normalized fluorescence intensity as a function of pH shows longer PC7A segment leads to slightly lower pH transition and sharper response. (FIG. 70D) A 3D plot of fluorescence intensity as a function of probe concentration and pH. Data from FIGS. 70B-70D were obtained in 20% serum-containing solutions.

Figure 71:
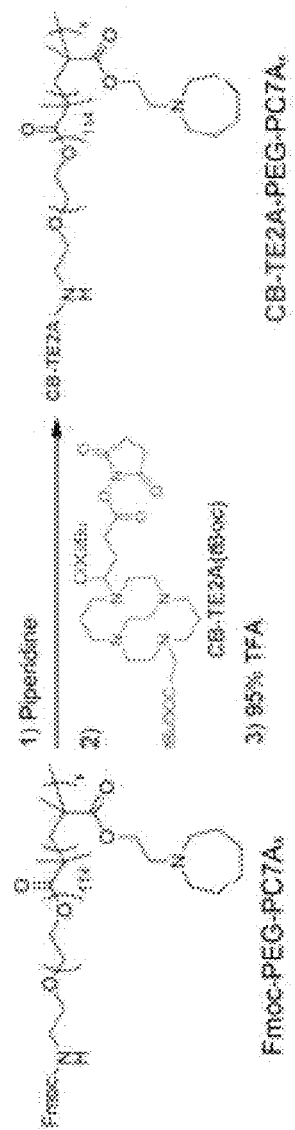

FIG. 71 shows the proposed synthetic route of chelator conjugated polymer, CB-TE2A-PEG-PC7A$_x$.

Figure 72:
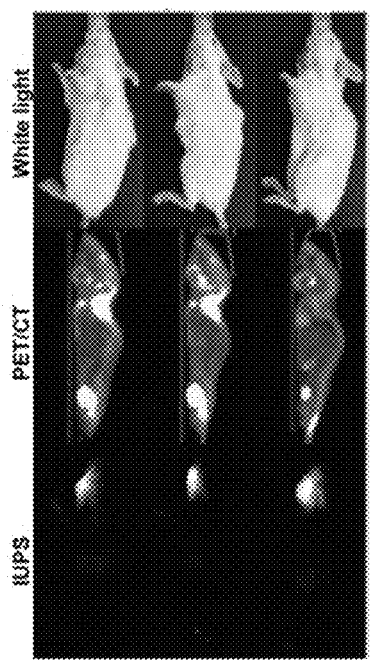

FIG. 72 shows mice bearing orthotopic HN5 tumors imaged by FDG-PET and I-UPS. Mice were imaged at sagittal position to show false positives from brown fat or neck muscles (arrows) in FDG-PET images.

Figure 73:
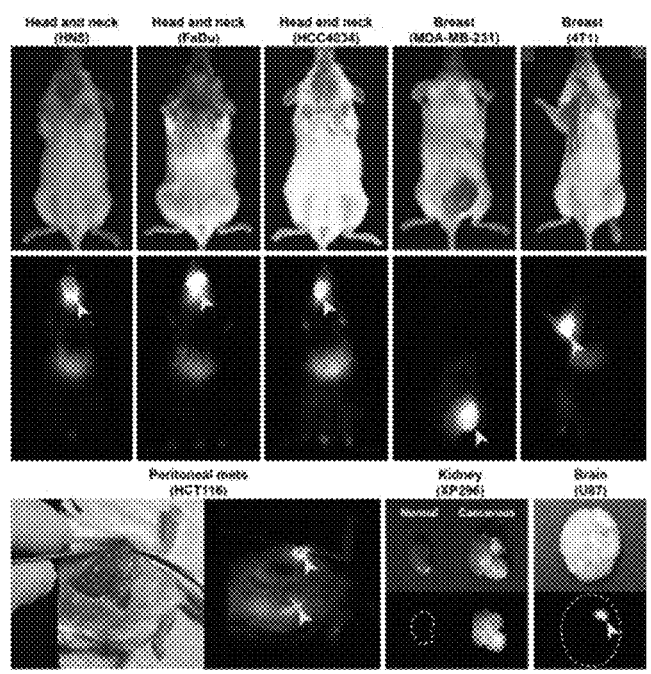

FIG. 73 shows tumor acidosis imaging by I-UPS with broad cancer specificity in diverse tumor models (head and neck, breast, colorectal peritoneal mets, kidney, brain). Yellow arrow heads indicate the location of tumors. I-$UPS_{6.9}$ (2.5 mg/kg) was i.v. injected 24 h before imaging by a SPY camera.

Figures 74A, 74B:
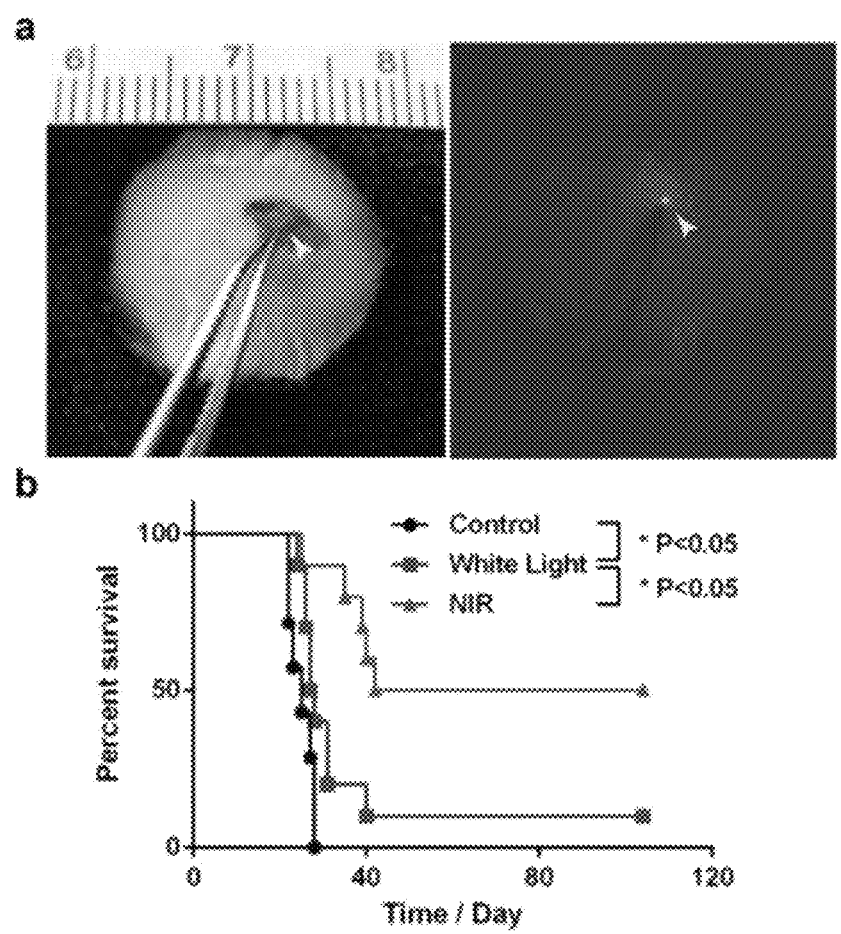

FIGS. 74A & 74B show (FIG. 74A) I-$UPS_{6.9}$-guided resection of orthotopic 4T1 breast tumors. Tumor foci (<1 million cells) was visible under SPY camera (right panel) but not by visual detection (left panel). (FIG. 74B) Kaplan-Meier curve demonstrates improved long-term survival by I-$UPS_{6.9}$-guided resection over white light (P<0.05) and untreated control groups (P<0.01).

Figure 75:
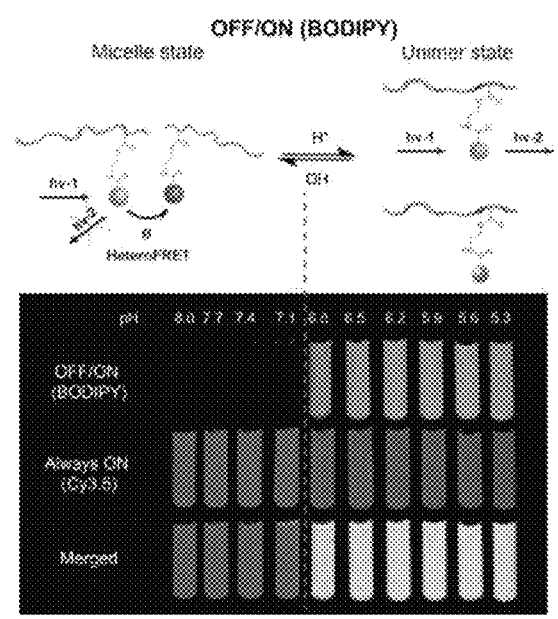

FIG. 75 shows UPS nanoprobe with Always-ON/OFF-ON dual reporter signals. $UPS_{6.9}$ is used as an example and BODIPY/Cy3.5 as FRET donor/acceptor pair.

Figure 76A:
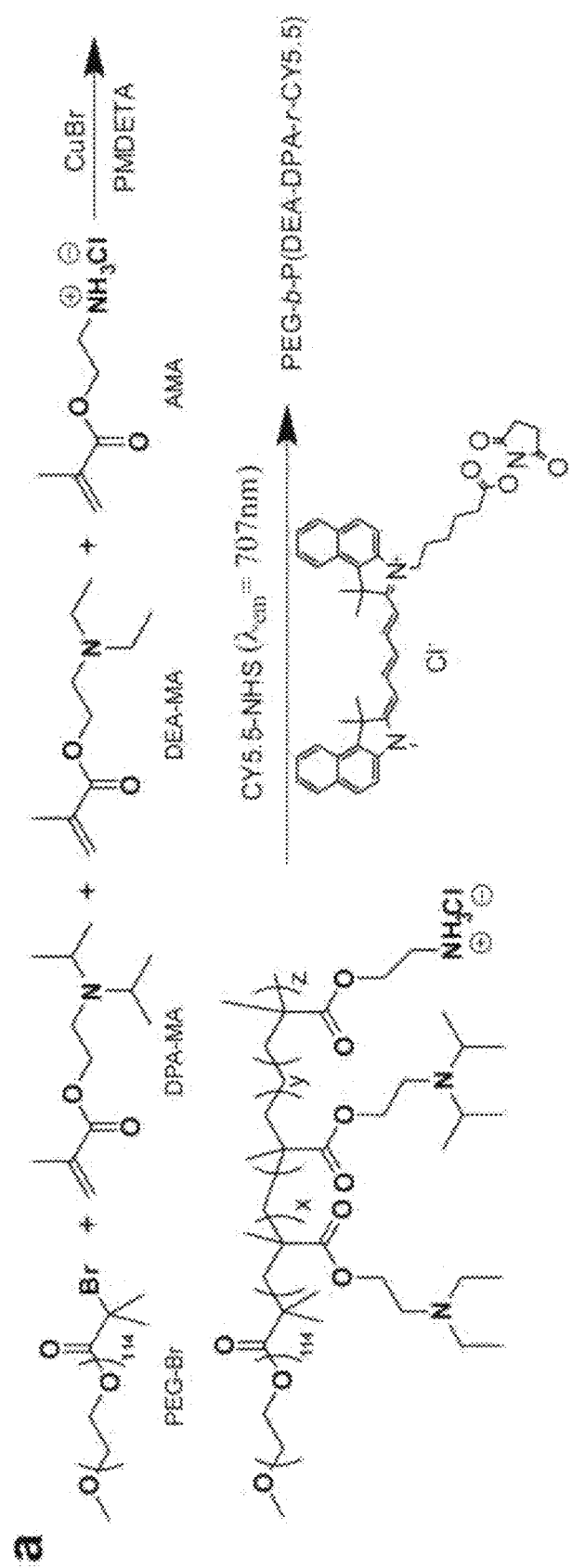

FIGS. 76A-76C show UPS nanoprobes with fine-tuned pH transitions. (FIG. 76A) Synthetic scheme of PEG-b-PR copolymers with varying molar fractions of DPA-MA and DEA-MA subunits in the PR block. (FIG. 76B) pH response of the UPS nanoprobes for different PR compositions. Cy5.5 was used as a model dye. (FIG. 76C) Transition pH as a function of molar percentage of DPA establishes a standard curve for rational design of UPS with pre-determined pH transition.

Figure 77:
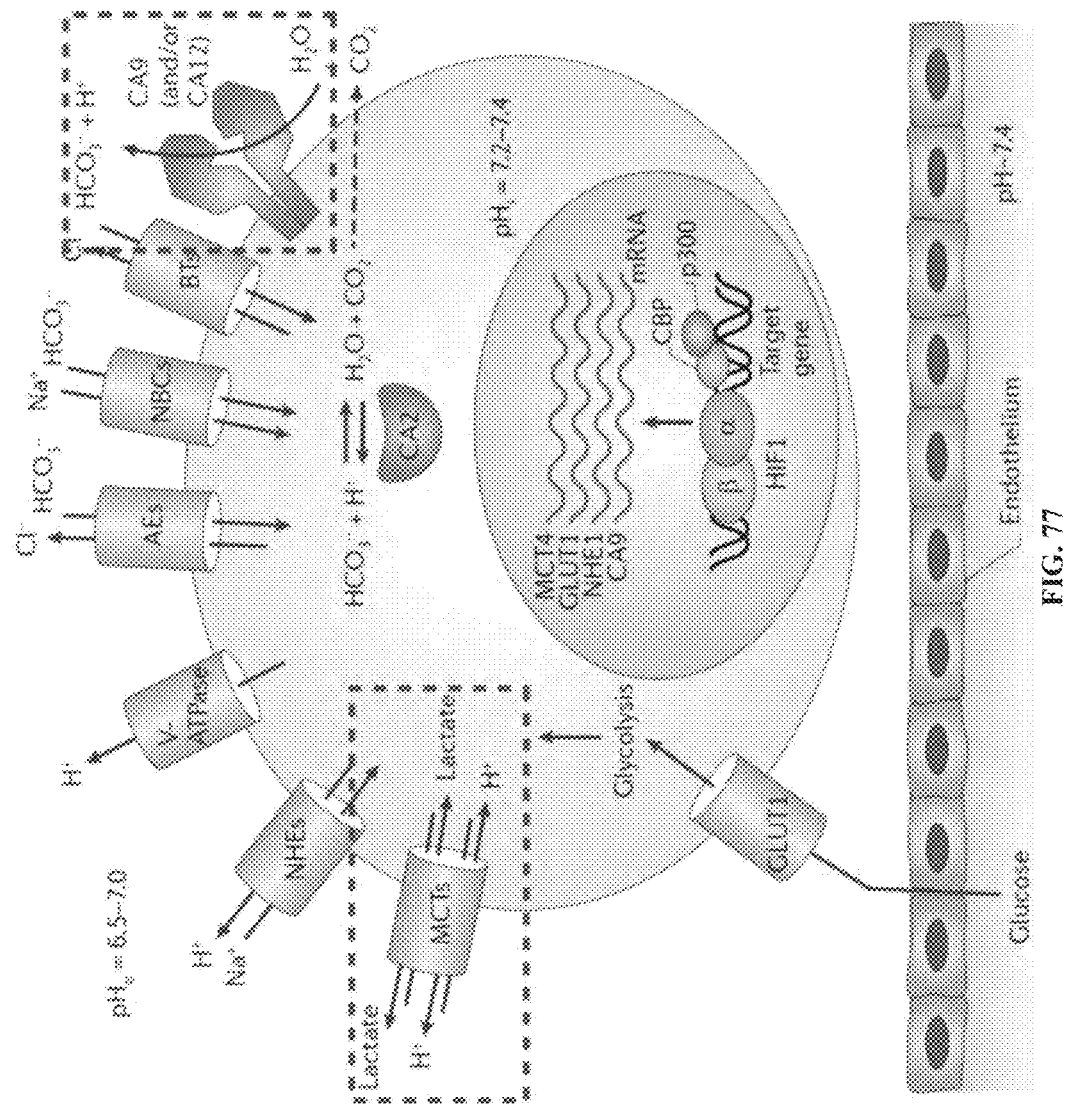

FIG. 77 shows pH regulatory machinery in a cancer cell. Proton pumping results in tumor acidosis in the microenvironment as well as raising the intracellular pH to promote cell proliferation and migration (Neri & Supuran, 2011).

FIGS. 78A-78E show UPS$_{6.9}$ nanoprobes can specifically image tumor pH$_e$ in A549 lung tumors. (FIG. 78A) Aerobic glycolysis converts glucose to lactate in cancer cells. 2-DG and CHC are metabolic inhibitors for glucose uptake and lactic acid secretion, respectively. (FIG. 78B) Effect of 2-DG or CHC on the rate of lactic acid secretion in A549 cells. (FIG. 78C) Acidification of A549 cell culture medium in the presence of 2-DG or CHC after 6 h incubation. *P<0.05, P<0.01, *P<0.001, compared with vehicle group. (FIG. 78D) Overlaid fluorescent images of A549 tumor-bearing mice at 24 h post-injection of UPS$_{6.9}$ (10 mg/kg). In the control groups, 2-DG (250 mg/kg) or CHC (250 mg/kg) was injected 12 h before UPS$_{6.9}$ administration. Cy5.5 (light spot) and autofluorescence (light background) are shown in the composite images. (FIG. 78E) NIR fluorescence intensity ratio between tumor and normal tissues (T/N ratio) as a function of time after UPS$_{6.9}$ injection. Data are presented as mean±s.d. (n=4).

Figures 79A, 79B, 79C:
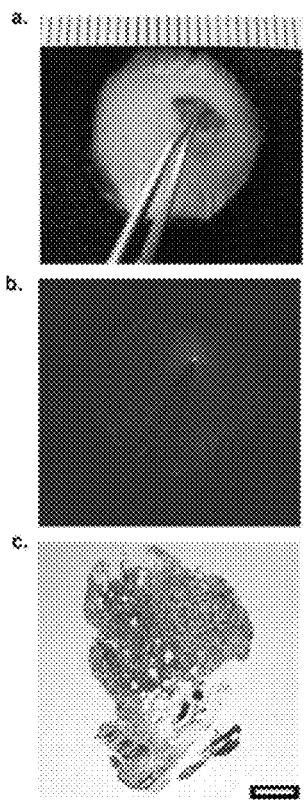

FIGS. 79A-79C show I-UPS imaging of orthotopic 4T1 breast tumors. Tumor foci (<1 million cells) was visible under SPY camera (heat mode, FIG. 79B) but not by visual detection (FIG. 79A). Tumor presence was verified by histology (FIG. 79C). The scale bar is 200 μm in FIG. 79C.

Figure 80:
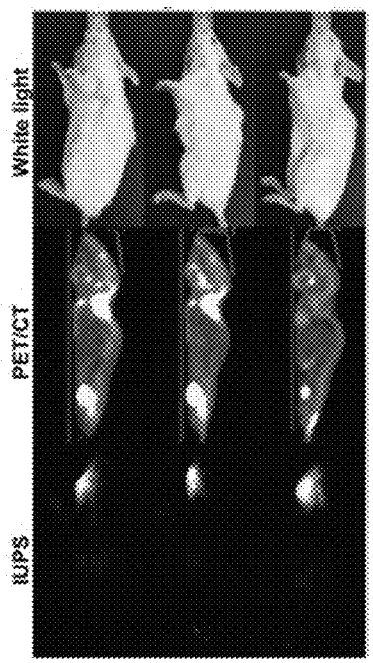

FIG. 80 shows mice bearing orthotopic HN5 tumors imaged by FDG-PET and I-UPS. Mice were imaged at sagittal position to show false positives from brown adipose tissue in the neck (2 out 3 mice) in FDG-PET images.

Figure 81:
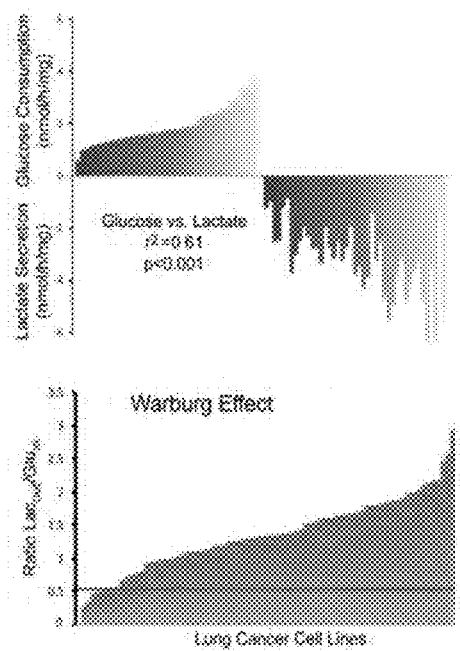

FIG. 81 shows the rates of glucose consumption and lactate secretion from a panel of 80 human non-small cell lung cancer cells. These lung cancer cells display a divergent glycolysis rates as represented by the ratio of Lac$_{out}$/Glu$_{in}$.

Figure 82:
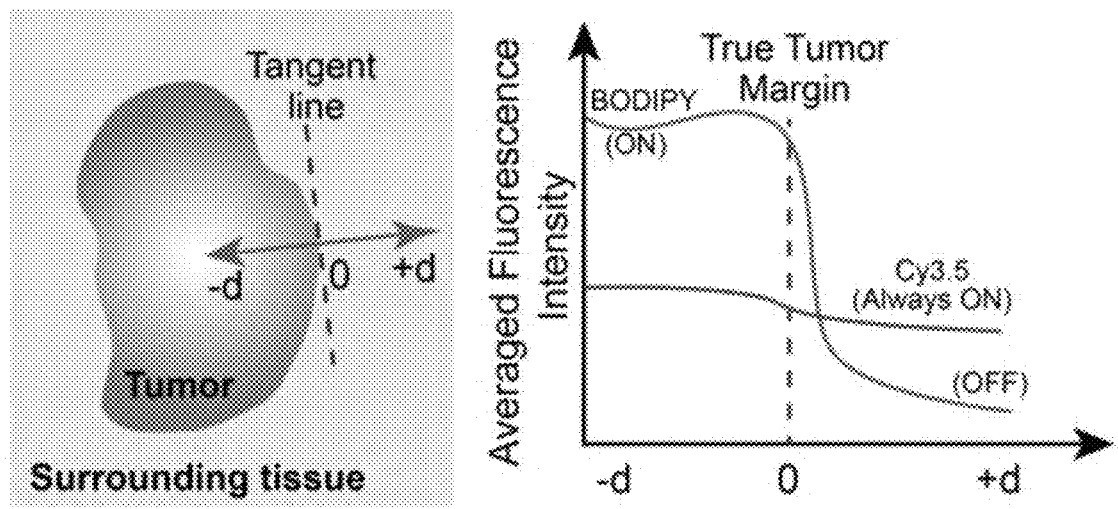

FIG. 82 shows schematic quantifying the BODIPY and Cy3.5 signals and correlating with true tumor margin delineated by histology. Fluorescence intensity along the perpendicular line to a tumor tangent point will be measured. Averaged intensity vs distance will be determined from multiple tangent points along tumor margins.

FIGS. 83A-B show comparison of PK/BD of two UPS nanoprobes with comparable size but different pH transitions.

Figures 84A, 84B, 84C:
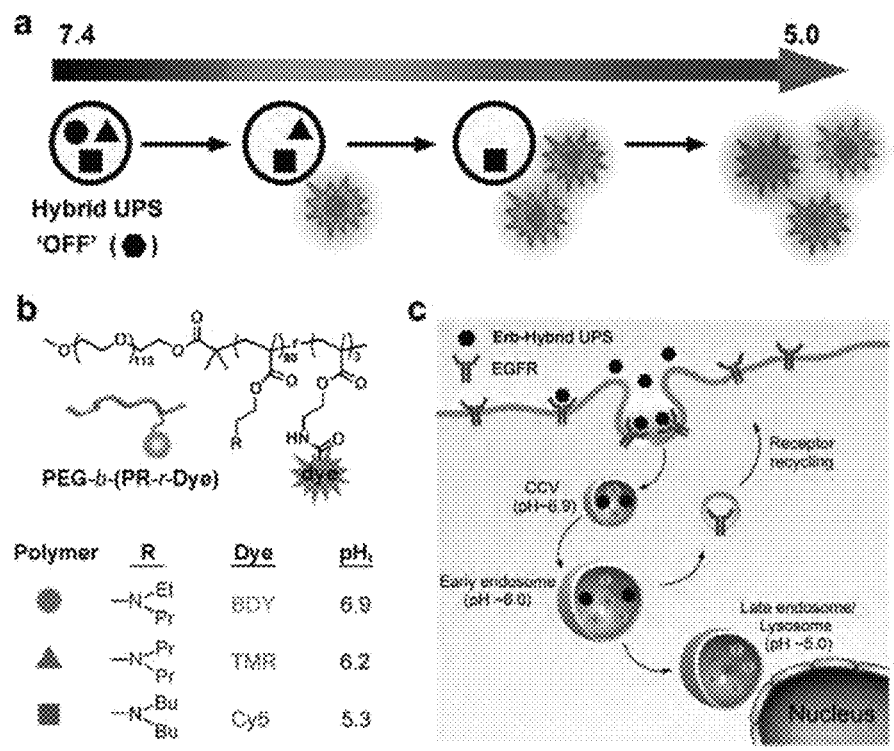

FIGS. 84A-84C show the schematic design and working principle of the multi-spectral hybrid UPS nanoprobe. FIG. 84A: The multi-spectral hybrid UPS nanoprobe is engineered by three PEG-b-PR block copolymers each encoded with different fluorescent dyes. The hybrid UPS nanoprobe stays "OFF" at neutral pH. When the pH is lowered, the PEG-b-(PR-r-dye) components disassemble and fluoresce sequentially to present different colors upon encountering subtle pH changes. FIG. 84B: The chemical structures of the PEG-b-PR block copolymers and fluorescent dye conjugated polymers. FIG. 84C: The internalization and activation of the multi-spectral hybrid UPS nanoprobe in live cells through the receptor-mediated endocytosis, such as endothelial growth factor receptor (EGFR). After internalization, the PEPA-BDY493 is turned ON by clathrin-coated vesicles (CCV, pH~ 6.8), then the PDPA-TMR is activated by early endosomes (pH~ 6.0), finally the PDBA-Cy5 is turned ON by the late endosome/lysosome (pH~ 5.0-5.5).

Figures 85A, 85B:
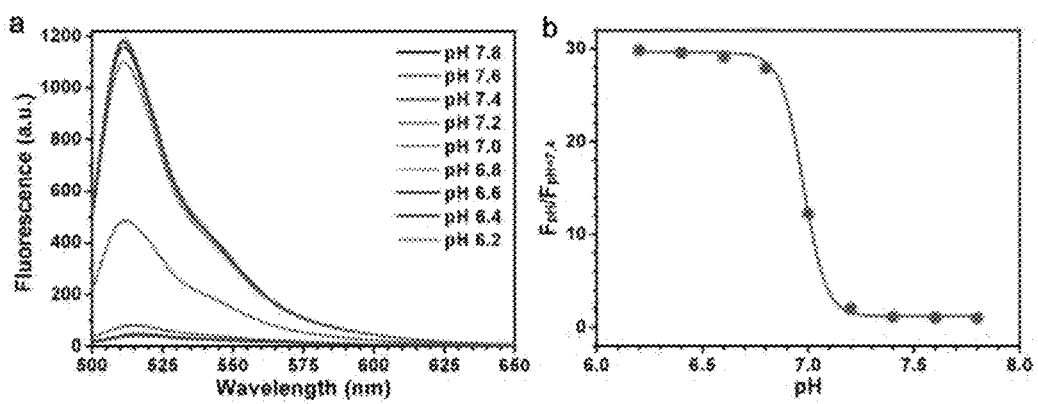

FIGS. 85A & 85B show (FIG. 85A) pH-dependent fluorescence emission spectra and (FIG. 85B) fluorescence intensity ratio of PEPA-BDY493 as a function of pH in 0.1 M PBS solution. The samples are excited at 488 nm, and the emission spectra are collected from 500 to 650 nm. The polymer concentrations are controlled at 0.1 mg/mL.

Figures 86A, 86B:
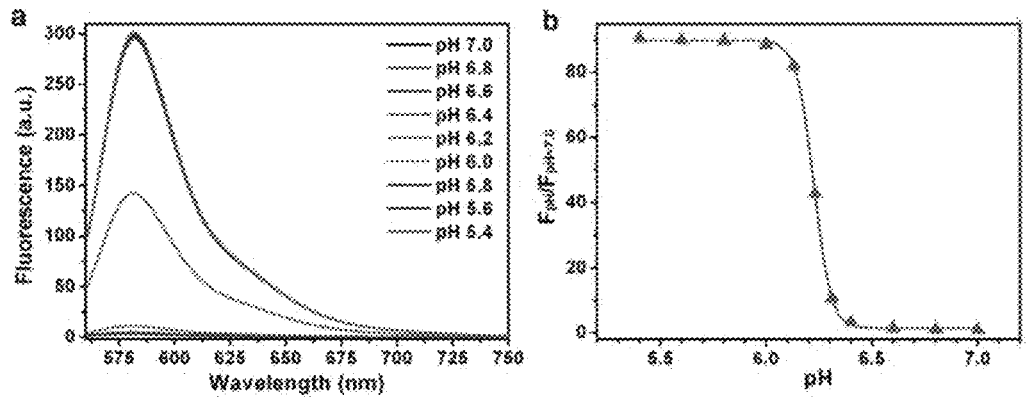

FIGS. 86A & 86B show (FIG. 86A) pH-dependent fluorescence emission spectra and (FIG. 86B) fluorescence intensity ratio of PDPA-TMR as a function of pH in 0.1 M PBS solution. The samples are excited at 545 nm, and the emission spectra are collected from 560 to 750 nm. The polymer concentrations are controlled at 0.1 mg/mL.

Figures 87A, 87B:
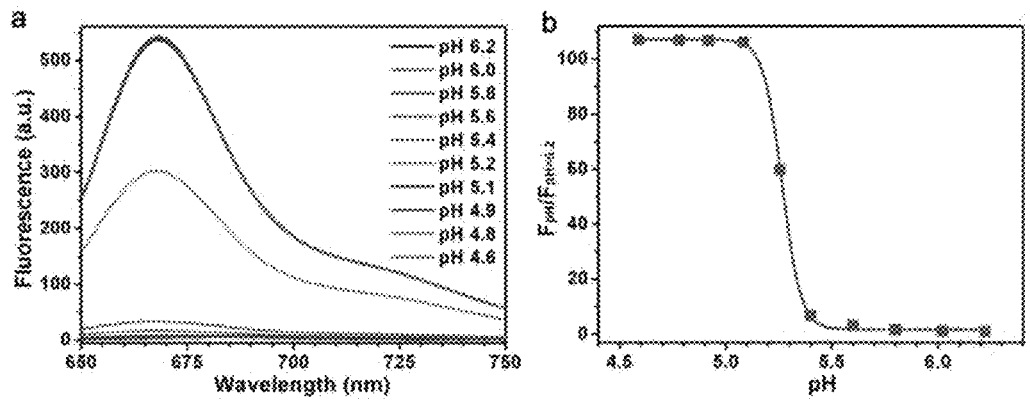

FIGS. 87A & 87B show (FIG. 87A) pH-dependent fluorescence emission spectra and (FIG. 87B) fluorescence intensity ratio of PDBA-Cy5 as a function of pH in 0.1 M PBS solution. The samples are excited at 640 nm, and the emission spectra are collected from 650 to 750 nm. The polymer concentrations are controlled at 0.1 mg/mL.

Figure 88:
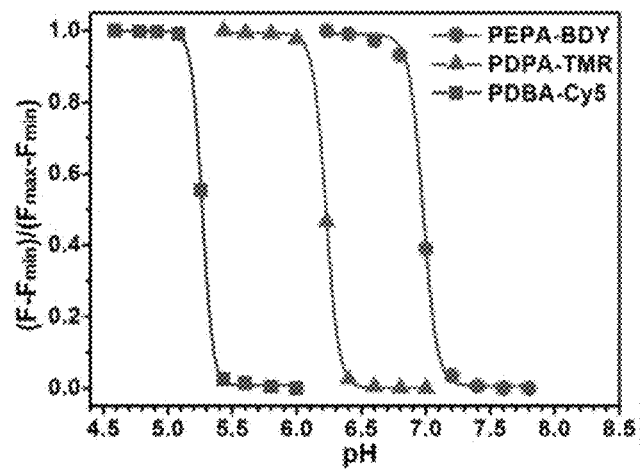

FIG. 88 shows normalized fluorescence intensity as a function of pH for PEPA-BDY493, PDPA-TMR, and PDBA-Cy5 micelles. The polymer concentrations were 100 μg/mL.

Figures 89A, 89B:
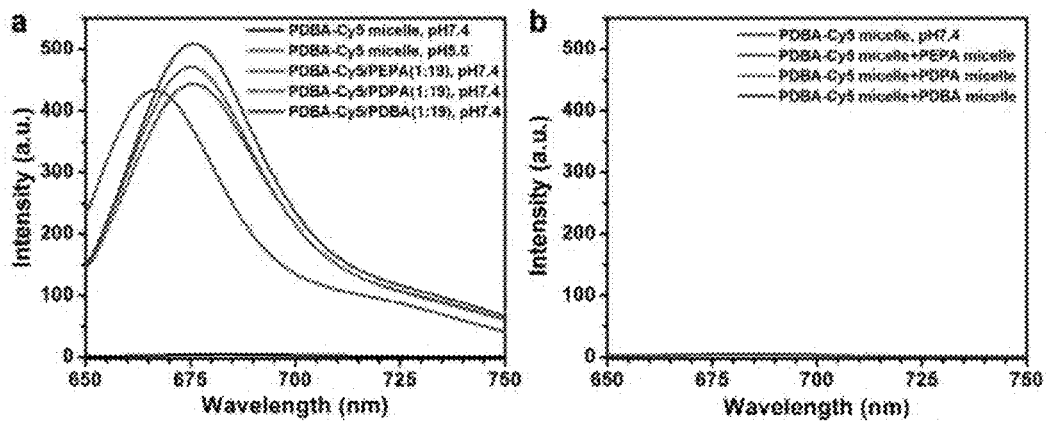

FIGS. 89A & 89B show fluorescence characterization of molecularly mixed micelles and micelle mixture. (FIG. 89A) Fluorescence intensity of molecularly mixed micelles of PDBA-Cy5 and PEG-b-(PR-r-AMA$_3$) with molar ratio of 1:19 at pH 7.4. (FIG. 89B) Fluorescence intensity of micelles mixture of PDBA-Cy5 micelle and PEG-b-(PR-r-AMA$_3$) micelle with molar ratio of 1:19 at pH 7.4.

Figures 90A, 90B, 90C, 90D:
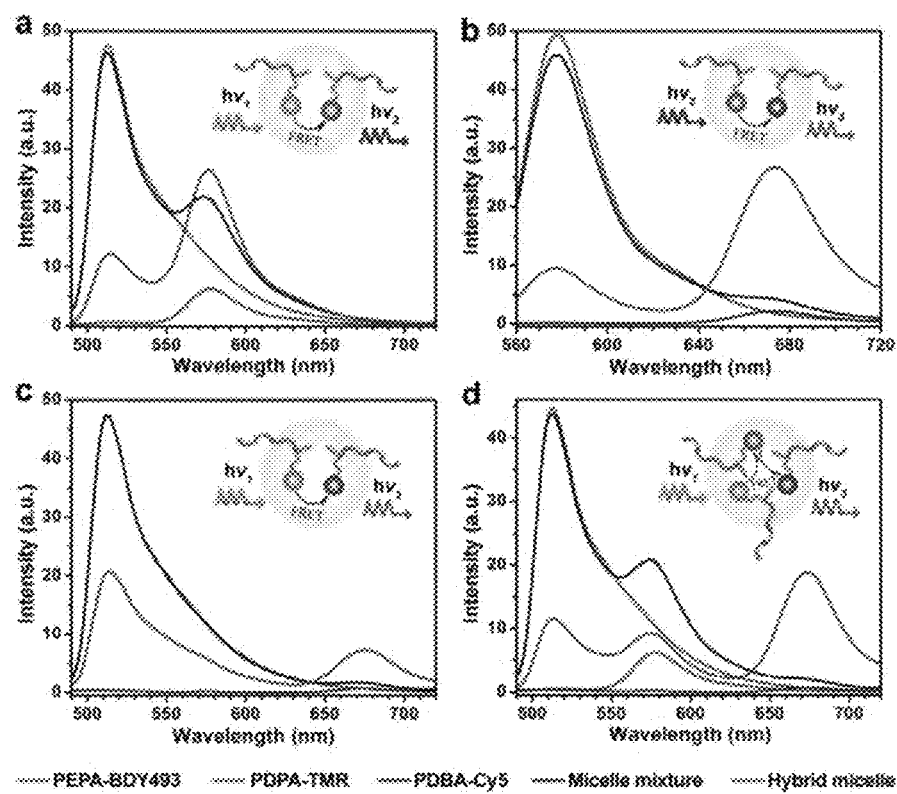

FIGS. 90A-90D show fluorescent resonance energy transfer (FRET) experiments demonstrate the formation of the multi-spectral hybrid UPS nanoprobe. The PEG-6-PR block copolymers are encoded with different dyes. Three exemplary PEG-b-(PR-r-Dye) block copolymers, including PEPA-BDY493, PDPA-TMR, and PDBA-Cy5 are synthesized with a low dye/polymer ratio (1:1) to minimize the homoFRET effect. FIG. 90A: The PEPA-BDY493, PDPA-TMR, PEPA-BDY493/PDPA-TMR (1:1) micelles, and micelle mixture of PEPA-BDY493 and PDPA-TMR are excited at 485 nm, then the emission spectra are collected from 490 to 720 nm. A strong FRET effect from PEPA-BDY493 to PDPA-TMR is observed, indicating the formation of the PEPA/PDPA hybrid nanoparticle. FIG. 90B: A strong FRET effect from PDPA-TMR to PDBA-Cy5 is observed, indicating the formation of the PDPA/PDBA hybrid nanoparticle. FIG. 90C: A strong FRET effect from PEPA-BDY493 to PDBA-Cy5 is observed, indicating the formation of the PEPA/PDBA hybrid nanoparticle. FIG. 90D: A strong sequential FRET effects from BDY493 to TMR, finally to Cy5 are observed, indicating the formation of the PEPA/PDPA/PDBA hybrid nanoparticle.

Figure 91:
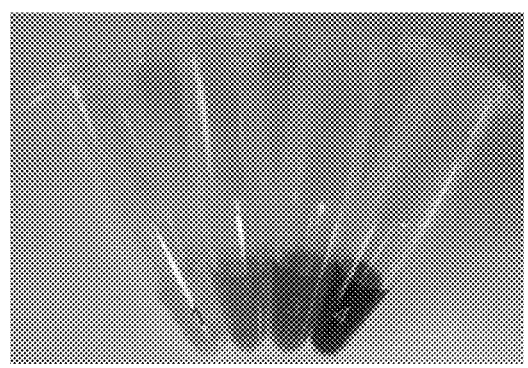

FIG. 91 shows representative images of dye-conjugated polymeric micelles, including PEPA-BDY493 (1), PDPA-TMR (2), PDBA-Cy5 (3), and three-in-one hybrid nanoprobe (4).

FIGS. 92A-92F show the in vitro characterization of the hybrid nanoprobe. (FIGS. 92A-92D) Fluorescence spectra of the hybrid nanoprobe in different pH buffers. The BDY493, TMR, and Cy5 signals are excited at 485, 545, and 640 nm, respectively. The emission spectra for BDY493, TMR, and Cy5 are collected from 490-750 nm, 560-750, and 650-750 nm, respectively. (FIG. 92E) The count rates and normalized fluorescence intensity of hybrid nanoprobe as a function of time are plotted. The count rates at different pH are determined by dynamic light scattering analysis. The multi-stage activation of the multi-spectral hybrid UPS nanoprobe is shown by green, red, and blue sigmoidal curves at different pH ranges. (FIG. 92F) Representative fluorescence images of multi-spectral UPS nanoprobe at different pH are captured. Yellow is the merged color of green and red signals. White is the merged color of blue, green, and red signals.

FIGS. 93A-93F show pH-dependent fluorescence emission spectra of hybrid nanoprobe. BDY493, TMR, and Cy5 signals were excited at 485, 545, and 640 nm, respectively.

The corresponding emission spectra were collected at 490-750, 560-750, and 650-750 nm, respectively.

Figure 94:
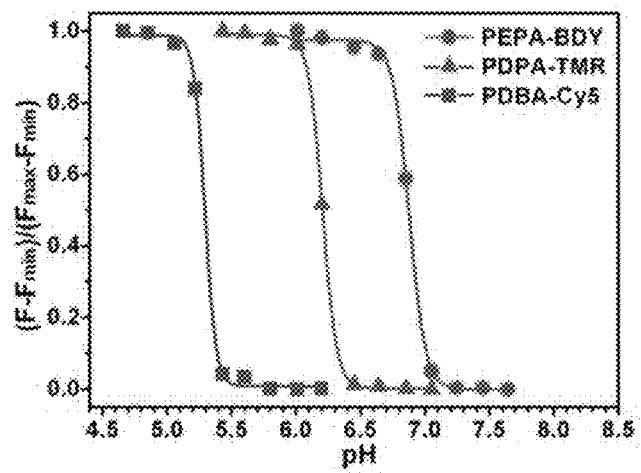

FIG. 94 shows normalized fluorescence intensity of PEPA-BDY493, PDPA-TMR, and PDBA-Cy5 components in hybrid UPS nanoprobe as a function of pH.

Figures 95A, 95B:
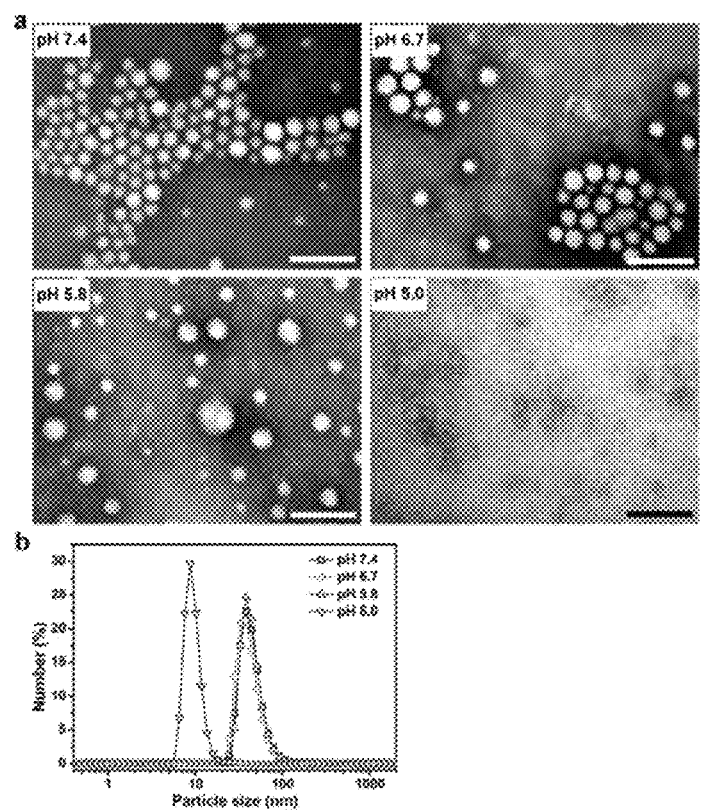

FIGS. 95A & 95B show (FIG. 95A) TEM and (FIG. 95B) DLS analyses of morphology and particle size distribution of hybrid nanoprobes at different pH solution. The scale bar is 100 nm in the TEM images.

Figure 96:
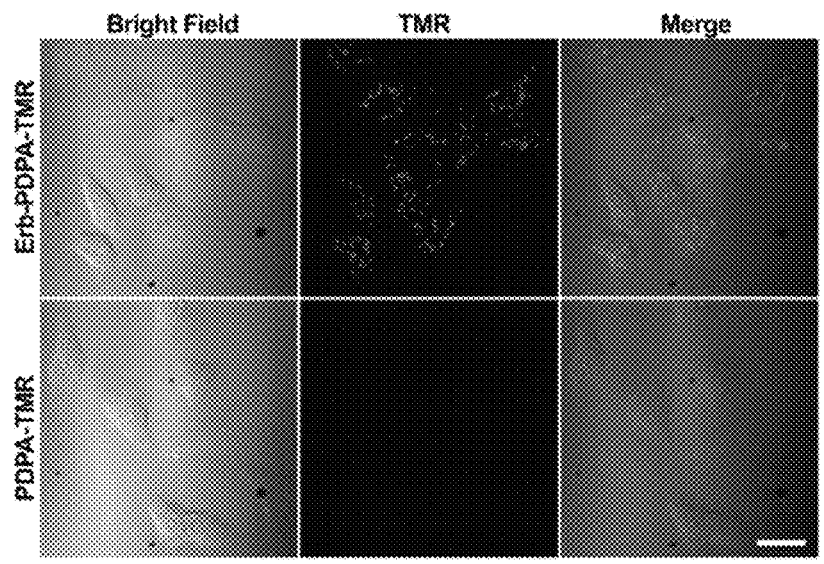

FIG. 96 shows specific fluorescence activation of Erbitux-conjugated PDPA-TMR nanoprobes in A549 cells. The cells were treated with Erbitux-conjugated PDPA-TMR micelle (upper) or PDPA-TMR micelles (lower) for 1 hour, respectively. The scale bar is 40 μm.

Figure 97:
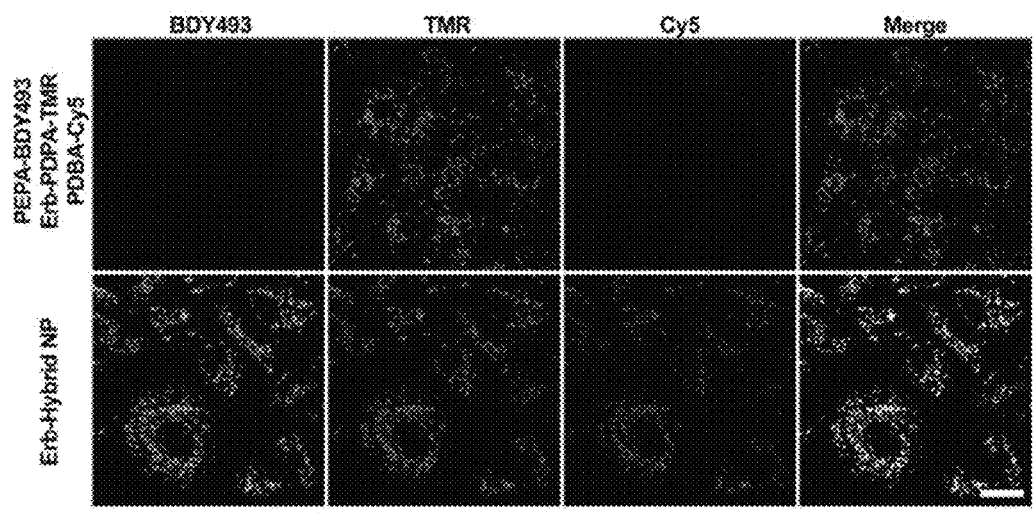

FIG. 97 shows synchronized uptake of Erbitux-encoded hybrid UPS nanoprobes in single endocytic organelle of A549 human lung cancer cells. Tumor cells were incubated with nanoprobes for 3 hours followed by confocal imaging. The scale bar is 40 μm.

Figure 98:
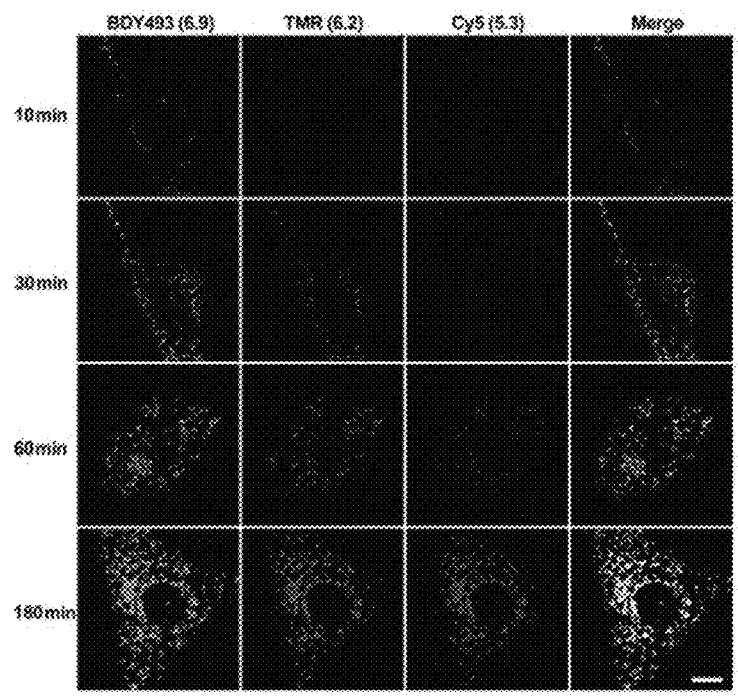

FIG. 98 shows multiplexed imaging of endosome maturation by multi-colored hybrid nanoprobes in lung cancer A549 cells. Scale bar is 20 μm.

Figure 99:
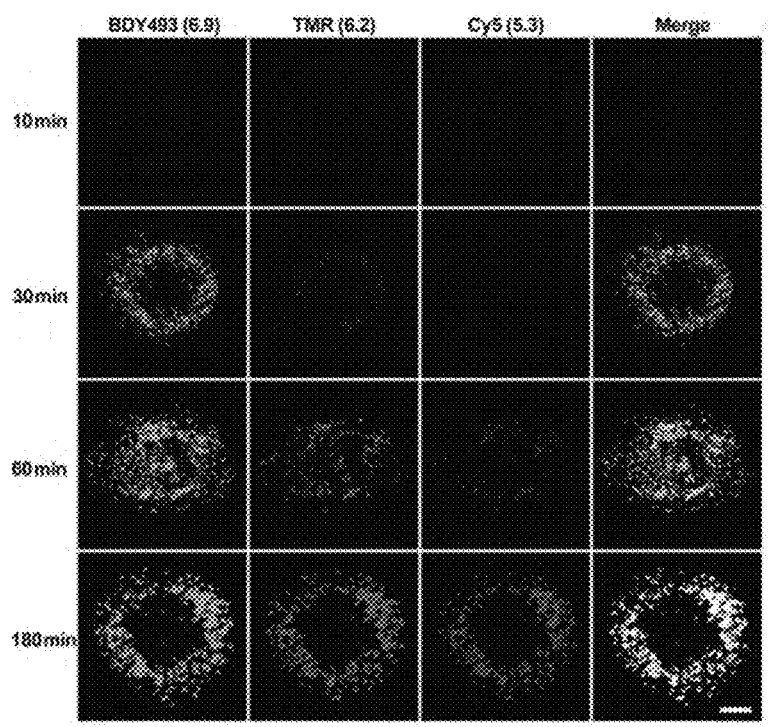

FIG. 99 shows multiplexed imaging of endosome maturation by multi-colored hybrid nanoprobes in head and neck cancer HN5 cells. Scale bar is 20 μm.

Figure 100:
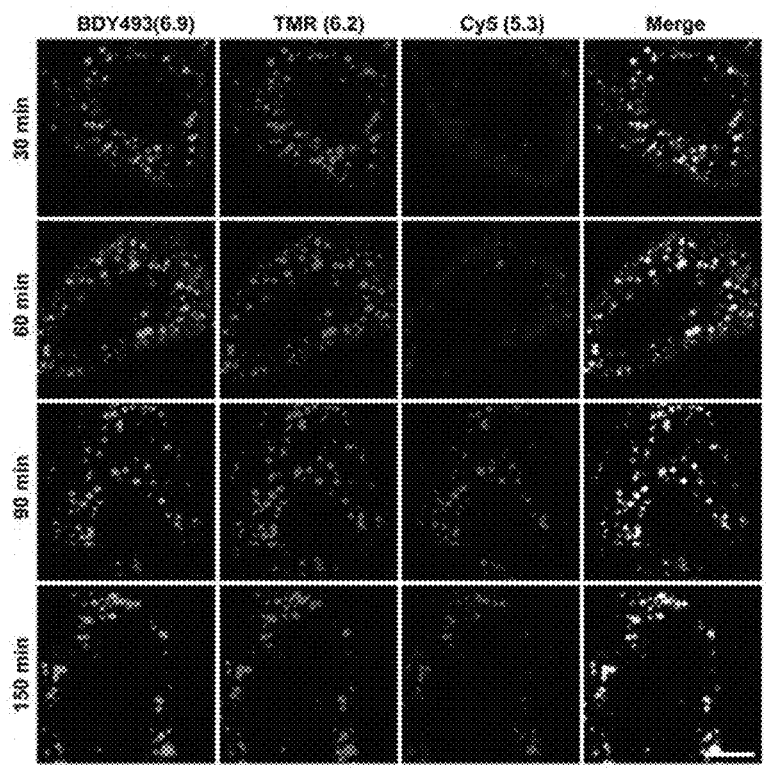

FIG. 100 shows multiplexed imaging of endosome maturation by multi-colored hybrid nanoprobes in human lung cancer H460 cell line, which has KRAS gene mutation. Scale bar is 20 μm.

Figure 101:
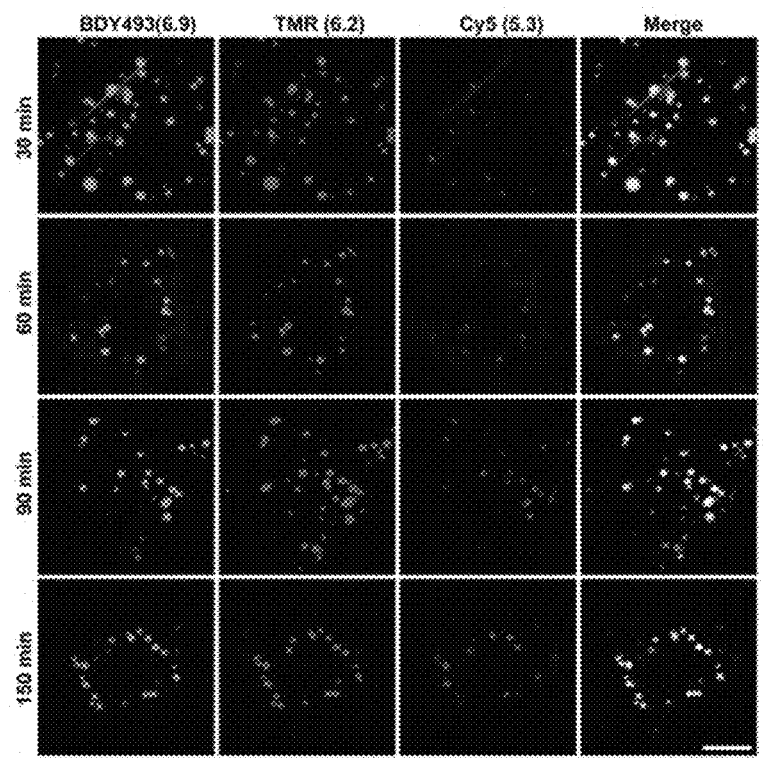

FIG. 101 shows multiplexed imaging of endosome maturation by multi-colored hybrid nanoprobes in human lung cancer A549 cell line, which has KRAS gene mutation. Scale bar is 20 μm.

Figure 102:
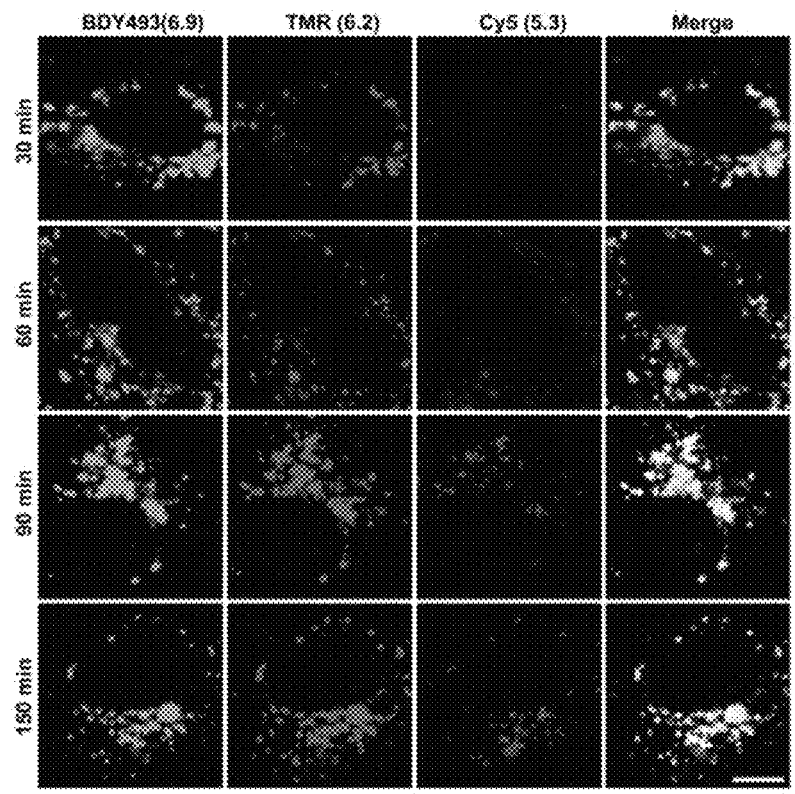

FIG. 102 shows multiplexed imaging of endosome maturation by multi-colored hybrid nanoprobes in human lung cancer H2882 cell line, which has P53 gene mutation. Scale bar is 20 μm.

Figures 103A, 103B:
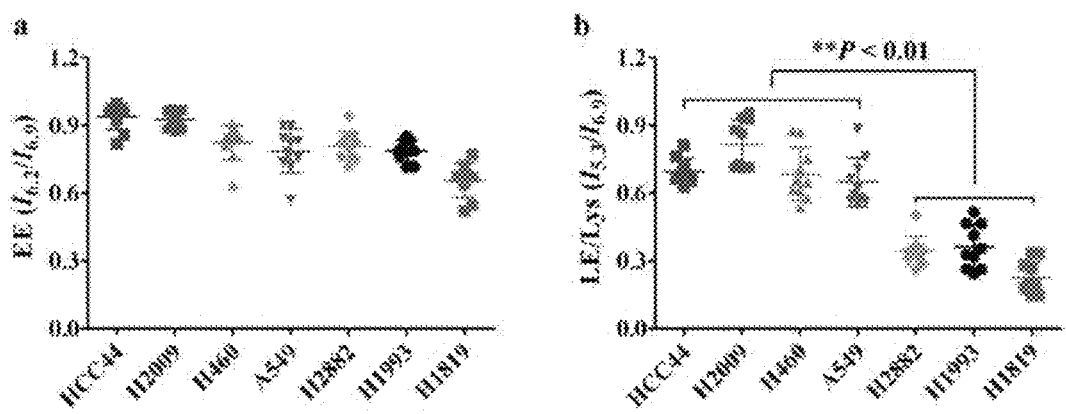

FIGS. 103A & 103B show organelle maturation in a panel of lung cancer cell lines. Quantification of maturation rates of early endosomes (FIG. 103A) and late endosomes/lysosomes (FIG. 103B) pinpoint Kras mutation being responsible for the phenotypic difference. The fluorescence intensity of PDPA-TMR ($I_{6.2}$) in early endosome (EE) at 30 min is normalized by PEPA-BDY493 signals ($I_{6.9}$). The fluorescence intensity of PDBA-Cy5 ($I_{5.3}$) in late endosome/lysosome (LE/Lys) at 75 min is normalized by PEPA-BDY493 signals ($I_{6.9}$). Significant difference between Kras mutated cell lines and Kras wild type cell lines indicates KRAS mutation is responsible for the late endosome/lysosome maturation. **P<0.01, paired, two-sided t-test; n=10.

Figures 104A, 104B, 104C, 104D:
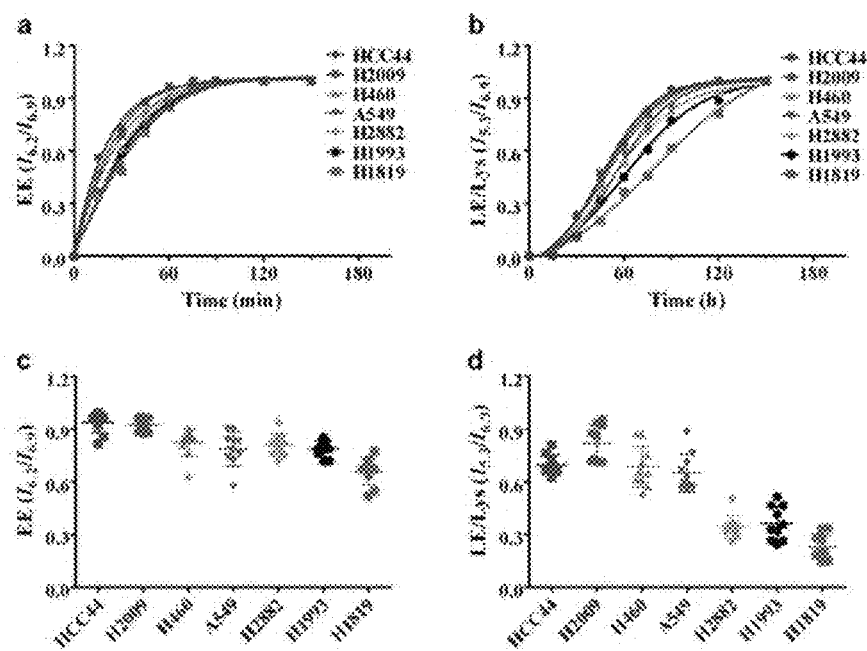

FIGS. 104A-104D show organelle maturation in a panel of lung cancer cell lines. Quantification of maturation rates of early endosomes (FIG. 104A) and late endosomes/lysosomes (FIG. 104B) pinpoint Kras mutation being responsible for the phenotypic difference. FIG. 104C: The fluorescence intensity of PDPA-TMR ($I_{6.2}$) in early endosome (EE) at 30 min is normalized by PEPA-BDY493 signals ($I_{6.9}$). FIG. 104D: The fluorescence intensity of PDBA-Cy5 ($I_{5.3}$) in late endosome/lysosome (LE/Lys) at 75 min is normalized by PEPA-BDY493 signals ($I_{6.9}$). Significant difference between K-ras mutated cell lines and K-ras wild-type cell lines indicates KRAS mutation is responsible for the late endosome/lysosome maturation. **P<0.01, paired, two-sided t-test; n=10.

Figures 105A, 105B:
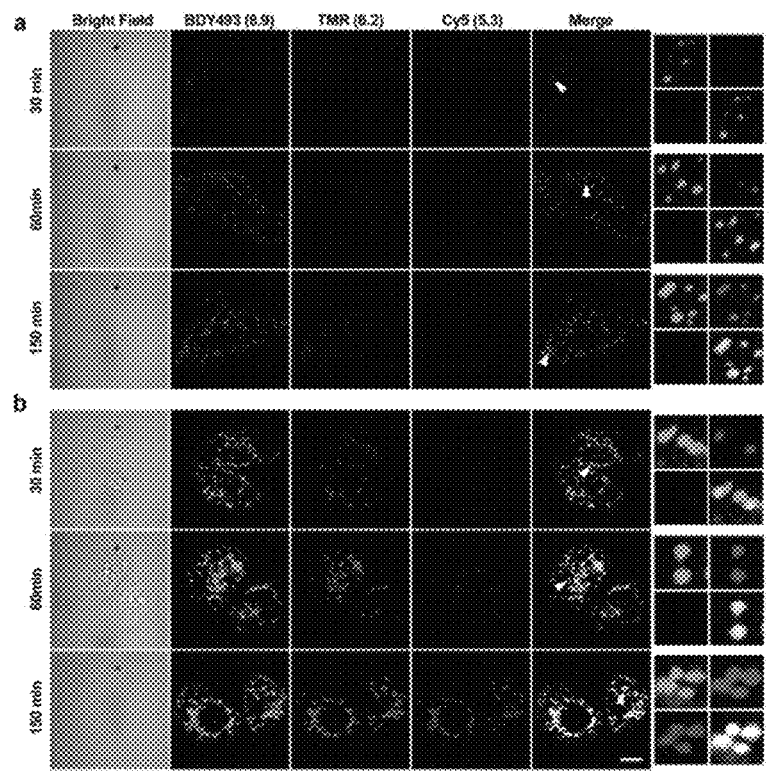

FIGS. 105A & 105B shows multistage pH imaging of organelle maturation during endocytosis using multi-spectral hybrid UPS nanoprobes in living cells. HBEC30 lung epithelial cells (FIG. 105A) and isogenic HCC4017 lung cancer cells (FIG. 105B) are incubated with 100 μg/mL Erbitux-conjugated hybrid UPS nanoprobe at 4° C. for 30 min, washed, and imaged in real time at 37° C. under a confocal microscope. The PEPA-BDY493, PDPA-TMR, and PDBA-Cy5 signals are excited at 488, 543, and 637 nm, respectively. FITC (515/30BP), TRITC (590/75BP), and Cy5 (650LP) filters are used for PEPA-BDY493, PDPA-TMR, and PDBA-Cy5 image capture, respectively. BDY493, TMR, and Cy5 are shown as green, red, and blue colors, respectively. The scale bar is 20 μm.

Figure 106:
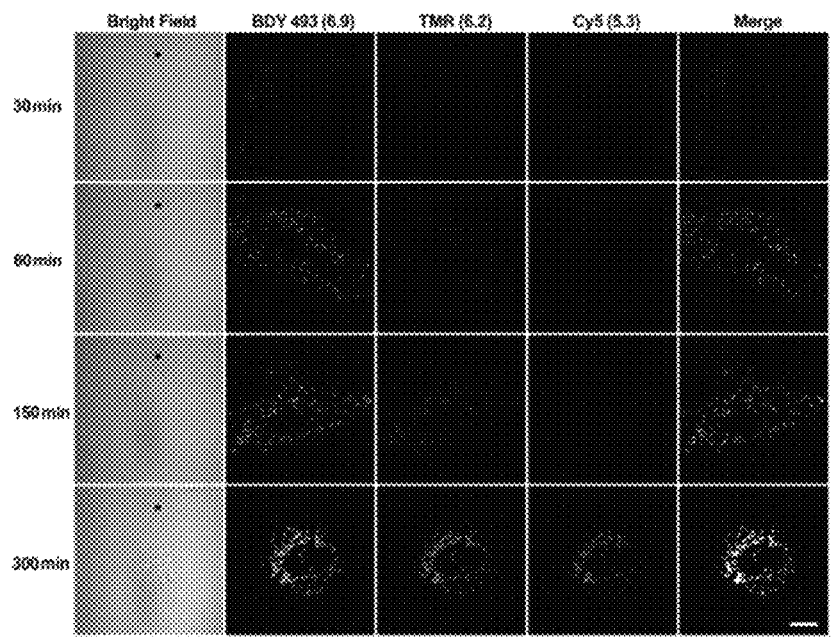

FIG. 106 shows multiplexed imaging of endosome maturation by multi-colored hybrid nanoprobes in HBEC30KT human epithelial cells. The scale bar is 20 μm.

Figure 107:
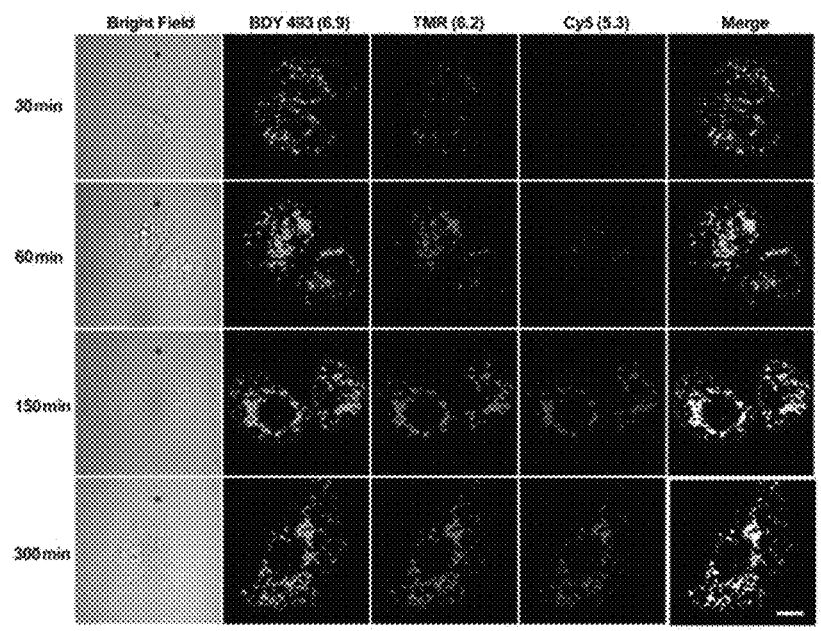

FIG. 107 shows multiplexed imaging of endosome maturation by multi-colored hybrid nanoprobes in human isogenic HCC4017 lung cancer cells. The scale bar is 20 μm.

Figure 108:
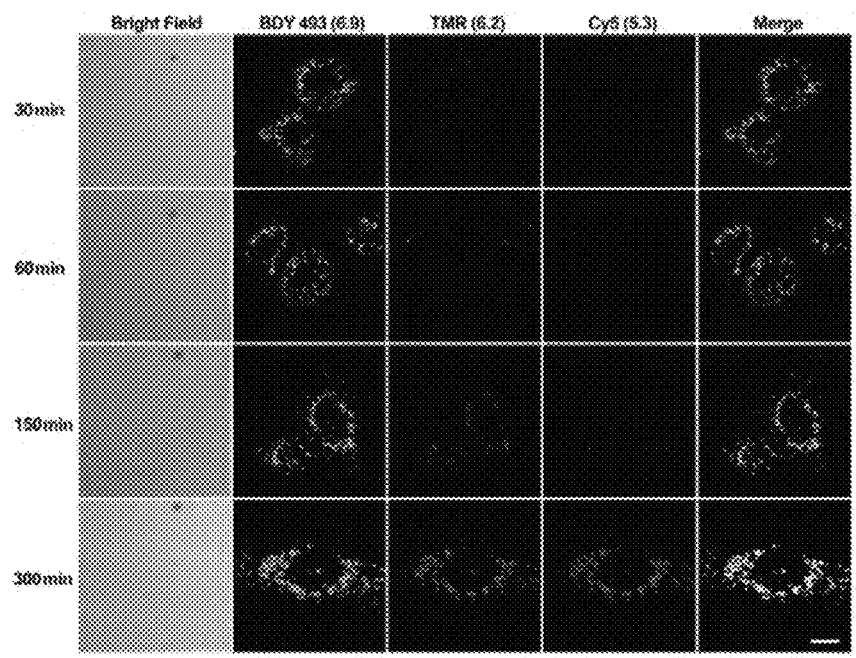

FIG. 108 shows multiplexed imaging of endosome maturation by multi-colored hybrid nanoprobes in HBEC30KT-5/2TP53 cells. The scale bar is 20 μm.

Figure 109:
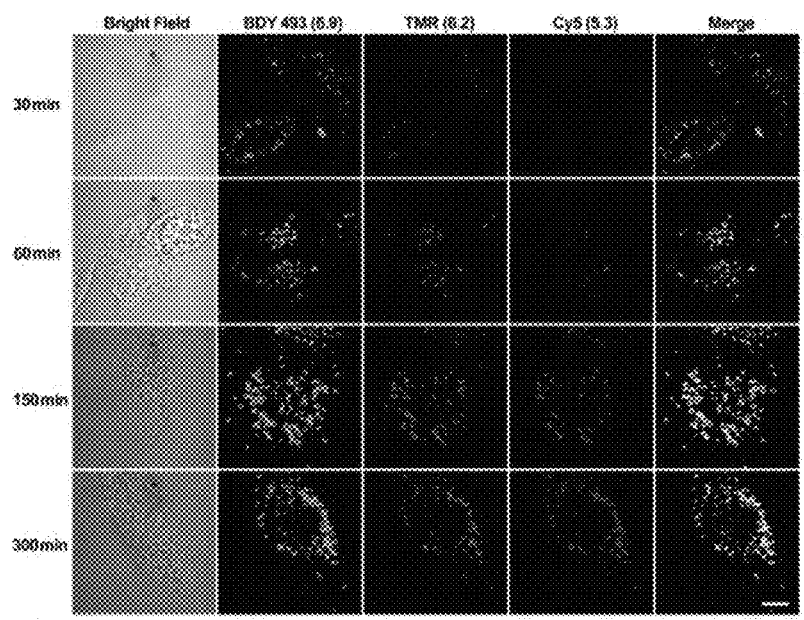

FIG. 109 shows multiplexed imaging of endosome maturation by multi-colored hybrid nanoprobes in HBEC30KT-shTP53/KRAS$^{G12V}$ cells. The scale bar is 20 μm.

Figure 110:
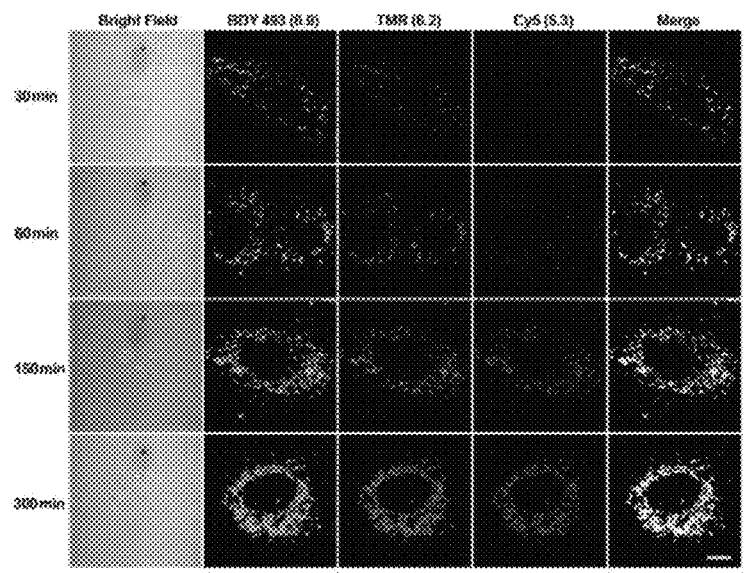

FIG. 110 shows multiplexed imaging of endosome maturation by multi-colored hybrid nanoprobes in HBEC30KT-shTP53/KRAS$^{G12V}$/shLKB1 cells. The scale bar is 20 μm.

Figures 111A, 111B, 111C, 111D:
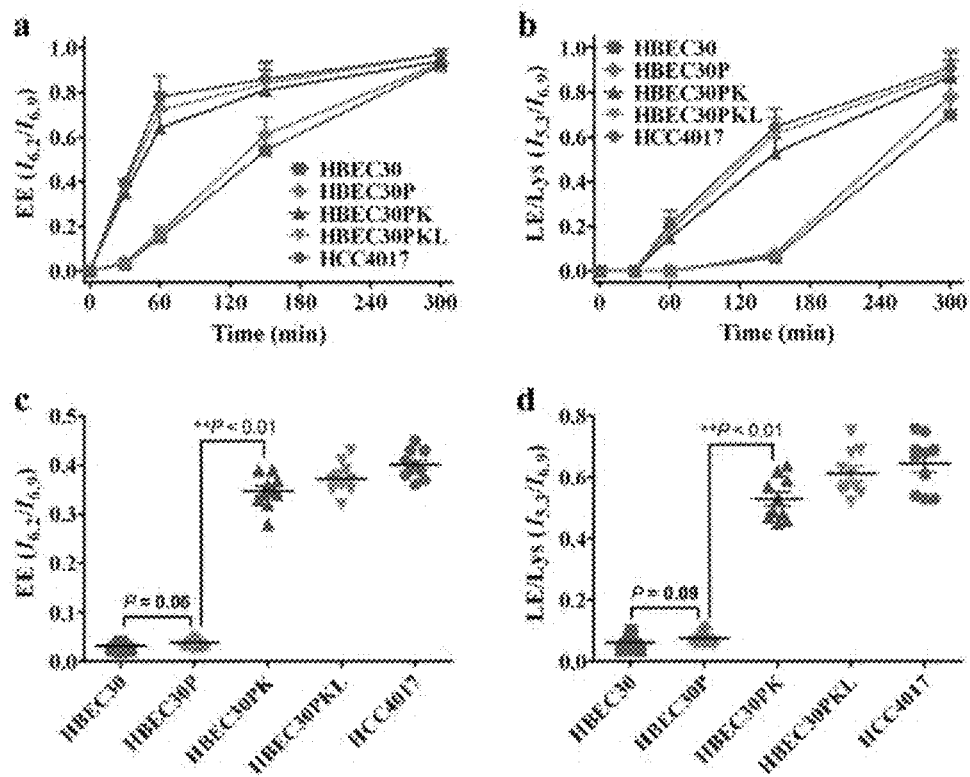

FIGS. 111A-111D show time-course organelle maturation in an isogenic progression series of HBEC30 cells. Quantification of maturation rates of early endosomes (FIG. 111A) and late endosomes/lysosomes (FIG. 111B) pinpoint Kras mutation being responsible for the phenotypic difference. FIG. 111C: The fluorescence intensity of PDPA-TMR ($I_{6.2}$) in early endosome (EE) at 30 min was normalized by PEPA-BDY493 signals ($I_{6.9}$). Significant difference between HBEC30KT-shTP53 and HBEC30KT-shTP53/KRAS$^{G12V}$ cells indicates KRAS mutation is responsible for the early endosome maturation. P<0.01, paired, two-sided t-test; n=10. FIG. 111D: The fluorescence intensity of PDBA-Cy5 ($I_{5.3}$) in late endosome/lysosome (LE/Lys) at 150 min was normalized by PEPA-BDY493 signals ($I_{6.9}$). Significant difference between HBEC30KT-shTP53 and HBEC30KT-shTP53/KRAS$^{G12V}$ cells indicates KRAS mutation is responsible for the late endosome/lysosome maturation. P<0.01, paired, two-sided t-test; n=10.

Figures 112A, 112B, 112C:
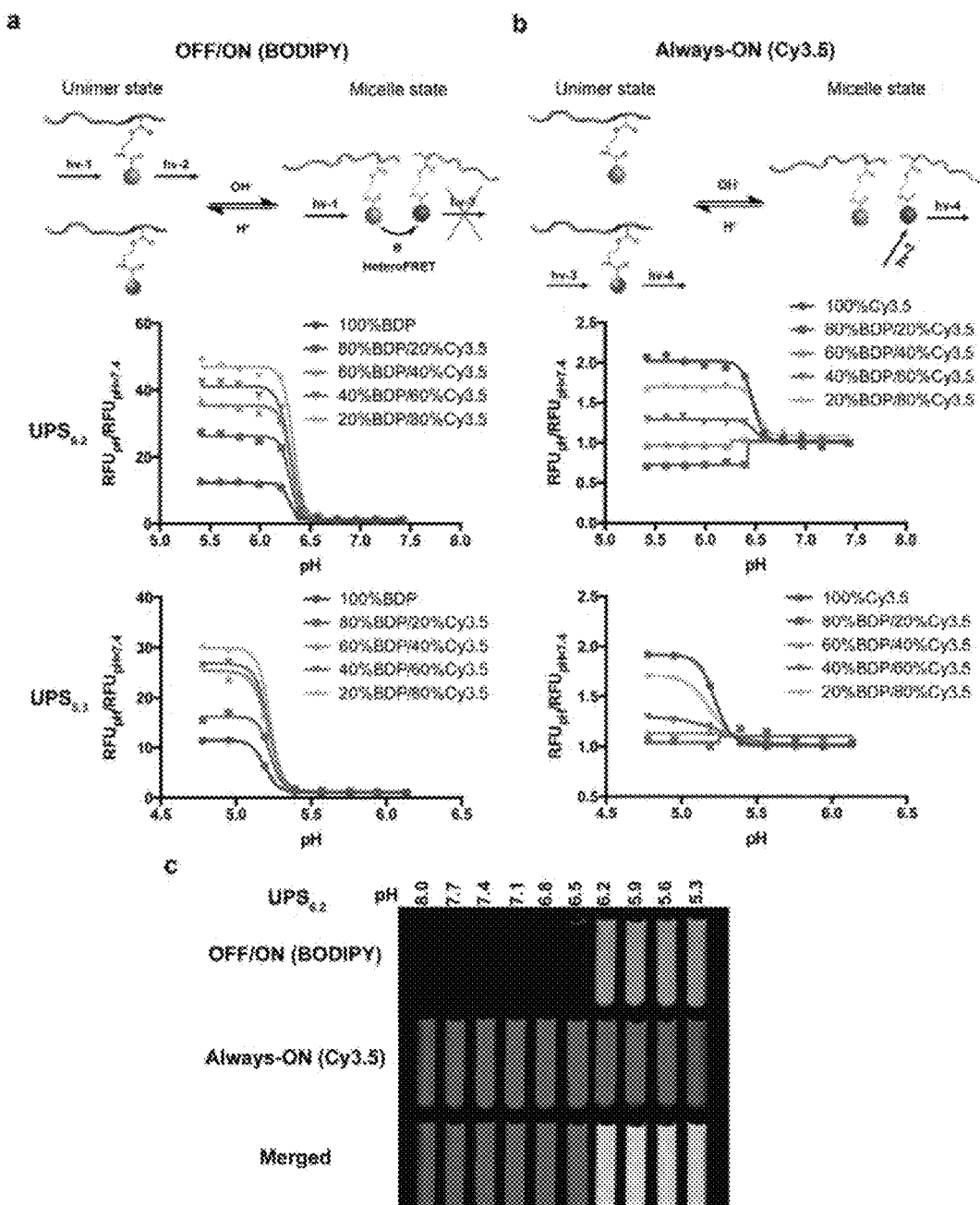

FIGS. 112A-112C show the syntheses and characterization of Always-ON/OFF-ON UPS nanoparticles. (FIG. 112A) and (FIG. 112B) Schematic of the dual-reporter nanoparticle. In the micelle state, the Always-ON dyes serve as the quencher for the ON/OFF fluorophores. When the micelle is disassembled, the Always-ON and ON/OFF fluorophores can fluoresce independently. The ON/OFF ratio of BODIPY (FIG. 112A) and Cy3.5 (FIG. 112B) varies when the ratio of polymers conjugated with these two dyes varies. Weight fraction of 60% BODIPY-conjugated copolymer with 40% Cy3.5-conjugated copolymer was chosen as the final combination. (FIG. 112C) Fluorescence signal amplification of UPS$_{6.2}$ nanoprobes as a function of pH. Images were captured on Maestro in vivo imaging system (CRI) using the green and yellow filters.

Figures 113A, 113B:
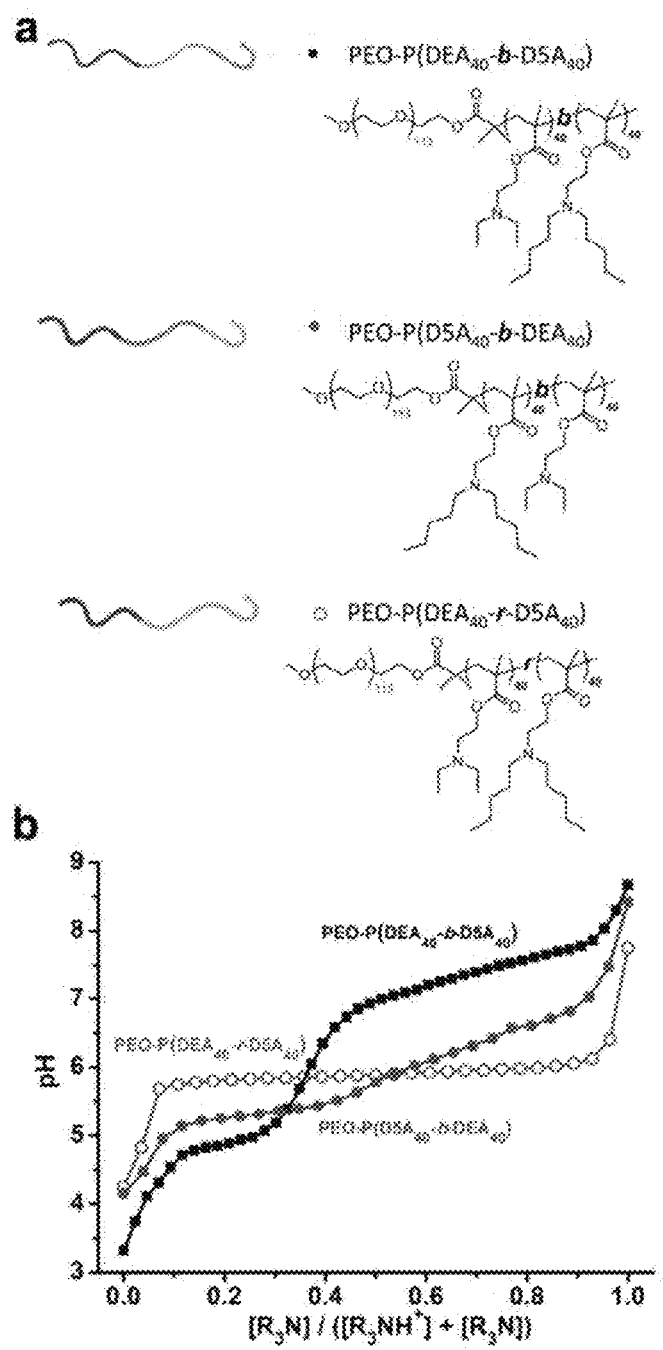

FIGS. 113A & 113B show the chemical structures of triblock copolymers PEO-6-P(DEA-b-D5A), PEO-b-P(D5A$_{40}$-b-DEA$_{40}$) and random block polymer PEO-b-P(DEA-r-D5A) (FIG. 113A). pH titration curves for PEO-b-P(D5A$_{40}$-b-DEA$_{40}$), PEO-b-P(DEA 40-b-D5A$_{40}$) and PEO-b-P(D5A$_{40}$-r-DEA$_{40}$) copolymers as a function of molar fraction of tertiary amino groups (FIG. 113B).

Figures 114A, 114B:
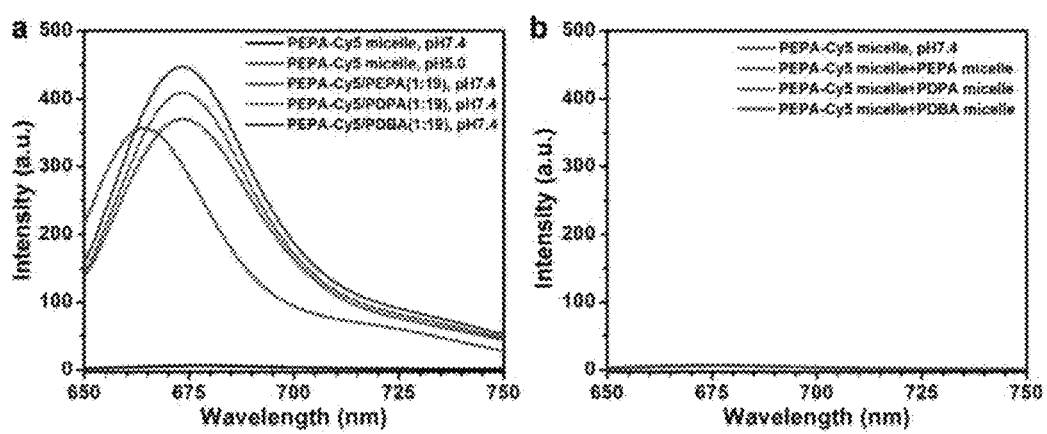

FIGS. 114A & 114B show fluorescence characterization of molecularly mixed micelles and micelle mixture. (FIG. 114A) Fluorescence intensity of molecularly mixed micelles of PEPA-Cy5 and PEG-b-(PR-r-AMA$_3$) with molar ratio of 1:19 at pH 7.4. (FIG. 114B) Fluorescence intensity of micelles mixture of PEPA-Cy5 micelle and PEG-b-(PR-r-AMA$_3$) micelle with molar ratio of 1:19 at pH 7.4.

DESCRIPTION OF ILLUSTRATIVE EMBODIMENTS

In some aspects, the present disclosure provides a polymer which can form a pH responsive nanoparticle which dissembles above a particular transition pH. In some embodiments, these polymers comprise a mixture of different monomers which allow specific tailoring of the desired pH transition point ($\Delta pH_{10-90\%}$) of less than 0.25 pH units as well as develop pH probes for a range of pH transition points from about a pH of 4 to about a pH of 8. The wide range of pH transition points allows for a wide range of application including but not limited to vesicular trafficking, imaging of the pH$_e$ of tumors, delivering drug compounds to specific tissues, improving the visualization of a tumor to improve the ability for a surgeon to resect the tumor tissue, or study the maturation or development of endosomes/lysosomes. In some aspects, the present disclosure provides methods of using these polymers in a pH responsive system as described above. Additional methods of using the polymers and the resultant pH responsive systems of the present disclosure are described in WO 2013/152059, which is incorporated herein by reference.

A. CHEMICAL DEFINITIONS

When used in the context of a chemical group: "hydrogen" means —H; "hydroxy" means —OH; "carboxy" means —C(=O)OH (also written as —COOH or —CO$_2$H); "halo" means independently —F, —Cl, —Br or —I; "amino" means —NH$_2$; "nitro" means —NO$_2$; "cyano" means —CN; in a monovalent context "phosphate" means —OP(O)(OH)$_2$ or a deprotonated form thereof; in a divalent context "phosphate" means —OP(O)(OH)O— or a deprotonated form thereof; "mercapto" means —SH; and "thio" means=S; "sulfonyl" means —S(O)$_2$—; and "sulfinyl" means —S(O)—.

In the context of chemical formulas, the symbol means a single bond, "=" means a double bond, and "≡" means triple bond. The symbol " ===== " represents an optional bond, which if present is either single or double. The symbol " ---- " represents a single bond or a double bond. Thus, for example, the formula

includes

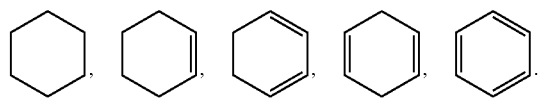

And it is understood that no one such ring atom forms part of more than one double bond. Furthermore, it is noted that the covalent bond symbol "—" when connecting one or two stereogenic atoms, does not indicate any preferred stereochemistry. Instead, it covers all stereoisomers as well as mixtures thereof. The symbol " ⌇ ", when drawn perpendicularly across a bond

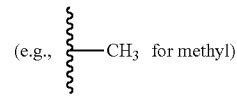

indicates a point of attachment of the group. It is noted that the point of attachment is typically only identified in this manner for larger groups in order to assist the reader in unambiguously identifying a point of attachment. The symbol " ◄ " means a single bond where the group attached to the thick end of the wedge is "out of the page." The symbol " ▬ " means a single bond where the group attached to the thick end of the wedge is "into the page". The symbol " ⌇ " means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

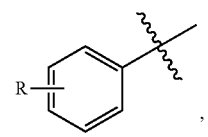

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

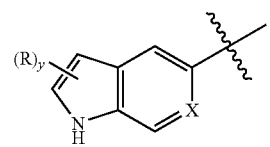

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms. (Cn-n') defines both the minimum (n) and maximum number (n') of carbon atoms in the group. Similarly, "alkyl$_{(C2-10)}$" designates those alkyl groups having from 2 to 10 carbon atoms.

The term "saturated" as used herein means the compound or group so modified has no carbon-carbon double and no carbon-carbon triple bonds, except as noted below. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl).

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups, —CH$_2$-(methylene), —CH$_2$CH$_2$—, —CH$_2$C(CH$_3$)$_2$CH$_2$—, and —CH$_2$CH$_2$CH$_2$—, are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the compound H—R, wherein R is alkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which one or more hydrogen atoms has been substituted with a halo group and no other atoms aside from carbon, hydrogen and halogen are present. The group, —CH$_2$Cl is a non-limiting example of a haloalkyl. The term "fluoroalkyl" is a subset of substituted alkyl, in which one or more hydrogen has been substituted with a fluoro group and no other atoms aside from carbon, hydrogen and fluorine are present. The groups, —CH$_2$F, —CF$_3$, and —CH$_2$CF$_3$ are non-limiting examples of fluoroalkyl groups.

The term "cycloalkyl" when used without the "substituted" modifier refers to a monovalent saturated aliphatic group with a carbon atom as the point of attachment, a linear or branched cyclo or cyclic structure, no carbon-carbon double or triple bonds, and no atoms other than carbon and hydrogen. As used herein, the cycloalkyl group may contain one or more branching alkyl groups (carbon number limit permitting) attached to the ring system so long as the point of attachment is the ring system. Non-limiting examples of cycloalkyl groups include: —CH(CH$_2$)$_2$ (cyclopropyl), cyclobutyl, cyclopentyl, or cyclohexyl. The term "cycloalkanediyl" when used without the "substituted" modifier refers to a divalent saturated aliphatic group with one or two carbon atom as the point(s) of attachment, a linear or branched cyclo or cyclic structure, no carbon-carbon double or triple bonds, and no atoms other than carbon and hydrogen.

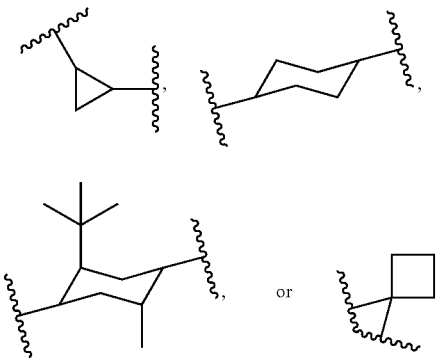

are non-limiting examples of cycloalkanediyl groups. The term "cycloalkylidene" when used without the "substituted" modifier refers to the divalent group =CRR' in which R and R' are taken together to form a cycloalkanediyl group with at least two carbons. Non-limiting examples of alkylidene groups include: =C(CH$_2$)$_2$ and =C(CH$_2$)$_5$. A "cycloalkane" refers to the compound H—R, wherein R is cycloalkyl as this term is defined above. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The following groups are non-limiting examples of substituted cycloalkyl groups: —C(OH)(CH$_2$)$_2$,

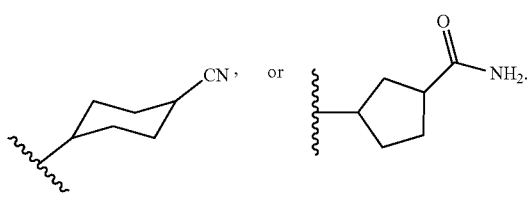 [SMILES: *C1CCC(C#N)CC1 ; "," ; "or" ; *C1CCC(C(N)=O)C1]

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —C$_6$H$_4$CH$_2$CH$_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

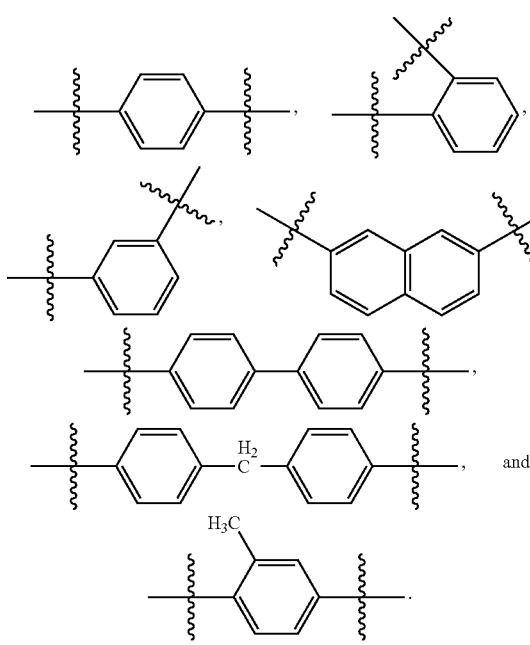

An "arene" refers to the compound H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "A-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

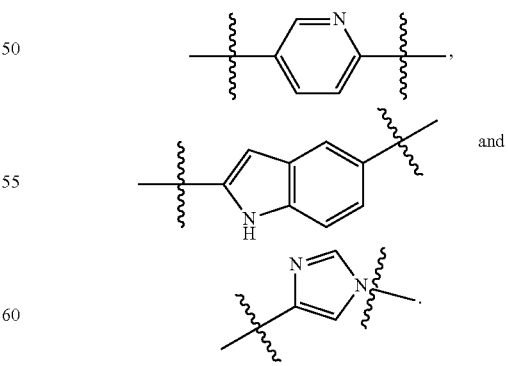

A "heteroarene" refers to the compound H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "acyl" when used without the "substituted" modifier refers to the group —C(O)R, in which R is a hydrogen, alkyl, cycloalkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C$_6$H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. When any of these terms are used with the "substituted" modifier one or more hydrogen atom (including a hydrogen atom directly attached the carbonyl or thiocarbonyl group, if any) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "alkoxy" when used without the "substituted" modifier refers to the group —OR, in which R is an alkyl, as that term is defined above. Non-limiting examples of alkoxy groups include: —OCH$_3$ (methoxy), —OCH$_2$CH$_3$ (ethoxy), —OCH$_2$CH$_2$CH$_3$, —OCH(CH$_3$)$_2$ (isopropoxy), and —OC(CH$_3$)$_3$ (tert-butoxy). The terms "cycloalkoxy", "alkenyloxy", "cycloalkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, cycloalkenyl, alkynyl, aryl, aralkyl, heteroaryl, heterocycloalkyl, and acyl, respectively. The term "alkoxydiyl" refers to the divalent group —O-alkanediyl-, —O-alkanediyl-O—, or -alkanediyl-O-alkanediyl-. The terms "alkylthio", "cycloalkylthio", and "acylthio" when used without the "substituted" modifier refers to the group —SR, in which R is an alkyl, cycloalkyl, and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy or cycloalkoxy group. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can each independently be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "cycloalkylamino", "alkenylamino", "cycloalkenylamino", "alkynylamino", "arylamino", "aralkylamino", "heteroarylamino", "heterocycloalkylamino" and "alkylsulfonylamino" when used without the "substituted" modifier, refers to groups, defined as —NHR, in which R is alkoxy, cycloalkyl, alkenyl, cycloalkenyl, alkynyl, aryl, aralkyl, heteroaryl, heterocycloalkyl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

B. EXTRACELLULAR PH$_E$

The present disclosure also relates to imaging the extracellular pH (pH$_e$) of a cell or group of cells. In particular, the extracellular environment could be of a tumor cell. Aerobic glycolysis (a.k.a. Warburg effect, FIG. 23A), where cancer cells preferentially take up glucose and convert it into lactic acids, has rekindled intense interest in imaging pH$_e$ of a tumor cell as a method of determine the presence of tumor tissue (Heiden et al., 2009). The clinical relevance of the Warburg effect has already been manifested by the wide clinical use of 2-$^{18}$F-deoxyglucose (FDG) for tumor diagnosis as well as monitoring treatment responses. In tumor microenvironment, lactic acids are preferentially accumulated in the extracellular space due to monocarboxylate transporters, which are elevated in cancer cell membranes (Halestrap & Prince 1999). The resulting acidification of extracellular pH (pH$_e$) in tumors promotes remodeling of extracellular matrix for increased tumor invasion and metastasis. Recently, Barber and coworkers described dysregulated pH in tumors as another "hallmark of cancer" (Webb et al., 2011).

Many previous studies have been performed to quantify the pH$_e$ in the tumor microenvironment (Gillies et al., 1994; Gillies et al., 2004; van Sluis et al., 1999 and Volk et al, 1993). FIG. 23B is a representative pH$_e$ study in 268 tumors from 30 different human cancer cell lines (Volk et al., 1993). Compared to blood pH (7.4), all the tumor pH$_e$ are acidic with an average of 6.84 ranging from 6.71 to 7.01. Although the acidity of tumor pH$_e$ is persistent, exploiting it for tumor-specific imaging is challenging due to the relatively small pH differences (i.e., <1 pH unit) making probes which possess a very narrow pH transition range of particular interest for this application.

In some embodiments, the present disclosure provides polymers and micelles which can be used in a pH responsive system that can image and physiological and/or pathological process that is affected or affects intracellular or extracellular pH including but not limited to infections, fistulas, ulcers, ketoacidosis from diabetes or other diseases, hypoxia, metabolic acidosis, respiratory acidosis, toxic ingestion, poisoning, bone turnover, degenerative diseases, wounds, and tissue damage from burns radiation or other sources.

C. SURGICAL IMAGING OF TUMOR MARGINS

Positive tumor margins, which are defined by the presence of cancer cells at the edge of surgical resection, are the most important indicator of tumor recurrence and survival of HNSCC patients after surgery (Woolgar & Triantafyllou 2005; McMahon el al., 2003; Ravasz et al., Atkins et al., 2012 and Iczkowski & Lucia 2011). In some embodiments, any cancer cell line which exhibits a different extracellular pH environment than the normal physiological pH of the environment can be imaged with a pH responsive system disclosed herein. Furthermore, by modifying the dye used in the pH responsive dyes, a variety of different commercially available surgical imaging systems can be used to measure the margins of the tumor. These systems include but are not limited to systems for open surgery (e.g., SPY Elite®), microsurgery (Carl Zeiss, Leica), laparoscopy (Olympus, Karl Storz), and robotic surgery (da Vinci®). Many of these clinical systems have fast acquisition times allowing real-time imaging during an operation. Furthermore, the mixed polymers disclosed herein as well as a homopolymer of the any of the individual monomers used to create the mixed polymers can be used in the pH responsive system for the imaging of a tumor during an operation.

D. BLOCK COPOLYMERS AND FLUORESCENT DYES

The pH-responsive micelles and nanoparticles disclosed herein comprise block copolymers and fluorescent dyes. A block copolymer comprises a hydrophilic polymer segment and a hydrophobic polymer segment. The hydrophobic polymer segment is pH sensitive. For example, the hydrophobic polymer segment may comprise an ionizable amine group to render pH sensitivity. The block copolymers form pH-activatable micellar (pHAM) nanoparticles based on the supramolecular self-assembly of these ionizable block copolymers. At higher pH, the block copolymers assemble into micelles, whereas at lower pH, ionization of the amine group in the hydrophobic polymer segment results in dissociation of the micelle. The ionizable groups may act as tunable hydrophilic/hydrophobic blocks at different pH values, which may directly affect the dynamic self-assembly of micelles.

For diagnostic or pH monitoring applications, a labeling moiety may be conjugated to the block copolymer. In some embodiments, the label (e.g., a fluorescent label) is sequestered inside the micelle when the pH favors micelle formation. Sequestration in the micelle results in a decrease in label signal (e.g., via fluorescence quenching). Specific pH conditions may lead to rapid protonation and dissociation of micelles into unimers, thereby exposing the label, and increasing the label signal (e.g., increasing fluorescence emission). The micelles of the disclosure may provide one or more advantages in diagnostic applications, such as: (1) disassociation of the micelle (and rapid increase in label signal) within a short amount of time (e.g., within minutes) under certain pH environments (e.g., acidic environments), as opposed to hours or days for previous micelle compositions; (2) increased imaging payloads; (3) selective targeting of label to the desired site (e.g., tumor or particular endocytic compartment); (4) prolonged blood circulation times; (5) responsiveness within specific narrow pH ranges (e.g., for targeting of specific organelles); and (6) high contrast sensitivity and specificity. For example, the micelles may stay silent (or in the OFF state) with minimum background signals under normal physiological conditions (e.g., blood circulation, cell culture conditions), but imaging signals can be greatly amplified when the micelles reach their intended molecular targets (e.g., extracellular tumor environment or cellular organelle).

Numerous fluorescent dyes are known in the art. In certain aspects of the disclosure, the fluorescent dye is a pH-insensitive fluorescent dyes. In some embodiments, the fluorescent dye is paired with a fluorescent quencher to obtain an increased signal change upon activation. The fluorescent dye may be conjugated to the copolymer directly or through a linker moiety. Methods known in the art may be used to conjugate the fluorescent dye to, for example, the hydrophobic polymer. In some embodiments, the fluorescent dye may be conjugated to amine of the hydrophobic polymer through an amide bond.

Examples of block copolymers and block copolymers conjugated to fluorescent dyes include:

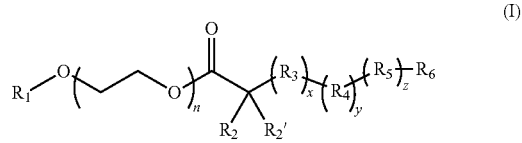

(I)

wherein: $R_1$ is hydrogen, alkyl$_{(C \leq 12)}$, cycloalkyl$_{(C \leq 12)}$, substituted alkyl$_{(C \leq 12)}$, substituted cycloalkyl$_{(C \leq 12)}$, or

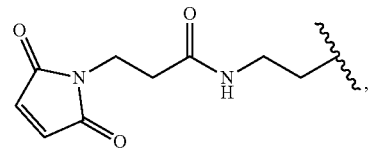 [SMILES: *CCNC(=O)CCN1C(=O)C=CC1=O]

or a metal chelating group; n is an integer from 1 to 250; $R_2$ and $R_2'$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; $R_3$ is a group of the formula:

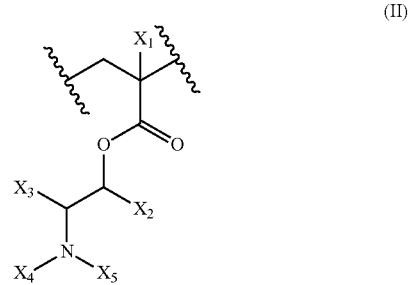

(II)

wherein: $X_1$, $X_2$, and $X_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and $X_4$ and $X_5$ are each independently selected from alkyl$_{(C \leq 12)}$, cycloalkyl$_{(C \leq 12)}$, aryl$_{(C \leq 12)}$, heteroaryl$_{(C \leq 12)}$ or a substituted version of any of these groups, or $X_4$ and $X_5$ are taken together and are alkanediyl$_{(C \le 12)}$, alkoxydiyl$_{(C \le 12)}$, alkylaminodiyl$_{(C \le 12)}$, or a substituted version of any of these groups; x is an integer from 1 to 100; $R_4$ is a group of the formula:

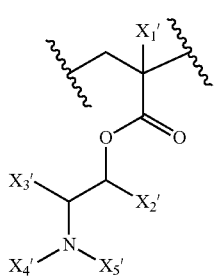

(III)

wherein: $X_1'$, $X_2'$, and $X_3'$ are each independently selected from hydrogen, alkyl$_{(C \le 12)}$, cycloalkyl$_{(C \le 12)}$, substituted alkyl$_{(C \le 12)}$, or substituted cycloalkyl$_{(C \le 12)}$; and $X_4'$ and $X_5'$ are each independently selected from alkyl$_{(C \le 12)}$, cycloalkyl$_{(C \le 12)}$, aryl$_{(C \le 12)}$, heteroaryl$_{(C \le 12)}$ or a substituted version of any of these groups, or $X_4'$ and $X_5'$ are taken together and are alkanediyl$_{(C \le 12)}$, alkoxydiyl$_{(C \le 12)}$, alkylaminodiyl$_{(C \le 12)}$, or a substituted version of any of these groups; y is an integer from 1 to 100; $R_5$ is a group of the formula:

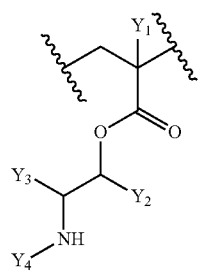

(IV)

wherein: $Y_1$, $Y_2$, and $Y_3$ are each independently selected from hydrogen, alkyl$_{(C \le 12)}$, cycloalkyl$_{(C \le 12)}$, substituted alkyl$_{(C \le 12)}$, or substituted cycloalkyl$_{(C \le 12)}$; and $Y_4$ is hydrogen, alkyl$_{(C \le 12)}$, acyl$_{(C \le 12)}$, substituted alkyl$_{(C \le 12)}$, substituted acyl$_{(C \le 12)}$, a dye, or a fluorescence quencher; z is an integer from 0-6; and $R_6$ is hydrogen, halo, hydroxy, alkyl$_{(C \le 12)}$, or substituted alkyl$_{(C \le 12)}$, wherein $R_3$, $R_4$, and $R_5$ can occur in any order within the polymer, provided that $R_3$ and $R_4$ are not the same group. In some embodiments, each monomer of $R_3$, $R_4$, and $R_5$ within the longer polymer can occur in any order within the polymer. In some embodiments, the specific composition of the polymer (molar fraction of the $R_3$, $R_4$, and $R_5$ monomers) is related to the specific pH transition point of the nanoparticle produced using that polymer.

E. MICELLE SYSTEMS AND COMPOSITIONS

The systems and compositions disclosed herein utilize either a single micelle or a series of micelles tuned to different pH levels. Furthermore, the micelles have a narrow pH transition range. In some embodiments, the micelles have a pH transition range of less than about 1 pH unit. In various embodiments, the micelles have a pH transition range of less than about 0.9, less than about 0.8, less than about 0.7, less than about 0.6, less than about 0.5, less than about 0.4, less than about 0.3, less than about 0.25, less than about 0.2, or less than about 0.1 pH unit. The narrow pH transition range advantageously provides a sharper pH response that can result in complete turn-on of the fluorophores with subtle changes of pH.

Accordingly, a single or series of pH-tunable, multicolored fluorescent nanoparticles having pH-induced micellization and quenching of fluorophores in the micelle core provide mechanisms for the independent control of pH transition (via polymers), fluorescence emission, or the use of fluorescence quenchers. The fluorescence wavelengths can be fine tuned from, for example, violet to near IR emission range (400-820 nm). Their fluorescence ON/OFF activation can be achieved within no more than 0.25 pH units, which is much narrower compared to small molecular pH sensors. In some embodiments, a narrower range for fluorescence ON/OFF activation can be achieved such that the range is no more than 0.2 pH units. In some embodiments, the range is no more than 0.15 pH units. Furthermore, the use of a fluorescence quencher may also increase the fluorescence activation such that the difference between the associated and disassociated nanoparticle is greater than 50 times the associated nanoparticle. In some embodiments, the fluorescence activation is greater than 75 times higher than the associated nanoparticle This multicolored, pH tunable and activatable fluorescent nanoplatform provides a valuable tool to investigate fundamental cell physiological processes such as pH regulation in endocytic organelles, receptor cycling, and endocytic trafficking, which are related to cancer, lysosomal storage disease, and neurological disorders.

The size of the micelles will typically be in the nanometer scale (i.e., between about 1 nm and 1 μm in diameter). In some embodiments, the micelle has a size of about 10 to about 200 nm. In some embodiments, the micelle has a size of about 20 to about 100 nm. In some embodiments, the micelle has a size of about 30 to about 50 nm.

F. TARGETING MOIETIES

The micelles and nanoparticles may further comprise a targeting moiety. The targeting moiety may be used to target the nanoparticle or micelle to, for example, a particular cell surface receptor, cell surface marker, or to an organelle (e.g., nucleus, mitochondria, endoplasmic reticulum, chloroplast, apoplast, or peroxisome). Such targeting moieties will be advantageous in the study of receptor recycling, marker recycling, intracellular pH regulation, endocytic trafficking.

The targeting moiety may be, for example, an antibody or antibody fragment (e.g., Fab' fragment), a protein, a peptide (e.g., a signal peptide), an aptamer, or a small molecule (e.g., folic acid). The targeting moiety may be conjugated to the block copolymer (e.g., conjugated to the hydrophilic polymer segment) by methods known in the art. The selection of targeting moiety will depend on the particular target. For example, antibodies, antibody fragments, small molecules, or binding partners may be more appropriate for targeting cell surface receptors and cell surface markers, whereas peptides, particularly signal peptides, may be more appropriate for targeting organelles.

G. FLUORESCENCE DETECTION

Various aspects of the present disclosure relate to the direct or indirect detection of micelle disassociation by detecting an increase in a fluorescent signal. Techniques for detecting fluorescent signals from fluorescent dyes are known to those in the art. For example, fluorescence confocal microscopy as described in the Examples below is one such technique.

Flow cytometry, for example, is another technique that can be used for detecting fluorescent signals. Flow cytometry involves the separation of cells or other particles, such as microspheres, in a liquid sample. The basic steps of flow cytometry involve the direction of a fluid sample through an apparatus such that a liquid stream passes through a sensing region. The particles should pass one at a time by the sensor and may categorized based on size, refraction, light scattering, opacity, roughness, shape, fluorescence, etc.

The measurements described herein may include image processing for analyzing one or more images of cells to determine one or more characteristics of the cells such as numerical values representing the magnitude of fluorescence emission at multiple detection wavelengths and/or at multiple time points.

H. KITS

The present disclosure also provides kits. Any of the components disclosed herein may be combined in a kit. In certain embodiments the kits comprise a pH-responsive system or composition as described above.

The kits will generally include at least one vial, test tube, flask, bottle, syringe or other container, into which a component may be placed, and preferably, suitably aliquoted. Where there is more than one component in the kit, the kit also will generally contain a second, third or other additional containers into which the additional components may be separately placed. However, various combinations of components may be comprised in a container. In some embodiments, all of the micelle populations in a series are combined in a single container. In other embodiments, some or all of the micelle population in a series are provided in separate containers.

The kits of the present disclosure also will typically include packaging for containing the various containers in close confinement for commercial sale. Such packaging may include cardboard or injection or blow molded plastic packaging into which the desired containers are retained. A kit may also include instructions for employing the kit components. Instructions may include variations that can be implemented.

I. SPECT AND PET

Radionuclide imaging modalities (positron emission tomography, (PET); single photon emission computed tomography (SPECT)) are diagnostic cross-sectional imaging techniques that map the location and concentration of radionuclide-labeled radiotracers. Although CT and MRI provide considerable anatomic information about the location and the extent of tumors, these imaging modalities cannot adequately differentiate invasive lesions from edema, radiation necrosis, grading or gliosis. PET and SPECT can be used to localize and characterize tumors by measuring metabolic activity.

PET and SPECT provide information pertaining to information at the cellular level, such as cellular viability. In PET, a patient ingests or is injected with a slightly radioactive substance that emits positrons, which can be monitored as the substance moves through the body. In one common application, for instance, patients are given glucose with positron emitters attached, and their brains are monitored as they perform various tasks. Since the brain uses glucose as it works, a PET image shows where brain activity is high.

Closely related to PET is single-photon emission computed tomography, or SPECT. The major difference between the two is that instead of a positron-emitting substance, SPECT uses a radioactive tracer that emits low-energy photons. SPECT is valuable for diagnosing coronary artery disease, and already some 2.5 million SPECT heart studies are done in the United States each year.

PET radiopharmaceuticals for imaging are commonly labeled with positron-emitters such as $^{11}C$, $^{13}N$, $^{15}O$, $^{18}F$, $^{82}Rb$, $^{62}Cu$, and $^{68}Ga$. SPECT radiopharmaceuticals are commonly labeled with positron emitters such as $^{99m}Tc$, $^{201}Tl$, and $^{67}Ga$. Regarding brain imaging, PET and SPECT radiopharmaceuticals are classified according to blood-brain-barrier permeability (BBB), cerebral perfusion and metabolism receptor-binding, and antigen-antibody binding (Saha et al., 1994). The blood-brain-barrier SPECT agents, such as $^{99m}TcO4$-DTPA, $^{201}Tl$, and [$^{67}Ga$]citrate are excluded by normal brain cells, but enter into tumor cells because of altered BBB. SPECT perfusion agents such as [$^{123}I$]IMP, [$^{99m}Tc$]HMPAO, [$^{99m}Tc$]ECD are lipophilic agents, and therefore diffuse into the normal brain. Important receptor-binding SPECT radiopharmaceuticals include [$^{123}I$]QNE, [$^{123}I$]IBZM, and [$^{123}I$]iomazenil. These tracers bind to specific receptors, and are of importance in the evaluation of receptor-related diseases.

J. EXAMPLES

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1: Methods and Materials for Preparation of Library of pH Responsive Nanoprobes 1. Materials The N-hydroxyl succinimidal (NHS) esters of different fluorophores and fluorescence quenchers were obtained as following: RhoG-NHS, TMR-NHS, ROX-NHS, BDY-NHS, BDY-TMR-NHS, BDY630-NHS, AMCA-x-NHS, MB-NHS, PPO-NHS, QSY$_{35}$, QSY$_7$ and QSY$_{21}$ ester were purchased from Invitrogen Company; Cy5-NHS, Cy5.5-NHS, Cy7.5-NHS ester were purchased from Lumiprobe Corporation; BHQ-1-NHS ester was purchased from Biosearch Technologies. PEO macroinitiator, MeO-PEO$_{114}$-Br, was prepared from 2-bromo-2-methyl propanoyl bromide and MeO-PEO$_{114}$-OH according to the procedure in Bronstein, et al., which is incorporated herein by reference. Bromopropane, bromobutane, bromopentane, ethanolamine, methacrylate chloride and sodium salts were purchased from Sigma-Aldrich. Monomers such as 2-(dimethylamino)ethyl methacrylate (DMA-MA), 2-(diethylamino)ethyl methacrylate (DEA-MA) and 2-aminoethyl methacrylate (AMA) were purchased from Polyscience Company. AMA was recrystallized twice with isopropanol and ethyl acetate (3:7). Monomer 2-(dibutylamino) ethyl methacrylate (DBA-MA)

was synthesized following a previously published procedure.[2] Syntheses of 2-(dipropylamino) ethyl methacrylate (DPA-MA) and 2-(dipentylamino) ethyl methacrylate (D5A-MA) are reported herein. AMA monomer was recrystallized twice with isopropanol and ethyl acetate (3:7) before use. Other solvents and reagents were used as received from Sigma-Aldrich or Fisher Scientific Inc.

2. Syntheses of New Methacrylate Monomers

New methacrylate monomers were synthesized following a published method. [2] Synthesis of 2-(dipropylamino) ethyl methacrylate (DPA-MA) is described here as an example. First, ethanolamine (12.2 g, 0.2 mol) and bromopropane (49.2 g, 0.4 mol) were dissolved in 400 mL acetonitrile, and $Na_2CO_3$ (53.0 g, 0.5 mol) was added to the solution. After overnight reaction, the solution was filtered to remove the precipitated NaBr salt and extra $Na_2CO_3$. $CH_3CN$ solvent was removed by rotovap. The resulting residue was distilled in vacuo (40-45° C. at 0.05 mm Hg) as a colorless liquid to obtain 2-(dipropylamino) ethanol. Then 2-(dipropylamino) ethanol (21.3 g, 0.1 mol), triethylamine (10.1 g, 0.1 mol), and inhibitor hydroquinone (0.11 g, 0.001 mol) were dissolved in 100 mL $CH_2Cl_2$ and methacryloyl chloride (10.4 g, 0.1 mol) was added dropwise into a three-neck flask. The solution was refluxed overnight. After reaction, the solution was filtered to remove the precipitated triethylamine-HCl salts, and $CH_2Cl_2$ solvent was removed by rotovap. The resulting residue was distilled in vacuo (47-53° C. at 0.05 mm Hg) as a colorless liquid. After synthesis, the monomer was characterized by $^1$H-NMR. All the NMR spectra were obtained in $CDCl_3$ using tetramethylsilane (TMS) as the internal reference on a Varian 500 MHz spectrometer. The characterization of the two new monomers is as follows:

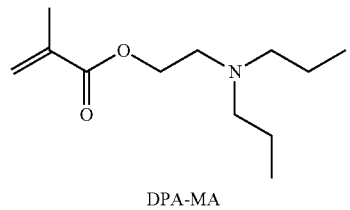

DPA-MA 2-(Dipropylamino) Ethyl Methacrylate (DPA-MA)

$^1$H NMR (TMS, $CDCl_3$, ppm): 6.10 (br, 1H, CHH=C($CH_3$)—), 5.54 (br, 1H, CHH=C($CH_3$)—), 4.07 (t, 2H, —OCH$_2$CH$_2$N—), 3.01 (t, 2H, —OCH$_2$CH$_2$N—), 2.68 (t, 4H, —N(CH$_2$CH$_2$CH$_3$)$_2$, 1.94 (s, 3H, CH$_2$=C(CH$_3$)—), 1.44 (m, 4H, —N(CH$_2$CH$_2$CH$_3$)$_2$), 1.01 (t, 6H, —N(CH$_2$CH$_2$CH$_3$)$_2$)

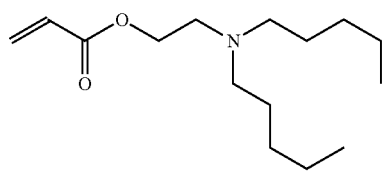

D5A-MA 2-(Dipentylamino) Ethyl Methacrylate (D5A-MA)

$^1$H NMR (TMS, $CDCl_3$, ppm): 6.10 (br, 1H, CHH=C(CH$_3$)—), 5.55 (br, 1H, CHH=C(CH$_3$)—), 4.20 (t, 2H, —OCH$_2$CH$_2$N—), 2.74 (t, 2H, —OCH$_2$CH$_2$N—), 2.45 (t, 4H, —N(CH$_2$CH$_2$CH$_2$CH$_2$CH$_3$)$_2$), 1.94 (s, 3H, CH$_2$=C(CH$_3$)—), 1.43 (m, 4H, —N(CH$_2$CH$_2$CH$_2$CH$_2$CH$_3$)$_2$), 1.30 (m, 4H, —N(CH$_2$CH$_2$CH$_2$CH$_2$CH$_3$)$_2$), 1.24 (m, 4H, —N(CH$_2$CH$_2$CH$_2$CH$_2$CH$_3$)$_2$), 0.88 (t, 6H, —N(CH$_2$CH$_2$CH$_2$CH$_2$CH$_3$)$_2$),

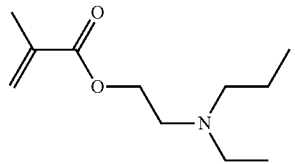

2-(Ethylpropylamino) Ethyl Methacrylate (EPA-MA)

$^1$H NMR (TMS, $CDCl_3$, ppm): 6.10 (s, 1H, CHH=C(CH$_3$)—), 5.54 (s, 1H, CHH=C(CH$_3$)—), 4.20 (t, 2H, —OCH$_2$CH$_2$N—), 2.75 (t, 2H, —OCH$_2$OH$_2$N—), 2.58 (q, 2H, —N(CH$_2$CH$_2$CH$_3$)(CH$_2$CH$_3$)), 2.44 (m, 2H, —N(CH$_2$CH$_2$CH$_3$)(CH$_2$CH$_3$)), 1.94 (s, 3H, CH$_2$=C(CH$_3$)—), 1.45 (m, 2H, —N(CH$_2$CH$_2$CH$_3$)(CH$_2$CH$_3$)), 1.02 (t, 3H, —N(CH$_2$CH$_2$CH$_3$)(CH$_2$CH$_3$)), 0.87 (t, 3H, —N(CH$_2$CH$_2$CH$_3$)(CH$_2$CH$_3$))

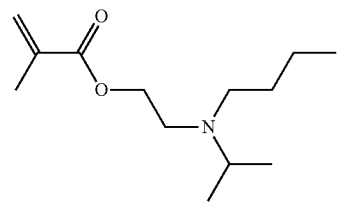 [SMILES: C=C(C)C(=O)OCCN(CCCC)C(C)C]

2-(Butyl(Isopropyl)Amino) Ethyl Methacrylate ($^m$D3.5A-MA)

$^1$H NMR (TMS, $CDCl_3$, ppm): 6.09 (s, 1H, CHH=C(CH$_3$)—), 5.53 (s, 1H, CHH=C(CH$_3$)—), 4.11 (t, 2H, —OCH$_2$CH$_2$N—), 2.92 (m, 1H, —N(CH$_2$CH$_2$CH$_2$CH$_3$)(CH(CH$_3$)$_2$), 2.64 (t, 2H, —OCH$_2$CH$_2$N—), 2.42 (t, 2H, —N(CH$_2$CH$_2$CH$_2$CH$_3$)(CH(CH$_3$)$_2$), 1.93 (s, 3H, CH$_2$=C(CH$_3$)—), 1.38 (m, 2H, —N(CH$_2$CH$_2$CH$_2$CH$_3$)(CH(CH$_3$)$_2$), 1.29 (m, 2H, —N(CH$_2$CH$_2$CH$_2$CH$_3$)(CH(CH$_3$)$_2$), 0.97 (d, 6H, —N(CH$_2$CH$_2$CH$_2$CH$_3$)(CH(CH$_3$)$_2$), 0.88 (t, 3H, —N(CH$_2$CH$_2$CH$_2$CH$_3$)(CH(CH$_3$)$_2$)

3. Syntheses of PEO-b-PR Block Copolymers

PEO-6-PR copolymers were synthesized by atom transfer radical polymerization (ATRP) as described in Zhou, et al., 2011, which is incorporated herein by reference. The dye free copolymers were used in polymer characterizations. Tables 1-3 summarize the characterization of each copolymer. PEO-6-PDPA is used as an example to illustrate the procedure. First, DPA-MA (1.70 g, 8 mmol), PMDETA (21 µL, 0.1 mmol) and MeO-PEO$_{114}$-Br (0.5 g, 0.1 mmol) were charged into a polymerization tube. Then a mixture of 2-propanol (2 mL) and DMF (2 mL) was added to dissolve the monomer and initiator. After three cycles of freeze-pump-thaw to remove the oxygen, CuBr (14 mg, 0.1 mmol) was added into the polymerization tube under nitrogen atmosphere, and the tube was sealed in vacuo. The polymerization was carried out at 40° C. for 8 hours. After polymerization, the reaction mixture was diluted with 10 mL THF, and passed through a neutral $Al_2O_3$ column to remove the catalyst. The THF solvent was removed by rotovap. The residue was dialyzed in distilled water and lyophilized to obtain a white powder.

TABLE 1

Coarse-tuned pH sensitive nanoprobes from Cy5-conjugated PEO-P($DEA_x$-$D5A_y$) copolymers.

| Polymers | $M_n$ (kDa) | $M_w$ (Da) | PDI | Yield (%) | $pH_t$ | $\Delta pH_{10\text{-}90\%}$ |
|---|---|---|---|---|---|---|
| PD5A | 26.9 | 32.6 | 1.21 | 85 | 4.38 | 0.19 |
| P($DEA_{20}$-$D5A_{60}$) | 21.3 | 26.3 | 1.23 | 90 | 5.19 | 0.65 |
| P($DEA_{40}$-$D5A_{40}$) | 21.3 | 25.8 | 1.20 | 95 | 5.99 | 0.64 |
| P($DEA_{60}$-$D5A_{20}$) | 22.3 | 26.4 | 1.19 | 90 | 6.88 | 0.47 |
| PDEA | 22.6 | 26.6 | 1.18 | 91 | 7.83 | 0.14 |

TABLE 2

Fine-tuned pH sensitive nanoprobes from Cy5-conjugated PEO-P($DPA_x$-$DBA_y$) copolymers.

| Polymers | $M_n$ (kDa) | $M_w$ (Da) | PDI | Yield (%) | $pH_t$ | $\Delta pH_{10\text{-}90\%}$ |
|---|---|---|---|---|---|---|
| PDBA | 22.5 | 26.8 | 1.19 | 80 | 5.27 | 0.20 |
| P($DPA_{20}$-$DBA_{60}$) | 19.7 | 21.4 | 1.09 | 94 | 5.46 | 0.19 |
| P($DPA_{40}$-$DBA_{40}$) | 21.7 | 24.7 | 1.14 | 78 | 5.70 | 0.20 |
| P($DPA_{60}$-$DBA_{20}$) | 23.9 | 27.9 | 1.17 | 83 | 5.91 | 0.18 |
| PDPA | 22.6 | 27.3 | 1.21 | 91 | 6.21 | 0.20 |

TABLE 3

Composition of the UPS library spanning the pH range from 4.4 to 7.4.

| Probe | Composition | $M_n$ (kDa) | $M_w$ (Da) | PDI | Yield (%) | $pH_t$ | $\Delta pH_{10\text{-}90\%}$ |
|---|---|---|---|---|---|---|---|
| 4.4 | PD5A | 26.9 | 32.6 | 1.21 | 85 | 4.38 | 0.19 |
| 4.7 | P($DBA_{28}$-$D5A_{52}$) | 20.2 | 23.3 | 1.15 | 82 | 4.67 | 0.15 |
| 5.0 | P($DBA_{56}$-$D5A_{24}$) | 20.0 | 25.9 | 1.29 | 84 | 4.96 | 0.18 |
| 5.3 | PDBA | 22.5 | 26.8 | 1.19 | 80 | 5.27 | 0.20 |
| 5.6 | P($DPA_{30}$-$DBA_{50}$) | 20.4 | 24.9 | 1.22 | 89 | 5.63 | 0.19 |
| 5.9 | P($DPA_{60}$-$DBA_{20}$) | 23.9 | 27.9 | 1.17 | 83 | 5.91 | 0.18 |
| 6.2 | PDPA | 20.1 | 23.3 | 1.21 | 91 | 6.21 | 0.20 |
| 6.5 | P($DEA_{21}$-$DPA_{79}$) | 21.8 | 24.3 | 1.12 | 87 | 6.45 | 0.19 |
| 6.8 | P($DEA_{39}$-$DPA_{61}$) | 20.3 | 23.2 | 1.14 | 82 | 6.76 | 0.20 |
| 7.1 | P($DEA_{58}$-$DPA_{42}$) | 23.1 | 25.2 | 1.09 | 85 | 7.08 | 0.21 |
| 7.4 | P($DEA_{76}$-$DPA_{24}$) | 22.5 | 25.4 | 1.13 | 87 | 7.44 | 0.18 |

4. Syntheses of PEO-b-(PR-r-Dye/FQ) Block Copolymers

AMA was used for the conjugation of dyes or fluorescence quenchers. Synthesis of PEO-b-(PR-r-AMA) copolymers followed the procedure described above. Three primary amino groups were introduced into each polymer chain by controlling the feeding ratio of AMA monomer to the initiator (ratio=3). After synthesis, PEO-b-(PR-r-AMA) (10 mg) was dissolved in 2 mL DMF. Then the NHS-ester (1.5 equivalences for Dye-NHS or FQ-NHS) was added. After overnight reaction, the copolymers were purified by preparative gel permeation chromatography (PLgel Prep 10 m 10E3 Å 300×250 columns by Varian, THF as eluent at 5 mL/min) to remove the free dye molecules. The produced PEO-b-(PR-r-Dye/FQ) copolymers were lyophilized and kept at −20° C. for storage.

5. Preparation of Micelle Nanoparticles

Micelles were prepared as has been previously described in Zhou, et al., 2011, which is incorporated herein by reference. In a typical procedure, 5 mg of PDPA-Cy5 was dissolved in 0.5 mL THF. Then, the solution was slowly added into 4 mL of Milli-Q deionized water under sonication. The mixture was filtered 4 times to remove THF using the micro-ultrafiltration system (MWCO=100 KD). Then, the deionized water was added to adjust the polymer concentration to 5 mg/mL as a stock solution. For the mixed micelles, different weight ratios of the PR-Dye and PR-FQ copolymers were dissolved in 0.5 mL THF, and the same procedure was used.

6. Fluorescence Characterization

The fluorescence emission spectra were obtained on a Hitachi fluorometer (F-7500 model). For each copolymer, the sample was initially prepared in Milli-Q water at the concentration of 2 mg/mL. Then the stock solution was diluted in 0.2 M citric-phosphate buffers (containing 0.15 M sodium chloride) with different pH values. The terminal polymer concentration was controlled at 100-200 µg/mL.

For the fluorescent images of 4.4-7.1-Cy5s, 5.0-BDY, 5.3-RhoG, 5.6-TMR, 5.9-ROX, 6.2-BDY630, 6.5-Cy5, 6.8-Cy5.5 and 7.1-Cy7.5 solutions at different pH values (100 µg/mL for each sample), the Maestro imaging system (CRI, Inc., Woburn, Mass.) was used by choosing a proper band pass excitation filter and a proper long-pass emission filter according to the instrument manual. For 4.4-AMCA and 4.7-MB, the images were taken by a camera under the irradiation of a handheld UV light (365 nm). All measurements were conducted at room temperature.

Example 2: Synthesis and Characterization of a Library of pH Responsive Polymer Micelles 1. Copolymer Syntheses by the ATRP Method.

The atom transfer radical polymerization (ATRP) method (Tsarevsky and Matyjaszewski, 2007; Ma, et al., 2003) with CuBr as a catalyst and N,N,N',N',N"-pentamethyldiethylenetriamine (PMDETA) ligand for the copolymer synthesis (FIG. 1) was used to prepare the copolymers for the study. The PEO-b-PR copolymers with homopolymeric PR block were synthesized using a single methacrylate monomer as previously described (Zhou, et al., 2011; Zhou, et al., 2012). In order to continuously fine tune the hydrophobicity of the PR segment, a copolymerization strategy using two methacrylate monomers with different hydrophobicity (FIG. 1) was employed. The molar fraction of the two monomers can be precisely controlled prior to polymerization, leading to a random copolymerized P($R_1$-r-$R_2$) block. A series of methacrylate monomers with different dialkyl chain lengths (e.g., ethyl, propyl, butyl and pentyl) were used in the current study. To introduce fluorophores or fluorescence quenchers, aminoethylmethacrylate (AMA-MA) (three repeating units per polymer chain) was also incorporated where the free amino groups were conjugated to dyes or FQs through activated N-hydroxyl succinimidyl (NHS) esters.

After syntheses, the copolymers were characterized with $^1$H NMR to verify the chemical compositions, and gel permeation chromatography to measure the number- and weight-averaged molecular weights and polydispersity (Tables 1-3, FIGS. 2-6).

2. Comparison of Copolymerization Vs. Molecular Mixture Strategy for $pH_t$ Control.

Initially, two different strategies on their abilities to control the $pH_t$ values of UPS nanoprobes were compared. The first strategy involves a molecular mixture of two different PEO-b-PR copolymers with different pH transitions. In this example, Cy5-conjugated PEO-b-poly[2-(diethylamino) ethyl methacrylate] (PDEA, all the copolymers were conjugated with Cy5 dye in the PR segment unless specified below) and PEO-b-poly[2-(dipentylamino)ethyl methacrylate] (PD5A) were used. The PDEA and PD5A nanoprobes had pH transitions at 4.4 and 7.8, respectively. A solvent evaporation procedure was used to produce a micelle nanoprobe consisting of both copolymers with the same molar percentage (i.e., 50%) in each micelle (this was verified by heteroFRET experiments). In the second strategy, the Cy5-conjugated PEO-b-poly[2-(diethylamino)ethyl methacrylate-r-2-(dipentylamino)ethyl methacrylate] copolymer (P(DEA$_{40}$-D5A$_{40}$)) was synthesized where the PR segment was composed of a random copolymer from two monomers (40 repeating units for each monomer, Table 1). The hydrodynamic diameters were 65 and 22 nm for PDEA/PD5A (molecular mixture) and P(DEA$_{40}$-D5A$_{40}$) (copolymer) micelles, respectively. The two micelle designs showed a drastically different pattern of fluorescence emission vs. pH relationships. For the PDEA/PD5A nanoprobes, distinctive behaviors of pH transitions was observed corresponding to individual copolymers where the fluorescence on/off transitions were at 4.4 and 7.8 (FIG. 7A, FIG. 8). This result suggests that chain entanglement between PDEA and PD5A within the micelle core is not sufficient to overcome individual polymer dissociation behaviors. In contrast, the P(DEA$_{40}$-D5A$_{40}$) nanoprobe showed a single pH transition at 6.0, about halfway between the PDEA and PD5A transitions.

To explore the control of transition pH, a series of P(DEA$_x$-D5A$_y$) copolymers with varying molar fractions of two monomers were synthesized. The resulting copolymers displayed different pH transitions (FIG. 7B, FIG. 9). Plot of $pH_t$ of nanoprobes as a function of the molar fraction of DEA monomer showed a linear correlation (FIG. 7C). Incorporation of higher percentage of less hydrophobic monomers (e.g., DEA-MA) resulted in higher pH transitions. The transition pH of the UPS nanoprobes can be primarily controlled by varying the hydrophobicity of the PR segment. This observation is in contrary to small molecular pH sensors, where electron withdrawing or donating groups are necessary for fine tuning (Urano, et al., 2009).

3. Monomer Compatibility Affects Sharpness of pH Transition.

Although P(DEA$_x$-D5A$_y$) nanoprobes with different monomer percentage allowed control of transition pH (FIGS. 7B-C), the sharpness of pH transitions was significantly broader than the corresponding nanoprobes with homopolymeric PR segment. More specifically, the $\Delta pH_{10-90\%}$ values (the pH range where fluorescence intensity increases from 10 to 90%) were 0.65, 0.64, and 0.47 for P(DEA$_x$-D5A$_y$) copolymers with 25, 50 and 75% of DEA-MA compositions, respectively, in comparison to 0.14 and 0.19 for PDEA and PD5A nanoprobes, respectively. The broad pH response from P(DEA$_x$-D5A$_y$) copolymers indicates the heterogeneous chain property from the monomers with large hydrophobicity differences.

Figure 10:
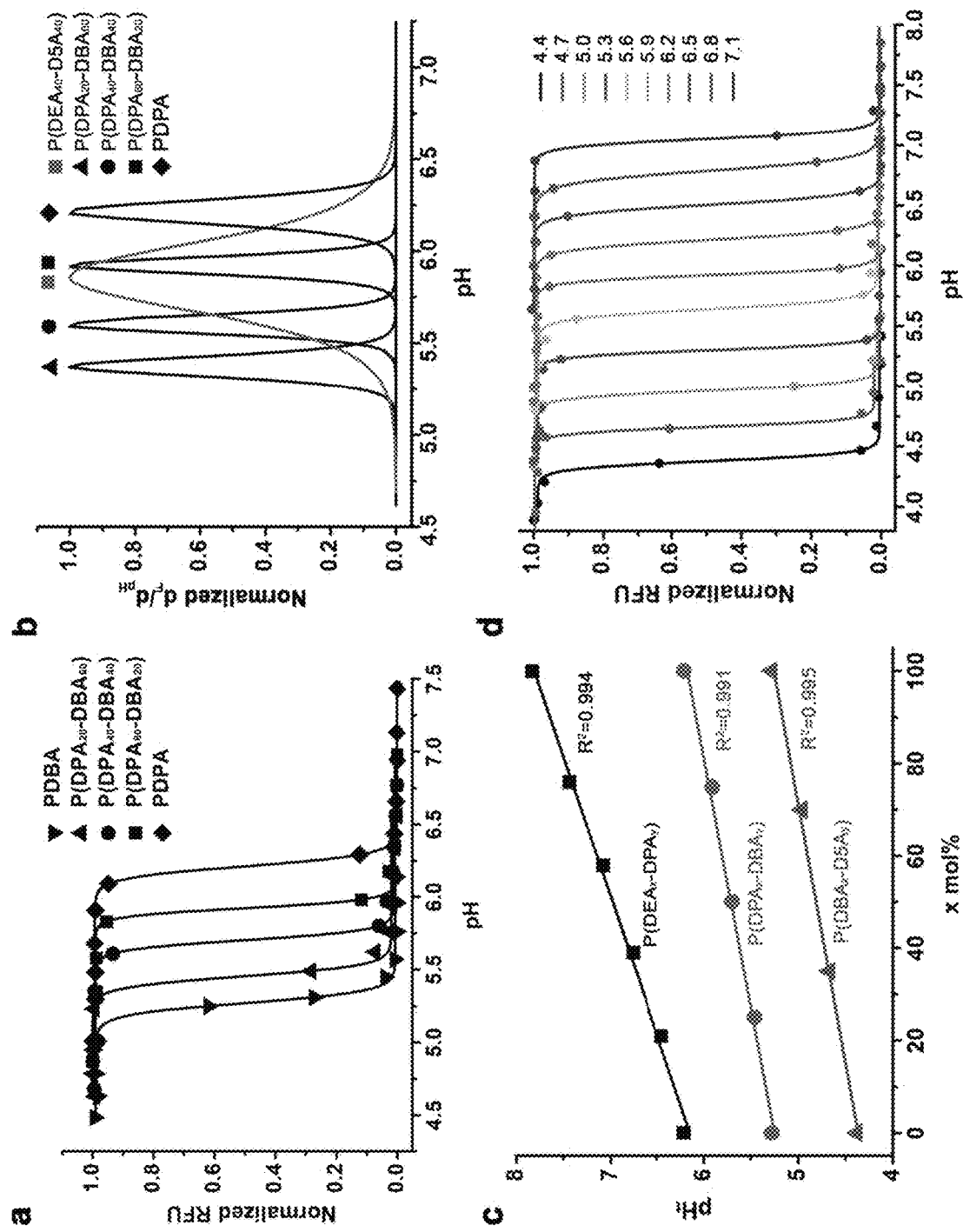

To improve the sharpness of pH transition, the use of monomers with closely matched hydrophobicity were investigated. As an example, 2-(dipropylamino)ethyl methacrylate (DPA-MA) and 2-(dibutylamino)ethyl methacrylate (DBA-MA) was chosen to produce a series of P(DPA$_x$-DBA$_y$) nanoprobes. The two monomers differ by one carbon on the nitrogen substituents (i.e., propyl vs. butyl). Copolymerization of the two monomers led to a more refined, tunable series of nanoprobes with sharp pH transitions (FIG. 10A, FIG. 11). The $\Delta pH_{10-90\%}$ values were 0.19, 0.20, and 0.18 for P(DPA$_x$-DBA$_y$) nanoprobes with 25, 50 and 75% of DPA-MA compositions, respectively. Each copolymer probe maintained the sharp pH transition (<0.25 pH unit). FIG. 10B shows a fluorescence derivative plot as a function of pH, which further illustrates the greatly increased sharpness of serial P(DPA$_x$-DBA$_y$) nanoprobes compared to a single P(DEA$_{40}$-D5A$_{40}$) nanoprobe in the same pH span. Plot of $pH_t$ values of the P(DPA$_x$-DBA$_y$) nanoprobes as a function of molar fraction of DPA-MA monomer also yielded a linear correlation (FIG. 10C). Similarly, standard curves for P(DBA$_x$-D5A$_y$) and P(DEA$_x$-DPA$_y$) series were established demonstrating linear relationships between $pH_t$ and molar fraction of the monomers. These standard curves allow for the rational design of UPS nanoprobes with any predetermined pH transitions (between 4.4-7.8) by choosing copolymers with correct PR compositions (i.e., selection of monomer pairs and specific molar fractions). For proof of concept, a UPS library consisting of 10 nanoprobes with 0.3 pH increment covering the entire physiologic range of pH (4.4-7.4) were generated while each nanoprobe maintained the sharp pH transitions (<0.25 pH unit between on and off states, FIG. 10D, FIGS. 12-13).

4. Use of Fluorescence Quenchers to Broaden Fluorophore Selection.

Previously, homo-FRET induced fluorescence decay is the main mechanism to achieve the on/off activatable design of the UPS nanoprobes was reported (Zhou, et al., 2012). This mechanism only applies to fluorophores (e.g., rhodamine and cyanine dyes) with small Stoke shifts (<40 nm). For dyes with large Stoke shifts (e.g., marina blue or PPO, $\Delta\lambda \geq 100$ nm), the fluorescence activation ratio ($R_F = F_{on}/F_{off}$, where $F_{on}$ and $F_{off}$ are the fluorescence intensity at on and off states, respectively) was less than 5. Moreover, for BODIPY® families of dyes, the pH transition was broad (>0.5 pH unit) with relatively low $R_F$ (<15) as a result of the photo-induced electron transfer (PeT) mechanism (Petsalakis, et al., 2008; Tal, et al., 2006; Dale and Rebek, 2006)

Figure 14:
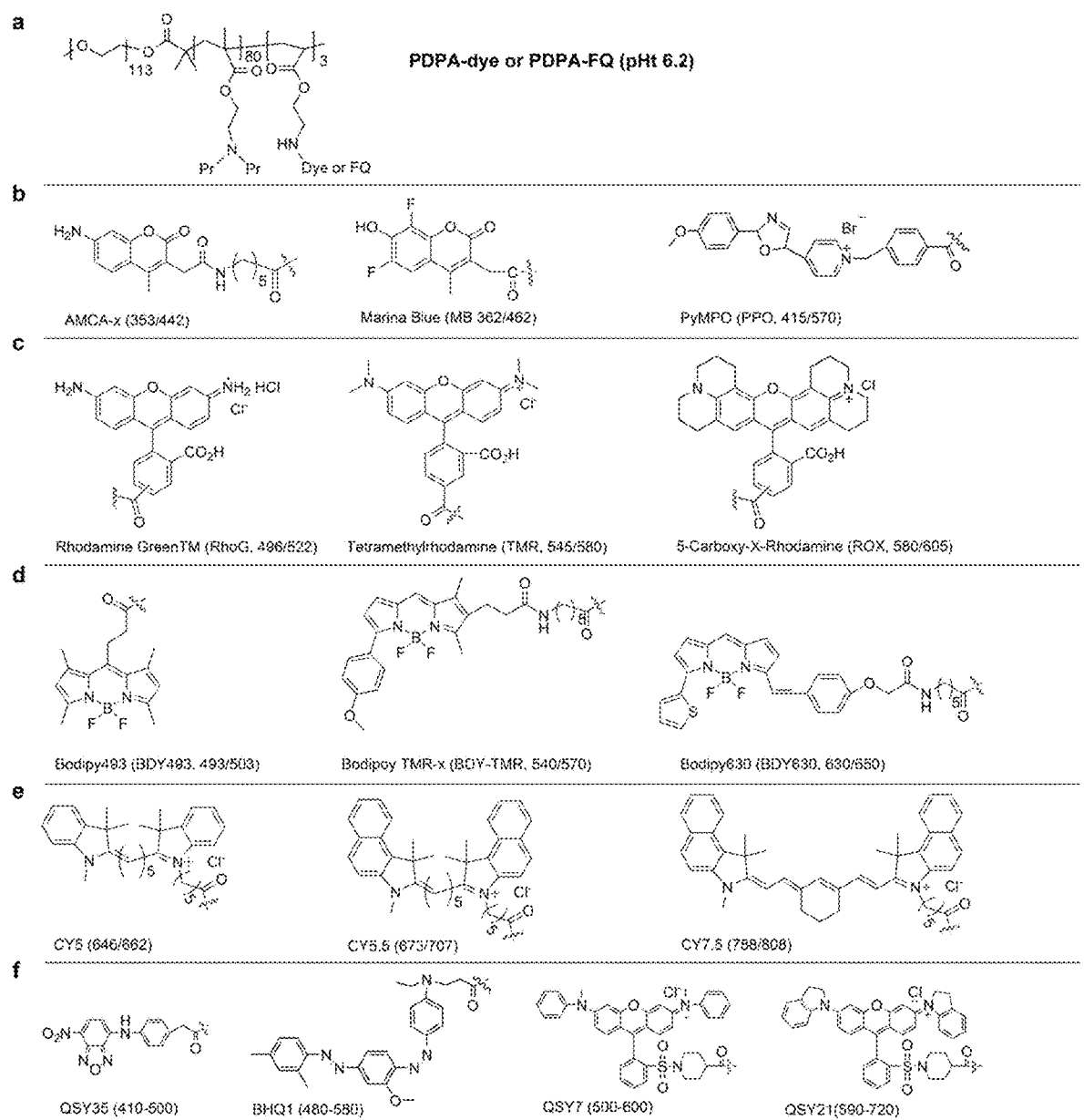

To overcome these limitations, the use of fluorescence quenchers (FQs) to broaden the fluorophore selection was investigated. Fluorescence quenchers have been widely used by many groups for the design of activatable imaging probes (Blum, et al., 2005; Fee, et al., 2009; Fevi, et al., 2010; Maxwell, et al., 2009). The mechanism is based on the fluorescence resonance energy transfer from desired fluorophores to the FQs, which subsequently dissipate the radiative energy into heat. In this design, a series of FQs that are sensitive to different emission wavelengths were prepared and conjugated onto the copolymer (FIG. 14). The UPS nanoprobes were produced by mixing the FQ-conjugated polymer with dye-conjugated polymer in the same micelle core. At the micelle state, the FQs are anticipated that the compounds would effectively quench the fluorophore signals and upon micelle dissociation, separation of FQs and fluorophores will result in significant increase in fluorescence emissions (FIG. 15A).

To evaluate the effectiveness of the FQ strategy, PEO-b-poly[2-(propylamino)ethyl methacrylate] (PDPA) were used as a model system and different FQs and fluorophores were conjugated to the copolymer. The PDPA nanoprobe had a pH transition at 6.2. First, the FQ strategy on fluorophores with large Stoke shift (e.g., AMCA: 353/442; marina blue or MB: 362/462; PyMPO or PPO: 415/570 was investigated. The two numbers refer to the excitation and emission wavelengths, respectively). Without the introduction of FQ-conjugated polymer, the PDPA-AMCA and PDPA-MB nanoprobes showed only 3-fold fluorescence activation between the on and off states at pH 5.0 and 7.4, respectively (FIG. 18A). Introduction of PDPA-QSY$_{35}$ to PDPA-AMCA or PDPA-MB resulted in significant increase in fluorescence activation, which reached a plateau when the molar fraction of PDPA-QSY$_{35}$ became 67% (FIG. 16A). At this composition, the R$_F$ values reached approximately 90-fold, which are 30 times higher than those without the FQs (FIG. 18B). Similarly, introduction of PDPA-QSY$_7$ (50 mol %) to PDPA-PPO nanoprobes increased the R$_F$ value from 6 to >130-fold, respectively (FIG. 18B).

For BODIPY® families of dyes, the PDPA-BDY493 and PDPA-TMR nanoprobes only yielded ~ 15-fold of fluorescence activations (FIG. 18C), which are not adequate in biological applications (e.g., during cellular imaging, an R$_F$ value >30 is necessary to suppress the background signals). Introduction of PDPA-BHQ1 (50 mol %) and PDPA-QSY$_7$ (50 mol %) to the PDPA-BDY493 and PDPA-TMR nanoprobes led to dramatically increased R$_F$ values (both >100-fold, FIG. 18D, FIG. 19). Interestingly, PDPA-BDY630 alone was able to achieve a 40-fold R$_F$ value. Addition of PDPA-QSY$_{21}$ further increased the R$_F$ value to over 250-fold (FIG. 18D)

Previous studies showed that rhodamine and cyanine dyes with small Stoke shifts (<40 nm) were able to produce UPS nanoprobes with large R$_F$ values through the homoFRET-induced fluorescence decay mechanism (Zhou, et al., 2012). Results from this study confirmed the previous report, where PDPA-dye copolymers alone reached >50-fold and >100-fold for rhodamine and cyanine dyes, respectively. Addition of FQ-conjugated copolymer further increased the R$_F$ values for these nanoprobes (FIG. 18F, FIGS. 20-22).

FIGS. 18E-F summarized the fluorescence activation ratios (R$_F$=F$_{5.0}$/F$_{7.4}$) for all the fluorophores used in PDPA nanoprobes with and without the introduction of fluorescence quenchers. Data show that with the addition of FQ-conjugated polymer, all the fluorophores (12 in total) showed universally high activation ratios (>50-fold) regardless of the Stoke shift or PeT mechanisms. In addition, introduction of FQ-conjugated polymer did not affect the sharpness of pH transitions (all the composite nanoprobes had <0.25 pH unit between on and off states, FIGS. 18B and 18D and FIGS. 22B-22D).

5. UPS Library Spanning Large pH Transitions and Fluorescence Emissions.

Based on the above results, a representative UPS library consisting of 10 nanoprobes each encoded with a different fluorophore was produced. The composition for each nanoprobe follows that from FIG. 10D (see Table 3 for details), which resulted in a collection with 0.3 pH increment in the pH span of 4 to 7.4. For each nanoprobe, a series of aqueous solutions of the copolymer at the same polymer concentration (i.e., 0.1 mg/mL) but different pH values were prepared. For 4.4-AMCA, 4.7-MB, 5.0-BDY and 6.2-BDY630 nanoprobes, the corresponding copolymers were mixed with the same equivalent of FQ-conjugated matching copolymers to achieve high on/off contrast. FIG. 24 shows the emission image of the UPS nanoprobe library at the excitation/emission wavelengths corresponding to each fluorophore.

Results from FIG. 24 illustrate the exquisite pH sensitivity of the UPS nanoprobes to the external environment spanning the entire physiologic pH of 4-7.4. In the lowest pH range, the 4.4-AMCA nanoprobe was off at pH 4.55 but can be turned on at pH 4.25. This nanoprobe can be useful in the detection of functional lysosomal pH where hydrolases require a lower pH for enzyme activity. The on/off characteristics of the nanoprobe make them particularly useful in high through screening applications to identify molecular pathways or small molecular perturbators that affect lysosomal functions. For the nanoprobes covering the higher pH range (e.g., 6.5-7.1), the nanoprobes can be useful for the imaging of the acidic pH$_e$ of tumors and correlate nanoprobe activation with glycolysis rates of the cancer cells (Wang, et al., 2014; Ko, et al. 2010). The nanoprobes in the intermediate range (e.g., 5.0-6.5) may be useful for the study of maturation of endosomes/lysosomes and establish organelle-specific compositions for subcellular imaging or drug delivery applications.

Example 3: Anion Driven Micelle Formation Methods

1. Syntheses of PEO-b-PR Block Copolymers

PEO-6-PR copolymers (Scheme 1) were synthesized by atom transfer radical polymerization (ATRP) as reported by Zhou, et al., 2011, which is incorporated herein by reference. The dye-free copolymers were used in polymer characterizations. PEO-6-PDPA (3) is used as an example to illustrate the procedure. First, DPA-MA (1.70 g, 8 mmol), PMDETA (21 μL, 0.1 mmol) and MeO-PEO$_{114}$-Br (0.5 g, 0.1 mmol) were charged into a polymerization tube. Then a mixture of 2-propanol (2 mL) and DMF (2 mL) was added to dissolve the monomer and initiator. After three cycles of freeze-pump-thaw to remove oxygen, CuBr (14 mg, 0.1 mmol) was added into the polymerization tube under nitrogen atmosphere, and the tube was sealed in vacuo. The polymerization was carried out at 40° C. for 8 hours. After polymerization, the reaction mixture was diluted with 10 mL THF, and passed through a neutral Al$_2$O$_3$ column to remove the Cu catalyst. The THF solvent was removed by rotovap. The residue was dialyzed in distilled water and lyophilized to obtain a white powder. Table 4 summarizes the characterization of each copolymer.

a.
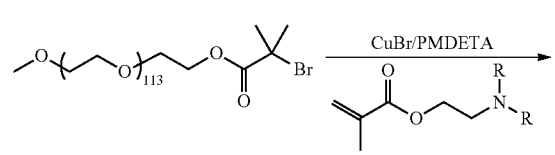
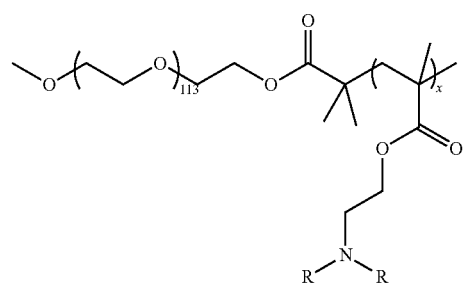
PEO-b-PR
b.
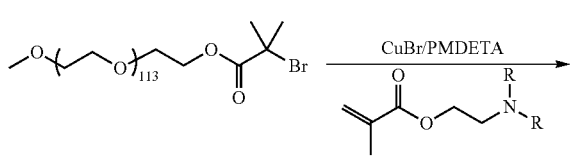
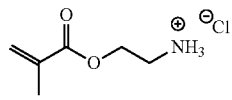
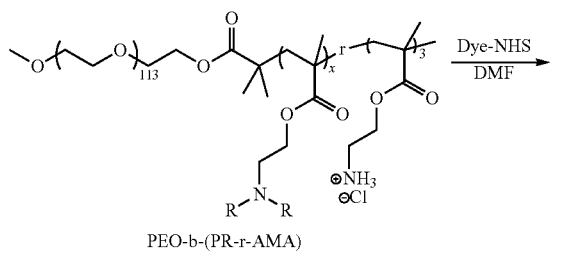
PEO-b-(PR-r-AMA)
-continued
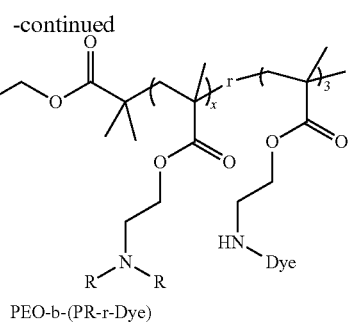
PEO-b-(PR-r-Dye)
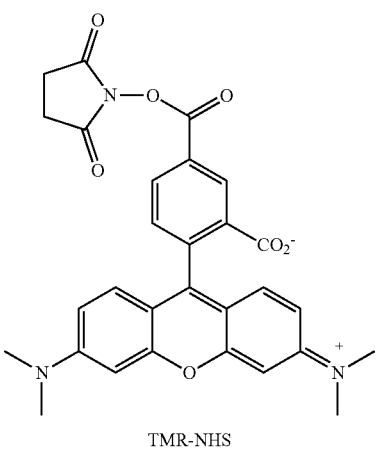
TMR-NHS
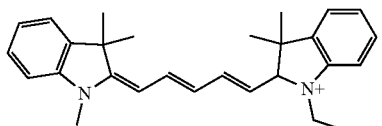
Cy5-NHS
R = Me 1
Et 2
Pr 3
Bu 4
Pe 5
TABLE 4
Characterization of PEO-b-(PR-r-AMA) block copolymers.
| Copolymer | PR name | Yield (%) | $M_{w,\, GPC}$ ($\times 10^{-4}$ D)[a] | $M_{n,\, GPC}$ ($\times 10^{-4}$ D)[a] | PDI[a] | Repeating units In the PR block | $M_{n,\, 1H\, NMR}$ ($\times 10^{-4}$ D)[b] |
|---|---|---|---|---|---|---|---|
| 1 | PDMA | 86 | 2.28 | 1.87 | 1.22 | 92 | 1.99 |
| 2 | PDEA | 87 | 2.42 | 1.97 | 1.23 | 88 | 2.17 |
| 3 | PDPA | 88 | 2.45 | 2.06 | 1.19 | 80 | 2.25 |

TABLE 4-continued

Characterization of PEO-b-(PR-r-AMA) block copolymers.

| Copolymer | PR name | Yield (%) | $M_{w, GPC}$ $(\times 10^{-4} D)^a$ | $M_{n, GPC}$ $(\times 10^{-4} D)^a$ | $PDI^a$ | Repeating units In the PR block | $M_{n, {}^1H NMR}$ $(\times 10^{-4} D)^b$ |
|---|---|---|---|---|---|---|---|
| 4 | PDBA | 78 | 2.84 | 2.32 | 1.22 | 72 | 2.47 |
| 5 | PD5A | 72 | 3.11 | 2.58 | 1.20 | 82 | 2.75 |

$^a$Number-average (Mn), weight-average molecular weight (Mw) and polydispersity index (PDI) (PDI = Mw/Mn) were determined by GPC using THF as the eluent.
$^b$Determined by $^1$H-NMR.

2. Syntheses of PEO-d-CPR-r-TMR/Cy5) Block Copolymers

AMA monomer was incorporated in the copolymers for the conjugation of dyes (Scheme Sib). Synthesis of PEO-b-(PR-r-AMA) copolymers followed the procedure described above. Three primary amino groups were introduced into each polymer chain by controlling the feeding ratio of AMA monomer to the initiator (ratio=3). In a representative procedure, PEO-b-(PR-r-AMA) (50 mg) was dissolved in 2 mL DMF. Then the NHS-ester (2.0 equivalence for TMR-NHS and 1.0 equivalence for Cy5-NHS) was added. After overnight reaction, the copolymers were purified by preparative gel permeation chromatography (PFgel Prep 10 m 10E3 Å 300×250 columns by Varian, THF as eluent at 5 mF/min) to remove the free dye molecules. The produced PEO-b-(PR-r-Dye) copolymers were lyophilized and kept at −20° C. during storage. It is important to note that the dye would undergo both Hetero FRET as well self-quenching when block copolymers self-assembled into micelles. So the dye conjugation number for each polymer chain is important for the FRET experiment. In the experiment, the conjugation number of TMR and Cy5 was controlled at 2 and 1 per polymer chain, respectively.

3. Preparation of Micelle Nanoparticles

For each copolymer, the stock solution of micelles was prepared following a solvent evaporation method as described in Nasongkla, et al. (2006), which is incorporated herein by reference. In the example of PEO-b-(PDPA-r-TMR) micelle solution, 20 mg of the copolymer was first dissolved in 1.0 mF THF and then added into 8 mF deionized water drop wise under sonication. The THF was removed through ultrafiltration with (100 KD) membrane for five times. Then deionized water was added to adjust the polymer concentration to 5 mg/mL as a stock solution. PEO-6-PDMA stock solution could be made by directly dissolve copolymer in deionized water.

Micelle solution samples for FRET experiment were prepared in a similar method. Preparation of PEO-b-(PDPA-TMR/Cy5) samples was described as a representative procedure. First, 0.1 mL PDPA-TMR and 0.1 mL PDPA-Cy5 stock solution was added to 1.8 mL deionized water. Then 1.8 μL of 1.0 M HCl was added to dissolve the water-insoluble block copolymer and adjust solution pH to 4. The Cl⁻ from HCl in the starting sample was <2 mM, which could be neglected for their ability to perturb micellization according to the experimental results.

4. FRET Experiment

The fluorescence emission spectra were obtained on a Hitachi fluorometer (F-7500 model). The samples were excited at 545 nm, and the emission spectra were collected from 560 to 750 nm. The FRET experiment for PEO-6-PDPA self-assembly behavior with the introduction of different anions followed similar procedure. $ClO_4^-$ was used as an example: 0.2 μL of 10 M $NaClO_4$ solution was added to 2.0 mL 0.5 mg/mL dye-conjugated PDPA (PDPA-TMR/PDPA-Cy5=1:1) solution at pH=4 and adjusted the $ClO_4^-$ concentration to 1 mM. Then small volume of 10 M $NaClO_4$ solution was added incrementally to increase the $ClO_4^-$ concentration to 3.2, 5.6, 10 mM. After 10 mM, solid $NaClO_4$ was added to the solution to increase the $ClO_4^-$ concentration to avoid sample dilution. The total volume of added $NaClO_4$ is less than 2 μL, which can be neglected compared to total volume of 2 mL. The fluorescence emission spectrum was collected after 4 min vortex following each addition of $NaClO_4$.

5. TEM and DLS Characterization

Samples for TEM and DLS analyses were prepared following procedures described above. The transition pH of PEO-6-PDPA was 6.1. First, 0.1 mL PDPA-TMR and 0.1 ml, PDPA-Cy5 stock solution was added to 1.6 mL deionized water. Solid $NaClO_4$ and NaCl were then added to the solution and dissolved after vortex. HCl and NaOH solution (1 M) were used to adjust the solution pH to 5.0 and 7.4. Deionized water was added to adjust the total volume to 2 mL. The morphology and size of nanoparticles were characterized by transmission electron microscopy (TEM, JEOL 1200EX model). Hydrodynamic diameter (Dh) was determined by dynamic light scattering (DLS, Malvern MicroV Model, He-Ne Laser, λ=632 nm).

6. Anion Competition Experiment

The preparation of micelle samples followed the same procedures described in FRET experiment. Solid NaCl and $Na_2SO_4$ powders were dissolved in the aqueous solution to achieve the initial anion concentration. The initial concentrations of Cl⁻ were 0, 50, 100, 200, 500, 1000 and 2000 mM. The initial concentrations of $SO_4^{2-}$ were 0, 25, 50, 100, 200 and 500 mM. The fluorescence emission spectra were collected 4 mins after vortex following the addition of $NaClO_4$. The results were fit with a sigmoidal curve. The half maximal FRET efficiency concentration of perchlorate was defined as $FC_{50}$ to quantify the competition ability of Cl⁻ and $SO_4^{2-}$.

7. $ClO_4^-$ Induced Micelle Self-assembly of PEG-b-PR Copolymers

A series of PEO-h-PR copolymers (1-5 in FIG. 25) with different alkyl side chains were used in this study. The preparation of micelle samples followed that described in the FRET experiment section. In this series of experiments, the ionic strength of the solution was buffered by using a 100 mM of NaCl concentration. This was used to minimize the ionic strength contribution from $NaClO_4$ since more hydrophobic PEO-h-PR copolymer (e.g., 5) requires less concentration to induce micelle self-assembly. After the experiments, the FRET efficiency was calculated as previously described in the FRET section.

Example 4: Anion Driven Micelle Formation
Results and Discussion

The discovery of the surprising chaotropic anion-induced micellization of protonated PEO-b-PR copolymers at pH below $pH_t$ (FIG. 25) is described. Surprisingly, an anti-Hofmeister trend was observed, where chaotropic anions resulted in micellization but not the kosmotropic anions (Zhang and Cremer, 2006; Parsons, et al., 2011; Kunz, et al., 2004), in contrary to their effects in protein aggregation (FIG. 26A).

First, a fluorescence energy resonance transfer (FRET) method to investigate the micelle self-assembly process was established. FRET is highly sensitive in detecting conformational and phase transitions of polymers/proteins because the energy transfer efficiency is inversely proportional to the sixth power of the donor-acceptor distance (Jares-Erijman and Jovin, 2003; Sapsford, et al., 2006). In the method, block copolymers were conjugated (1-5 in FIG. 25, Table 4) (Tsarevsky and Matyjaszewski, 2007; Ma, et al., 2003) with either a donor or acceptor dye. PEO-b-poly(dipropylaminoethyl methacrylate) (3, $pH_t$=6.1) was chosen as a model copolymer, and tetramethyl rhodamine (TMR, $\lambda_{ex}/\lambda_{em}$=545/580 nm)/Cy5 ($\lambda_{ex}/\lambda_m$=647/666 nm) as donor/acceptor, respectively (Ha, et al., 1999; Grunwell, et al., 2001)

At pH 4, the tertiary amines in 3 ($pH_t$=6.1) were protonated and the resulting copolymers were soluble in water as dispersed cationic unimers. No FRET effect was observed due to the large distance between the unimers (therefore TMR and Cy5) in solution. Addition of chaotropic anions (e.g., $ClO_4^-$, $SCN^-$ or $I^-$) resulted in the decrease of fluorescence intensity from TMR and increase of emission intensity of Cy5 (FIG. 27), indicating the formation of polymeric micelles. Micelle formation was hypothesized to bring TMR and Cy5 to close proximity within the micelle core, thereby dramatically increasing FRET efficiency (FIG. 26B). In contrary, kosmotropic anions (e.g., $SO_4^{2-}$, $H_2PO_4^-$) did not lead to any FRET transfer (FIG. 28) even at concentrations close to their solubility limits (Table 5).

TABLE 5

Saturated solubility of sodium salts of Hofmeister anions.

| Salt | Saturated solubility (M) | Salt | Saturated solubility (M) |
|---|---|---|---|
| $NaClO_4$ | 17.2 | NaBr | 8.8 |
| NaSCN | 17.1 | NaCl | 6.1 |
| NaI | 11.9 | $NaH_2PO_4$ | 7.2 |
| $NaNO_3$ | 5.0 | $Na_2SO_4$ | 1.4 |

Solubility data were obtained from solubility handbook by Khaled Gharib from open sources:
[1] srdata. nist. gov/solubility/index. aspx
[2] food. oregonstate. edu/learn/sugar. html
[3] world-wide-web at kayelaby. npl. co. uk/
[4] chemfinder. cambridgesoft. com The FRET effects were quantified to compare different anions in their abilities to induce micellization (FIG. 26C). FRET efficiency was normalized as $(FA/FD)/(FA/FD)_{max}$, where FA and FD were the fluorescence intensity of TMR and Cy5 at different anion concentrations, respectively; $(FA/FD)_{max}$ was the maximum value of FA/FD (3.3) at high $ClO_4^-$ concentrations. FRET efficiency was plotted as a function of concentration for different anions. Results displayed an anti-Hofmeister trend where chaotropic anions were able to induce unimer association (i.e., micellization) whereas the kosmotropic anions were not (FIG. 26C). This observation is in contrary to the classical Hofmeister effect in protein solubilisation, where kosmotropic ions are known to induce protein aggregation in water but not the chaotropic ions (Hofmeister, 1888; Collins and Washabaugh, 1985)

Copolymer 3 displayed different detection sensitivity toward the chaotropic anions. Data show FRET sensitivity followed the order of $ClO_4^->SCN^->I^->NO_3^-$. $FC_{50}$ is defined as the anion concentration that the FRET efficiency was at 50%. The values of $FC_{50}$ were 11, 68 and 304 mM for $ClO_4^-$, $SCN^-$, and $I^-$, respectively. For $NO_3^-$, only weak FRET effect was observed at its saturation concentration (~3 M). More detailed examination shows that only 3-fold $ClO_4^-$ concentration change (i.e., from 6 to 18 mM, FIG. 26C) was necessary to increase FRET efficiency from 10% to 90%. This narrowed concentration dependence suggests an increased cooperative response similar to the ultra-pH response as reported previously (Zhou, et al., 2011; Zhou, et al., 2012; Huang, et al., 2013; Wang, et al., 2013).

Figure 29:
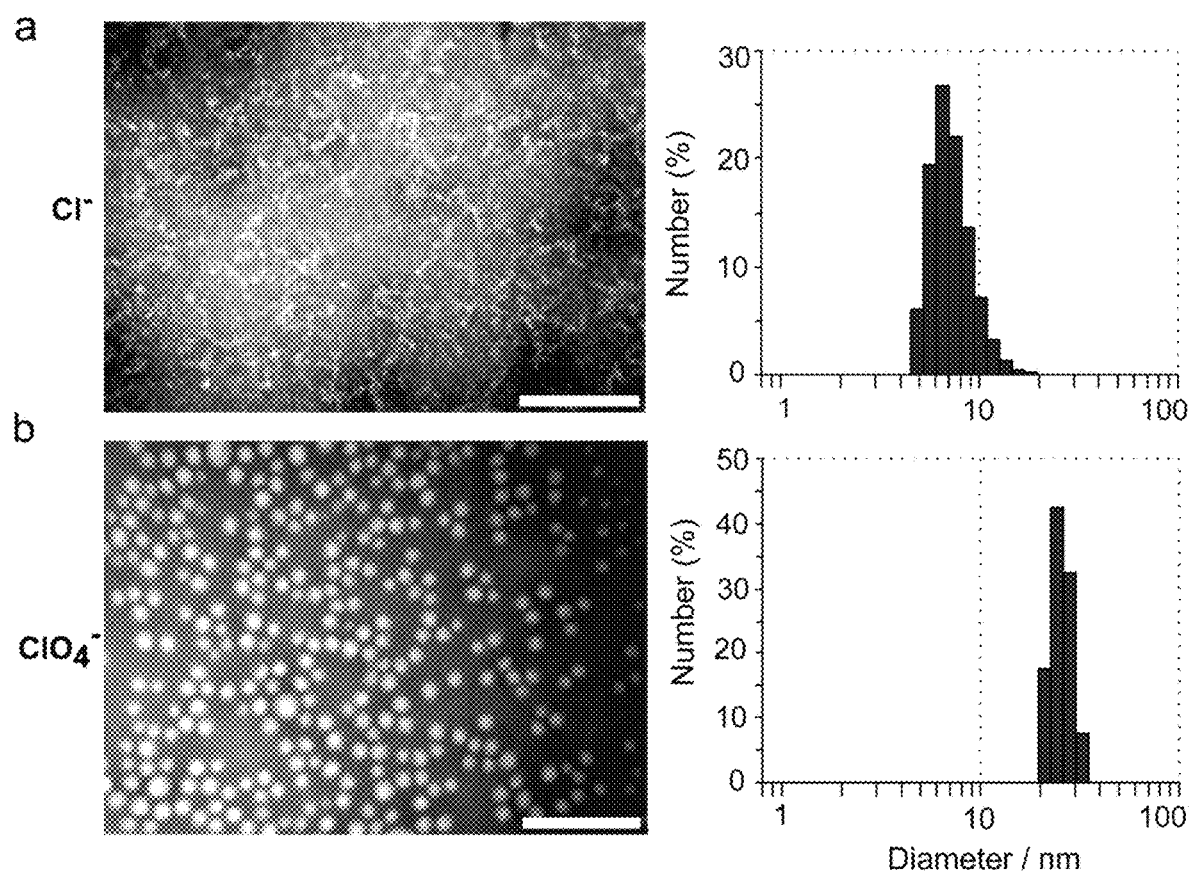
Figure 30:
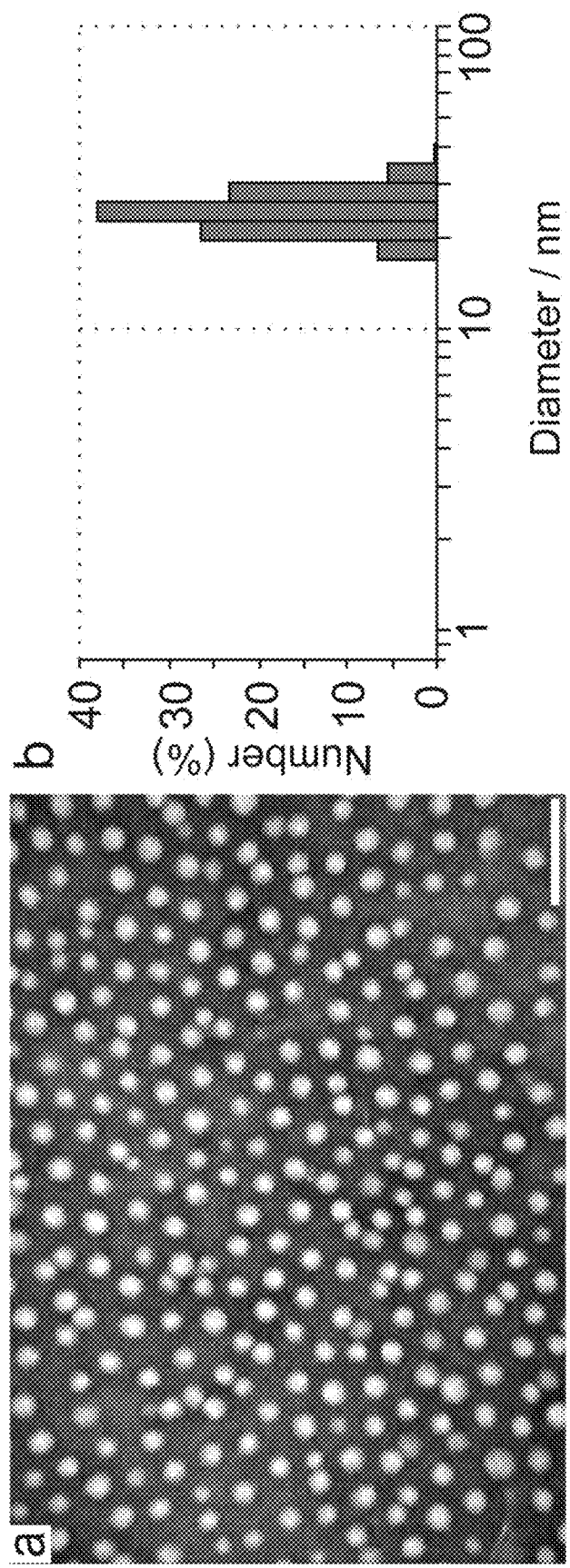
Figure 31:
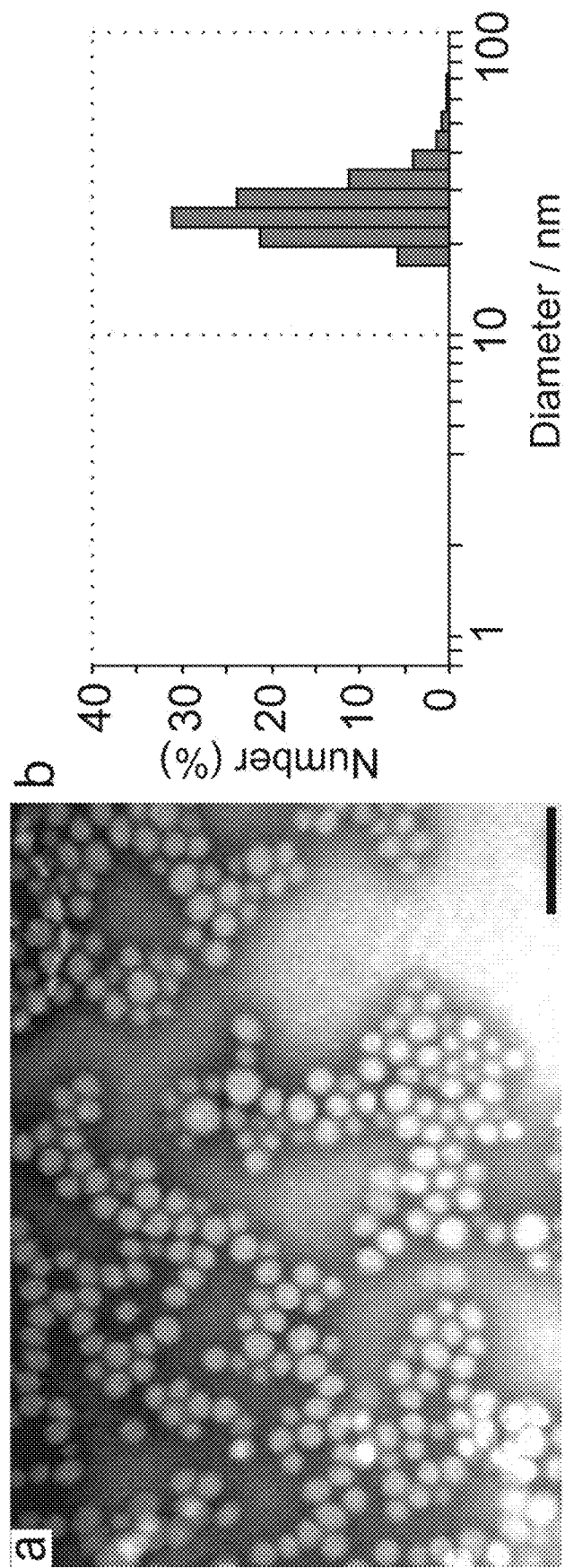
Figure 32:
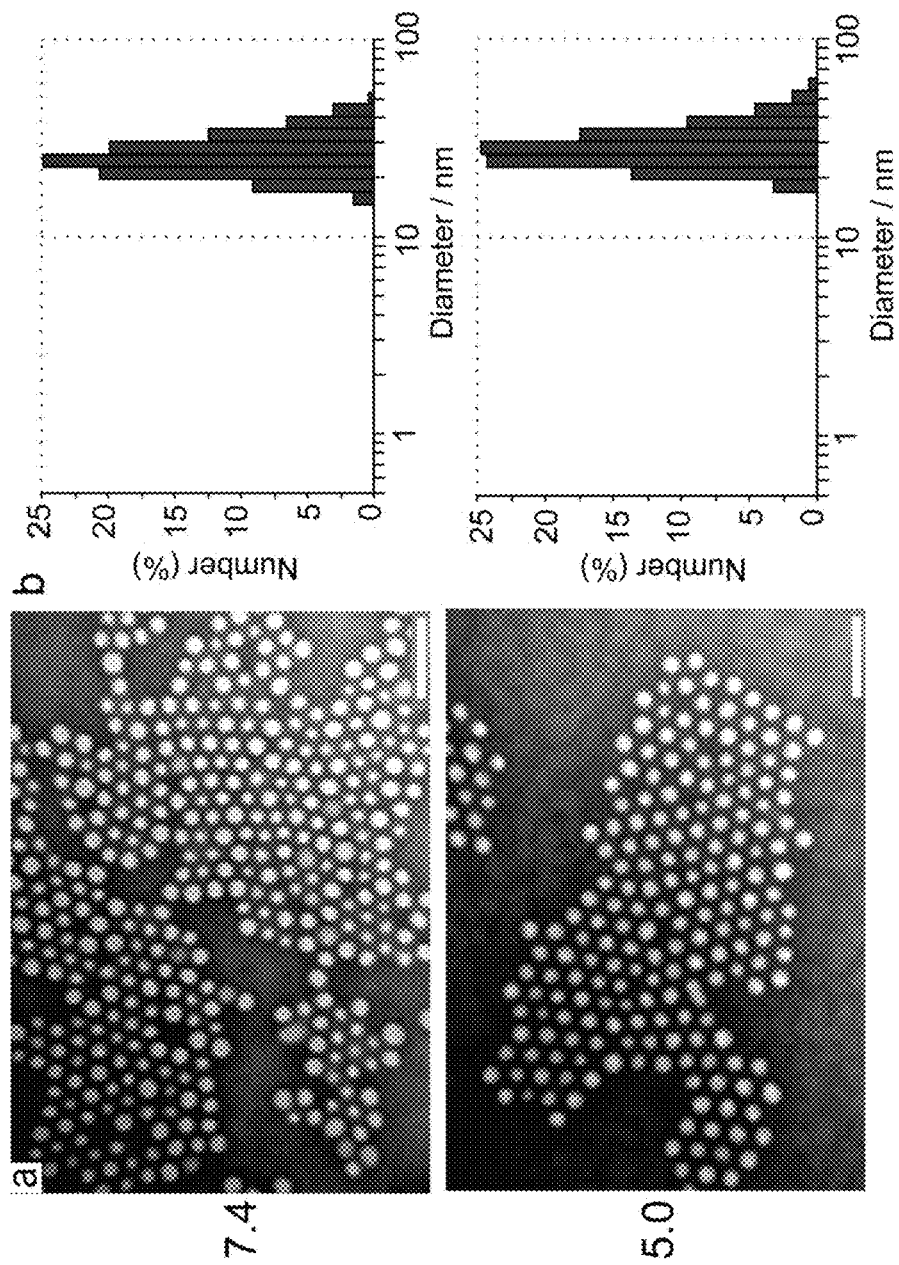

To further confirm chaotropic anion-induced micellization, transmission electron microscopy (TEM) and dynamic light scattering (DLS) was employed to investigate the changes in morphology and hydrodynamic diameter during micelle transition, respectively. The chloride anion ($Cl^-$) was used as a negative control. In the presence of 50 mM $Cl^-$, copolymer 3 stayed as a unimer at pH 5.0 (below its $pH_t$ at 6.1, FIG. 29A). In contrast, copolymer 3 self-assembled into spherical micelles when $Cl^-$ was replaced with $ClO_4^-$ (FIG. 29B). DLS analyses showed increase of hydrodynamic diameters from 7±2 to 26±3 nm when the anions were changed from $Cl^-$ to $ClO_4^-$, respectively (FIG. 29). This size increase reflects the transition of copolymer 3 from unimer state to the micelle state, consistent with the FRET and TEM data. At pH 7.4, copolymer 3 was present as spherical micelles with hydrodynamic diameters at 27±2 and 28±3 nm in the presence of $Cl^-$ and $ClO_4^-$ anions, respectively (FIGS. 30-31). For non-ionizable amphiphilic block copolymers such as PEO-b-poly(D,L-lactic acid) (PEO-b-PLA), neither pH change nor $ClO_4^-$ addition had any effects on the micelle state (FIG. 32).

The chaotropic anion-induced self-assembly were then studied in the presence of competing kosmotropic or borderline anions. Copolymer 3 was dissolved at pH 4 with different initial concentrations of competing $SO_4^{2-}$ or $Cl^-$. Then chaotropic anions $ClO_4^-$ were added to induce micellization (FIGS. 33-36). FIG. 37A shows the representative example of FRET efficiency as a function of $ClO_4^-$ concentration. Addition of $SO_4^{2-}$ anions was able to decrease the sensitivity of $ClO_4^-$ in micelle induction. The $FC_{50}$ values were quantified to evaluate the effect of competing anions (FIG. 37B). A bell curve as a function of the ionic strength of the competing anions was observed. At low ionic strength (<0.1 M), addition of competing anions decreased the ability of $ClO_4^-$ to induce micelle formation, consistent with their competition with the ammonium groups of the PR segment. At high ionic strength (>0.5 M) of $SO_4^{2-}$ or $Cl^-$, however, an enhancement of $ClO_4^-$ induced self-assembly was observed. This effect can be attributed to the more ordered bulk water structures at high kosmotropic ion concentrations, which makes the hydrophobic association during micelle self-assembly more favorable.

Finally, the effect of hydrophobic strength of PR segment on chaotropic anion-induced micellization (FIG. 38A) was investigated. A series of PEO-b-PR copolymers (1-5 in FIG. 25) bearing different alkyl chain lengths from methyl to pentyl groups on the tertiary amines were synthesized. Results showed a clear dependence of $ClO_4^-$-induced self-assembly on the hydrophobicity of the PR segment (FIG. 39). With the least hydrophobic side chains (i.e., methyl in 1), no micellization was observed even at the highest $ClO_4^-$ concentrations (1 M). In contrary, the most hydrophobic side chains (pentyl in 5) resulted in the most sensitive micellization induction by $ClO_4^-$. The $FC_{50}$ values were 2, 4, 35, 134 mM when the side chains were pentyl, butyl, propyl and ethyl groups, respectively (FIG. 38A).

Results from the above studies illustrate a highly unusual micelle self-assembly process from block copolymers with tertiary ammonium groups induced by chaotropic anions. There are several unique features in the current nanosystem: first, chaotropic anions were able to form stable ion pairs with positively charged ammonium groups in the hydrophobic micelle core environment. Assuming majority of the ammonium groups are in the ionized state, this translates into ~60,000 ion pairs per micelle with an estimated core size of 14 nm (calculation based on 800 polymer chains per micelle, (Wang, et al., 2013) 70-80 repeating units of amino group-containing monomers per polymer chain and PEO shell size of 6 nm) (Leontidis, 2002). Second, only chaotropic anions were able to induce micelle formation whereas the kosmotropic ($SO_4^{2-}$) and borderline ($Cl^-$) anions did not posses this ability. This trend appears to counter that in classical protein solubilization studies. Third, the ability of chaotropic anions to induce micellization appears to show positive cooperativity similar to ultra-pH sensitive response. Previous studies had showed that fluorescence activation (10% to 90% response) occurred within 0.25 pH unit (<2-fold in [$H^+$]). This study show FRET transfer happened in a span of 3-fold [$ClO_4$] change. Lastly, competition experiments with kosmotropic and borderline anions illustrated a bell curve behavior, which points to the complexity and subtle nature of the micelle self-assembly process in the current system.

An empirical model (FIG. 38B) was built to depict the factors that contribute to the micelle self-assembly process. Without being bound by theory, the hydrophobic interactions from increasing alkyl chain lengths are hypothesized to provide the dominant driving force for micelle formation. This is supported by the lack of micelle formation when the side chain of the tertiary amines is methyl group (as indicated by the dashed line on the left arm of FIG. 38B). Similarly, neutralized copolymer 1 did not form micelles at pH above its $pH_t$ (Zhou, et al, 2011) Meanwhile, anions also play a critical role in micellization. Kosmotropic anions, which are known to have strong hydration shells and weak polarization characteristics are energetically less favorable in the formation of ion pairs and stabilization of ion pairs in the hydrophobic core (Collins, 1997; Underwood and Anacker, 1987). Chaotropic anions, with their strong polarizability and low energy cost at removing hydration sheath allows for formation of stable ion pairs in the hydrophobic micelle core (Zhang and Cremer, 2009).

Example 5: Sentinel Lymph Node Detection

1. Identification of at Risk Sentinel Lymph Nodes by UPS6.9

The $UPS_{6.9}$ nanoprobes also demonstrated the ability to identify at risk sentinel lymph nodes. FIG. 42A shows the identification of a representative sentinel lymph node on the side of the neck near the primary tumor site by the SPY Elite® camera. Eight lymph nodes were identified in 4 different animals (2 per animal) with primary head and neck cancers. These nodes were in the cervical basin draining the primary head and neck tumors in the mice and anatomically corresponded to cervical nodes typically found in mice. All the eight nodal structures were identified by $UPS_{6.9}$ only; they were too small to be seen with white light being a millimeter or less in size and closely associated with cervical fat and salivary glands but were bright when visualized with the SPY camera. H&E analysis by a clinical pathologist validated the identified structures as lymph nodes. One out of eight nodes showed the presence of HN5 cancer cells, as indicated by the black arrows in FIG. 42B bottom panel. In several cases, nodal recurrence of tumors was observed in mice that had had complete resection of their primary tumors. Large tumors appeared in the side of the neck instead of the primary tumor site. These data suggest the importance of identification of at risk lymph nodes to achieve complete resection of the tumors. The fact that single nodes draining the tumors were identified, and that the majority did not contain cancer cells suggests, these nodes represent SLN collecting activated polymer probes draining into lymphatics from the primary tumor sites.

Example 6: Development of pH-Activated Indocyanine Green-Encoded Nanosensor (PINS)

1. Preparation of PINS and Nanosensor Characteristics

A pH-activatable indocyanine green-encoded nanosensor (PINS) comprising a micelle of poly(ethylene glycol)-b-poly(ethylpropylaminoethyl methacrylate) copolymers (PEG-b-(PEPA$_x$-r-ICG$_y$), where x and y indicate the number of random repeating units of EPA monomer and ICG dye, respectively; FIGS. 43A-43I) was synthesized. Hydrophobic micellization and homoFRET-induced fluorescence quenching (Zhou et al., 2011 and Zhou et al., 2012) rendered dramatically sharpened pH response. Systematic optimization of PEPA segment length and ICG conjugation number (FIGS. 44A-44F) led to an optimal PINS composition with sharp pH transition at 6.9, high fluorescence activation ratio, optimal particle size (25 nm), and an average of 800 ICG per nanoprobe for signal amplification. Compared to reported pH-sensitive probes (e.g., small molecular dyes, (Urano et al., 2009) peptides, (Weerakkody et al., 2013) or PeT nanoprobes (Diaz-Fernandez et al., 2006) with 10-fold signal change over 2 pH), the PINS design achieved >100-fold signal increase over 0.15 pH span at 6.9. Additional polymers linked to ICG dye were prepared and are characterized in Table 6.

TABLE 6

Mixed Alkyl Monomer Co-polymers Characteristics.

| Polymers | $M_n$ (kDa) | $M_w$ (Da) | PDI | Yield (%) | $pH_t^a$ | $\Delta pH_{10-90\%}$ |
|---|---|---|---|---|---|---|
| P(DEA$_{22}$-EPA$_{78}$) | 20.7 | 26.4 | 1.28 | 86 | 7.10 | 0.15 |
| P(DEA$_{11}$-EPA$_{89}$) | 21.1 | 27.1 | 1.28 | 88 | 7.01 | 0.16 |
| PEPA$_{100}$ | 21.2 | 26.6 | 1.25 | 87 | 6.92 | 0.15 |
| P(DPA$_{10}$-EPA$_{90}$) | 20.5 | 24.8 | 1.21 | 83 | 6.82 | 0.14 |
| P(DPA$_{21}$-EPA$_{79}$) | 20.9 | 25.9 | 1.24 | 82 | 6.72 | 0.16 |

$^a$pH$_t$ was determined by the titration curve of Probe-ICG

Initial dose-response study with the nanosensor was performed in mice bearing human head and neck HN5 orthotopic tumor xenografts similar to those due with other pH responsive systems described herein. The PINS was intravenously injected through the tail vein and a clinical SPY Elite® camera was used to image the animals (FIGS. 45A-45E). The 2.5 mg/kg amount was chosen for use as the imaging dose due to the large tumor contrast over noise ratio (CNR=27) over a persisted time window (12-24 h). The stable time window is advantageous for oncologic surgery over small molecular tracers with transient windows (2-3 h) (Choi et al., 2013) due to fast renal clearance. Injection of free ICG at the equivalent dye dose as in 2.5 mg/kg PINS showed no observable tumor contrast (FIG. 45B).

Tumor acidosis imaging by PINS improved sensitivity and specificity of tumor detection compared to FDG-PET where brain and brown adipose tissues led to false positives mimicking clinical observations (FIG. 46B and FIGS. 47A-47E) (Cook et al., 2004 and Fukui et al., 2005). Although FDG-PET detected large HN5 tumors (~200 mm$^3$), the PET method was not successful at detecting small tumor nodules (~15 mm$^3$, Table 7). Multiple different tumor sizes were detectable using PINS with high tumor to normal tissue contrast (CNR>20). Furthermore, PINS was able to delineate tumor margins at submillimeter spatial resolutions (FIG. 46B and FIGS. 47A-47E).

TABLE 7

Characterization of PEPA$_x$-ICG$_1$ copolymers with different repeating units of PEPA segment but the same ICG content and the resulting nanoprobe properties.

| copolymer | M$_n$ (kDa)$^a$ | Repeat unit$^b$ | Particle size (nm) | pH$_t$ | ΔpH$_{10\text{-}90\%}$ | FI$_{HS6.0}$$^c$ |
|---|---|---|---|---|---|---|
| PEPA$_{40}$-ICG$_1$ | 13.5 | 43 | 21.9 ± 1.7 | 6.96 | 0.30 | 32.3 |
| PEPA$_{60}$-ICG$_1$ | 16.8 | 62 | 24.8 ± 0.9 | 6.94 | 0.25 | 37.0 |
| PEPA$_{80}$-ICG$_1$ | 19.7 | 79 | 25.3 ± 0.8 | 6.92 | 0.18 | 45.3 |
| PEPA$_{100}$-ICG$_1$ | 25.1 | 102 | 26.0 ± 1.1 | 6.92 | 0.15 | 49.3 |
| PEPA$_{120}$-ICG$_1$ | 29.1 | 119 | 27.6 ± 1.0 | 6.91 | 0.13 | 51.6 |

$^a$Number-averaged molecular weights (M$_n$) were determined by GPC using THF as the eluent;
$^b$Repeating unit was calculated based on integrations of —CH$_2$—O— groups on PDPA to the methylene groups on PEG using $^1$H NMR;
$^c$ Determined as ICG fluorescence emission intensity in 50% human serum.

To assess the breadth of tumor detection, three orthotopic head and neck tumors (HN5, FaDu and HCC4034, a tumor xenograft from a patient of B.D.S), a subcutaneous breast tumor (MDA-MB-231), an intramammary orthotopic breast tumor (triple negative 4T1), a peritoneal metastasis model from HCT116 colorectal cancer cells, a patient derived xenograft of kidney cancer, and an ortho topic brain tumor from U87 glioma cells were imaged. All the tumors were established in NOD-SCID mice except 4T1 tumors in immunocompetent BalB/C mice. Bright fluorescent illumination was observed across all the tumor types (FIG. 48). Ex vivo imaging revealed high contrast ratios of tumor over muscle (20-50 fold) with high cancer specificity (FIGS. 49A & 49B). Using HN5 tumor model, the compatibility of PINS imaging with multiple clinical cameras was demonstrated (FIGS. 50A-50F).

Using the SPY camera, real-time tumor acidosis guided surgery (TAGS) in mice bearing HN5 head and neck or 4T1 breast cancers was performed. PINS (2.5 mg/kg) was injected intravenously 12-24 h before surgery. In a representative operation in HN5 tumor-bearing mice, after resection of the primary tumor, the residual tumor was clearly visible by the SPY camera (middle left panel in FIG. 51A) but not under white light (top left panel). To investigate the accuracy of margin delineation, non-survival surgery in 9 mice bearing HN5 head and neck tumors were analyzed using a double blind protocol. The surgeon resected the tumors under PINS illumination and marked the tissue specimen (2-3 mm in size) as either primary tumor, tumor margin or negative muscle tissue based on fluorescence. The specimens were then frozen sectioned and stained with H&E. Histological evaluation was performed independently by a clinical pathologist (FIG. 52). Using histology as the gold standard, PINS fluorescent assessment had a 95% confidence of detection accuracy between 89.5% and 100% (n=27). Long-term survival surgery outcomes show improved loco-regional control and overall survival with TAGS over white light surgery (WLS), debulking surgery and untreated controls (FIG. 51B). Debulking surgery with macroscopically positive margins typically provides no survival benefit for head and neck cancer and served as a control for the adequacy of WLS. WLS was superior to the debulking and untreated controls (P<0.0001) which showed equivalent survival, indicating good unbiased technique. TAGS led to the best outcome, with 13 out of 18 animals (72%) showing cures 150 days post-operatively (P<0.0001 vs. WLS, FIG. 51B).

To mimic clinical scenarios where identifying occult cancerous nodules may take precedence over tumor margins, small orthotopic breast tumors were established in immunocompetent female BalB/C mice. 5×10$^4$ triple negative 4T1 breast cancer cells were injected in the inguinal mammary pad. With an estimated doubling time of 24 h, the nodule size represents <1 million 4T1 cells in the foci on day 4. PINS under SPY camera was able to identify the 4T1 foci, which was confirmed by histology (FIGS. 53A-53C). Tumor could not be detected with visual inspection or palpation. For the white light control, the tumor was allowed to grow to ~25 mm$^3$ to be visible, and carefully resected the primary tumor and surrounding margin. TAGS resulted in superior visualization, improving survival after resection over the untreated control and WLS (P<0.05, FIG. 53D), demonstrating superb imaging sensitivity with PINS.

Tumor response to small molecular inhibitors targeting different tumor acidosis pathways was evaluated by PINS (FIGS. 54A-54C). Four inhibitors were selected: acetazolamide for carbonic anhydrase IX (CAIX),V) (Neri & Supuran, 2011) α-cyano-4-hydroxycinnamate (CHC) for monocarboxylate transporter (MCT) (Sonveaux et al., 2008), cariporide for sodium proton ex changer 1 (NHE1) (Cardone et al., 2005) and pantoprazole as a proton pump inhibitor (PPI) (Vishvakarma & Singh, 2011). The PINS was injected intravenously to BalB/C mice bearing 4T1 tumors following inhibitor administration. NIR imaging 24h after PINS injection showed drastic inhibition (74.2%) by CAIX inhibitor acetazolamide over PBS control. Moderate inhibition (29.3%) by MCT inhibitor CHC was also observed. No significant inhibition was noticed by cariporide or pantoprazole. The PINS response is consistent with the previously reported antitumor efficacy of CAIX inhibitors in 4T1 tumors (Lou et al., 2011 and Pacchiano et al., 2011). Compared to $^1$H/$^{31}$P$^{19}$ or hyperpolarization $^{13}$C MRI methods (Gallagher et al., 2008), PINS imaging offers a simple and convenient reporter assay for the mechanistic investigation of tumor acidosis and development of drugs that target dysregulated pH of solid cancers (Neri & Supuran, 2011 and Parks et al., 2013).

Safety evaluation of the PINS in immunocompetent C57BL/6 mice showed temporary body weight loss at high dose (FIG. 55A and Tables 8 & 9). The maximum tolerated dose is at 250 mg/kg, 100-fold higher than the imaging dose. Mice were sacrificed on day 1, 7 and 28 at 200 and 250 mg/kg. Liver and kidney functions were measured (FIGS. 55B-55D). Liver enzyme levels (ALT and GOT) increased on day 1 after PINS injection and returned to normal after 7 days. Histology analysis (FIG. 56) showed microsteatosis in the liver in the 250 mg/kg group at day 1 and returned to normal by 28 days. Other major organs (e.g., kidney, heart, spleen, brain) are normal.

TABLE 8

Log-rank p-values for pairwise treatment comparisons among different groups in survival surgery.

| | | Debulking | White light | TAGS |
|---|---|---|---|---|
| Head and neck surgery | Control | 0.347 | <0.0001 | <0.0001 |
| | Debulking | — | <0.0001 | <0.0001 |
| | White light | — | — | <0.0001 |
| Breast surgery | Control | — | 0.0501 | <0.0001 |
| | White light | — | — | 0.0116 |

TABLE 9

Tolerability and survival of C57BL/6 mice following bolus injection of PINS.

| | 7 Days | Morbidity reaction type and degree$^a$ | | |
|---|---|---|---|---|
| Dose (mg/kg) | mortality: n death/total n (% deaths) | Reduced feces | Lack of mobility (<6 h) | Lack of appetite (<6 h) |
| 150 | 0/5 (0%) | − | recovered soon | recovered soon |
| 200 | 0/10 (0%) | + | + | + |
| 250 | 0/15 (0%) | ++ | ++ | ++ |
| 300 | 4/5 (80%) | +++ | +++ | +++ |

$^a$Reaction degree was recorded as: − no reaction; + mild reaction; ++ intermediate reaction; +++ strong reaction.

2. Materials and Methods

Characterization of Monomer and Polymer of PINS.

Syntheses of 2-(ethylpropylamino)ethyl methacrylate (EPA-MA) and poly(ethylene glycol)-b-poly(ethylpropylaminoethyl methacrylate) copolymers (PEG-h-(PEPA)) were described in the method section above. Below are the chemical characterizations of the monomer and copolymer:

2-(Ethylpropylamino) Ethyl Methacrylate (EPA-MA)

$^1$H NMR (TMS, CDCl$_3$, ppm): 6.10 (s, 1H, CHH=C(CH$_3$)—), 5.54 (s, 1H, CHH=C(CH$_3$)—), 4.20 (t, 2H, —OCH$_2$CH$_2$N—), 2.75 (t, 2H, —OCH$_2$CH$_2$N—), 2.58 (q, 2H, —N(CH$_2$CH$_2$CH$_3$)(CH$_2$CH$_3$)), 2.44 (m, 2H, —N(CH$_2$CH$_2$CH$_3$)(CH$_2$CH$_3$)), 1.94 (s, 3H, CH$_2$=C(CH$_3$)—), 1.45 (m, 2H, —N(CH$_2$CH$_2$CH$_3$)(CH$_2$CH$_3$)), 1.02 (t, 3H, —N(CH$_2$CH$_2$CH$_3$)(CH$_2$CH$_3$)), 0.87 (t, 3H, —N(CH$_2$CH$_2$CH$_3$)(CH$_2$CH$_3$)). $^{13}$CNMR (CDCl$_3$, ppm): 167.42, 136.36, 125.35, 63.20, 56.31, 51.51, 48.32, 20.54, 18.33, 12.09, 11.82. [M+H]$^+$: 200.2 (calculated 200.3).

Poly(Ethylene Glycol)-b-Poly(Ethylpropylaminoethyl Methacrylate) (PEO-b-P(EPA)$_{100}$)

$^1$H NMR (TMS, CDCl$_3$, ppm): 3.99 (b, 204H, —COOCH2-), 3.83-3.45 (m, 450H, —CH2CH2O—), 3.38 (s, 3H, CH3O—), 2.68 (b, 204H, —OCH2CH2N), 2.55 (b, 204H, N(CH$_2$CH$_2$CH$_3$)(CH2CH3)), 2.41 (b, 204H, —N(CH$_2$CH$_2$CH$_3$)(CH$_2$CH$_3$)), 1.78-1.90 (m, 270H, CCH3C & C(CH3)2), 1.45 (m, 204H, —N(CH2CH2CH3)(CH$_2$CH$_3$)), 1.02 (m, 306, —N(CH$_2$CH$_2$CH$_3$)(CH$_2$CH$_3$)), 0.88 (b, 306H, —N(CH$_2$CH$_2$CH$_3$)(CH$_2$CH$_3$)). $^{13}$CNMR (CDCl$_3$, ppm): 177.73, 177.33, 176.61, 70.58, 63.26, 63.13, 56.21, 51.09, 45.05, 44.70, 38.69, 31.92, 30.33, 29.69, 29.36, 28.90, 23.72, 22.98, 22.69, 20.62, 16.53, 14.13, 12.18, 11.91.

Fluorescence Activation of PINS.

Fluorescence intensity of PINS in different pH buffer solutions was measured on a Hitachi fluorimeter (F-7500 model). For each PINS composition, a stock solution in MilliQ water at the concentration of 2.5 mg/mL was prepared. The stock solution was then diluted with either 80 mM phosphate-buffered saline (PBS) buffer with different pH values or 50% human serum in 80 mM PBS buffer with different pH values. The final micelle concentration was controlled at 0.05 mg/mL in PBS or 0.025 mg/mL in 50% human serum. The nanoprobe solution was excited at 780 nm and the emission spectra were collected from 800 nm to 900 nm. The emission intensity at 815 nm in PBS and 830 nm in 50% human serum was used to quantify the pH-response of the nanoprobes. Fluorescent images of PINS solution (0.05 mg/mL) in test tubes at different pH values were taken by a SPY Elite® imaging system.

Shelf-Life Study.

Freshly prepared nanoprobe aqueous solution (5 mg/mL) was mixed with equal volume of 20% sucrose aqueous solution to generate 2.5 mg/mL stock solution in 10% sucrose. The stock solution was divided and sealed in several test tubes and frozen in a −20° C. freezer. Samples were thawed at designated time point to test the fluorescence activation in PBS or 50% human serum as described above.

Cell Culture.

The cancer cell lines used for in vivo tumor models include HN5, FaDu, HCC4034 human head and neck cancers, MDA-MB-231 and 4T1 breast cancers, U87 glioma, and HCT116 colorectal cancer cells. HN5 and FaDu cell lines were obtained from Michael Story's lab; HCC4034 was established by John Minna's lab from a resected tumor of a head and neck patient of Dr. Baran Sumer; MD-MBA-231, 4T1 and HCT116 were obtained from David Boothman lab; U87 was obtained from Dawen Zhao lab. All cells lines were tested for mycoplasma contamination before use. Negative status for contamination was verified by Mycoplasma Detection Kit from Biotool. Cells were cultured in DMEM with 10% fetal bovine serum and antibiotics.

Animal Models.

Animal protocols related to this study were reviewed and approved by the Institutional Animal Care and Use Committee. Female NOD-SCID mice (6-8 weeks) were purchased from UT Southwestern Medical Center Breeding Core. For orthotopic head and neck tumors, HN5, FaDu or HCC4034 cells (2×10$^6$ per mouse) were injected into the submental triangle area. One week after inoculation, animals with tumor size 100-200 mm$^3$ were used for imaging studies. Subcutaneous breast tumor model was established by injecting MDA-MB-231 (2×10$^6$ per mouse) cells on the right flank. Peritoneal metastasis was established by intraperitoneal injection of HCT-116 (2×10$^6$ per mouse) cells followed by gentle massage on the abdomen. Orthotopic U87 glioma bearing mice were established by intracranial injection of U87 cells. Mice bearing XP296 patient-derived kidney xenograft were provided by the James Brugarolas lab. Female BalB/C mice (6-8 weeks) were purchased from UT Southwestern Medical Center Breeding Core. Orthotopic breast tumor model was established in BalB/C mice by injection of 4T1 (5×10$^4$ per mouse) cells into the right thoracic mammary glands.

Dose-Response Study.

HN5-tumor-bearing mice (3 for each group) were injected with 1.0, 2.5 or 5.0 mg/kg PINS isotonic solution. The control group was injected with 0.08 mg/kg free ICG dye (equivalent to the dye content in 2.5 mg/kg PINS). At designated time point, mice were anesthetized with 2.5% isofluorane and imaged with SPY Elite®. Fluorescence intensity was measured by Image J. Contrast to noise ratios (CNR) were calculated by the following equation:

$$CNR = \frac{FI(\text{Tumor}) - FI(\text{Normal Tissue})}{\text{s.d.(Normal Tissue)}}$$

FI(Tumors) and FI(Normal Tissue) are the fluorescence intensities of the tumor and normal tissues, respectively. The background noise was measured as the standard deviation of the normal tissue fluorescence.

In Vivo and Ex Vivo Fluorescence Imaging.

Nanoprobes (2.5 mg/kg for all tumor models except 3.0 mg/kg for U87 and XP296) were administered intravenously via the tail veins of tumor-bearing mice. After 24 h, the animals were imaged by the SPY Elite® clinical camera. For ex vivo imaging, tumors and main organs were harvested and imaged. Fluorescence intensities of the tumors and organs were normalized to the muscle tissue of comparable size.

Example 7: Use of Micelles to Evaluate Endocytic Organelles and their Use in Signaling and Proliferation 1. Preparation of the pH Responsive Systems In order to evaluate the physiological roles of organelles, a series of amphiphilic block copolymers PEO-b-P($R_1$-r-$R_2$), where PEO is poly(ethylene oxide) and P($R_1$-r-$R_2$) is an ionizable random copolymer block were synthesized (FIG. 57A and FIG. 58). The molecular composition of each copolymer is shown in Table 10. At high pH (e.g., 7.4 in phosphate-buffered saline), these copolymers self-assemble into core-shell micelle structures (diameter 30-60 nm, surface electrostatic potential −2 to 0 mV, Table 10 and FIG. 59). At pH below the apparent $pK_a$ of each copolymer, micelles dissociate into unimers due to the protonation of tertiary amines. The previous studies exploited the sharp pH-dependent micelle transitions for the development of a series of tunable, ultra-pH sensitive fluorescence sensors (Ma, et al., 2014).

Herein are described UPS nanoparticles that have exquisite pH-tunable buffer capacity at a narrow pH interval in a broad range of pH (4.0 to 7.4). FIG. 57B shows the pH titration curves of three exemplary $UPS_{4.4}$, $UPS_{5.3}$, and $UPS_{6.2}$ nanoparticles (each subscript indicates the pKa of the corresponding copolymer, Table 10) in the presence of 150 mM NaCl. Results showed that $UPS_{4.4}$, $UPS_{5.3}$, and $UPS_{6.2}$ (2 mg/mL) were able to buffer the pH at their apparent $pK_a$ at 4.4, 5.3 and 6.2, respectively, when HCl (0.4 M) was added into the polymer solution. In contrast, chloroquine (CQ), a widely used small molecular base in biological studies, showed a broad pH response in the range of pH 6 to 9 ($pK_a$=8.3), as well as polyethyleneimines as a broad pH buffer (Suh et al., 1994). Determination of buffer capacity from the pH titration curves (FIG. 57C and FIG. 60) showed exquisite buffer strengths at specific pH in the range of pH 4.0-7.4. More specifically, the maximal values for $UPS_{4.4}$, $UPS_{5.6}$, and $UPS_{7.1}$ nanoparticles were 1.4, 1.5 and 1.6 mmol HCl per 40 mg of nanoparticle, which are 339-, 75- and 30-fold higher than CQ at pH 4.4, 5.6 and 7.1, respectively (FIG. 57C). This collection of UPS nanoparticles provides a unique set of pH-specific "proton sponges" for the functional range of organelle pH from early endosomes (E.E., 6.0-6.5) (Weisz, 2003) to late endosomes (L.E., 5.0-5.5) (Weisz, 2003) to lysosomes (4.0-4.5) (Casey et al., 2010).

2. pH Buffering Capacity and Proton Pumping Rates

For simultaneous imaging and buffering studies, a new nanoparticle design with a dual fluorescence reporter was established: an "always ON" reporter to track intracellular nanoparticle distribution regardless of the pH environment, and a pH-activatable reporter (OFF at extracellular medium pH 7.4 and ON at specific organelle pH post endocytosis). Initial attempts at conjugating a dye (e.g., Cy3.5) on the terminal end of PEO succeeded in an always ON signal, however, the resulting nanoparticles were unstable as a result of dye binding to serum proteins. To overcome this limitation, a heteroFRET design using a pair of fluorophores that were introduced in the core of micelles was employed. As an example, a FRET pair (e.g., BODIPY and Cy3.5 as donor and acceptor, respectively) was conjugated to the PR segment of the UPS6.2 copolymer. Mixing of the two dye-conjugated copolymers (optimal molar ratio of donor/acceptor=2:1) within the same micelle core allowed the heteroFRET-induced fluorescence quenching of donor dye (e.g., BODIPY) in the micelle state (pH>pKa), but fluores-

TABLE 10

Chemical compositions and physical properties of UPS nanoparticles.

| | Composition[a] | $D_h$ (nm)[b] | PDI[b] | ξ (mV)[c] | $pK_a$[d] | $pH_t$[e] |
|---|---|---|---|---|---|---|
| $UPS_{4.4}$ | P(D5A$_{80}$) | 47.5 ± 3.0 | 0.13 ± 0.01 | −1.1 ± 0.2 | 4.35 | 4.39 |
| $UPS_{4.7}$ | P(DBA$_{28}$-D5A$_{52}$) | 62.4 ± 2.9 | 0.08 ± 0.01 | −0.5 ± 0.1 | 4.65 | 4.71 |
| $UPS_{5.0}$ | P(DBA$_{56}$-D5A$_{24}$) | 54.6 ± 1.2 | 0.10 ± 0.01 | −1.3 ± 0.4 | 4.93 | 5.02 |
| $UPS_{5.3}$ | P(DBA$_{80}$) | 42.3 ± 2.6 | 0.12 ± 0.02 | −0.7 ± 0.1 | 5.31 | 5.32 |
| $UPS_{5.6}$ | P(DPA$_{30}$-DBA$_{50}$) | 49.8 ± 2.6 | 0.11 ± 0.01 | −2.1 ± 0.4 | 5.58 | 5.61 |
| $UPS_{5.9}$ | P(DPA$_{60}$-DBA$_{20}$) | 49.2 ± 1.3 | 0.11 ± 0.01 | −0.9 ± 0.1 | 5.89 | 5.91 |
| $UPS_{6.2}$ | P(DPA$_{80}$) | 44.3 ± 1.2 | 0.10 ± 0.01 | −1.6 ± 1.8 | 6.19 | 6.22 |
| $UPS_{6.5}$ | P(DEA$_{21}$-DPA$_{79}$) | 42.0 ± 1.3 | 0.12 ± 0.02 | −0.9 ± 0.6 | 6.45 | 6.50 |
| $UPS_{6.8}$ | P(DEA$_{39}$-DPA$_{61}$) | 35.2 ± 1.3 | 0.11 ± 0.01 | −1.4 ± 0.6 | 6.77 | 6.79 |
| $UPS_{7.1}$ | P(DEA$_{58}$-DPA$_{42}$) | 32.7 ± 1.3 | 0.13 ± 0.01 | −0.9 ± 1.1 | 7.05 | 7.08 |

[a]Only the composition of the PR segment is shown. The subscripts indicate the number of repeating unit for each monomer.
[b]The hydrodynamic diameter ($D_h$) and polydispersity index (PDI) were analyzed by dynamic light scattering analysis.
[c]Surface electrostatic potential (ξ) of the UPS nanoparticles was analyzed by the Zeta Sizer.
[d]The apparent $pK_a$ values for UPS nanoparticles were measured by pH titration experiments in the presence of 150 mM NaCl.
[e] The transition pH ($pH_t$) was measured from Cy5-conjugated UPS nanoprobes based on fluorescence intensity.

cence recovery in the unimer state after micelle disassembly at lower pH (FIG. 61A upper panel). To generate the "always ON" signal, the weight fraction of Cy3.5-conjugated copolymer in the micelles was kept low (e.g., 40%) to avoid homoFRET-induced fluorescence quenching for the acceptor dye in the micelle state (Zhou, et al., 2012) (FIG. 61B). The resulting UPS nanoparticle showed constant fluorescence intensity in the Cy3.5 channel across a broad pH range, while achieving ultra-pH sensitive activation at specific pH for BODIPY signal (FIG. 61C). Since both fluorophores were embedded within the micelle core, the resulting UPS nanoparticles were stable and free from protein bindings.

$UPS_{6.2}$ and $UPS_{5.3}$ were chosen for imaging and buffering study since their apparent $pK_a$'s correspond to early endosomes to late endosomes and to lysosomes transitions, respectively (Weisz, 2003). HeLa cells were incubated with an increasing dose (100, 400 and 1,000 µg/mL) of $UPS_{6.2}$ or $UPS_{5.3}$ for 5 min at 37° C. to allow particle uptake via endocytosis (Conner & Schmid, 2003), then washed with fresh medium (10% FBS in DMEM). At 100 µg/mL, half maximal $UPS_{6.2}$ activation (BODIPY channel) was observed by 30 min and half maximal $UPS_{5.3}$ activation by 60 min (FIGS. 62A & 62B for $UPS_{6.2}$; FIGS. 63A & 63B for $UPS_{5.3}$). In contrast, at 1,000 µg/mL, activation of BODIPY signal was delayed by at least 60 min despite clear indication of particle uptake in the HeLa cells by the Cy3.5 signal (FIGS. 62A & 62B and FIGS. 63A & 63B). In situ quantitation of the endosomal pH with Lysosensor showed dose-dependent sustained pH plateaus at pH 6.2 and 5.3 upon exposure of cells to 400 and 1,000 µg/ml $UPS_{6.2}$ (FIG. 62C) and $UPS_{5.3}$ (FIG. 63C), respectively. For either nanoparticle, 100 µg/ml dose was insufficient to delay organelle acidification.

To further quantify the acidification rates, the number of micelle nanoparticles per HeLa cell was measured based on the fluorescence intensity of internalized UPS divided by the cell number (see methods below). Data shows an increasing number of nanoparticles at higher incubation doses (Table 11). Based on the number of amino groups per micelle (64,000) and an average of 200 endosomes/lysosomes per cell (Holtzman, 1989), the acidification rate was calculated as approximately 150-210 protons per second for each organelle. This result is consistent with calculations based on 2 protons per ATP hydrolyzed per V-ATPase (Deamer et al., 1999), 3 ATP molecules consumed per rotation (Cross & Muller, 2004), 2.4 revolutions per second (Imamura et al., 2003) and an average of 20 V-ATPases per organelle (Imamura et al., 2003).

3. pH Thresholds for Two Different Modes of mTORC1 Activation

Figures 64A, 64B, 64C, 64D, 64E, 64F:
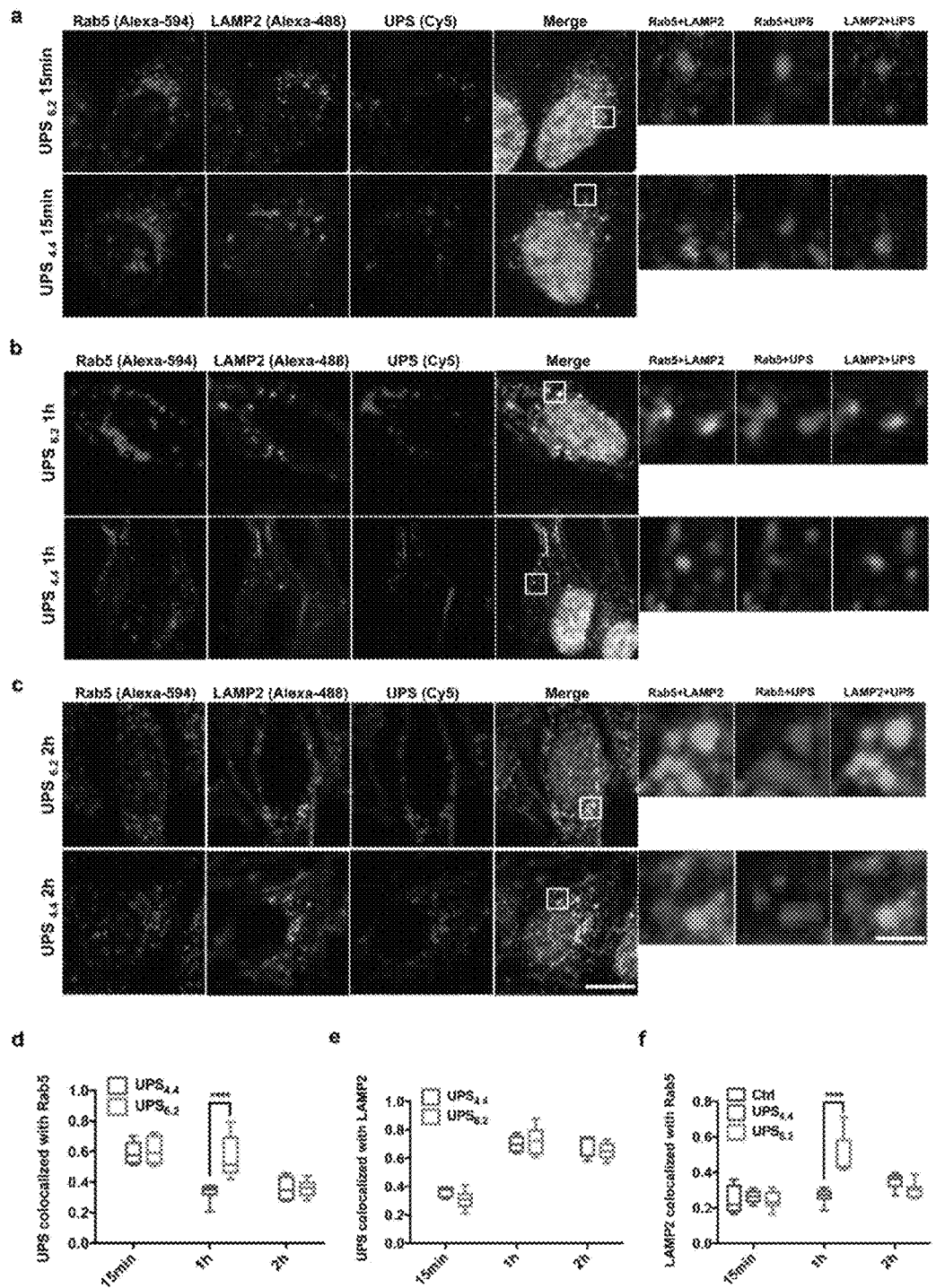

The consequences of UPS buffering of luminal pH on endosome protein coat maturation and endo/lysosome-dependent signal transduction were examined. For this purpose, UPS nanoparticles that discretely report and buffer at pH 6.2, 5.3, 5.0, 4.7 and 4.4 were selected. This range covers established luminal pH values in early endosomes, late endosomes and lysosomes. A discriminating feature of early endosome biogenesis is recruitment of the Rab5 GTPase (Huotari, & Helenius, 2011), which corresponds to a luminal pH range of 6.0-6.5 (Weisz, 2003). Fully mature lysosomes are LAMP2 positive with a luminal pH range of 4.0-4.5 (Casey et al., 2010). To enable quantitation of colocalization of UPS positive endosomes with endosomal maturation markers, Cy5-encoded $UPS_{6.2}$ and $UPS_{4.4}$ were developed with a low dye/polymer ratio that allowed for detectable fluorescence in the micelle state (Wang et al., 2014) (FIG. 64A). Within 15 min at a concentration of 1,000 µg/mL, over 60% of $UPS_{6.2}$ and $UPS_{4.4}$ positive endosomes were also Rab5 positive (FIGS. 64A & 64D). $UPS_{4.4}$ positive endosomes further transitioned to a Rab5 negative/LAMP2 positive maturation state within 60 min (FIGS. 64B and 64E-64F). Notably, $UPS_{6.2}$ positive endosomes also became LAMP2 positive in a similar timeframe despite inhibition of the luminal acidification that normally accompanies this transition (FIGS. 64B & 64D). However, $UPS_{6.2}$ delayed release of Rab5, resulting in transient accumulation of anomalous Rab5/LAMP2 positive endosomes at 60 min (FIGS. 64B & 64F). These observations indicate the presence of a regulatory mechanism that recruits LAMP2 to nascent endolysomes independent of the luminal pH and the presence of a luminal pH-sensitive Rab5 release mechanism.

To examine the consequence of luminal pH clamping on endo/lysosome biology, a key regulatory system was evaluated which has recently reported to be linked to lysosome biogenesis—namely nutrient dependent activation of cell growth via mammalian target of rapamycin complex 1 (mTORC1). In mammalian cells, mTORC1 localizes to endo/lysosomal membranes in response to internalized free amino acids (Sancak et al., 2010). Furthermore, the physical interactions between the V-ATPase and Rag GTPases on endo/lysosomal membranes are needed for mTORC1 activation in response to nutrient availability (Zoncu et al., 2011). To evaluate amino-acid induced mTORC1 activation, two quantitative reporters of mTORC1 pathway activation were employed: phosphorylation/activation of the mTORC1 substrate p70S6 kinase (p70S6K) and nuclear/cytoplasmic distribution of the mTORC1 substrate TFEB.

TABLE 11

Quantification of acidification rates of endocytic organelles by the UPS nanoparticles.

| | $[UPS]_{med}$ (µg/mL) | $D_h/\xi$ (nm/mV)[a] | No. UPS/cell ($\times 10^2$)[b] | Plateau pH (mean ± SD) | $t_p$ (min)[c] | Proton rate ($\times 10^2$/sec)[d] |
|---|---|---|---|---|---|---|
| $UPS_{6.2}$ | 100 | 42.3 ± 2.6/ | 4.7 | n.d. | n.d. | N/A |
| | 400 | −0.7 ± 0.1 | 17 | 6.2 ± 0.1 | 51 | 1.8 |
| | 1,000 | | 24 | 6.2 ± 0.1 | 84 | 1.5 |
| $UPS_{5.3}$ | 100 | 44.3 ± 1.2/ | 4.6 | n.d. | n.d. | N/A |
| | 400 | −1.6 ± 1.8 | 17 | 5.4 ± 0.1 | 43 | 2.1 |
| | 1,000 | | 24 | 5.3 ± 0.1 | 68 | 1.9 |

[a]Hydrodynamic diameter ($D_h$) and zeta potential ($\xi$) were measured in the PBS buffer at pH 7.4.
[b]Calculated based on 800 copolymer chains per micelle.
[c]$t_p$ is measured as the time interval where the pH was buffered at the plateau value.
[d]The rate of proton pumping into each endocytic organelle.

Figures 65A, 65B, 65C, 65D, 65E:
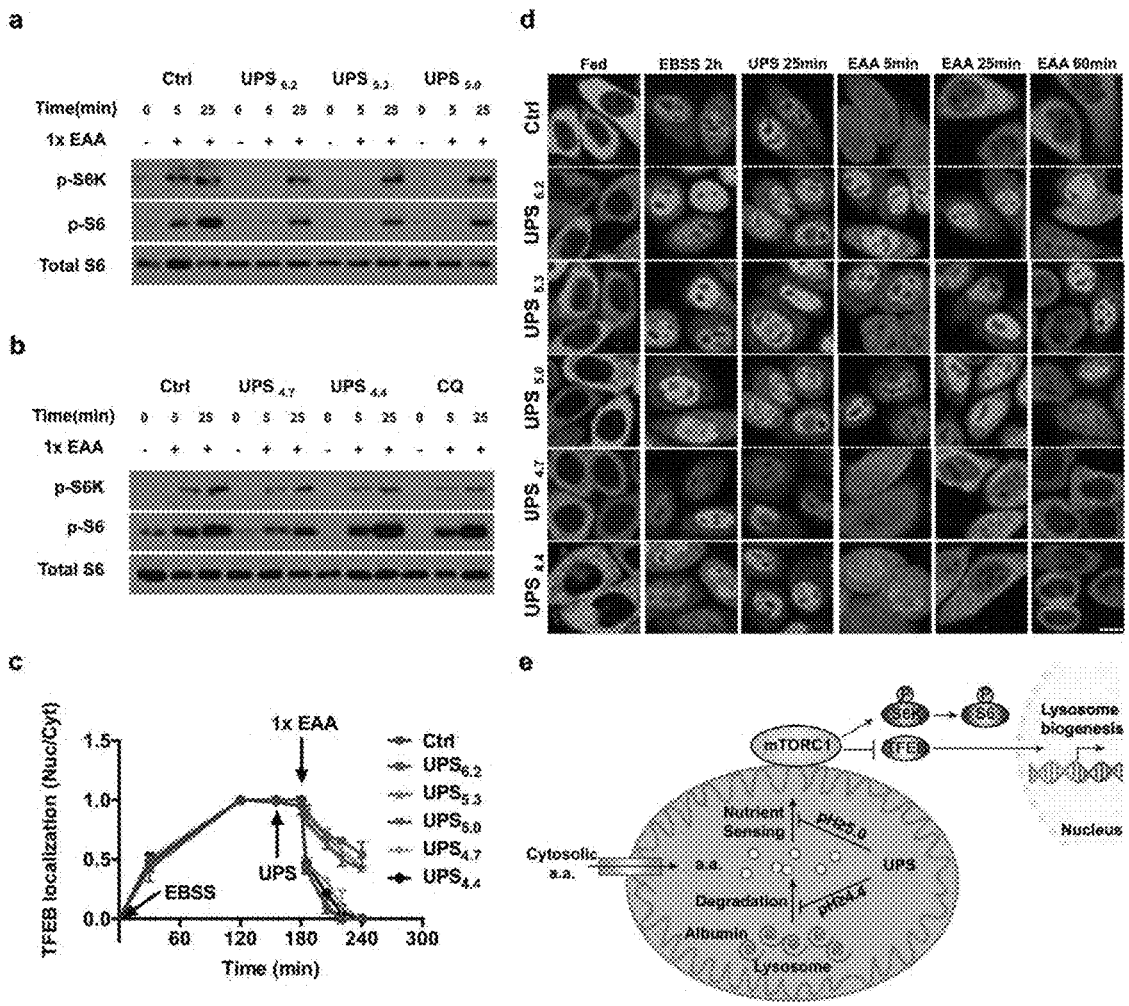

Incubation of HeLa cells for 2 h in a nutrient-free balanced salt solution (EBSS) was sufficient to inhibit mTORC1 activity as indicated by reduced accumulation of activation site phosphorylation on both p70S6K and its substrate S6. Addition of essential amino acids was sufficient to induce pathway activation within 5 min (FIG. 65A and FIGS. 66A & 66B). Pretreatment with 1,000 µg/ml of $UPS_{4.7}$, or $UPS_{4.4}$ had little to no effect on the mTORC1 response to free amino acids. In contrast, pretreatment with 1,000 µg/ml $UPS_{6.2}$, $UPS_{5.3}$ and $UPS_{5.0}$ both delayed and significantly suppressed the mTORC1 pathway response to free amino acids (FIGS. 65A & 65B and FIGS. 66A & 66B). The selective UPS inhibition of the mTORC1 pathway response was mirrored by TFEB nuclear/cytoplasm distribution. Phosphorylation of this transcription factor by mTORC1 results in nuclear exclusion, thereby inhibiting the TFEB transcriptional program in nutrient replete conditions (Pena-Llopis et al., 2011, Settembre et al., 2012 and Roczniak-Ferguson et al., 2012). In Hela cells, with stable expression of GFP-tagged TFEB, pretreatment with $UPS_{6.2}$, $UPS_{5.3}$ and $UPS_{5.0}$ inhibited redistribution of TFEB to the cytoplasm upon addition of free amino acids. In contrast, in cells pretreated with $UPS_{4.7}$ and $UPS_{4.4}$, TFEB redistribution proceeded normally (FIGS. 65C & 65D).

The above data suggest acidification of endosomes below a threshold of pH 5 is necessary for free amino acid-induced activation of mTORC1. Similar experiments were performed employing bovine serum albumin (BSA) as a macromolecular nutrient source rather than free amino acids. Similar to free amino acids, BSA exposure was sufficient to reactivate mTORC1 following nutrient starvation (FIGS. 67A-67D). However, in contrast to free amino acids, $UPS_{4.4}$ delayed mTORC1 activation in response to BSA (FIGS. 67A & 67D). Given that cells treated with $UPS_{4.4}$ responded normally to free amino acids, the delayed response was surmised to BSA is the consequence of inhibition of the proteolysis of BSA by acid hydrolases in the lysosome. Consistent with this, significant inhibition of cathepsin B activity in the presence of $UPS_{4.4}$ was found (FIG. 66C). Together, these observations indicate that distinct lysosomal pH thresholds are required for acid hydrolase activity versus free amino acid sensing (FIG. 65E).

4. Modulating Cellular Metabolite Pools by Buffering Lysosomal pH

Lysosomes recycle intracellular macromolecules and debris to produce metabolic intermediates deployed for energy production or for construction of new cellular components in response to the nutrient status of the cellular environment (Settembre et al, 2013). Abnormal accumulation of large molecules, including lipids and glycoproteins in lysosomes are associated with metabolic disorders. To broadly assess alterations associated with highly selective perturbation of lysosomal acidification, accumulation of small metabolites in cells was quantified by loaded with $UPS_{4.4}$ under nutrient starved versus nutrient replete growth conditions. Following a 12 h exposure to 0, 200, and 400 µg/ml of $UPS_{4.4}$, HeLa cells were lysed and intracellular metabolites were quantified using liquid chromatography-triple quadrupole mass spectrometry (LC/MS/MS). Sixty-eight metabolites were quantifiable from $3 \times 10^6$ HeLa cells, revealing a number of dose-dependent and nutrient-dependent consequences of pH arrest at 4.4 in lysosomes (FIG. 68A). Under nutrient replete conditions, as the dose of $UPS_{4.4}$ increased, the relative abundance of most metabolites also increased when normalized to cellular protein content. This included most amino acids (FIG. 68B upper panel), consistent with an inhibition of the anabolic signals required to use them for protein synthesis and/or defects in lysosomal export of amino acids. In nutrient deprived conditions, $UPS_{4.4}$ enhanced the relative abundance of nucleotides and their precursors (e.g., bottom cluster in FIG. 68A) and massively suppressed the second messenger cAMP. The loss of many essential amino acids including lysine, valine, methionine, and arginine was also observed, consistent with the inhibition of starvation-induced catabolism of macromolecules like albumin (FIG. 68B lower panel). These results suggest mechanistic connections between organelle acidification and metabolite pools, and fortify the hypothesis that proper lysosomal acidity is required for homeostasis of numerous metabolic pathways, either in the presence or absence of nutrients (FIG. 68C).

5, Effects of NSCLC Cells to Endo/Lysosomal pH Arrest

Figures 69A, 69B, 69C, 69D, 69E, 69F, 69G:
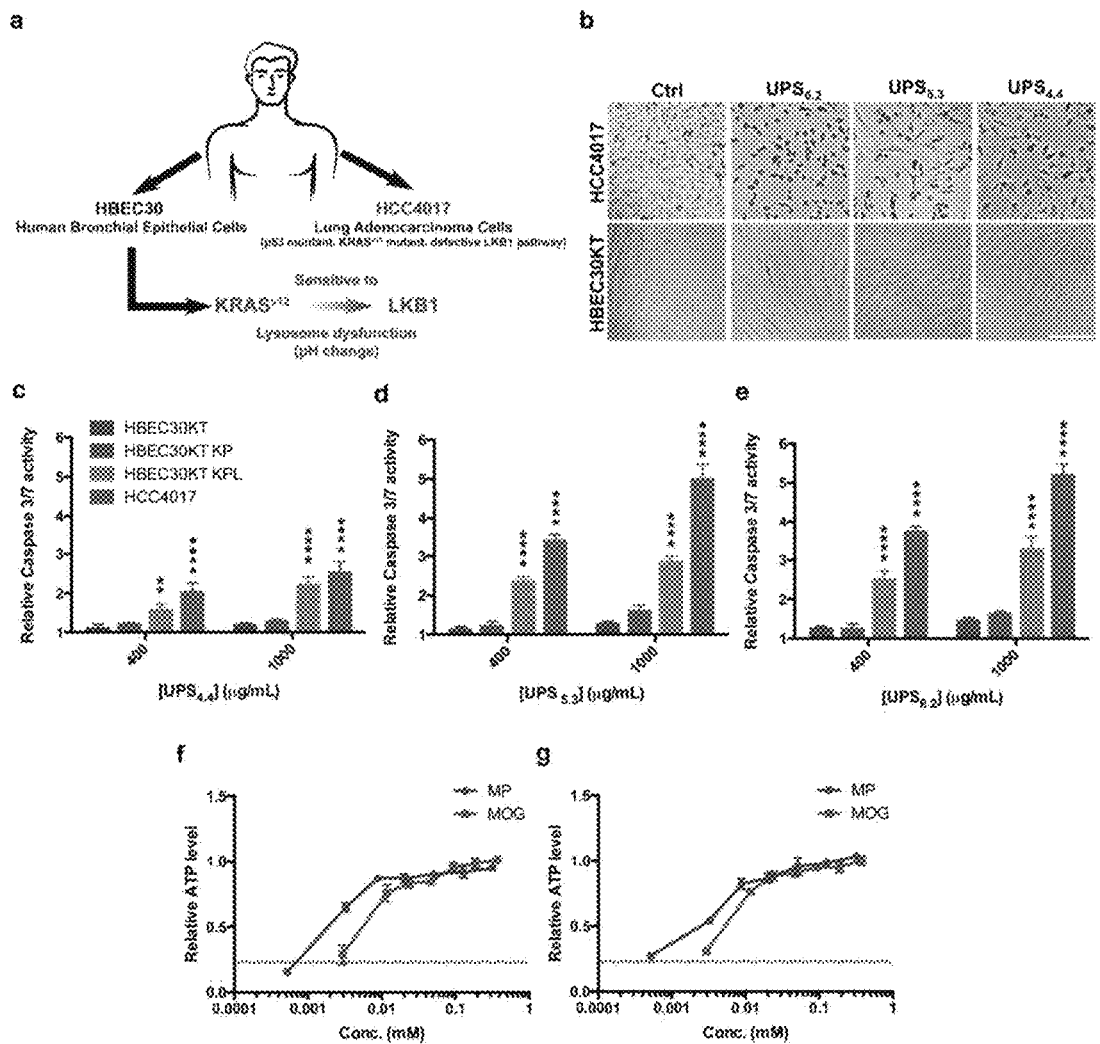

The inventors recently described a selective metabolic vulnerability in non-small cell lung cancer (NSCLC) cells, whereby co-occurring mutations in the KRAS oncogene and LKB1 tumor suppressor result in cellular addiction to lysosomal catabolism for maintenance of mitochondrial health (Kim et al., 2013). Genetic or chemical inhibition of V-ATPase activity was sufficient to selectively induce programmed cell death in this oncogenic background. This was proposed to be a direct consequence of inhibition of a lysosome-dependent supply of TCA cycle substrates for ATP production. The UPS library afforded an opportunity to directly test this hypothesis in the absence of confounders associated with the pleiotropic contributions of V-ATPases to cytosolic pH and mTORC1/AMPK protein complexes in cancer cells (Zoncu et al., 2011 Zhang et al., 2014). As a model system, normal (HBEC30KT) and tumor-derived (HCC4017) cell lines from the same patient were employed together with an isogenic progression series in which the KRAS and LKB1 lesions were artificially introduced into the normal cell background (FIG. 69A) (Ramirez et al., 2004). A comparison of cell number and morphology between HCC4017 and HBEC30KT treated with $UPS_{6.2}$, $UPS_{5.3}$ and $UPS_{4.4}$ at high dose revealed highly selective toxicity of these UPS nanoparticles to HCC4017 (FIG. 69B). The expression of oncogenic KRAS together with inhibition of LKB1 was sufficient to induce sensitivity of bronchial epithelial cells to UPS-induced programmed cell death (FIGS. 69C-69E). Importantly, this phenotype was rescued in both the tumor-derived cells (FIG. 69G) and the genetically engineered cells (FIG. 69G) upon addition of cell permeable analogs of TCA cycle substrates (methyl pyruvate and α-ketoglutarate). Thus selective vulnerability of KRAS/LKB1 co-mutant NSCLC cells to lysosomal function arises from addiction to catabolism of extracellular macromolecules. Moreover, the higher cytotoxicity by $UPS_{6.2}$ over $UPS_{4.4}$ indicates mTORC1 inhibition further contributed to the lethality in these cells.

6. Discussion

Luminal acidification is a hallmark of maturation of endocytic organelles in mammalian cells conferring distinctive cellular functions such as receptor recycling, organelle trafficking and protein/lipid catabolism at different stages (Maxfield & McGraw, 2004 and Yeung et al., 2006). Existing tools or reagents (e.g., chloroquine, $NH_4Cl$, bafilomycin A1) are cell permeable and block a broad range of pH activities. Consequently, biological interrogations on endosome/lysosome functions using these agents may suffer from compounded, non-specific pH effect as well as contributions from perturbation of other acidic organelles (such as the Golgi). In contrast, current UPS nanoparticles enter cells exclusively through endocytosis; furthermore, they allow for robust and fine-scale buffering of luminal pH at operator-predetermined thresholds along the endocytic pathway. The exquisite pH-specific buffer effect, together with previously reported ultra-pH sensitive fluorescence response (Zhou et al., 2011 and Zhou et al., 2012), are unique nanoscale property in self-assembled systems, where hydrophobic micellization (phase transition) dramatically sharpens the pH transition leading to cooperative protonation of tertiary amines. As a result, the UPS nanoparticles yielded a high resolution buffer effect within 0.3 pH unit. The buffered pH range (centered around apparent p$K_a$) of the UPS platform can be fine-tuned by the hydrophobicity of the PR segment, unlike small molecular pH buffers/sensors that are mostly controlled by electron withdrawing/donating substituents (Urano, et al., 2008). The unique pH-specific, tunable "proton sponge" effect is distinct from other low resolution polybase buffers (e.g., polyethyleneimines, FIG. 57C). To further achieve simultaneous imaging and buffering capability, an always-ON/OFF-ON composition was constructed employing a heteroFRET strategy. This nanoparticle design permitted the first measurement of acidification rates of the endocytic organelles (150-210 protons per second) in the HeLa cells, which is in the same order of magnitude with estimations (240-310) based on literature data.

Detailed evaluation of the UPS library illustrated how perturbation of luminal pH of endocytic organelles impacted multiple cell physiological processes, which contributes to the understanding of endosome biology and bio-nano interactions. More specifically, the "perturb and report" characteristics of the library allowed for time-resolved quantitation of endosome maturation, and uncovered previously unappreciated consequences of luminal pH on endosomal coat protein exchange. Notably, the recruitment of the "mature" lysosome marker, LAMP2, was found to occur independently of luminal acidification. On the other hand, release of the early endosome marker Rab5 is delayed by luminal alkalization, resulting in the de novo accumulation of Rab5/LAMP2 positive endosomes. This indicates the presence of currently undescribed, but explorable, pH-sensitive and pH-insensitive mechanisms governing endosome/lysosome biogenesis. The ability to fine-tune UPS buffering capacity also allowed discrimination of distinct pH thresholds required for free amino acid versus albumin dependent activation of mTORC1 pathway. Without wishing to be bound by any theory, it is believed that the acidification to pH 5.0 or below is required to release free amino acids for "inside-out" communication with V-ATPase protein complexes, or for induction of conformational changes in V-ATPase during amino acid sensing (Zoncu et al., 2011). Similarly, acidification to pH 4.4 or below is used in albumin dependent activation of mTORC1, most likely due to the need for hydrolase activation and subsequent protein catabolism. The scalability of UPS synthesis enabled broad-spectrum quantitation of the cellular metabolite milieu upon inhibition of lysosomal consumption of extracellular macromolecules. The exclusive uptake of UPS within endocytic organelles afforded the opportunity to specifically evaluate the participation of endosomal/lysosomal pH in growth regulatory signaling pathways and cell metabolism.

7. Methods

1. Chemicals;

The Cy5-NHS, BODIPY-NHS and Cy3.5-NHS esters were purchased from Lumiprobe Corp. (FL, USA). Monomers 2-(diethylamino) ethyl methacrylate (DEA-MA) and 2-aminoethyl methacrylate (AMA) were purchased from Polyscience Company. Monomers 2-(dibutylamino) ethyl methacrylate (DBA-MA) (Zhou et al., 2011), 2-(dipropylamino) ethyl methacrylate (DPA-MA) and 2-(dipentylamino) ethyl methacrylate (D5A-MA) (Li et al., 2014) were prepared according to the method described in the inventor's previous work, as well as the PEO macroinitiator (MeO-PEO$_{114}$-Br)[1]. N,N,N',N'',N'''-Pentamethyldiethylenetriamine (PMDETA) was purchased from Sigma-Aldrich. Amicon ultra-15 centrifugal filter tubes (MWCO=100 K) were obtained from Millipore (MA). Other reagents and organic solvents were analytical grade from Sigma-Aldrich or Fisher Scientific Inc.

2. Cells, Culture Media and Biological Reagents

The NSCLC cell line HCC4017 and its matched normal bronchial epithelial cell line HBEC30KT were developed from the same patient. The generation of these cell lines and the corresponding HBEC30KT oncogenic progression series was as previously reported (Ramirez, et al., 2004). HCC4017 and all HBEC30-derived cell lines were cultured in ACL4 medium (RPMI 1640 supplemented with 0.02 mg/ml insulin, 0.01 mg/ml transferrin, 25 nM sodium selenite, 50 nM hydrocortisone, 10 mM HEPES, 1 ng/ml EGF, 0.01 mM ethanolamine, 0.01 mM O-phosphorylethanolamine, 0.1 nM triiodothyronine, 2 mg/ml BSA, 0.5 mM sodium pyruvate) with 2% fetal bovine serum (FBS, Atlanta Biologicals) and 1% antibiotics (GIBCO). HeLa and GFP-TFEB HeLa cells were cultured in DMEM (Invitrogen) with 10% FBS and 1% antibiotics (Invitrogen). Earle's Balanced Salt Solution (EBSS, 10x, Sigma) was diluted to 1x with Milli-Q water supplemented with 2.2 g/L sodium bicarbonate (Sigma). Antibodies were from Cell Signaling (S6K-pT389, S6K, S6-Ribosomal-Protein-pS235/236, S6 Ribosomal Protein, Rab5 and Rab7) and Abcam (LAMP2). Other biological agents include Hoechst 33342 (Invitrogen), LysoSensor Yellow/Blue DND 160 (Invitrogen), Magic Red™ Cathepsin B Assay Kit (Immunochemistry Technology), Bafilomycin A1 (Sigma), Chloroquine (Sigma) and BCA Protein Assay Kit (Thermo).

3. Syntheses of Dye-Conjugated PEO-b-(P($R_1$-r-$R_2$)) Block Copolymers

Aminoethyl methacrylate (AMA) was used for the conjugation of dyes. Three primary amino groups were introduced into each polymer chain by controlling the feeding ratio of AMA monomer to the initiator (molar ratio=3). After synthesis, PEO-b-(PR-r-AMA) (10 mg) was dissolved in 2 mL DMF. Then the Dye-NHS ester (1.5 equivalences for Dye-NHS) was added. After overnight reaction, the copolymers were purified by preparative gel permeation chromatography (PLgel Prep 10 μm $10^3$ Å, 300×25 mm column by variant, THF as eluent at 5 mL/min) to remove the free dye molecules. The resulting copolymers were lyophilized and kept at −20° C. for storage. The only difference for the syntheses of block copolymers for always-ON/OFF-ON UPS nanoparticles is that three AMA groups were introduced into a polymer chain for BODIPY conjugation, while one AMA group was introduced for Cy3.5 conjugation.

4. Preparation and Characterization of UPS Nanoparticle Micelles

In a typical procedure, 10 mg UPS polymer was dissolved in 500 μL THF (without dye conjugation) or methanol (with dye-conjugation). For always-on/OFF-ON UPS nanoparticles, BODIPY-conjugated polymer and Cy3.5-conjugated polymer was mixed with the indicated weight ratio (FIG. 112) to determine the best combination that yields high ON/OFF ratio in BODIPY channel and stable always-on signal in Cy3.5 channel. The solution was added to 10 mF Milli-Q water drop by drop. Four to five filtrations through a micro-ultrafiltration system (<100 kDa, Amicon Ultra filter units, Millipore) were used to remove the organic solvent. The aqueous solution of UPS nanoprobes was sterilized with a 0.22 µm filter unit (Millex-GP syringe filter unit, Millipore). Transmission electron microscopy (TEM, JEOL 1200 EX model, Tokyo, Japan) was used to examine micelle size and morphology. Dynamic light scattering (DLS, Malvern Nano-ZS model, He-Ne laser, λ=633 nm) was used to determine the hydrodynamic diameter (Dh) of 100 µg/mL micelle PBS solutions. The presented data were averaged from five independent measurements. The zeta-potential was measured using a folded capillary cell (Malvern Instruments, Herrenberg, Germany). The presented data were averaged from three independent measurements.

5. Quantitation of Cellular Uptake of UPS Nanoprobes

HeLa cells ($1 \times 10^6$ per well) were seeded in 6-well tissue culture dishes. After 12 to 16 h, the cells were exposed to $UPS_{6.2}$-TMR and/or $UPS_{5.3}$-TMR for 5 min in serum free DMEM, and then washed three times with PBS. Following an additional 2h incubation in DMEM+10% FBS, the UPS nanoprobes were extracted from cells with methanol. UPS nanoprobe micelles disassociate into unimers in methanol. A Hitachi fluorometer (F-7500 model) was used to determine RFU of the UPS-TMR unimer solutions at 570 nm. The dose of internalized UPS nanoprobes was calculated from the RFU and a standard curve of the UPS-TMR solutions.

6. Measurement of Endo/lysosomal pH

HeLa cells were plated in 4- or 8-well Nunc™ Lab-Tek™ II Chambered Coverglass (Thermo Scientific) and allowed to grow for 48 h. The cells were then loaded with 25 µM LysoSensor Yellow/Blue DND-160 and 1,000 µg/mL UPS nanoprobes in serum-free medium at 37° C. for 5 min. The cells were washed twice and immediately imaged. Imaging was performed using an epifluorescent microscope (Deltavision, Applied Precision) equipped with a digital monochrome Coolsnap HQ2 camera (Roper Scientific, Tucson, Ariz.). Fluorescence images were collected using SoftWoRx v3.4.5 (Universal Imaging, Downingtown, Pa.). Data were recorded at excitation/emission wavelengths of 360/460 nm and 360/520 nm. The single band pass excitation filter for DAPI (360 nm) is 40 nm, and the band pass of emission filters for DAPI (460 nm) and FITC (520 nm) is 50 nm and 38 nm, respectively. Cell fluorescence ratios were determined by image analysis of the stored single wavelength images using ImageJ software. For each cell, a region of interest was defined as the punctae in cytosol that emitted fluorescent signals from both UPS nanoprobes and LysoSensor. Fluorescent intensity ratio was calculated for each intracellular punctate as $R=(F_1-B_1)/(F_2-B_2)$ where $F_1$ and $F_2$ are the fluorescence intensities at 360/520 and 360/460 respectively, and $B_1$ and $B_2$ are the corresponding background values determined from a region on the same images that was near the punctae in the cytosol. To calibrate the relationship between R and pH, we used a modified protocol established by Diwu et al. (1999). Cells were loaded with LysoSensor and then permeabilized with 10 µM monensin and 10 µM nigericin. These cells were treated for 30 min with the equilibration buffers consisting of 5 mM NaCl, 115 mM KCl, 1.2 mM $MgSO_4$, and 25 mM MES (MES buffer) varied between pH 4.0 and 7.4. The cells were kept in the buffer until imaging.

7, Colocalization Analysis

Images from the immunofluorescence assay were taken by using spinning disk confocal microscope (Andor). Z-stack images were used after deconvolution in the colocalization analysis. The data was analyzed using the Coloc module of Imaris 7.7 (Bitplane). The thresholded Mander's coefficient was used as an indicator of the proportion of the colocalized signal over the total signal (Manders et al., 1993 and Bolte & Cordelieres, 2006).

8. Metabolomic Analysis

HeLa cells were grown in 100 mm dishes until 80% confluent, and separated into nutrient replete and nutrient deplete groups. The medium for cells in the nutrient deplete group was changed to EBSS before being washed with saline twice. Then 200 or 400 µg/mL $UPS_{4.4}$ (final concentration) or same volume of water (as control, each condition contains 6 replicates) was added to both groups and was left for overnight. Following this, cells were washed twice with ice cold saline, then overlaid with 500 µL of cold methanol/water (50/50, v/v). Cells were transferred to an Eppendorf tube and subjected to three freeze-thaw cycles. After vigorous vortexing, the debris was pelleted by centrifugation at 16,000×g and 4° C. for 15 min. Pellets were used for protein quantitation (BCA Protein Assay Kit, Thermo). The supernatant was transferred to a new tube and evaporated to dryness using a SpeedVac concentrator (Thermo Savant, Holbrook, N.Y.). Metabolites were reconstituted in 100 µL of 0.03% formic acid in analytical-grade water, vortex-mixed and centrifuged to remove debris.

Thereafter, the supernatant was transferred to a HPLC vial for the metabolomics study. Targeted metabolite profiling was performed using a liquid chromatography-mass spectrometry/mass spectrometry (LC/MS/MS) approach. Separation was achieved on a Phenomenex Synergi Polar-RP HPLC column (150×2 mm, 4 µm, 80 Å) using a Nexera Ultra High Performance Liquid Chromatograph (UHPLC) system (Shimadzu Corporation, Kyoto, Japan). The mobile phases employed were 0.03% formic acid in water (A) and 0.03% formic acid in acetonitrile (B). The gradient program was as follows: 0-3 min, 100% A; 3-15 min, 100%-0% A; 15-21 min, 0% A; 21-21.1 min, 0%-100% A; 21.1-30 min, 100% A. The column was maintained at 35° C. and the samples kept in the autosampler at 4° C. The flow rate was 0.5 mL/min, and injection volume 10 µL. The mass spectrometer was an AB QTRAP 5500 (Applied Biosystems SCIEX, Foster City, Calif.) with electrospray ionization (ESI) source in multiple reaction monitoring (MRM) mode. Sample analysis was performed in positive/negative switching mode. Declustering potential (DP) and collision energy (CE) were optimized for each metabolite by direct infusion of reference standards using a syringe pump prior to sample analysis. The MRM MS/MS detector conditions were set as follows: curtain gas 30 psi; ion spray voltages 5000 V (positive) and −1500 V (negative); temperature 650° C.; ion source gas 1 50 psi; ion source gas 2 50 psi; interface heater on; entrance potential 10 V. In total, 69 water soluble endogenous metabolites were confidently detected above the baseline set by cell-free samples. Dwell time for each transition was set at 3 msec. Cell samples were analyzed in a randomized order, and MRM data was acquired using Analyst 1.6.1 software (Applied Biosystems SCIEX, Foster City, Calif.).

Chromatogram review and peak area integration were performed using MultiQuant software version 2.1 (Applied Biosystems SCIEX, Foster City, Calif.). Although the numbers of cells were similar and each sample was processed identically and randomly, the peak area for each detected metabolite was normalized against the protein content of that sample to correct any variations introduced from sample handling through instrument analysis. The normalized area values were used as variables for the multivariate and univariate statistical data analysis. The chromatographically co-eluted metabolites with shared MRM transitions were shown in a grouped format, i.e., leucine/isoleucine. All multivariate analyses and modeling on the normalized data were carried out using SIMCA-P (version 13.0.1, Umetrics, Umea, Sweden). The pre-processed datasets were evaluated by unsupervised hierarchical clustering with complete-linkage method.

Example 8: Dual Imaging Methods with PET and Fluorescence Imaging

1. Development of Ultra-pH Sensitive (UPS) Nanoprobes with Fluorescent Reporter

Figure 70A:
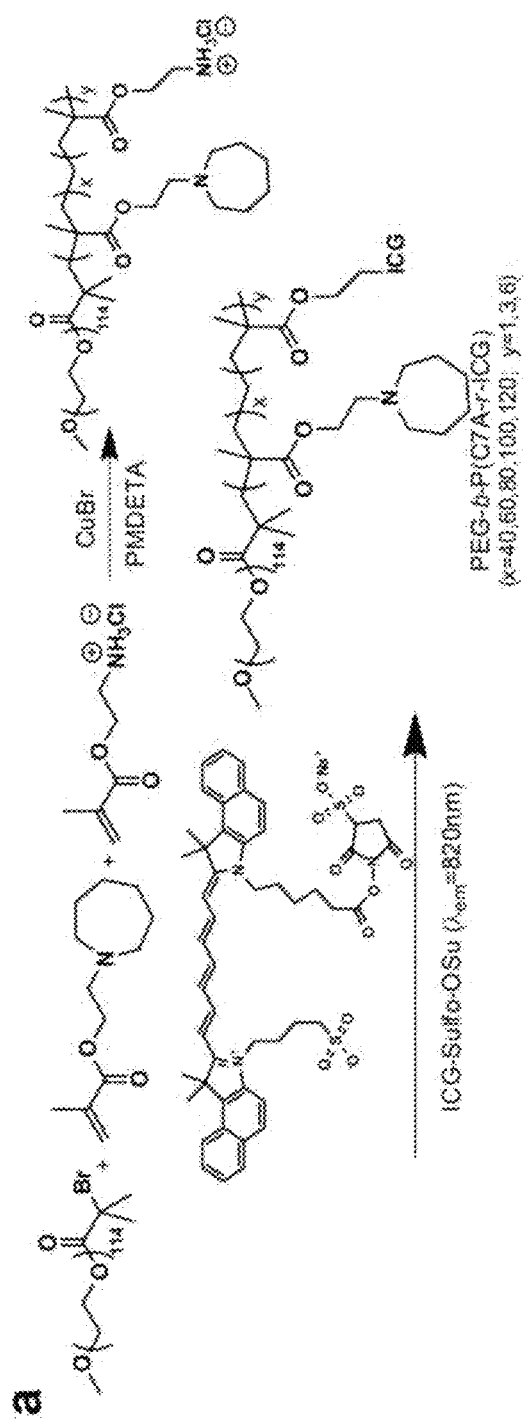

Recently ICG-functionalized UPS nanoprobes were developed by the inventors with a pH transition at 6.9. PEG-b-PEPA was synthesized using atom-transfer radical polymerization method with varying repeating units in the PEPA segment (40-120, FIG. 70A). ICG, an FDA approved near infrared dye was then conjugated to the PEPA segment with different dye densities (1, 3 and 6 ICGs per polymer chain). At blood pH (7.4) or interstitial pH (7.2) of normal tissues, the I-UPS$_{6.9}$ nanoprobe remains silent (FIG. 70D) as a result of homoFRET-induced fluorescence quenching (Zhou et al., 2012 and Zhou et al., 2011). At these pHs, UPS$_{6.9}$ was present as self-assembled micelles with a diameter of 25.3±1.5 nm by dynamic light scattering analysis and a spherical morphology by TEM (data not shown). The effect of polymer chain length and ICG density on the transition pH, sharpness of response, fluorescence activation ratio and diameter of the nanoprobes were investigated. FIG. 70B shows a representative study on varying PEPA segment length. Data show increasing the repeating unit of PEPA from 40 to 120 resulted in sharper pH transitions (e.g. $\Delta pH_{ON/OFF}$ decreased from 0.30 to 0.13, respectively) and slightly lower pH transitions (from 6.96 to 6.91, respectively). The particle size also increased with PC7A length (15 to 30 nm). Three ICGs per polymer chain allowed the most optimal dye density with high fluorescence activation ratio and bright fluorescence intensity at the on state. Based on these data, the UPS composition with 100 repeating unit of PC7A and 3 ICG dyes per chain were selected. The resulting UPS nanoprobes have sharp pH transition ($\Delta pH_{ON/OFF}$=0.15), high fluorescence activation ratio (>100 fold between on and off states) (FIG. 70C), and optimal particle size (25 nm) for tumor penetration. Using this strategy broad tumor specificity with large tumor-to-normal tissue ratio in a broad set of animal tumors with diverse cancer types and organ sites was demonstrated (Wang et al., 2014). Tumor-specific imaging was accomplished in tumors as small as 1 mm³. Additionally, the I-UPS$_{6.9}$ nanoprobe is stable in serum containing (20% FBS) medium over 48 hours and maintains a sharp pH response and high fluorescence activation ratio (FIGS. 70B-70D)

2. Introduce $^{64}$Cu as the Radioactive Tracer to UPS Nanoprobes for PET Imaging Comparing to other nonstandard PET nuclides, $^{64}$Cu ($t_{1/2}$=12.7 h; β+ 0.653 MeV, 17.4%) has been widely used in many imaging agents based on nanoparticles, antibodies and peptides due to is low positron range, commercial availability, and reasonably long decay half-life (Rossin et al., 2008 and Haubner & Wester, 2004). The stability between the metal and the chelator is important to the outcome of the radiopharmceutical modality design. Many chelators have been developed as the chelating ligands for $^{64}$Cu such as 1,4,7,10-tetraazacyclododecane-tetraacetic acid (DOTA) and 1,4,7-triazacyclononane-triacetic acid (NOTA) and etc (Wadas et al., 2007). Among them, CB-TE2A (FIG. 71) has been reported by Sun and coworkers to form one of the most stable complexes with $^{64}$Cu (Sun et al., 2002), and the Cu(II)-CB-TE2A complex is more resistant to reductive metal loss than are other tetramacrocyclic complexes (Woodin et al., 2005). CB-TE2A will be used as the chelator for induction of $^{64}$Cu to the UPS. An NHS ester functionalized CB-TE2A will be prepared following the procedure reported in the paper (Liu et al., Angew Chem Int Ed Engl., 48:7346-7349, 2009). On the nanoprobe side, primary amino group will be introduced to the PEG terminal of the polymer chains. NH$_2$—PEG-PC7A will be synthesized by the route described in FIG. 71. Commercially available Fmoc-PEG-OH will be used to make the macroinitiators for ATRP. After deprotection of the polymer after ATRP, the primary amino groups can be regenerated and used for the conjugation to the NHS ester functionalized CB-TE2A. The hybrid micelles will be formed from a mixture of CB-TE2A-PEG-PC7A and PEG-PC7A-ICG by sonication and solvent evaporation method. The hybrid micelles will be labeled with $^{64}$Cu by incubating $^{64}$CuCl$_2$ and micelles in buffered solution followed by ultrafiltration.

3. Compare the Imaging Efficacy of Dual Modality UPS and PET with FDG Only.

Preliminary results in orthotopic HN5 head and neck tumor-bearing mice showed strong false positive signals from interscapular BAT in two out of three mice, while I-UPS fluorescence delineated tumors with high specificity (FIG. 72). Clinically, BAT or tensed neck muscles in head and neck cancer patients can lead to misinterpretation as abnormality in PET imaging due to elevated glucose consumption. By introduce $^{64}$Cu to the UPS nanoprobes, the distribution of the PET nuclides is anticipated to be shifted by targeting tumor acidosis and therefore eliminate the potential false positives from PET with FDG.

In order to compare whether dual modality UPS can provide more accurate tumor detection over FDG by PET scan, activated BAT will be used as a model to evaluate the imaging efficacy. After an orthotopic head and neck tumor models in mice is established, the tumor bearing mice will cold treated before PET imaging to active BAT (Wang et al., 2012). To be specific, the tumor bearing mice will be fasted 12 h and placed in a pre-chilled cage in a 4° C. cold room for 4 h before PET imaging. The mice will be evenly divided into three groups and will be injected with the following agents respectively through tail vein: 1) FDG; 2) dual modality UPS; 3) propranolol and FDG. Propranolol is a (3 adrenoceptor inhibitor which will suppress BAT activation and serve as the negative control. PET images will be acquired and reconstructed into a single frame using the 3D Ordered Subsets Expectation Maximization (OSEM3D/MAP) algorithm. Regions of interest (ROI) will be drawn manually encompassing the tumor/BAT in all planes containing the tissue. The target activity will be calculated as percentage injected dose per gram (% ID/g). Standardized uptake value (SUV) will also be calculated for tumors, interscapular BAT as well as surrounding normal tissues for evaluation of potential false positives. Histology will serve as the gold standard for verdict of the presence of cancerous tissue or BAT. All tissues which show a positive signal in head and neck region from either FDG group or UPS group will all be collected for paraffin embedding and sectioning. H&E staining will be prepared from these slides for histology validation to correlate with the results from each group. Each specimen will be assigned as FDG+/− (from PET), $^{64}$Cu-UPS+/− (from PET), cancer cell+/− (from histology) and BAT+/−(from histology). Statistical analysis will be used to judge whether dual modality UPS significantly improve detection accuracy.

Example 9: Cancer Surgery and Tumor Removal Process with UPS Nanoprobes

1. Broad Cancer-Specific Imaging of Multiple Tumor Types with UPS Nanoprobes

One advantage of the I-UPS design is its compatibility with existing operating room camera systems that have already been approved for ICG-based imaging in open surgery (SPY Elite® by Novadaq), microsurgery (Leica, Carl Zeiss), laparoscopy (Karl Storz, Olympus), and robotic surgery (da Vinci®), lowering barriers for clinical translation. Using the SPY camera, the feasibility of the I-UPS$_{6.9}$ nanoprobe to image tumor acidosis in multiple cancer types was investigated, including the head and neck (human HN5, FaDu and HCC4034 orthotopic xenografts in SCID mice; HCC4034), breast (human MDA-MB-231 in SCID mice and murine 4T1 in BALB/C mice), kidney (human orthotopic XP296 tumors in SCID mice), brain (human glioblastoma U87 xenograft), and peritoneal metastasis from the GI tract (human colorectal HCT-116 tumors in SCID mice, FIG. 73). Results show high tumor/normal tissue contrast (T/N ratio >20) in this broad set of tumors. In particular, I-UPS signals were lacking in typical false positive tissues in the head and neck (e.g., brown fat) as well as brain parenchyma (likely due to the blood-brain-barriers (Hawkins & Davis, 2005 and Kreuter, 2001) that prevent UPS uptake). These results demonstrate the robustness of extracellular acidic pH as a cancer target and the broadly applicable and cancer-specific detection by the I-UPS nanoprobes.

Example 10: Dual Fluorescence Reporter UPS Nanoprobes

1, UPS Nanoprobes with Dual Fluorescence Reporters

To independently evaluate nanoprobe dose and pH activation in tumor acidosis imaging, UPS nanoprobes with a dual fluorescence reporter will be constructed: an "Always ON" reporter to track nanoparticle distribution regardless of pH, and a pH-activatable reporter. Initial attempts at conjugating a dye (e.g., Cy5.5) to the terminal end of PEO (such as the surface of UPS nanoprobes) succeeded in an Always ON signal, however, the resulting nanoparticles were unstable because of dye binding to serum proteins. To overcome this limitation, a heteroFRET design using a pair of fluorophores that are introduced in the core of the micelles will be employed. For example, a FRET pair (e.g., BODIPY and Cy3.5 as donor and acceptor, respectively) were separately conjugated to the PR segment of the UPS$_{6.9}$ copolymer. Mixing of the two dye-conjugated copolymers (optimal molar ratio of donor/acceptor=2:1) within the same micelle core allowed the heteroFRET-induced fluorescence quenching of the donor dye (e.g., BODIPY, $\lambda_{ex}/\lambda_{em}$=493/503 nm) in the micelle state (pH>pK$_a$), but fluorescence recovery in the unimer state after micelle disassembly at lower pH (FIGS. 76A-C). To generate the "always ON" signal, the weight fraction of Cy3.5-conjugated copolymer in the micelles was kept low (e.g., 40%) to avoid homoFRET-induced fluorescence quenching for the acceptor dye (Cy3.5, $\lambda_{ex}/\lambda_{em}$=591/604 nm) in the micelle state (Zhou et al., 2011; 2012). The resulting UPS nanoparticle show constant fluorescence intensity in the Cy3.5 channel across a broad pH range, while achieving ultra-pH sensitive activation at 6.9 of the BODIPY signal (FIG. 75). Since both fluorophores are embedded within the micelle core, the resulting UPS nanoparticles are stable and free from protein fouling.

In the current study, the heteroFRET design and BODIPY/Cy3.5 pair will be employed to introduce Always-ON/OFF-ON dual reporters in the UPS nanoprobes. After micelle formation, the nanoprobes will first be characterized by dynamic light scattering (DLS, Malvern Zetasizer Nano-ZS model) for hydrodynamic diameter (Dh) and zeta-potential. Size and morphology of UPS nanoprobes will be further analyzed by transmission electron microscopy (TEM, JEOL 1200 EX model) and correlated with DLS results. For study of fluorescence activation in response to pH, micelles will be prepared in different pH buffers (pH will be controlled from 6.0 to 7.4 with 0.1 pH increment) at a concentration of 0.1 mg/mL. The nanoprobes will be excited at corresponding wavelengths of the fluorophores on a Hitachi fluorometer (F-7500 model), and the emission spectra will be collected. The emission intensity will be used to quantify the ON/OFF ratio. The critical micelle concentration (CMC) will be measured using the pyrene method (Kalyanasundaram & Thomas, 1977 and Winnik, 1993). Stability of the dual reporter UPS nanoprobes in fresh mouse serum will also be tested as previously described (Wang et al., 2014).

2. UPS Nanoprobes with pH Transitions from 6.5 to 7.1.

A finely tunable series of UPS nanoprobes from 6.5 to 7.1 will be synthesized to target tumor pH$_e$ with different degrees of acidosis. A random copolymer strategy for the construction of a UPS library with operator-predetermined pH transitions (4.0-7.4) and sharp pH response is reported herein and in (Ma et al., 2014). Three design criteria must be met: (1) In the PEO-b-PR copolymer, a random PR block (P(R$_1$-r-R$_2$), where R$_1$ and R$_2$ are monomers with different alkyl chain lengths on the tertiary amine) must be used to ensure a single pH transition. A blocked PR segment (P(R$_1$-b-R$_2$)) resulted in two pH transitions reflecting the different ionization behaviors of the R$_1$ and R$_2$ blocks; (2) monomers with closely matched hydrophobicity in R$_1$ and R$_2$ are necessary to achieve sharp pH response. In one non-limiting example, the $\Delta$pH$_{OFF/ON}$ is <0.25 pH when adjacent alkyl groups are used (e.g., R$_1$/R$_2$=ethyl/propyl) whereas $\Delta$pH$_{OFF/ON}$ is >0.5 pH when R$_1$/R$_2$ are ethyl/pentyl groups; (3) the hydrophobicity of P(R$_1$-r-R$_2$) segment can be fine-tuned by controlling the molar fraction of R$_1$ and R$_2$ monomers, which leads to precisely controlled transition pH.

Based on the above criteria, a series of PEO-b-P(DEA$_x$-r-DPA$_y$) copolymers with varying ratios of the two monomers, diethylaminoethyl methacrylate (DEA-MA) and diisopropylaminoethyl methacrylate (DPA-MA) (FIG. 76A) will be synthesized. The total repeating unit will be controlled at 100 (x+y=100). Aminoethyl methacrylate (AMA-MA) will be introduced (z=3 per chain) for fluorophore conjugation. FIG. 76B shows the data on pH-dependent UPS activation using Cy5.5, a representative dye. Results indicate a finely tuned series of UPS nanoprobes in the pH range of 6.3 and 7.8. All nanoprobes maintained the sharp pH response ($\Delta$pH$_{OFF/ON}$<0.25). Plot of transition pH vs. DPA molar percentage (quantified by $^1$H NMR) shows a linear correlation (FIG. 76C). This correlation will be used as a standard curve to determine the composition of PEO-b-P(DEA$_x$-r-DPA$_y$) copolymers to target pH transitions at 6.5, 6.7, 6.9 and 7.1. For each transition pH, a nanoprobe with ICG conjugation for SPY imaging or dual fluorescence reporters for mechanistic studies will be produced.

Example 11: Analysis of pH Regulatory
Mechanisms in Tumor Progression 1. pH Regulatory Mechanism of Tumor Acidosis in Different Glycolytic Phenotypes at Different Stages of Tumor Progression Using the dual reporter UPS nanoprobes described herein, tumors with divergent glycolysis propensity will be investigate to determine different pH regulatory pathways employed to achieve tumor acidosis. More specifically, whether highly glycolytic tumors will predominantly employ monocarboxylate transporters (e.g., MCT1/4) for pH regulation whereas glycolysis-impaired tumors utilize carbonic anhydrase IX in tumor acidosis will be investigated. Competent glycolysis head and neck cancer cells (e.g., HN5 or FaDu) will be used as positive controls, and create isogenic, glycolysis-impaired tumors by stable knockdowns of key glycolytic enzymes (e.g., LDHA or PKM2). Previous studies have shown that shRNA knockdown of LDHA or PKM2 selectively inhibits glycolysis and reprograms the cells toward the OXPHOS pathway (Christofk el al., 2008; Fantin el al., 2006). Small molecular inhibitors (e.g., suicide inhibitor for MCT1/4, or aryl sulfonamides for CAIX) will be used in combination with immunohistochemistry of MCT1/4 and CAIX. The pattern of UPS activation will be correlated with the spatial expression of pH regulatory proteins in tumor sections.

2. Mechanistic Investigation of Tumor Acidosis by Perturbation with Small Molecular Inhibitors Tumor bioenergetics involves enhancement of glycolytic machinery or mitochondrial oxidative phosphorylation (OXPHOS) pathways. Several molecular mechanisms are responsible for maintaining an alkaline $pH_i$ in cancer cells and acidic $pH_e$ in tumor microenvironment (FIG. 77). The pH regulatory machinery involves the interplay of multiple proteins, including monocarboxylate transporters (MCT1 and MCT4) (Enerson & Drewes, 2003 and Halestrap & Price, 1999), carbonic anhydrases (CAIX and CAXII) (Supuran, 2008 and Supuran, 2010), anion exchangers (AE1, 2 and 3) (Sterling, et al., 2002; Morgan, 2004), $Na^+$-bicarbonate exchangers (NBCs) (Pouyssegur et al., 2006), $Na^+/H^+$ exchangers (NHEs) (Pouyssegur et al., 2006), and V-ATPase (Perez-Sayans et al., 2009).

To examine the acidosis mechanism in tumors with different glycolytic phenotypes, the inventors will first start with inhibitors of the two main regulatory proteins in the acidosis process: suicide CHC inhibitor for MCT1/4 (FIGS. 78A-78E) and acetazolamide for CAIX. The dual reporter UPS nanoprobes described herein will be administered intravenously to perturb the pH regulation in the tumor microenvironment and use the dual reporter UPS nanoprobes for imaging spatiotemporal response of acidification. Three groups of mice will be used with subcutaneous lung tumors that have different glycolysis phenotypes: 1) orthotopic HN5 or FaDu tumors with competent glycolysis rates; 2) orthotopic HN5 or FaDu tumors with impaired glycolysis by shRNA knockdown of LDHA (Fantin et al., 2006). The tumor size will be controlled at ~200 $mm^3$ for all groups. The mice from each group will then be divided into four sub-groups. Each sub-group of mice will receive: 1) PBS; 2) CHC inhibitor; 3) acetazolamide or 4) both CHC inhibitor and acetazolamide, respectively followed by administration of dual reporter UPS. At 1, 2, 4, 12 and 24 h post UPS injection, the BODIPY (OFF-ON) fluorescence intensity (FI) and Cy3.5 distribution (Always ON) from each tumor will be measured by a Maestro small animal imaging system (PerkinElmer) and quantified by ImageJ. By comparing the FI(subgroup1) among the three different groups, whether cancer cells with divergent glycolysis rates all produce acidic $pH_e$ in the tumor microenvironment will be determined. By calculating the ratio of FI(subgroup2/3/4)/FI (subgroup1) from the same group, how each pathway contributes to the overall acidosis for the tumors with different glycolysis rates will be determined. At the end of each experiment, tumors will be collected and frozen sections will be prepared from the specimen. For each tumor section, a BODIPY image for activated nanoprobes and a Cy3.5 image for absolute probe distribution will be captured. The relative contribution of MCT1/4 or CAIX to the tumor acidosis will be normalized from the ratio of activated ON/OFF BODIPY vs always ON Cy3.5 fluorescent intensity. The frozen section will be stained by H&E or antibodies to correlate with the expression profiles of MCT1/4 or CAIX in tumors. Hypoxic biomarker HIF1α will be also stained to compare the distribution patterns with activated nanoprobes.

3. Investigate the Intratumoral Heterogeneity of Tumor Acidosis at Different Stages of Tumor Progression.

It is known that a continuum of bioenergetic remodeling exists along tumor progression (Jose et al., 2011). Small tumors have a tendency of low conversion of glucose to lactate but relatively high conversion of glutamine to lactate, whereas large tumors have high glucose and oxygen utilization rate despite low oxygen and glucose supply (Eigenbrodt et al., 1998). Data show that the I-UPS method can detect very small tumor foci (<1 mm or one million 4T1 cancer cells in BalB/C mice, FIG. 79A-79C) as a bright punctate under SPY camera. This result demonstrates that I-UPS has the adequate sensitivity to detect small tumor nodules at an early stage of development.

To monitor the potential switching of tumor acidosis mechanism during tumor growth, HN5 and HN5 glycolysis-impaired models will be studied and evaluate the nanoprobe activation at different stages of tumor growth. When the tumors grow to sizes of 10, 100, 500 and 1000 $mm^3$, the animals will first be imaged without injection of MCT1/4 or CAIX inhibitors. Afterwards, CHC inhibitor or acetazolamide will be injected intravenously to block the corresponding pH regulation pathway and the animals will be imaged again to compare the fluorescence intensity before and after perturbation. The percentage decrease in fluorescence intensity as a result of CHC inhibitor or acetazolamide will be quantified and correlated with the expression levels of MCT1/4 or CAIX in tumor sections, respectively. Vasculature (anti-CD31) and hypoxia (pimonidazole) stains will also be performed to assess impact of the vascularization and hypoxia on UPS activation at different stages of tumor progression as described in (Wang et al., 2014).

Example 11: UPS Imaging in Detecting Tumors
with Divergent Glycolytic Phenotypes 1. Mouse Tumor Models with Divergent Glycolysis Rates.

In one series, orthotopic head and neck tumors (HN5, FaDu, or HCC4034, FIG. 73) will be established and their isogenic, glycolysis-impaired tumors by stable knockdowns of LDHA described herein. In another series, several non-small cell lung cancer cell lines with constitutively high vs. low glycolysis rates from a panel of 80 cell lines previously established will be selected. Using these animal models with divergent glycolytic phenotypes, the hypothesis that acidosis imaging by I-UPS nanoprobes allows higher cancer specificity will be tested particularly for glycolysis-impaired tumors over FDG-PET. In addition, the false positive signals from both imaging methods in normal tissues will be investigated.

2. Comparison of I-UPS and FDG-PET Imaging in Normal and Glycolysis-Impaired Tumor Models of the Head and Neck.

A series of orthotropic head and neck tumor models in mice with competent glycolysis and impaired glycolysis will be established. Specifically, $10^6$ of selected head and neck cancer cells (HN5, FaDu or HCC4034) will be injected in the submental triangle region in SCID mice and let tumors grow to ~200 mm$^3$. The mice will be divided into two groups: one group will be injected with scrambled short hairpin RNA (shRNA$_{scr}$) as the competent glycolysis group; the other group will be injected with lactate dehydrogenase (LDHA) knockdown short hairpin RNA (shRNA$_{LDHA}$) (Fantin et al., 2006) to block lactate formation as the glycolysis-impaired group. Mice will be fasted for 12 h prior to PET imaging. Each mouse will receive 150 µCi of FDG in 150 µL in saline intravenously via tail vein injection. PET images will be acquired one hour post-injection for 15 mins. PET images will be reconstructed into a single frame using the 3D Ordered Subsets Expectation Maximization (OSEM3D/MAP) algorithm. Regions of interest (ROI) will be drawn manually encompassing the tumor in all planes containing the tissue. The target activity will be calculated as percentage injected dose per gram (% ID/g). Standardized uptake value (SUV) will also be calculated for tumors as well as surrounding normal tissues and other organs of interests (e.g., brain, kidney, heart, and tonsil) for evaluation of potential false positives. Preliminary data in orthotopic HN5 head and neck tumor-bearing mice showed strong false positive signals from brown adipose tissues (Christofk et al., 2008; Fantin et al., 2006) in two out of three mice, while UPS detected tumors with high specificity (FIG. 80). Clinically, interscapular brown adipose tissue or tensed neck muscles in head and neck cancer patients can also lead to misinterpretation as abnormality in PET imaging due to elevated glucose consumption (Mirbolooki, 2011; Wang et al., 2012). Histology in the normal tissues will be preformed to verify the tissue origin of the false positive signals.

After PET imaging, mice will be kept overnight to deactivate the radioactive tracer ($^{18}$F, $t_{1/2}$=110 min). I-UPS (2.5 mg/kg) will then be injected through the tail vein. Mice will be imaged using a SPY Elite® surgical camera 24 hours after injection. After whole body imaging, mice will be dissected to remove major organs (e.g., heart, liver, kidney, lung, brain, spleen, etc.). Ex vivo imaging of tumors and normal tissues will be imaged by the SPY Elite® surgical camera. Tumor to normal tissue ratio (T/N) will be quantified using Image J software for all fluorescent images. Between the two divergent glycolytic animal groups, how the glycolysis degrees impact % ID/g or SUV for PET imaging and T/N for fluorescent imaging will be compared. After fluorescence imaging, the major organs of the animals will be frozen sectioned and stained with H&E. A clinical pathologist will verify the presence of malignance and tissue origin of false positive signals.

3. Investigation of I-UPS Imaging Specificity in Non-Small Ceil Long Tumor Models.

In addition to head and neck cancer models, the imaging specificity of I-UPS and FDG-PET in selected lung cancer models with divergent glycolysis rates will also be investigated. As part of the lung cancer SPORE, the glucose consumption rate and lactate secretion rate for a panel of over 80 non-small cell lung cancer (NSCLC) cells in cell culture (FIG. 81) has been previously quantified. Plot of glycolysis rates (Lactate$_{out}$/Glucose$_{in}$) vs cell lines illustrates cell autonomous, constitutively divergent glycolytic phenotypes across the NSCLC cells. Based on this data, two groups of lung cancer cells with high and low glycolysis rates will be selected. Specifically, H2170, HCC515 and H2347 will be chosen as the high glycolytic panel (Lactate$_{out}$/Glucose$_{in}$~2.0), and H228, H1755 and HCC78 will be chosen as the low panel (Lactate$_{out}$/Glucose$_{in}$<0.5). These cell lines are available from the UTSW/MDACC lung SPORE and have been shown to produce subcutaneous tumors in SCID mice. In a typical procedure, 2×10$^6$ lung cancer cells will first be injected subcutaneously at the left flank of the mice to form tumor xenografts in SCID mice. When the tumors grow to ~200 mm$^3$, the mice will be imaged with PET first, followed by fluorescent imaging after injection of I-UPS nanoprobes using the procedures described above. The I-UPS imaging outcomes will be compared with those from FDG-PET. In particular, whether I-UPS imaging will stay silent in verified false positive tissues from FDG-PET (e.g., brown fat, thoracic muscle by histology) will be evaluated and also whether I-UPS imaging is able to illuminate lung tumors with constitutively low glycolysis rates that are potentially undetected by FDG-PET.

Example 12: Optimize UPS Nanoprobe Activation Relative to Microscopic Tumor Margins in Cancer Tumors 1. Quantify UPS Activation Profile and Correlate with Microscopic Tumor Margins.

For selected tumor models, nanoprobes with the Always ON/OFF-ON dual reporter will be injected intravenously. Starting at 15 mins, 1, 4 and 24 h post-injection, tumor and surrounding tissue will be collected and frozen sections will be prepared from the specimen. For each tumor section, a BODIPY image will be captured for activated nanoprobes and a Cy3.5 image for absolute probe distribution. The frozen section will be stained by H&E to identify the true tumor margin (current clinical gold standard). For larger tumors, multiple images will be captured and stitch them together for holistic comparison.

For quantitative image analysis, (1) a tangent line from a true tumor margin point (zero point) identified by the histology image will be drawn (FIG. 82), (2) draw another line perpendicular to the tangent line, (3) quantify BODIPY and Cy3.5 fluorescence intensity (e.g., ±500 µm from the zero point) along the perpendicular line using ImageJ program, (4) repeat steps 1 to 3 from multiple margin points for each tumor slice and average multiple linear profiles, and (5) plot averaged fluorescence intensity vs. distance in the BODIPY and Cy3.5 channels. FIG. 82 illustrates the schematic of margin analysis by the dual reporter nanoprobes.

By comparing the H&E image and BODIPY (pH activatable reporter) map, the probes will be determined to see if the probes can delineate the tumor margin through pH activation by glycolytic cancer cells. Some specific questions that will be addressed include: (1) what is the distribution and nature of the lactate secreting cells and is lactate secretion and thus the accuracy of the margins affected by tumor size, type, and stage and (2) whether UPS nanoprobes will be able to discriminate pH heterogeneity within and/or across tumor borders and whether residual cancer cells infiltrating into the normal tissue can be detected beyond the margin due to the lack of EPR effect. By comparing the CFP and Cy3.5 (always ON reporter) maps, the distribution of the probes inside the tumor will be determined vs. the normal tissue around the tumor over time. By comparing BODIPY and Cy3.5 signals, the probe activation ($I_{BODIPY}/I_{Cy3.5}$) will be determined relative to probe accumulation ($I_{Cy3.5}$). Without wishing to be bound by any theory, it is believed to determine whether dose accumulation via EPR effect or pH activation drives margin delineation. This set of curves for a series of dual reporter probes with different pH transitions from 6.3 to 7.1 will establish and investigate whether tuning the pH transition changes the sensitivity and specificity of tumor margin delineation. The optimal I-UPS is universal will be examined or is dependent on the type and/or size of the tumor. Finally, CFP-labeled cancer cells will be used to further test the sensitivity and specificity of the probes for the detection of cancer cells infiltrating into the normal tissue beyond the margin.

2. Antitumor Efficacy and Long-Term Survival Studies.

Orthotopic tumor xenografts (HN5 and FaDu for head and neck cancer, 4T1 and MD-MBA-231 for breast cancer) will be used to evaluate the antitumor efficacy of I-UPS-guided resections. For each study, I-UPS nanoprobes will be intravenously injected 24 h before surgery. The animals will be divided into 4 groups (n=10 or 15 for each group): (1) no surgery; (2) tumor debulking control (where visible tumor is partially removed); (3) white light surgery with complete removal (based on surgeon's best estimation) and (4) SPY-guided tumor resection. These experimental groups will allow exploration of the difference between conventional surgery under white light and fluorescent surgery. Pilot studies have been performed using the I-UPS$_{6.9}$ probes (FIGS. 74A & 74B and 78A-78E). Similar experiments for optimized I-UPS probes in additional tumor models (e.g., FaDu and MDA-MB-231) will be carried out.

After surgery, the Kaplan-Meier survival curves will be determined to compare the antitumor efficacy between each group. For all resected animals, tumor occurrence at the primary site will be examined and recorded. In addition, the effects of surgery on the swallowing function of the mice will be estimated. Without wishing to be bound by any theory, it is believed that the greater the amount of normal tissue that is removed during tumor extirpation, the greater the resultant functional deficit to the animal and therefore swallowing. The mice will be weighed both pre- and post-operatively. Daily weights will be recorded post-operatively for 1 week and twice a week thereafter. Percentage body weight lost will be used as a proxy for feeding and swallowing function. Weights will be normalized to the initial weight to account for animal growth.

Example 13: Biological Profile and Pharmacokinetics

1. Pharmacokinetic/Biodistribution (PK/BD) Studies.

Previous studies using $^3$H-labelled PEG-b-PC7A (UPS$_{6.9}$) and PEG-b-PDPA (UPS$_{63}$) show that the resulting UPS nanoparticles have significantly different PK/BD profiles (FIG. 83) despite similar hydrodynamic diameters (25.3±1.5 vs. 24.9±0.8 nm, respectively), zeta potential (−0.7±1.1 vs. −3.5±0.6 mV), and PEG length (both 5 kD). The α-phase half-lives were 1.0±0.2 and 4.3±0.7 h (P<0.05), and (5-phase half-lives were 7.5±0.3 and 19.6±2.1 h (P<0.01) for UPS$_{6.9}$ and UPS$_{63}$ nanoparticles, respectively. Biodistribution studies at 24 h after nanoparticle injection showed liver and spleen were the major organs for the clearance of both nanoparticles. The faster clearance of UPS$_{6.9}$ over UPS$_{6.3}$ was attributed to its higher transition pH and higher susceptibility in UPS activation and clearance from blood.

In this study, the PK/BD studies will first be perform for the optimized I-UPS composition described herein using $^3$H-labelled copolymers as previously established (n=5 for each group). Blood will be collected at 2 min, 0.5, 1, 3, 6, 12 and 24 h after injection. At the end of the experiment, animals will be sacrificed and tumor tissue and major organs (heart, liver, spleen, kidney, etc.) will be removed. Dissected organs will be weighed, homogenized and treated with scintillation mixtures. Both the blood and tissue samples will be quantified by a liquid scintillation counter (Beckman LS 6000 IC). The UPS distribution in different organs/tissues will be calculated as the percentage of injected dose per gram of tissue. In addition to blood and tissue samples, urine and feces samples will also be collected to analyze the clearance of I-UPS via kidney secretion and GI tract. These experiments will be performed in metabolic cages in a designated animal facility on campus.

2. Assessment of Innate Immunity Response.

To evaluate whether I-UPS may cause strong innate immunity, I-UPS nanoprobes will be intravenously injected at 1×, 10× and 50× of the imaging dose in immunocompetent C57BL/6 mice (n=5 for each group). At 2, 6 and 24 h, blood samples (100 μL) from the tail vein will be collected. Serum will be separated and the cytokine profiles analyzed. The current Luminex™ multiplex assay can detect 23 cytokines (e.g., IFN-α and -β, IL-2, IL-4, IL-12, IL-17, etc) from 25 μL of serum. PBS will be used as a negative control. If a significant increase is observed in cytokines, more detailed analysis on immune response will be performed (e.g., examining neutrophil or other leukocyte production, complement activation, inflammatory response in the spleen and lymph nodes) over longer time frame such as 2-4 weeks.

Example 14: UPS Nanoparticles Containing Multiple Different Polymers

1. Use of Micelles with Multiple Different Polymers

Initially, a series of amphiphilic block copolymers PEG-b-PR, where PEG is poly (ethylene glycol) and PR is an ionizable segment (Scheme 1 and Table 12) were synthesized

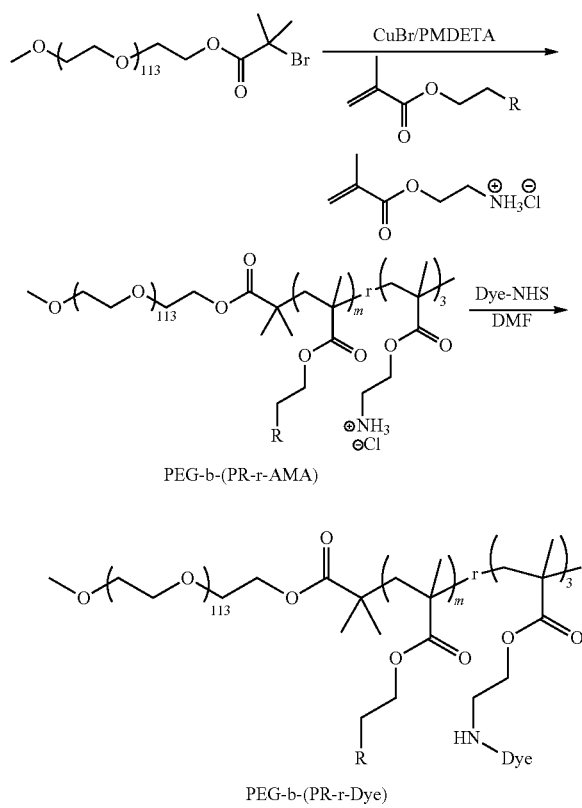

Scheme 1: Synthesis of Ionizable Segment

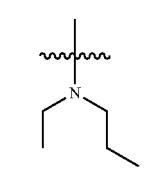
R = Dye-NHS, PEG-b-(PR-r-Dye)

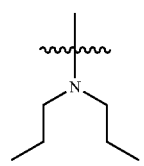
BODIPY 493, PEG-b-PEPA-BDY

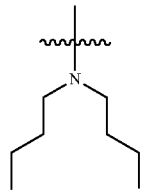
TMR, PEG-b-PDPA-TMR

Cy5, PEG-b-PDBA-Cy5

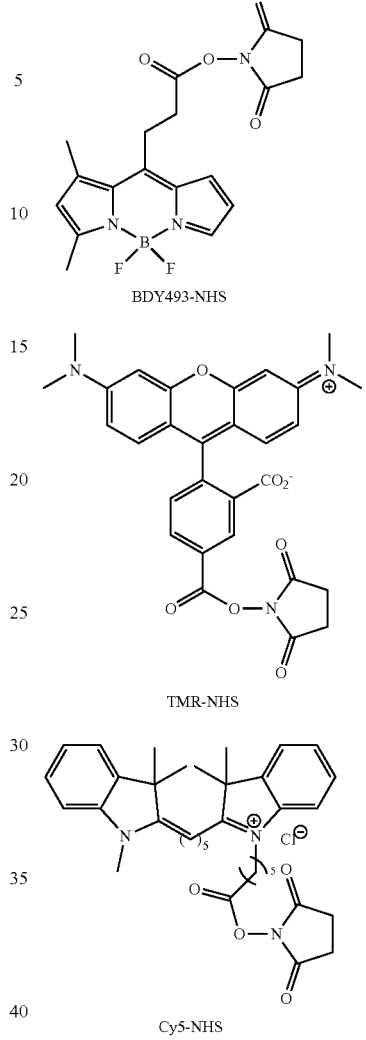

BDY493-NHS

TMR-NHS

Cy5-NHS

TABLE 12

Characterization of PEG-b-(PR-r-AMA$_3$) diblock copolymers.

| Copolymer | $M_n$, $^1$H-NMR (kD)$^a$ | $M_n$, GPC (kD)$^b$ | $M_w$, GPC (kD)$^b$ | PDI$^b$ |
|---|---|---|---|---|
| PEG$_{114}$-b-P(EPA$_{75}$-r-AMA$_3$) | 20.8 | 20.1 | 24.9 | 1.24 |
| PEG$_{114}$-b-P(DPA$_{81}$-r-AMA$_3$) | 22.8 | 22.3 | 25.6 | 1.15 |
| PEG$_{114}$-b-P(DBA$_{75}$-r-AMA$_3$) | 23.5 | 22.8 | 26.5 | 1.16 |

$^a$Number-averaged molecular weight ($M_n$) as determined by $^1$H-NMR.
$^b$Number-averaged ($M_n$), weight-averaged molecular weight ($M_w$), and polydispersity index(PDI = $M_w/M_n$) were determined by GPC using THF as the eluent.

The PEG-b-PR copolymers were encoded with different fluorophores. Three exemplary PEPA-BDY493, PDPA-TMR, and PDBA-Cy5 fluorescent polymers were selected and characterized in terms of dye conjugation number and efficiency as well as quantum yield (FIG. 84B and Table 13). The PEPA-BDY493, PDPA-TMR, and PDBA-Cy5 nanoprobes had pH transitions at 6.9, 6.2, and 5.3, which cover the pH changes during endocytic pathway from clathrin-coated vesicle (CCV) to early endosome (pH~ 6.0), then to late endosome/lysosome (pH~ 5.0-5.5) (Huotari & Helenius, 2011). The particle sizes of these nanoparticles were 25-35 nm with narrow distribution. The fluorescent activation ratios ($R_F$) were 30, 91, and 107 fold for PEPA-BDY493, PDPA-TMR, and PDBA-Cy5 nanoprobes with sharp pH response ($\Delta pH_{10-90\%}$=0.18-0.22, Table 14 and FIGS. 85-88). Using the sonication method, a hybrid UPS nanoprobe system consists of three components PEPA-BDY493, PDPA-TMR, and PDBA-Cy5 was engineered, as shown in FIGS. 84A-84C. Without wishing to be bound by any theory it is believed that the three fluorescent polymers will self-assembled into a homogenous hybrid UPS nanoprobe at higher pH. After endocytosis, the hybrid UPS nanoprobe will sequentially disassemble and fluoresce at the individual $pH_t$ of each polymer (e.g., 6.9, 6.2, 5.3) to tract the endosomal maturation process associated with subtle pH changes at single organelle resolution in living cells (FIG. 84C).

TABLE 13

Measurement of conjugation efficiency and quantum yields of dye-conjugated copolymers.

| | Dye conjugation | | Quantum yield ($\Phi_F$)[a] | |
|---|---|---|---|---|
| PR-Dye | Number | Efficiency (%) | Free dye[b] | Conjugated dye | Mixture[d] |
| PEPA-BDY493 | 2.2 | 73 | 0.90 | 0.05/0.68[c] | 0.87 |
| PDPA-TMR | 2.1 | 70 | 0.68 | 0.26 | 0.65 |
| PDBA-Cy5 | 2.2 | 73 | 0.28 | 0.24 | 0.27 |

[a]In methanol unless noted otherwise.
[b]Obtained from literature.
[c]In methanol with 0.5% 1M HCl.
[d]Mixture of free dye with dye-free PDPA copolymer.

TABLE 14

Characterization of PEG-b-(PR-r-Dye) nanoprobes.

| Copolymer | Particle size (nm) | $pH_t$ | $\Delta pH_{10-90\%}$ | $R_F$ ($F_{on}/F_{off}$)[a] |
|---|---|---|---|---|
| PEPA-BDY493 | 24.65 ± 1.55 | 6.95 | 0.22 | 30 |
| PDPA-TMR | 30.15 ± 2.15 | 6.20 | 0.18 | 91 |
| PDBA-Cy5 | 35.49 ± 2.92 | 5.26 | 0.20 | 107 |

[a] Determined by fluorescence emission intensity of different dyes.

To demonstrate the formation of homogenous hybrid nanoparticle, a series of homoFRET and heteroFRET experiments were designed and performed. The homoFRET experiment involves a molecular mixture of one fluorescent PEG-b-PR polymer and another label-free PEG-6-PR polymer with different pH transitions. In this example, PEPA-Cy5 were used and mixed up with PEPA, PDPA, or PDBA polymer at the molar ratio of 1:19 for the labeled versus label-free polymer. Results showed the successful formation of molecularly mixed micelle of PEPA-Cy5 with PEPA, PDPA or PDBA polymer in the same micelle which indicated by the recovery of the Cy5 fluorescent signal through overcoming homoFRET effect (FIGS. 114A & 114B) (Zhou et al., 2012). In contrast, the micelle mixture of PEPA-Cy5 and another label-free micelle showed no Cy5 signal recovery. The same result was also observed in the molecularly mixed micelle of PDBA-Cy5 and another label-free PEG-b-PR polymer (FIGS. 89A & 89B). All these results indicated that the PEPA, PDPA, and PDBA polymers can form a homogenous hybrid nanoprobe.

To further verify the formation of the hybrid nanoprobe, the fluorescence transfer effect was examined from copolymers encoded with different hetero-FRET dyes: PEPA-BDY493, PDPA-TMR, and PDBA-Cy5. To minimize the homoFRET effect, each copolymer was encoded with one dye in the hydrophobic PR segment. Two or three copolymers were dissolved in THF and then were added dropwise into water to produce a molecularly mixed micelle as described herein. In the pair of PEPA-BDY and PDPA-TMR (molar ratio=1:1), the fluorescence intensity at BDY493 emission wavelength (510 nm) in the molecularly mixed micelle decreased over 4-fold as compared to PEPA-BDY493 alone micelle solution. Moreover, the fluorescence intensity at TMR emission (580 nm) increased over 4-fold for mixed micelle solution over PDPA-TMR micelle solution (FIG. 90A). The other three sets of hetero-FRET polymers: (i) PDPA-TMR and PDBA-Cy5, (ii) PEPA-BDY493 and PDBA-Cy5; (iii) PEPA-BDY493, PDPA-TMR and PDBA-Cy5 were also extensively investigated (FIGS. 90B-90D). In the set of PEPA-BDY493, PDPA-TMR and PDBA-Cy5 fluorescent polymers, the sequential FRET effect from BDY493 to TMR was observed, finally to Cy5 dye (FIG. 90D). The fluorescence intensity at BDY493 emission in hybrid nanoprobe decreased over 4-fold as compared to PEPA-BDY493 alone micelle solution, while the Cy5 signal increased over 25-fold for hybrid nanoprobe over PDBA-Cy5 micelle. These results clearly demonstrated that the three PEG-b-PR copolymers can self-assembled into a homogenous hybrid UPS nanoprobe.

Figures 92A, 92B, 92C, 92D, 92E, 92F:
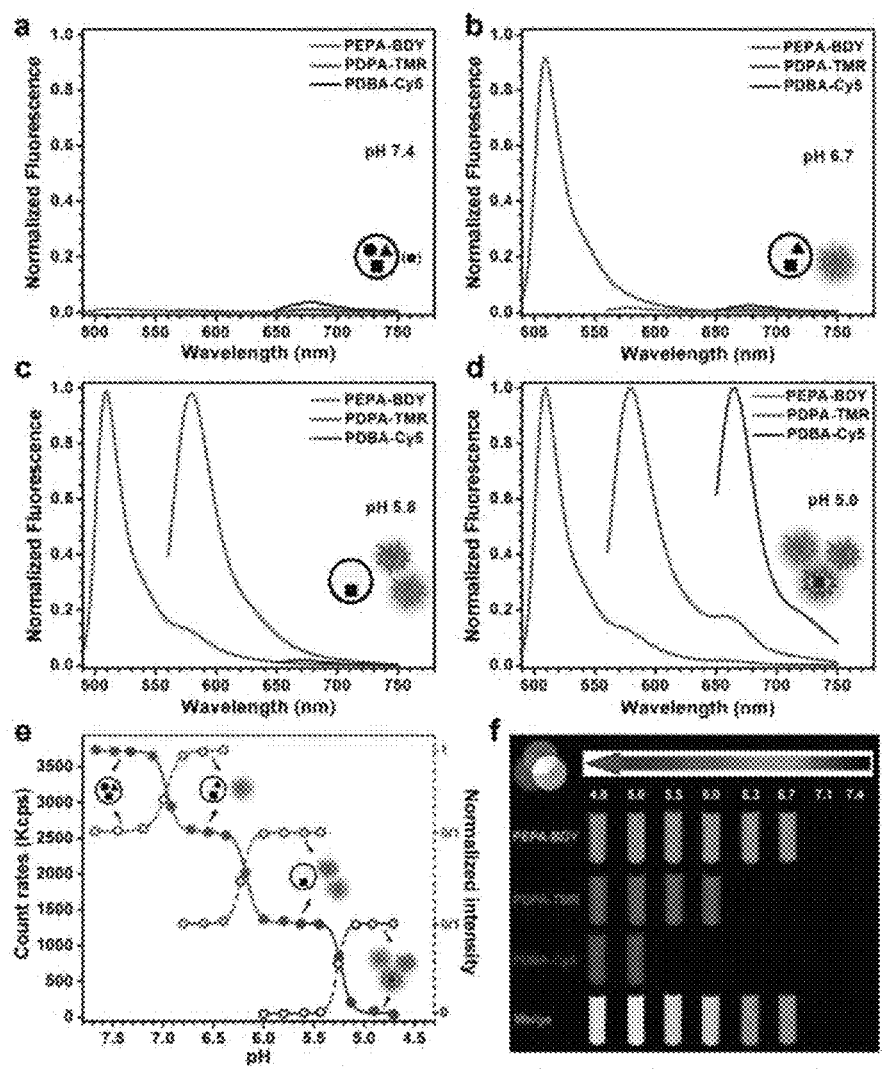
Figures 93A, 93B, 93C, 93D, 93E, 93F:
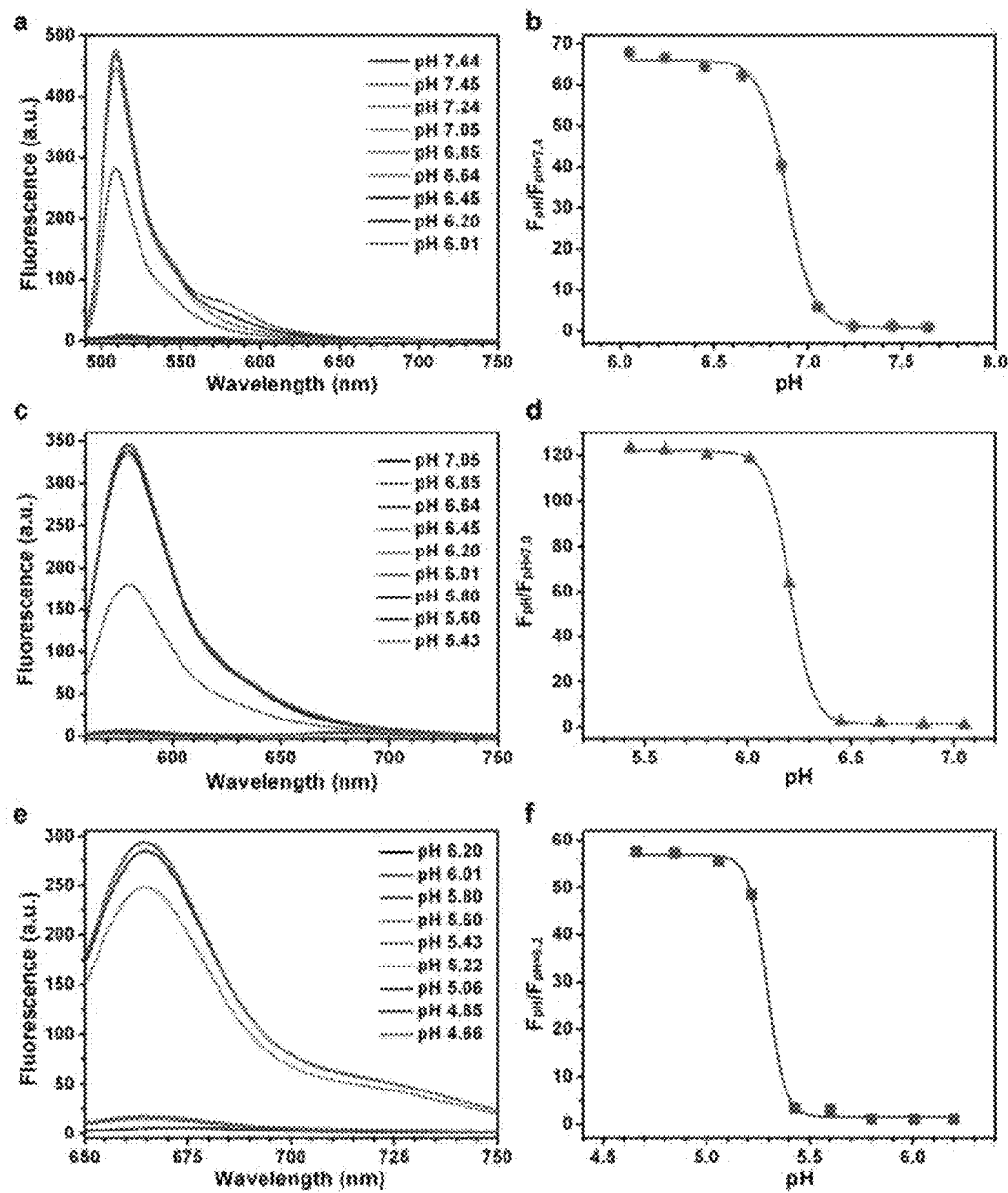

After demonstrating the formation of hybrid UPS nanoprobe, a hybrid nanoprobe system was produced using PEPA-BDY493, PDPA-TMR and PDBA-Cy5 fluorescent polymers each PR chain conjugated with ~2.2 dyes (FIG. 91). The fluorescence emission spectra at different excitation wavelength (485, 545, 640 nm) and different pH (7.4, 6.7, 5.8, and 5.0) were collected and plotted (FIGS. 92A-92D and FIG. 93A-93F and FIG. 94). Results showed that all the three fluorescent polymer components kept "silent" at the neutral pH. When the pH decreased to 6.7, the PEPA-BDY component was firstly released and activated to produce the green signal, while the other two components still stayed "OFF". When the pH was lowered to 5.8, the PDPA-TMR signal was activated to produce the red signal and the PDBA-Cy5 component was completely "silent" in this stage. Finally, the PDBA-Cy5 was activated when the solution pH was decreased to 5.0. In this stage, all three fluorescent polymers were fully activated. The particle sizes of hybrid UPS nanoprobe were ~30-40 nm at pH between 7.4 and 5.8, and dropped to 8.7 nm as unimers at pH 5.0 determined by dynamic light scattering analysis (DUS). Similar observation was made by TEM analysis (FIGS. 95A & 95B). The $pH_t$ values for PEPA-BDY493, PDPA-TMR, and PDBA-Cy5 components in hybrid UPS nanoprobe were 6.9, 6.2, and 5.3, which were consistent with their corresponding single component nanoprobes. Overall, the fluorescence activation ratios for PEPA-BDY493, PDPA-TMR, and PDBA-Cy5 were 74, 123, and 30 with sharp pH response ($\Delta pH_{10-90\%}$=0.20-0.25, Supplementary Table S4). Using DES analysis, the count rates of the hybrid nanoprobe versus pH values were plotted and also observed the multi-stage activation pattern as shown in FIG. 92E. In each stage, one fluorescent polymer will be released, fluoresce, and finally all the polymers will dissociate indicated by the count rates reached to zero. The multi-stage activation of hybrid UPS nanoprobe at different pH was also imaged and verified by Maestro CRI imaging system as shown in FIG. 92F.

To check the synchronized cell uptake of three components in hybrid UPS nanoprobe, the UPS nanoprobe was functionalized with 5% Erbitux (humanized EGFR antibody) (Adams & Weiner, 2005) through thiol-maleimide linkage as described herein. The Erb-encoded hybrid nanoprobe had three distinct pH transitions at 6.9, 6.2, and 5.3 with $\Delta pH_{10-90\%}$ values of 0.20-0.25. The fluorescence ON/OFF activation ratios of the hybrid nanoprobe were 200, 191, and 35-fold for BDY493, TMR, and Cy5 channels, respectively. To investigate the specificity of Erb-encoded UPS nanoprobe, the A549 cells were incubated with Erb-encoded PDPA-TMR nanoprobe. Fifteen minutes after Erb-encoded PDPA-TMR incubation, punctate fluorescence activation was observed inside the cells. At 1 h, an over 250-fold fluorescence increase in the Erb-encoded PDPA-TMR nanoprobe was observed over PDPA-TMR nanoprobe control group, demonstrating the high specificity to EGFR biomarker (FIG. 96). After verifying the specificity of the Erb-conjugated UPS nanoprobe, the synchronized uptake of Erb-encoded hybrid UPS nanoprobe was checked (FIG. 97). A549 cells were incubated with Erb-encoded hybrid UPS nanoprobe for 3 h, and imaged by a confocal microscope. In the control group, A549 cells were incubated with the cocktail of PEPA-BDY493, Erb-encoded PDPA-TMR, and PDBA-Cy5 three nanoprobes. The synchronized uptake of Erb-encoded hybrid nanoprobes in single endocytic organelle was observed, while only Erb-encoded PDPA-TMR nanoprobe in the control group was internalized and activated inside the cells. Importantly, all the punctate blue and red fluorescent dots were colocalized with a subset of green fluorescent dots, indicating that the hybrid nanoprobes can be utilized for the evaluation of endocytic organelle maturation.

To track endosome maturation in real-time, the A549 cells were incubated with Erb-encoded hybrid UPS nanoprobe for 30 min at 4° C. to allow for specific cell binding, then the medium was removed and washed thrice. The intracellular uptake and activation of hybrid nanoprobe at 37° C. was imaged by confocal microscope. As expected, the PEPA-BDY493 component was firstly released and activated to produce the green fluorescent dots at 10 min, and the intensity increased and reached a plateau after 30 min incubation (FIG. 98). Then, the red PDPA-TMR signals started to emerge at 20-30 min. All the red dots were colocalized with a subset of green dots at this stage. Finally, the PDBA-Cy5 component was activated with pseudocolored blue dots at 90-180 min, and all the blue dots were colocalized with a subset of red dots at this period. The endocytic organelles can be divided into three populations: (i) green dots (6.2<pH<6.9); (ii) yellow dots (5.3<pH<6.2); (iii) white dots (pH<5.3), which indicated pH~6.8 for clathrin-coated vesicle, pH~6.0 for early endosome and pH 5.0-5.5 for late endosome/lysosome, respectively. Similarly, the sequential activation was observed inside the single acidic organelle in HN5 head-neck cancer cell line (FIG. 99). Thus, the hybrid UPS nanoprobe successfully reported spatiotemporal pH changes along the specific endocytic pathway in single organelle resolution.

Having demonstrated the unique capability of the hybrid UPS nanoprobe, the unique oncogenic signature that is responsible for the dramatic increase of acidification rates during organelle maturation was investigated. Seven lung cancer cell lines with different gene mutation background were selected and evaluated (Table 15). The cells were incubated with 100 μg/mL Erb-encoded hybrid UPS nanoprobe at 4° C. for 30 min, washed three times and then imaged in real time at 37° C. to track the nanoprobe activation rates which indicates the organelle acidification capacity (FIGS. 100-102). Results showed that the activation rates of KRAS mutated cells including HCC44, H2009, H460, and A549 are significantly faster than KRAS wild type cells (H2882, H1991, and H1819). To normalize the uptake difference in different cell lines, the fluorescence intensity of PDPA-TMR (early endosome) and PDBA-Cy5 (late endosome/lysosome) signals were divided by PEPA-BDY493 signal, which was activated at as early as 15 min. The $I_{6.2}/I_{6.9}$ and $I_{5.3}/I_{6.9}$ as a function of time were plotted (FIGS. 103A & 103B and FIGS. 104A-104D). At 30 min, no significant activation difference of TMR channel ($I_{6.2}/I_{6.9}$) was observed. At 75 min, the $I_{5.3}/I_{6.9}$ ratios for KRAS mutated cells reached to 70% blue-positive organelles, while KRAS wild type cells only had less than 40% blue-positive organelles. These results indicated that KRAS mutation would be responsible for the lysosome catabolism associated with pH regulation.

TABLE 15

| Cell lines and their gene mutation background | | |
|---|---|---|
| Cell line | KRAS status | P53 status |
| HCC44 | Mutate (M) | M |
| H2009 | M | M |
| H460 | M | Wild Type (WT) |
| A549 | M | WT |
| H2882 | WT | M |
| H1993 | WT | M |
| H1819 | WT | WT |

Given that the KRAS mutation is probably responsible for the upregulated acidification rate of lysosome, the hybrid UPS nanoprobe was utilized to directly capture the organelle pH correlates with gene mutations. As a model system, tumor-derived (HCC4017) and normal bronchiole epithelia-derived (HBEC30KT) cell lines from the same lung cancer patient together with an isogenic progression series of HBEC30KT with stepwise stable suppression of TP53 (HBEC30KT-shTP53), stable expression of $KRAS^{G12V}$ (HBEC30KT-shTP53/$KRAS^{G12V}$), and stable suppression of LKB1 (HBEC30KT-shTP53/$KRAS^{G12V}$/shLKB1) were selected and imaged (Ramirez et al., 2004). FIGS. 105A & 105B showed the dramatic difference on the faster maturation rates of endocytic organelles in malignant HCC4017 cells over HBEC30KT epithelial cells (FIGS. 106 & 107). Genotyping of the parental tumor and HCC4017 cell line revealed mutations in TP53, LKB1 and KRAS. The data is consistent with previous findings that KRAS/LKB1 mutated cells rely on lysosomal catabolism for growth and survival (Kim et al., 2013). To further pinpoint which oncogenic signature is responsible for the difference in organelle maturation, the fluorescence activation pattern of hybrid nanoprobe in the isogenic progression series of HBEC30KT were imaged (FIGS. 108-110). The $I_{6.2}/I_{6.9}$ and $I_{5.3}/I_{6.9}$ as a function of time were plotted (FIGS. 111A-111D). Results clearly indicated that KRAS mutation is responsible for the dramatic increase in the acidification and maturation of endocytic organelles.

2. Method and Materials

1. Synthesis and Characterization of Hybrid Nanoprobes

Dye conjugated PEG-b-PR and maleimide-terminated PEG-b-PDPA (Mal-PEG-PDPA) block copolymers were synthesized by the atom transfer radical polymerization method. The hybrid nanoprobes were prepared following a previously published procedure (Wang et al., 2014). In a typical procedure, 5 mg of each PEG-b-PEPA-BDY493, PEG-b-PDPA-TMR, and PEG-b-PDBA-Cy5 polymer were dissolved in 1 mL THF. Then, the mixture was added into 10 mL of Milli-Q water under sonication. The mixture was filtered four times to remove THF using a micro-ultracentrifugation system. Then, the distilled water was added to adjust the final polymer concentration to 5 mg/mL. To prepare the Erbitux-conjugate hybrid nanoprobe, 0.6 mg Mal-PEG-PDPA, 4 mg of each PEG-6-PEPA-BDY493, PEG-6-PDPA-TMR, and PEG-6-PDBA-Cy5 polymer were dissolved in 1 mL THF, and the same procedure as described above was used to prepare the 5% maleimide-modified hybrid nanoprobe. Meanwhile, the Erbitux Fab'-SH fragment (3 mg, $M_w$=55 kDa) was prepared following the published procedure. Then, the maleimide-modified hybrid nanoprobe and Erbitux Fab'-SH solution were mixed and reacted in 100 mM phosphate buffered saline (PBS, pH 7.4) containing 1 mM EDTA overnight at room temperature. Then, the mixture was filtered six times to remove free Fab'-SH using a micro-ultracentrifugation system (MWCO=100K, Millipore). Then, 100 mM PBS (pH 7.4) was added to adjust the final polymer concentration to 5 mg/mL. Transmission electron microscopy was carried out with 1% phosphotungstic acid negative staining and visualized on a JEOL 1200EX electron microscope (JEOL 1200EX). The particle size and distribution of the nanoparticles were determined by dynamic light scattering (DLS) analysis. The mean count rates of the nanoparticles as a function of pH values were also determined by DLS analysis.

2. Fluorescence Activation of UPS Nanoprobes

Fluorescence emission spectra of the hybrid UPS nanoprobes in different pH buffer solutions were obtained on a Hitachi fluorometer (F-7500 model). The final polymer concentration was adjusted to 100 µg/mL using 100 mM PBS with different pH values. The hybrid nanoprobe was excited at 485, 545, and 640 nm, respectively. The corresponding emission spectra were collected at 490-750, 560-750, and 650-750 nm, respectively. The emission peaks at 510, 580, and 710 nm were used to quantify the fluorescence activation ratios for BDY493, TMR, and Cy5 channels. Fluorescent images of the hybrid nanoprobe solution (100 µg/mL) at different pH values were captured on a Maestro imaging system (CRI) using blue (515 nm LP), green (580 nm LP), and orange (645 nm LP) filters. Then, the images were spectrally unmixed using the standard fluorescent spectra of individual dyes to obtain the multicolor images.

3. Cell Culture

The lung cancer cell line A549 and head and neck cancer cell line HN5 were culture in DMEM (Invitrogen) containing 10% fetal bovine serum (Invitrogen), 100 IU/mL penicillin, and 100 µg/mL streptomycin (Invitrogen). The HBEC30KT progression series and HCC4017 cells were cultured in ACL4 medium supplemented with 2% fetal bovine serum and antibiotics at 37° C. in 5% $CO_2$ atmosphere.

4. Cell Imaging

A549 and HN5 cells were plated in glass bottom dishes (MatTek, MA) in 2 mL complete DMEM medium. To test the specificity of Erbitux-conjugated nanoprobes, the A549 cells in complete medium were kept at 4° C. for 10 min, then 100 µg/mL of Erb-PDPA-TMR micelle was added and kept for 30 min at 4° C. for epidermal growth factor receptor (EGFR) binding, then the medium was removed and washed with ice-cold PBS three times. Thereafter, cells were incubated with complete medium for 2 h at 37° C. The confocal images were captured by a Nikon ECLIPSE TE2000-E confocal microscope with a 60× objective lens.

To demonstrate the synchronized uptake of three components in the hybrid nanoprobe, the A549 cells in complete medium were kept at 4° C. for 10 min, then 100 µg/mL of Erb-conjugated hybrid nanoprobe was added and kept for 30 min at 4° C. for EGER binding. The medium was removed and washed thrice. Thereafter, cells were incubated with complete medium for 3 h at 37° C. BDY493, TMR, and Cy5 were excited at 488, 543, and 633 nm, respectively. The FITC (515±15 nm), TRITC (590±25 nm) and Cy5 (650 nm LP) filters were used for BDY493, TMR, and Cy5 imaging, respectively. For control group, PEPA-BDY493, Erb-PDPA-TMR, and PDBA-Cy5 micelles were prepared, mixed up, and incubated with A549 cells. The same procedure was utilized for the cell imaging.

To track endosome maturation process, the cell samples were prepared using the same procedure described above. Confocal images were captured by a Nikon ECLIPSE TE2000-E confocal microscope with a 100× objective lens at 0, 15, 30, 60 min, 2.5, and 5 hrs after incubation at 37° C. The BDY493, TMR, and Cy5 three channels were excited and collected using the same setting described above. The images were analyzed using Image-J software. Five independent measurements were presented as the mean±standard deviation.

5. Statistical Analysis

Data were expressed as mean±s.d. Differences between groups were assessed using paired, two-sided Student t-test. $P<0.05$ was considered significant, and **$P<0.01$ was considered highly significant.

6. Materials

Tetramethylrhodamine succinimidyl ester (TMR-NHS) and BODIPY®493/503 succinimidyl ester (BDY493-NHS) were purchased from Invitrogen Inc. Cy5 NHS ester (Cy5-NHS) was purchased from Lumiprobe Company. Monomers including 2-(dipropylamino) ethyl methacrylate (DPA-MA), and 2-(dibutylamino) ethyl methacrylate (DBA-MA) were reported recently (Zhou et al., 2011; Ma et al., 2014). 2-aminoethyl methacrylate (AMA) was purchased from Polyscience Company. AMA was recrystallized twice with isopropanol and ethyl acetate (3:7). PEG macroinitiator, MeO-$PEG_{114}$-Br, was prepared from α-bromoisobutyryl bromide and MeO-$PEG_{114}$-OH according to the procedure in literature (Zhou et al., 2011). Other solvents and reagents were used as received from Sigma-Aldrich or Fisher Scientific Inc.

7. Synthesis of PEG-h-(PR-r-Dye) Block Copolymers

PEG-b-(PR-r-AMA) copolymers (Scheme 1) were first synthesized by atom transfer radical polymerization (ATRP) method. The primary amino groups were introduced into each polymer chain by controlling the feeding ratio of the AMA monomer to the initiator (ratio=3). The dye-free copolymers were used in polymer characterizations (Table 12). PEG-b-P(DPA-r-AMA) was used as an example to illustrate the procedure. First, DPA-MA (1.7 g, 8 mmol), AMA (50 mg, 3 mmol), PMDETA (21 µL, 0.1 mmol), and MeO-$PEG_{114}$-Br (0.5 g, 0.1 mmol) were charged into a polymerization tube. Then a mixture of 2-propanol (2 mL) and DMF (2 mL) was added to dissolve the monomer and initiator. After three cycles of freeze-pump-thaw to remove oxygen, CuBr (14.4 mg, 0.1 mmol) was added into the reaction tube under nitrogen atmosphere, and the tube was sealed in vacuo. The polymerization was carried out at 40° C. for 12 hours. After polymerization, the reaction mixture was diluted with 10 mL THF, and passed through an $Al_2O_3$ column to remove the catalyst. The THF solvent was removed by rotovap. The residue was dialyzed in distilled water and lyophilized to obtain a white powder. The resulting PEG-b-(PR-r-AMA) copolymers were characterized by 500 MHz $^1$H-NMR, gel permeation chromatography (Viscotech GPCmax, PLgel 5 µm MIXED-D columns by Polymer Labs, THF as eluent at 1 mL/min). Table 12 enlists the yield, molecular weights ($M_n$ and $M_w$) and polydispersity index (PDI) of each copolymer.

Synthesis of dye-conjugated copolymers followed a representative procedure described below. For TMR conjugation, PEG-b-P(DPA-r-AMA) (50 mg) was first dissolved in 2 mL DMF. Then, TMR-NHS ester (1.5 equivalents to the molar amount of the primary amino group) was added. The reaction mixture was stirred at room temperature for 24 hours. The copolymers were purified by preparative gel permeation chromatography (PLgel Prep µm 10E3 Å 300× 25 mm columns by Varian, THF as eluent at 5 mL/min) to remove the free dye molecules. The produced PEG-b-P (DPA-TMR) copolymers were lyophilized and stored at −20° C. for further research. The dye conjugation efficiency and quantum yield were determined according to the procedure in the literature (Ma et al., 2014).

8. Preparation of the Micelle Nanoparticles

Micelles were prepared following a previously published procedure. In a typical procedure, 10 mg of PDPA-TMR was dissolved in 0.5 mL THF. Then, the mixture was slowly added into 4 mL of Milli-Q water under sonication. The mixture was filtered 4 times to remove THF using the micro-ultrafiltration system. Then, the distilled water was added to adjust the polymer concentration to 5 mg/mL as a stock solution. For the multi-color hybrid nanoparticle, 5 mg of PEPA-BDY, 5 mg of PDPA-TMR, and 5 mg of PDBA-Cy5 were dissolved in 1 mL THF. Then, the same procedure was used to prepare the hybrid nanoparticle. The nanoparticles were characterized by transmission electron microscopy (TEM, JEOL 1200 EX model) for micelle size and morphology, dynamic light scattering (DLS, Malvern Zetasizer Nano-ZS, $\lambda$=632 nm) for hydrodynamic diameter (Dh).

For Erbitux-conjugated hybrid nanoprobe, 4 mg of PEPA-BDY, 4 mg of PDPA-TMR, 4 mg of PDBA-Cy5, and 0.6 mg of MAL-PEG-PDPA were dissolved in 1 mL THF. Then, the same procedure was used to prepare the Mal-hybrid nanoprobe. After micelle formation, an excess amount of Erbitux Fab'-SH fragment (55 kD) in PBS buffer containing 1 mM EDTA was added. The conjugation was allowed to occur overnight under $N_2$ atmosphere followed by ultracentrifugation six times to remove free Fab'-SH. The resulting Erb-conjugated hybrid nanoprobe was adjusted to 5 mg/mL polymer concentration for cell imaging studies. The Erb-conjugated PDPA-TMR micelle was also prepared using the same procedure.

9. Fluorescence Characterization

The fluorescence emission spectra in different pH buffer solutions were obtained on a Hitachi fluorometer (F-7500 model). For each polymeric micelle, the sample (5 mg/mL) was prepared in Milli-Q water. Then, the solution was diluted in 100 mM phosphate buffered saline (PBS) with different pH values. The final polymer concentration was controlled at 0.1 mg/mL.

To demonstrate whether different polymer can form a homogenous hybrid micelle, we examined the fluorescence properties of hybrid micelles using fluorescence resonance energy transfer (FRET) experiments. For each nanoprobe, the sample (5 mg/mL) was prepared in Milli-Q water. The solution was diluted to 100 µg/mL in 100 mM PBS buffer (pH 7.4). Then, the nanoprobe was excited by a proper excitation light ($\lambda_{ex}$=485, 545, and 640 nm), and the emission spectra were collected.

The fluorescent images of hybrid nanoprobe solutions (0.1 mg/mL) at different pH were captured on Maestro in vivo imaging system (CRI Inc. Woburn, Mass.) using a proper band pass excitation filter and a proper long-pass emission filter.

10. Cell Culture

Human lung small cell lung cancer A549 cells and head and neck cancer HN5 cells were cultured in DMEM medium (Invitrogen, CA) supplemented with 10% fetal bovine serum (FBS), 100 IU/mL penicillin and 100 µg/mL streptomycin at 37° C. in 5% $CO_2$ atmosphere.

Tumor-derived (HCC4017) and normal bronchiole epithelia-derived (HBEC30) cell lines from the same lung cancer patient were obtained. The normal bronchial epithelial cells were immortalized by stable expression of CDK4 and hTERT to produce HBEC30KT. Series cell lines of HBEC30KT derivatives with stepwise stable suppression of p53 (HBEC30KT-shTP53), stable expression of $KRAS^{G12V}$ (HBEC30KT-shTP53/$KRAS^{G12V}$), and stable suppression of LKB1 (HBEC30KT-shTP53/$KRAS^{G12V}$/shLKB1) were also obtained.

The HBEC30KT progression series and HCC4017 cells were cultured in ACL4 medium supplemented with 2% fetal bovine serum (FBS), 100 IU/mL penicillin and 100 µg/mL streptomycin at 37° C. in 5% $CO_2$ atmosphere.

11. Multi-Stage Activation of Erbitux-Conjugated Hybrid Nanoprobes in Living Cells A549 and HN5 Cells were plated in glass bottom dishes (MatTek, MA) in 2 mL complete DMEM medium. To test the specificity of Erbitux-conjugated nanoprobes, the A549 cells were incubated with complete medium containing Erb-PDPA-TMR micelle for 1 hour at 37° C., then the medium was removed and washed 3 times. The confocal images were captured by a Nikon ECLIPSE TE2000-E confocal microscope with a 60× objective lens.

To demonstrate the synchronized uptake of three components in the hybrid nanoprobe, the A549 cells in complete medium were kept at 4° C. for 10 min, then 100 µg/mL of Erb-conjugated hybrid nanoprobe was added and kept for 30 min at 4° C. for epidermal growth factor receptor (EGFR) binding. The medium was removed and washed with ice-cold PBS three times. Thereafter, cells were incubated with complete medium for 3 hours at 37° C. BDY493, TMR, and Cy5 were excited at 488, 543, and 633 nm, respectively. The FITC (515±15 nm), TRITC (590±25 nm) and Cy5 (650 nm LP) filters were used for BDY493, TMR, and Cy5 imaging, respectively. For control group, PEPA-BDY493, Erb-PDPA-TMR, and PDBA-Cy5 micelles were prepared, mixed up, and incubated with A549 cells. The same procedure was utilized for the pulse-chase study.

12. Tracking Endosome Maturation During Endocytosis Using Erbitux-Conjugated Hybrid Nanoprobes Pulse chase experiments were utilized to track endosome maturation process. Cells in complete medium were kept at 4° C. for 10 min, and then 100 µg/mL of Erb-conjugated hybrid nanoprobe was added and kept for 30 min at 4° C. for EGFR binding. The medium was removed and washed with ice-cold PBS three times. Thereafter, cells were incubated with complete medium at 37° C. Confocal images were captured by a Nikon ECLIPSE TE2000-E confocal microscope with a 100× objective lens at 0, 15, 30, 60 min, 2.5, and 5 hrs after addition of micelles. BDY493, TMR, and Cy5 were excited at 488, 543, and 633 nm, respectively. The FITC (515±15 nm), TRITC (590±25 nm) and Cy5 (650 nm LP) filters were used for BDY493, TMR, and Cy5 imaging, respectively. The images were analyzed using Image-J software. Five independent measurements were presented as the mean±standard deviation.

Example 15: Syntheses of Triblock Copolymer PEO-b-P(R$_1$-b-R$_2$)

PEG-b-P(R$_1$-b-R$_2$) triblock copolymers were synthesized by ATRP method following similar procedures previously reported. PEO-b-P(D5A-b-DEA) is used as an example to illustrate the procedure. First, D5A-MA (0.54 g, 2 mmol), PMDETA (12 µL, 0.05 mmol) and MeO-PEO$_{114}$-Br (0.25 g, 0.05 mmol) were charged into a polymerization tube. Then a mixture of 2-propanol (1 mL) and DMF (1 mL) was added to dissolve the monomer and initiator. After three cycles of freeze-pump-thaw to remove the oxygen, CuBr (7 mg, 0.05 mmol) was added into the polymerization tube under nitrogen atmosphere, and the tube was sealed in vacuo. After polymerization carrying out at 40° C. for 8 hours, deoxygenized DEA-MA (0.368, 2 mmol) was injected to the reaction solution via air-tight syringe and the reaction mixture was stirred at 40° C. for additional 8 hours. After polymerization, the reaction mixture was diluted with 10 mL THF, and passed through a neutral Al$_2$O$_3$ column to remove the catalyst. The THF solvent was removed by rotovap. The residue was dialyzed in distilled water and lyophilized to obtain a white powder. PEO-b-P(DEA-6-D5A) can also be synthesized by reversing the feeding sequence of DEA and D5A. The pH titration experiments showed two distinctive ionization transitions for the PEO-b-P(D5A$_{40}$-b-DEA$_{40}$) or PEO-b-P(DEA$_{40}$-b-D5A$_{40}$). In contrast, only one pH transition was observed for the corresponding random PR block copolymers (FIGS. 113A & 113B).

All of the compositions and methods disclosed and claimed herein can be made and executed without undue experimentation in light of the present disclosure. While the compositions and methods of this disclosure have been described in terms of certain embodiments, it will be apparent to those of skill in the art that variations may be applied to the compositions and methods and in the steps or in the sequence of steps of the methods described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference.

WO 2013/152059
Adams & Weiner, Nat Biotechnol, 23:1147-1157, 2005.
Albertazzi, L.; Storti, B.; Marchetti, L.; Beltram, F. *J. Am. Chem. Soc.* 2010, 132, 18158.
Alberts, B.; Johnson, A.; Lewis, J.; Raff, M.; Roberts, K.; Walter, P. *Molecular Biology of the Cell;* 5th ed.; Garland Science: New York, 2008.
Almutairi, A.; Guillaudeu, S. J.; Berezin, M. Y.; Achilefu, S.; Fréchet, J. M. J. *J. Am. Chem. Soc* 2007, 130, 444.
Ananthapadmanabhan, K. P.; Goddard, E. D.; Turro, N. J.; Kuo, P. L. *Langmuir* 1985, 1, 352.
Atkins, et al., J. Surg. Res., 177, 109-115, 2012.
Atkins, P.; De Paula, J. *Physical Chemistry*, Oxford University Press, 2009.
Benjaminsen, R. V.; Sun, H. H.; Henriksen, J. R.; Christensen, N. M.; Almdal, K.; Andresen, T. L. *ACS Nano* 2011, 5, 5864.
Berezin, M. Y.; Achilefu, S. *Chem. Rev.* 2010, 110, 2641.
Blum, G.; Mullins, S. R.; Keren, K.; Fonovic, M.; Jedeszko, C.; Rice, M. J.; Sloane, B. F.; Bogyo, M. *Nat. Chem. Biol.* 2005, I, 203.
Bolte & Cordelières, J. Microsc. 224, 213-232, 2006.
Cardone et al., Nat. Rev. Cancer 5, 786-795, 2005.
Casey et al., Nat. Rev. Mol. Cell Biol., 11:50-61, 2010.
Choi et al., Nat. Biotechnol. 31, 148-153, 2013.
Christofk et al., Nature, 452:230-233, 2008.
Collins and Washabaugh, Q. Rev. Biophys. 18:323-422, 1985.
Collins, Biophys. J. 1997, 72, 65-76.
Conner & Schmid, Nature, 422:37-44, 2003.
Cook et al., Semin. Nucl. Med. 34, 122-133, 2004.
Cross & Muller, FEBS Lett., 576:1-4, 2004.
Dacosta et al., Best Pract. Res. Clin. Gastroenterol., 20, 41-57, 2006.
Dai, S.; Ravi, P.; Tam, K. C. *Soft Matter* 2008, 4, 435.
Dale, T. J.; Rebek, J. J. *Am. Chem. Soc.* 2006, 128, 4500.
de Silva, A. P.; Gunaratne, H. Q. N.; Gunnlaugsson, T.; Huxley, A. J. M.; McCoy, C.; P.; Rademacher, J. T.; Rice, T. E. *Chem. Rev.* 1997, 97, 1515.
de Silva, A. P.; Gunaratne, H. Q. N.; McCoy, C. P. *Chem. Commun.* 1996, 2399.
Deamer et al., Membrane permeability: 100 years since Ernest Overton. (Academic Press, San Diego, Calif., USA; 1999).
Demaurex, N. News Physiol. Sci. 2002, 17, 1-5.
Demchenko, A. P. *Introduction to Fluorescence Sensing;* Springer Science: New York, 2008.
Diaz-Fernandez et al., *Chemistry* 12, 921-930, 2006.
Diaz-Fernandez, Y.; Foti, F.; Mangano, C.; Pallavicini, P.; Patroni, S.; Perez-Gramatges, A.; Rodriguez-Calvo, S. *Chem. Eur. J.* 2006, 12, 921.
Diwu et al., Chem. Biol., 6: 411-418, 1999.
Draga et al., Anal. Chem., 82, 5993-5999, 2010.
Eigenbrodt et al., Anticancer Res., 18:3267-3274, 1998.
Enerson & Drewes, J. Pharm. Sci., 92:1531-1544, 2003.
Fantin et al., Cancer Cell, 9:425-434, 2006.
Fernandez-Suarez, M.; Ting, A. Y. *Nat. Rev. Mol. Cell Biol.* 2008, 9, 929.
Folkman, J., *Nat. Rev. Drug Discovery*, 2007, 6, 273-286.
Fukui et al., Radiographics 25, 913-930, 2005.
Gallagher et al., Nature 453, 940-943, 2008.
Gatenby, R. A.; Gillies, R. J., *Nat. Rev. Cancer*, 2004, 4, 891-899.
Gatenby, R. A.; Gillies, R. J., *Nat. Rev. Cancer*, 2008, 8, 56-61.
Giepmans, B. N. G.; Adams, S. R.; Ellisman, M. H.; Tsien, R. Y. *Science* 2006, 312, 111.
Gil, E. S.; Hudson, S. M. *Prog. Polym. Sci.* 2004, 29, 1173.
Gillies et al., Am. J. Physiol., 267, C195-C203, 1994.
Gillies et al., Med. Biol. Mag., 23, 57-64, 2004.
Gross, S.; Piwnica-Worms, D. *Cancer Cell* 2005, 7, 5.
Grunwell, et al., *J. Am. Chem. Soc.* 2001, 123, 4295-4303.
Ha, et al., *Proc. Natl. Acad. Sci. U.S.A.* 1999, 96, 893-898
Haka et al., *Cancer Res.*, 66, 3317-3322, 2006.
Halestrap & Price, Biochem. J., 343 Pt 2, 281-299, 1999.
Han, J. Y.; Burgess, K. *Chem. Rev.* 2010, 110, 2709.
Hanahan, D.; Weinberg, R. A., *Cell,* 2011, 144, 646-674.
Haubner & Wester, Curr Pharm Des., 10:1439-1455, 2004.
Hawkins & Davis, Pharmacological Reviews, 57:173-185, 2005.
Heiden et al., Science, 324, 1029-1033, 2009.

Hofmeister, *Pathol. u. Pharmakol*, 25, 1888.
Holtzman, E. Lysosomes. (Springer, New York, N.Y., USA), 1989.
Huang, X. et. al, *ACS Nano*, 2010, 4, 5887-5896.
Huotari & Helenius, EMBO J, 30:3481-3500, 2011.
Iczkowski and Lucia, Prostate Cancer, 2011, 673021, 2011.
Imamura et al., Proc. Natl. Acad. Sci. U.S.A., 100: 2312-2315, 2003.
Izumi et al., *Cancer Treat. Rev.* 2003, 29, 541.
Jares-Erijman and Jovin, *Nat Biotech* 2003, 21, 1387-1395.
Jelley, E. E. *Nature* 1936, 138, 1009.
Johansson, M. K.; Cook, R. M. *Chem. Eur. J.* 2003, 9, 3466.
Jose et al., Biochim. Biophys. Acta, 1807:552-561, 2011.
Joyce, J. A., *Cancer Cell*, 2005, 7, 513-520.
Kairdolf, B. A.; Nie, S. J. Am. Chem. Soc. 2011, 133, 7268.
Kalyanasundaram & Thomas, J. Am. Chem. Soc., 99:2039-2044, 1977.
Kanter et al., Am. J. Obstet. Gynecol., 200, 512 e511-515, 2009.
Kim et al., Cell, 155:552-566, 2013.
Kleiter, M. M. et. al., *Int. J. Radiat. Oncol. Biol. Rhys.*, 2006, 64, 592-602.
Kobayashi, H.; Choyke, P. L. *Acc. Chem. Res.* 2010, 44, 83.
Kobayashi, H.; Ogawa, M.; Alford, R.; Choyke, P. L.; Urano, Y. *Chem. Rev.* 2010, 110, 2620.
Kreuter, Advanced Drug Delivery Reviews, 47:65-81, 2001.
Kubben et al., Lancet Oncol., 12, 1062-1070, 2011.
Kunz, et al., *Curr. Opin. Colloid Interface Sci.* 2004, 9, 1-18.
Lakowicz, J. R. *Principles of Fluorescence Spectroscopy;* 3rd ed.; Springer: New York City, 2006.
Lee, E. S.; Shin, H. J.; Na, K.; Bae, Y. H. *J. Controlled Release* 2003, 90, 363.
Lee, S.; Park, K.; Kim, K.; Choi, K.; Kwon, I. C. *Chem. Commun.* 2008, 4250.
Lee, S.; Ryu, J. H.; Park, K.; Lee, A.; Lee, S. Y.; Youn, I. C.; Ahn, C. H.; Yoon, S. M.; Myung, S. J.; Moon, D. H.; Chen, X.; Choi, K.; Kwon, I. C.; Kim, K. *Nano Lett.* 2009, 9, 4412.
Lee, S.; Xie, J.; Chen, X. Y. *Curr. Top. Med Chem.* 2010, 10, 1135.
Leontidis, *Curr. Opin. Colloid Interface Sci.* 2002, 7, 81-91.
Levi, J.; Kothapalli, S. R.; Ma, T. J.; Hartman, K.; Khuri-Yakub, B. T.; Gambhir, S. S. *J. Am. Chem. Soc.* 2010, 132, 11264.
Li et al., Angew. Chem. Int. Ed. Engl., 53:8074-8078, 2014.
Li, C.; Xia, J. A.; Wei, X. B.; Yan, H. H.; Si, Z.; Ju, S. H. *Adv. Funct. Mater.* 2010, 20, 2222.
Liu et al., ACS Nano, 4, 2755-2765, 2010.
Liu et al., Angew Chem Int Ed Engl., 48:7346-7349, 2009.
Lodder et al., Eur. Radiol., 21, 98-106, 2011.
Lopez Arbeloa, I.; Ruiz Ojeda, P. *Chem. Rhys. Lett.* 1982, 87, 556.
Lou et al., Cancer Res. 71, 3364-3376, 2011.
Lovell, J. F.; Liu, T. W. B.; Chen, J.; Zheng, G. *Chem. Rev* 2010, 110, 2839.
Ma, et al., J. Am. Chem. Soc., 136:11085-11092, 2014.
Ma, et al., *Macromolecules* 2003, 36, 3475.
Manders et al., J. Microsc., 169: 375-382, 1993.
Maxfield & McGraw, Nat. Rev. Mol. Cell Biol. 5, 121-132, 2004.
Maxfield, F. R.; McGraw, T. E. *Nat. Rev Mol. Cell Biol.* 2004, 5, 121.
Maxwell, D.; Chang, Q.; Zhang, X.; Barnett, E. M.; Piwnica-Worms, D. *Bioconjug. Chem.* 2009, 20, 702.
McElroy et al., World J. Surg., 32, 1057-1066, 2008.
McMahon et al., Br. J. Oral Maxillofac. Surg., 41, 224-231, 2003.
Merk, et al., *Langmuir* 2014, 30, 4213-4222.
Mirbolooki, EJNMMI Research, 1:30, 2011.
Mo et al., Anal. Chem., 81, 8908-8915, 2009.
Modi, S.; Swetha, M. G.; Goswami, D.; Gupta, G. D.; Mayor, S.; Krishnan, Y. *Nat. Nanotech.* 2009, 4, 325.
Morgan, Mol. Membr. Biol., 21:423-433, 2004.
Nasongkla, N.; Bey, E.; Ren, J. M.; Ai, H.; Khemtong, C.; Guthi, J. S.; Chin, S. F.; Sherry, A. D.; Boothman, D. A.; Gao, J. M., *Nano. Lett.* 2006, 6, 2427-2430.
Neri & Supuran, Nat. Rev. Drug Discov. 10, 767-777, 2011.
Neri & Supuran, Nat. Rev. Drug Discov., 10:767-777, 2011.
Nguyen and Tsien, Nat. Rev. Cancer, 13, 653-662, 2013.
Nishi, T.; Forgac, M. *Nat. Rev. Mol. Cell Biol.* 2002, 3, 94.
Ogawa, M.; Kosaka, N.; Choyke, P. L.; Kobayashi, H. *ACS Chem. Biol.* 2009, 4, 535.
Ohgaki, R.; van Ijzendoorn, S. C. D.; Matsushita, M.; Hoekstra, D.; Kanazawa, H. *Biochemistry* 2010, 50, 443.
Pacchiano et al., J. Med. Chem. 54, 1896-1902, 2011.
Packard, B. Z.; Komoriya, A.; Toptygin, D. D.; Brand, L. J. *Phys. Chem. B* 1997, 101, 5070.
Parks et al., Nat. Rev. Cancer 13, 611-623, 2013.
Parsons, et al., *Rhys. Chem. Chem. Rhys.* 2011, 13, 12352-12367.
Pena-Llopis et al., EMBO J., 30: 3242-3258, 2011.
Perez-Sayans et al., Cancer Treat. Rev., 35:707-713, 2009.
Petsalakis, I. D.; Lathiotakis, N. N.; Theodorakopoulos, G. *J. Mol. Struct.: THEOCHEM* 2008, 867, 64.
Pouyssegur et al., Nature, 441:437-443, 2006.
Ramanujam et al., Photochem. Photobiol, 64, 720-735, 1996.
Ramirez, et al., Cancer Res, 64: 9027-9034, 2004.
Ravasz et al., J. Craniomaxillofac. Surg., 19, 314-318, 1991.
Riess, G. *Prog. Polym. Sci.* 2003, 28, 1107.
Roczniak-Ferguson et al., Sci Signal 5, ra42, 2012.
Rodman et al., Exp. Cell Res., 192:445-452, 1991.
Rossin et al., J Nucl Med., 49:103-111, 2008.
Ruckenstein, E.; Nagarajan, R. *J. Phys. Chem.* 1975, 79, 2622.
Sancak et al., Cell 141: 290-303, 2010.
Sapsford, et al., *Angew. Chem. Int. Ed* 2006, 45, 4562-4589.
Scheibe, G. *Z. Angew. Chem.* 1936, 49, 563.
Schomacker et al., Lasers Surg. Med., 12, 63-78, 1992.
Schwarz et al., Cancer, 115, 1669-1679, 2009.
Settembre et al., EMBO J., 31:1095-1108, 2012.
Settembre et al., Nat. Rev. Mol. Cell Biol., 14:283-296, 2013.
Sonveaux et al., J. Clin. Invest. 118, 3930-3942, 2008.
Srikun, D.; Albers, A. E.; Chang, C. *J. Chem. Sci.* 2011, 2, 1156.
Sterling, et al., Cell Physiology, 283:0 522-1529, 2002.
Suh et al., *Bioorg. Chem.,* 22: 318-327, 1994.
Sun et al., J Med Chem., 45:469-477, 2002.
Supuran, Bioorg. Med. Chem. Lett., 20:3467-3474, 2010.
Supuran, Nat. Rev. Drug Discov., 7:168-181, 2008.
Swartz, M. A.; et. al.; *Cancer Res.,* 2012, 72, 2473-2480.
Tal, S.; Salman, H.; Abraham, Y.; Botoshansky, M.; Eichen, Y. Chem. Eur. J. 2006, 12, 4858.
Tran et al., Hepatogastroenterology, 59, 1994-1999, 2012.
Tsarevsky and Matyjaszewski, *Chem. Rev.* 2007, 107, 2270.
Tsien, R. Y. *Nat. Rev. Mol. Cell Biol.* 2003, 4, SS16.
Ueno, T.; Nagano, T. *Nat. Methods* 2011, 8, 642.
Underwood and Anacker, J. *Colloid Interface Sd.* 1987, 117, 242-250.
Urano, et al., Nat. Med., 15:104-109, 2008.
Urano, Y.; Asanuma, D.; Hama, Y.; Koyama, Y.; Barrett, T.; Kamiya, M.; Nagano, T.; Watanabe, T.; Hasegawa, A.; Choyke, P. L.; Kobayashi, H. *Nat. Med.* 2009, 15, 104.

Vahrmeijer et al., *Nat. Rev. Clin. Oncol.*, 10, 507-518, 2013.
Valdes-Aguilera, O.; Neckers, D. C. *Acc. Chem. Res.* 1989, 22, 171.
Valeur, B. *Molecular fluorescence: principles and applications*; Wiley-VCH, 2002.
van Sluis et al., Magn. Reson. Med., 41, 743-750, 1999.
Vishvakarma & Singh, Biomed. Pharmacother. 65, 27-39, 2011.
Vogel, S. S.; Thaler, C.; Koushik, S. V. *Sci. STKE* 2006, 2006, re2.
Volk et al., Br. J. Cancer, 68, 492-500, 1993.
Wadas et al., Curr Pharm Des. 13:3-16, 2007.
Wang et al., J Vis Exp., 2012.
Wang et al., Journal of Visualized Experiments: JoVE, 2012.
Wang et al., Nat. Mater., 13:204-212, 2014.
Wang, et al., *Angew. Chem. Int. Ed.* 2008, 47, 9726-9729.
Wasielewski, M. R. *Chem. Rev.* 1992, 92, 435.
Webb et al., Nat. Rev. Cancer, 11, 671-677, 2011.
Webb, B. A.; Chimenti, M.; Jacobson, M. P.; Barber, D. L., *Nat. Rev. Cancer*, 2011, 11, 671-677.
Weerakkody et al., Proc. Natl. Acad. Sci. U.S.A. 110, 5834-5839, 2013.
Weis, S. M., Cheresh, D. A., *Nat. Med*, 2011, 17, 1359-1370.
Weissleder, R.; Pittet, M. J. *Nature* 2008, 452, 580.
Weisz, Cytol., 226:259-319, 2003.
Weller, A. *Pure Appl. Chem.* 1968, 16, 115.
West, W.; Pearce, S. *J. Phys. Chem.* 1965, 69, 1894.
Winnik, Chem. Rev., 93:587-614, 1993.
Woodin et al., Eur J Inorg Chem., 4829-4833, 2005.
Woolgar and Triantafyllou, Oral Oncol., 41, 1034-1043, 2005.
Yang C. et. al, *Cancer Res.* 2009, 69, 7986-93.
Yeung et al., Curr. Opin. Cell Biol. 18, 429-437, 2006.
Yezhelyev et al., *J. Am. Chem. Soc.* 2008, 130, 9006.
Yu et al., *ACS Nano* 2011, 5, 9246.
Zhang and Cremer, *Curr. Opin. Chem. Biol.* 2006, 10, 658-663.
Zhang and Cremer, *Proc. Natl. Acad. Sci. U.S.A.* 2009, 106, 15249-15253.
Zhang et al., Cell Metab. 20:526-540, 2014.
Zhang, J.; Campbell, R. E.; Ting, A. Y.; Tsien, R. Y. *Nat. Rev. Mol. Cell Biol.* 2002, 3, 906.
Zhang, X.; Lin, Y.; Gillies, R. J. *J. Nucl. Med* 2010, 51, 1167.
Zhou, et al., J. Am. Chem. Soc., 134:7803-7811, 2012.
Zhou, K. et. al., *Angew. Chem. Int. Ed.* 2011, 50, 6109-6114
Zhou, K.; Lu, Y.; Li, J.; Shen, L.; Zhang, G.; Xie, Z.; Wu, C. *Macromolecules* 2008, 41, 8927
Zoncu et al., Science, 334:678-683, 2011.

What is claimed is:

1. A polymer of the formula:

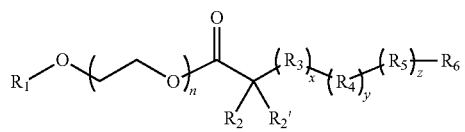
(I)

wherein:
R$_1$ is hydrogen, alkyl$_{(C≤12)}$, cycloalkyl$_{(C≤12)}$, substituted alkyl$_{(C≤12)}$, substituted cycloalkyl$_{(C≤12)}$, or

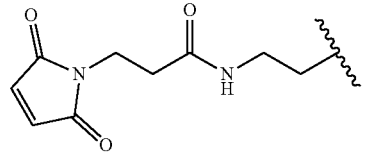, or a metal chelating group;
n is an integer from 1 to 500;
R$_2$ and R$_2$' are each independently selected from hydrogen, alkyl$_{(C≤12)}$, cycloalkyl$_{(C≤12)}$, substituted alkyl$_{(C≤12)}$, or substituted cycloalkyl$_{(C≤12)}$;
R$_3$ is a group of the formula:

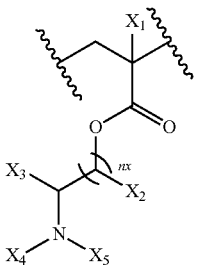
(II)

wherein:
n$_x$ is 1-10;
X$_1$, X$_2$, and X$_3$ are each independently selected from hydrogen, alkyl$_{(C≤12)}$, cycloalkyl$_{(C≤12)}$, substituted alkyl$_{(C≤12)}$, or substituted cycloalkyl$_{(C≤12)}$; and
X$_4$ and X$_5$ are each independently selected from alkyl$_{(C≤12)}$, cycloalkyl$_{(C≤12)}$, aryl$_{(C≤12)}$, heteroaryl$_{(C≤12)}$ or a substituted version of any of these groups, or X$_4$ and X$_5$ are taken together and are alkanediyl$_{(C≤12)}$, alkoxydiyl$_{(C≤12)}$, alkylaminodiyl$_{(C≤12)}$, or a substituted version of any of these groups;
x is an integer from 1 to 150;
R$_4$ is a group of the formula:

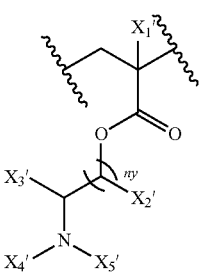
(III)

wherein:
n$_y$ is 1-10;
X$_1$', X$_2$', and X$_3$' are each independently selected from hydrogen, alkyl$_{(C≤12)}$, cycloalkyl$_{(C≤12)}$, substituted alkyl$_{(C≤12)}$, or substituted cycloalkyl$_{(C≤12)}$; and $X_4'$ and $X_5'$ are each independently selected from alkyl$_{(C \leq 12)}$, cycloalkyl$_{(C \leq 12)}$, aryl$_{(C \leq 12)}$, heteroaryl$_{(C \leq 12)}$ or a substituted version of any of these groups, or $X_4'$ and $X_5'$ are taken together and are alkanediyl$_{(C \leq 12)}$, alkoxydiyl$_{(C \leq 12)}$, alkylaminodiyl$_{(C \leq 12)}$, or a substituted version of any of these groups;

y is an integer from 1 to 150;

$R_5$ is a group of the formula:

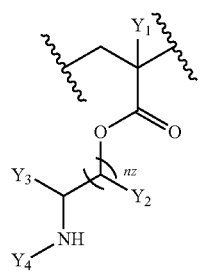

(IV)

wherein:
$n_z$ is 1-10;
$Y_1$, $Y_2$, and $Y_3$ are each independently selected from hydrogen, alkyl$_{(C \leq 12)}$, cycloalkyl$_{(C \leq 12)}$, substituted alkyl$_{(C \leq 12)}$, or substituted cycloalkyl$_{(C \leq 12)}$; and
$Y_4$ is with the following structure:

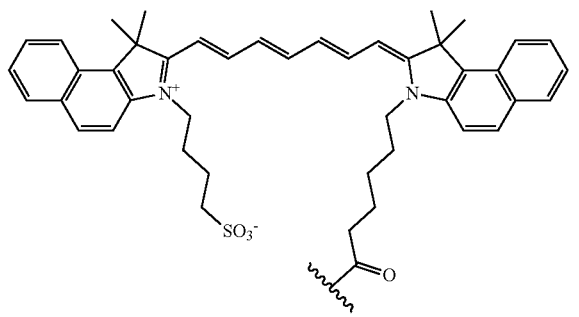

z is an integer from 0-6; and
$R_6$ is hydrogen, halo, hydroxy, alkyl$_{(C \leq 12)}$, or substituted alkyl$_{(C \leq 12)}$,
wherein $R_3$, $R_4$, and $R_5$ can occur in any order within the polymer, provided that $R_3$ and $R_4$ are not the same group.

2. The polymer according to claim 1, wherein $R_1$ is hydrogen.

3. The polymer according to claim 1, wherein $R_1$ is alkyl$_{(C \leq 6)}$.

4. The polymer of claim 3, wherein $R_1$ is methyl.

5. The polymer according to claim 1, wherein $R_1$ is

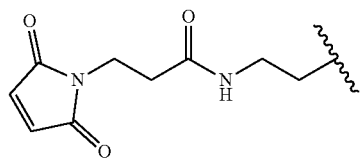

6. The polymer according to claim 1, wherein $R_1$ is a metal chelating group selected from DOTA, TETA, Diamsar, NOTA, NETA, TACN-TM, DTPA, TRAP, NOPO, AAZTA, DATA, HBED, SHBED, BPCA, CP256, DFO, PCTA, HEHA, PEPA, or a derivative thereof.

7. The polymer according to claim 1, wherein $R_1$ is a metal chelating group.

8. The polymer of claim 7, wherein the metal chelating group is a nitrogen containing macrocycle.

9. The polymer of claim 7, wherein the nitrogen containing macrocycle is a compound of the formula:

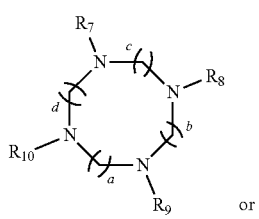

(VA)

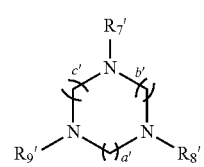

(VB)

wherein:
$R_7$, $R_8$, $R_9$, $R_{10}$, $R_7'$, $R_8'$, and $R_9'$ are each independently selected from hydrogen, alkyl$_{(C \leq 12)}$, acyl$_{(C \leq 12)}$, -alkanediyl$_{(C \leq 12)}$-acyl$_{(C \leq 12)}$, or a substituted version of any of these groups; or a linker, wherein the linker is an alkanediyl$_{(C \leq 12)}$ C(O)NH— or a substituted alkanediyl$_{(C \leq 12)}$-C(O)NH—; or $R_7$ is taken together with one of $R_8$, $R_9$, or $R_{10}$ and is alkanediyl$_{(C \leq 6)}$; or $R_8$ is taken together with one of $R_7$, $R_9$, or $R_{10}$ and is alkanediyl$_{(C \leq 6)}$; or $R_9$ is taken together with one of $R_7$, $R_8$, or $R_{10}$ and is alkanediyl$_{(C \leq 6)}$; or $R_{10}$ is taken together with one of $R_7$, $R_8$, or $R_9$ and is alkanediyl$_{(C \leq 6)}$; or $R_7'$ is taken together with one of $R_8'$ or $R_9'$ and is alkanediyl$_{(C \leq 6)}$; or $R_8'$ is taken together with one of $R_7'$ or $R_9'$ and is alkanediyl$_{(C \leq 6)}$; or $R_9'$ is taken together with one of $R_7'$ or $R_8'$ and is alkanediyl$_{(C \leq 6)}$; and a, b, c, d, a', b', and c' are each independently selected from 1, 2, 3, or 4.

10. The polymer of claim 9, wherein a, b, c, d, a', b', and c' are each independently selected from 2 or 3.

11. The polymer according to claim 7, wherein the metal chelating group is:

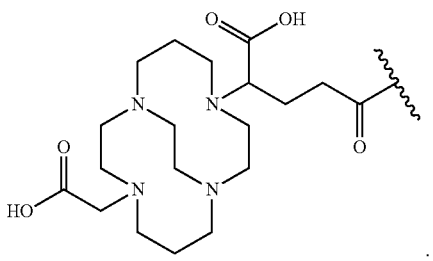 [SMILES: *C(=O)CCC(C(=O)O)N1CCCN2CCN(CCCN(CC(=O)O)CC2)CC1]

12. The polymer according to claim 7, wherein the metal chelating complex is bound to a metal ion.

13. The polymer of claim 12, wherein the metal ion is a radionuclide or radiometal.

14. The polymer of claim 12, wherein the metal ion is suitable for PET or SPECT imaging.

15. The polymer of claim 12, wherein the metal chelating complex is bound to a transition metal ion.

16. The polymer of claim 15, wherein the transition metal is a copper(II) ion.

17. The polymer of claim 16, wherein the copper(II) ion is a $^{64}Cu^{2+}$ ion.

18. The polymer of claim 17, wherein the metal chelating complex is:

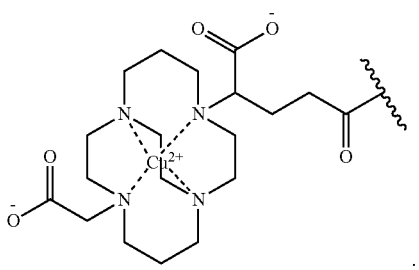

19. The polymer of claim 12, wherein the metal ion is a copper ion, a gallium ion, a scandium ion, an indium ion, a lutetium ion, a ytterbium ion, a zirconium ion, a bismuth ion, a lead ion, a actinium ion, or a technetium ion.

20. The polymer of claim 19, wherein the metal ion is an isotope selected from $^{99m}Tc$, $^{60}Cu$, $^{61}Cu$, $^{62}Cu$, $^{64}Cu$, $^{86}Y$, $^{90}Y$, $^{89}Zr$, $^{44}Sc$, $^{47}Sc$, $^{66}Ga$, $^{67}Ga$, $^{68}Ga$, $^{111}In$, $^{177}Lu$, $^{225}Ac$, $^{212}Pb$, $^{212}Bi$, $^{213}Bi$, $^{111}In$, $^{114m}In$, $^{114}In$, $^{186}Re$, or $^{188}Re$.

* * * * *